US012606564B2

(12) United States Patent
Lee et al.

(10) Patent No.: US 12,606,564 B2
(45) **Date of Patent: *Apr. 21, 2026**

(54) ADENOSINE RECEPTOR ANTAGONIST COMPOUNDS

(71) Applicant: ILDONG PHARMACEUTICAL CO., LTD., Seoul (KR)

(72) Inventors: Yoon-Suk Lee, Hwaseong-si (KR); Sung-Wook Kwon, Hwaseong-si (KR); Kyung-Sun Kim, Hwaseong-si (KR); Jeong-Geun Kim, Hwaseong-si (KR); Jeong-Ah Kim, Hwaseong-si (KR); An-Na Moon, Hwaseong-si (KR); Sun-Young Park, Hwaseong-si (KR); Jun-Su Ban, Hwaseong-si (KR); Dong-Keun Song, Hwaseong-si (KR); Ju-Young Jung, Hwaseong-si (KR); Soo-Jin Lee, Hwaseong-si (KR)

(73) Assignee: ILDONG PHARMACEUTICAL CO., LTD., Seoul (KR)

( * ) Notice: Subject to any disclaimer, the term of this patent is extended or adjusted under 35 U.S.C. 154(b) by 887 days.

This patent is subject to a terminal disclaimer.

(21) Appl. No.: 17/777,881

(22) PCT Filed: Nov. 19, 2020

(86) PCT No.: PCT/IB2020/000971

§ 371 (c)(1),
(2) Date: May 18, 2022

(87) PCT Pub. No.: WO2021/099838

PCT Pub. Date: May 27, 2021

(65) Prior Publication Data

US 2023/0159534 A1 May 25, 2023

(30) Foreign Application Priority Data

Nov. 19, 2019 (KR) ........................ 10-2019-0149117

(51) Int. Cl.

| | |
|---|---|
| ***A61P 35/00*** | (2006.01) |
| ***A61K 31/519*** | (2006.01) |
| ***A61K 45/06*** | (2006.01) |
| ***A61P 21/00*** | (2006.01) |
| ***A61P 25/08*** | (2006.01) |
| ***A61P 25/14*** | (2006.01) |
| ***A61P 25/16*** | (2006.01) |
| ***A61P 25/18*** | (2006.01) |
| ***A61P 25/24*** | (2006.01) |
| ***A61P 25/28*** | (2006.01) |
| ***A61P 29/00*** | (2006.01) |
| ***A61P 35/02*** | (2006.01) |
| ***C07D 487/04*** | (2006.01) |

(52) U.S. Cl.

CPC ............ *C07D 487/04* (2013.01); *A61K 45/06* (2013.01)

(58) Field of Classification Search

None

See application file for complete search history.

(56) References Cited

U.S. PATENT DOCUMENTS

| | | | | |
|---|---|---|---|---|
| 6,124,300 | A | 9/2000 | Rajagopalan et al. | |
| 7,589,097 | B2 | 9/2009 | Gillespie et al. | |
| 11,806,350 | B2 * | 11/2023 | Kim | A61K 31/519 |
| 2004/0116447 | A1 | 6/2004 | Gillespie et al. | |
| 2006/0111373 | A1 | 5/2006 | Gillespie et al. | |

FOREIGN PATENT DOCUMENTS

| | | | | |
|---|---|---|---|---|
| EP | 1 349 857 | B1 | 6/2010 | |
| JP | 2004517861 | A | 6/2004 | |
| JP | 2004517874 | A | 6/2004 | |
| JP | 2011525898 | A | 9/2011 | |
| WO | WO-9901454 | A1 * | 1/1999 | A61K 31/47 |
| WO | 01/002400 | A1 | 1/2001 | |
| WO | 02/055082 | A1 | 7/2002 | |
| WO | 02/055083 | A1 | 7/2002 | |
| WO | WO-2004094426 | A1 * | 11/2004 | C07D 473/00 |
| WO | WO-2008153947 | A2 * | 12/2008 | C07D 473/00 |
| WO | 2009/156737 | A1 | 12/2009 | |
| WO | 2011/006074 | A1 | 1/2011 | |
| WO | 2011/050160 | A1 | 4/2011 | |

(Continued)

OTHER PUBLICATIONS

Simsek et al., Immunological Agents Used in Cancer Treatment, Eurasian J Med 2019; 51 (I): 90-4, Available Online Date: Nov. 30, 2018 (Year: 2018).*

S. Gessi et al Biochimica et Biophysica Acta 1808 (2011) 1400â1412 (Year: 2011).*

Jin et al., Nature Reviews Drug Discovery | vol. 22 | Mar. 2023 | 213-234 (Year: 2023).*

Communication dated Sep. 9, 2024 issued by the Japanese Patent Office in application No. 2022-554968.

Christopher J. Langmead, et al., "Identification of Novel Adenosine A2A Receptor Antagonists by Virtual Screening", Journal of Medicinal Chemistry, vol. 55, 2012, pp. 1904-1909.

(Continued)

*Primary Examiner* — Kortney L. Klinkel
*Assistant Examiner* — Alison Azar Salamatian
(74) *Attorney, Agent, or Firm* — Sughrue Mion, PLLC

(57) ABSTRACT

Adenosine receptor (e.g., A2A and/or A1 receptor) antagonist compounds and compositions including the adenosine receptor antagonist compounds are disclosed. Methods of using the compounds and compositions for modulating (e.g., inhibiting or antagonizing) A2A and/or A1 receptor in a biological system are also disclosed. The compounds and compositions find use in various therapeutic applications including the treatment of cancer and in immuno-oncology. The compounds and compositions find use in various therapeutic applications including the treatment of central nervous system or neurodegenerative diseases, such as Parkinson's disease.

34 Claims, No Drawings

(56) References Cited

FOREIGN PATENT DOCUMENTS

| | | | |
|---|---|---|---|
| WO | 2017/046604 | A1 | 3/2017 |
| WO | 2019086074 | A1 | 5/2019 |
| WO | 2019/168847 | A1 | 9/2019 |
| WO | 2021/099079 | A1 | 5/2021 |
| WO | 2021/099518 | A1 | 5/2021 |

OTHER PUBLICATIONS

Office Action issued Jul. 13, 2023 in Chinese Application No. 202080080922.1.
Office Action issued Sep. 13, 2023 in Canadian Application No. 3,158,731.
Extended European Search Report issued Sep. 29, 2023 in European Application No. 20890594.3.
Roger J. Gillespie, et al., "Antagonists of the human adenosine A2A receptor. Part 3:Design and synthesis of pyrazolo[3,4-d]pyrimidines, pyrrolo[2,3-d]pyrimidines and 6-arylpurines", Bioorganic & Medicinal Chemistry Letters, 2008, vol. 18, pp. 2924-2929.
International Search Report for PCT/IB2020/000971 dated Apr. 12, 2021 [PCT/ISA/210].
Written Opinion for PCT/IB2020/000971 dated Apr. 12, 2021 [PCT/ISA/237].

* cited by examiner

ADENOSINE RECEPTOR ANTAGONIST COMPOUNDS

CROSS REFERENCE TO RELATED APPLICATIONS

This application is a National Stage of International Application No. PCT/IB2020/000971 filed Nov. 19, 2020, claims the priority based on Korean Application Number 10-2019-0149117, filed Nov. 19, 2019, which application is incorporated herein by reference in its entirety.

INTRODUCTION

Adenosine carries out many biological functions through particular cell receptors and is associated with a variety of biological activities including immune functions and inflammation.

There are four types of adenosine receptor (A1, A2A, A2B, and A3), and they are connected to the heteromeric G protein. Each of the A2A receptor and A2B receptor is connected to Gs subtype of Ga proteins. When these receptors are stimulated, the receptor format changes, and such a change induces the discharge of the Gs subunit activated by the Gβ ρ dimer, and then hydrolysis of the adenosine triphosphate (ATP) in the cell to produce cyclic adenosine monophosphate (cAMP). The cAMP synthesis activates protein kinase A (PKA) and phosphorylation of other proteins. In the T cell, mainly type I PKA isoform exists around the T cell receptor (TCR), and if activation of PKA increases due to the increased cAMP levels, the TCR signal transmission process is inhibited, thereby contributing to the occurrence of various illnesses.

Cancer cells produce significantly more adenosine than is produced by normal cells. In cancer cells, high-density adenosine induces activation of the A2A receptor to inhibit the immune system thereby and protect the cells. In the micro-environment of a tumor, the concentration of adenosine can be at 50 μM, an increase over normal cells, and lead to immunosuppression of T-cell function and activation. An A2A receptor antagonist can be used to adjust the cancer cell's inhibition of the immune system to induce anticancer effects.

A2A receptor antagonists are in development for immuno-oncology therapies. A2A receptor antagonists can enhance antitumor immunity. The A2A receptor is widely produced in white blood cells. When a T cell's A2A receptor becomes activated, TCR-mediated cytotoxicity and production of cytokines decreases, proliferation of T cells is inhibited, and expansion of Treg cells is induced. In immuno-oncology, the immunity checkpoint inhibitors of PD-1 or PD-L1 (e.g., antibody inhibitors) are widely used. However, statistically only 20% to 30% of patients produce PD-1/PD-L1, and thus there are many patients who do not benefit from the efficacy of such inhibitors. Treatments involving immunity checkpoint inhibitors in combination with A2A receptor antagonists are of interest.

Control of adenosine receptors is of interest for treatment of various indications. Modulating activity of the adenosine A1 receptor is of interest for treatment of nervous system disorders, asthma, heart failure, renal failure, and the like; antagonizing the adenosine A2A receptor is of interest for the treatment of Parkinson's disease, and the like; modulating activity of the adenosine A2B receptor is of interest for the treatment of chronic lung disorders such as asthma, cancer, in immuno-oncology and the like; and modulating the adenosine A3 receptor is of interest for treatment of asthma and chronic obstructive lung disorders, glaucoma, cancer, cerebral apoplexy, and the like.

SUMMARY

The present disclosure provides adenosine receptor (e.g., A2A and/or A1 receptor) antagonist compounds and compositions including said compounds. The present disclosure also provides methods of using said compounds and compositions for modulating (e.g., inhibiting or antagonizing) A2A and/or A1 receptor in a biological system. The compounds and compositions find use in various therapeutic applications including the treatment of cancer and in immuno-oncology. The compounds and compositions find use in various therapeutic applications including the treatment of central nervous system or neurodegenerative diseases, such as Parkinson's disease.

In a first aspect, the present disclosure provides an A2A and/or A1 antagonist compound of formula (I):

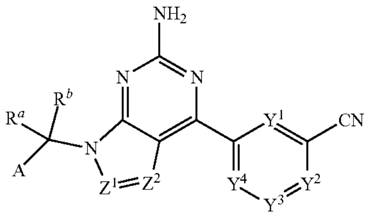

(I)

wherein:

- $Z^1$ and $Z^2$ are independently selected from CR and N, wherein at least one of $Z^1$ and $Z^2$ is N;
- R is H, $(C_1\text{-}C_3)$alkyl, or substituted $(C_1\text{-}C_3)$alkyl;
- $Y^1$ to $Y^4$ are independently selected from $CR^{10}$ and N, wherein at least two of $Y^1$ to $Y^4$ are independently $CR^{10}$;
- each $R^{10}$ is independently selected from H, $(C_1\text{-}C_8)$alkyl, substituted $(C_1\text{-}C_8)$alkyl, $(C_2\text{-}C_8)$alkenyl, substituted $(C_2\text{-}C_8)$alkenyl, $(C_2\text{-}C_8)$alkynyl, substituted $(C_2\text{-}C_8)$alkynyl, $(C_1\text{-}C_3)$haloalkyl, $(C_1\text{-}C_8)$alkoxy, substituted $(C_1\text{-}C_8)$alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol;
- $R^a$ and $R^b$ are each independently selected from H, F, $(C_1\text{-}C_3)$alkyl, and substituted $(C_1\text{-}C_3)$alkyl, or $R^a$ and $R^b$ are cyclically linked and together with the carbon atom to which they are attached form a cyclopropyl or substituted cyclopropyl; and
- A is phenyl, substituted phenyl, pyridyl or substituted pyridyl;
- or a solvate, a hydrate, a prodrug, and/or a stereoisomer thereof, or a pharmaceutically acceptable salt thereof.

In a second aspect, the present disclosure provides a pharmaceutical composition comprising a compound, or a pharmaceutically acceptable salt thereof as described herein (e.g., a compound of formula (I)-(XVIb)), and a pharmaceutically acceptable excipient.

In a third aspect, the present disclosure provides methods of modulating (e.g., inhibiting or antagonizing) an adenosine A2A and/or A1 receptor, comprising contacting a sample or cell or biological system with an effective amount of a compound as described herein (e.g., a compound of formula (I)-(XVIb) or a pharmaceutically acceptable salt thereof).

Also provided are methods of treating cancer that include administering to a subject having cancer a therapeutically effective amount of an A2A and/or A1 receptor antagonist compound (e.g., as described herein). In some embodiments, the method further includes co-administering to the subject an additional active agent, such as an immune checkpoint inhibitor. Also provided are methods of treating a central nervous system or neurodegenerative disease that includes administering to a subject having or at risk from a central nervous system or neurodegenerative disease a therapeutically effective amount of an A2A and/or A1 receptor antagonist compound (e.g., a compound of formula (I)-(XVIb) or a pharmaceutically acceptable salt thereof, as described herein).

DETAILED DESCRIPTION

Adenosine Receptor Antagonist Compounds

As summarized above, the present disclosure provides A2A and/or A1 receptor antagonist compounds and compositions. The compounds can modulate adenosine A2A and/or A1 receptor in cells and biological systems of interest. The compounds find use in a variety of therapeutic applications, including treatment of cancer and in immuno-oncology, and the treatment of central nervous system or neurodegenerative diseases, such as Parkinson's Disease.

The compounds of this disclosure can be described as cyano-substituted fused pyrimidine compounds that include a core structure having a 2-amino-pyrimidine ring fused to a five-membered heterocycle ring. The core structure can itself be further substituted with a benzonitrile substituent (e.g., a 3-cyano-phenyl) or a derivative thereof (e.g., a cyano-pyridyl substituent). The fused five membered heterocycle ring can be further substituted with an optionally substituted benzyl group. In some cases, the compounds have a 9H-purin-2-amine or a 1H-pyrazolo[3,4-d]pyrimidin-6-amine core structure that is further substituted as described herein.

In some embodiments, the compound is a benzonitrile-substituted fused pyrimidine compound, e.g., of the formula:

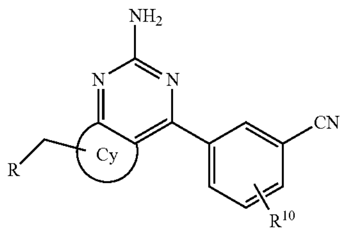

or a derivative thereof (e.g., a derivative compound where the 3-benzonitrile group is replaced with a cyano-pyridyl group), where Cy is a fused five membered heterocycle ring (e.g., heteroaryl or heterocycloalkyl ring) that contains at least one hetero atom selected from nitrogen, oxygen, and sulfur; R is an optionally substituted phenyl group; and $R^{10}$ is one or more optional substituents. In some embodiments, R is a phenyl substituted by $R^{11}$, $R^{12}$, and/or $R^{13}$ groups each independently selected from halogen, hydroxyl group, thiol group, carbonyl group, amide group, nitro group, amino group, substituted or unsubstituted $(C_1\text{-}C_5)$alkyl group, substituted or unsubstituted $(C_2\text{-}C_5)$alkenyl group, substituted or unsubstituted $(C_2\text{-}C_5)$alkynyl group, substituted or unsubstituted $(C_1\text{-}C_3)$haloalkyl group, and substituted or unsubstituted $(C_1\text{-}C_3)$aminoalkyl group or substituted or unsubstituted $(C_1\text{-}C_5)$alkoxy group, and $R^{10}$ is one or more groups independently selected from hydrogen, halogen, hydroxyl group, thiol group, substituted or unsubstituted $(C_1\text{-}C_5)$alkyl group, substituted or unsubstituted $(C_2\text{-}C_5)$alkenyl group, substituted or unsubstituted $(C_2\text{-}C_5)$alkynyl group, substituted or unsubstituted $(C_1\text{-}C_3)$haloalkyl group, substituted or unsubstituted $(C_1\text{-}C_5)$alkoxy group, or cyano group.

In some embodiments, the aforementioned $R^{11}$ and $R^{13}$ are each independently hydrogen, halogen, $(C_1\text{-}C_5)$alkyl group, or $(C_1\text{-}C_3)$haloalkyl group, the aforementioned $R^{12}$ is hydrogen or amino group, and each aforementioned $R^{10}$ is independently hydrogen, halogen, $(C_1\text{-}C_5)$alkyl group, or cyano group. Further embodiments of the formula above are described herein.

Aspects of the present disclosure include A2A and/or A1 receptor antagonist compounds of formula (I):

(I)

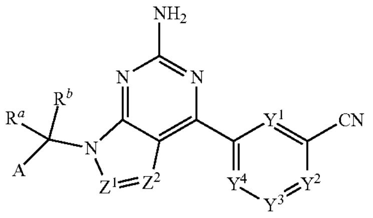

wherein:

$Z^1$ and $Z^2$ are independently selected from CR and N, wherein at least one of $Z^1$ and $Z^2$ is N;

R is H, $(C_1\text{-}C_3)$alkyl, or substituted $(C_1\text{-}C_3)$alkyl;

$Y^1$ to $Y^4$ are independently selected from $CR^{10}$ and N, wherein at least two of $Y^1$ to $Y^4$ are independently $CR^{10}$;

each $R^{10}$ is independently selected from H, $(C_1\text{-}C_8)$alkyl, substituted $(C_1\text{-}C_8)$alkyl, $(C_2\text{-}C_8)$alkenyl, substituted $(C_2\text{-}C_8)$alkenyl, $(C_2\text{-}C_8)$alkynyl, substituted $(C_2\text{-}C_8)$alkynyl, $(C_1\text{-}C_3)$haloalkyl, $(C_1\text{-}C_8)$alkoxy, substituted $(C_1\text{-}C_8)$alkoxy, $-CONH_2$, substituted amido, $-NH_2$, substituted amino, $-CO_2H$, cyano, halogen, hydroxyl, $-NO_2$, $-SO_3H$, $-SO_2NH_2$, substituted sulfonamide, and thiol;

$R^a$ and $R^b$ are each independently selected from H, F, $(C_1\text{-}C_3)$alkyl, and substituted $(C_1\text{-}C_3)$alkyl, or $R^a$ and $R^b$ are cyclically linked and together with the carbon atom to which they are attached form a cyclopropyl or substituted cyclopropyl; and A is phenyl, substituted phenyl, pyridyl or substituted pyridyl;

or a solvate, a hydrate, a prodrug, and/or a stereoisomer thereof, or a pharmaceutically acceptable salt thereof.

In some embodiments of formula (I), $Y^1$ to $Y^4$ are independently selected from $CR^{10}$ and N, wherein at least three of $Y^1$ to $Y^4$ are independently $CR^{10}$.

In some embodiments of formula (I), $Z^1$ is CR and $Z^2$ is N such that the compound is of formula (Ia):

(Ia)

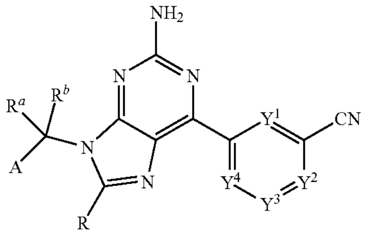

or a solvate, a hydrate, a prodrug, and/or a stereoisomer thereof, or a pharmaceutically acceptable salt thereof.

In some embodiments of formula (Ia), R is $(C_1\text{-}C_3)$alkyl. In some embodiments of formula (Ia), R is H.

In some embodiments of formula (I), $Z^1$ is N and $Z^2$ is CR such that the compound is of formula (Ib):

(Ib)

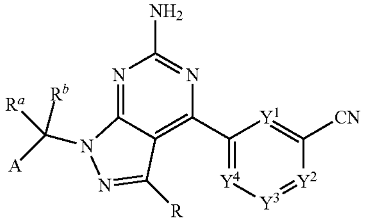

or a solvate, a hydrate, a pro rug, and/or a stereoisomer thereof, or a pharmaceutically acceptable salt thereof.

In some embodiments of formula (Ib), R is $(C_1\text{-}C_3)$alkyl. In some embodiments of formula (Ib), R is H.

In some embodiments of formula (I)-(Ib), A is phenyl. In some embodiments of formula (I)-(Ib), A is substituted phenyl. In some embodiments of formula (I)-(Ib), A is phenyl or phenyl substituted with one, two or three $R^{20}$ groups, each $R^{20}$ is independently selected from $(C_1\text{-}C_8)$alkyl, substituted $(C_1\text{-}C_8)$alkyl, $(C_2\text{-}C_8)$alkenyl, substituted $(C_2\text{-}C_8)$alkenyl, $(C_2\text{-}C_8)$alkynyl, substituted $(C_2\text{-}C_8)$alkynyl, $(C_1\text{-}C_3)$haloalkyl, $(C_1\text{-}C_8)$alkoxy, substituted $(C_1\text{-}C_8)$alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol.

In some embodiments of formula (I)-(Ib), A is pyridyl. In some embodiments of formula (I)-(Ib), A is substituted pyridyl. A can be an optionally substituted pyridyl that is a 2-pyridyl, 3-pyridyl or 4-pyridyl. In some embodiments of formula (I)-(Ib), A is pyridyl or pyridyl substituted with one, two or three $R^{20}$ groups, each $R^{20}$ is independently selected from $(C_1\text{-}C_8)$alkyl, substituted $(C_1\text{-}C_8)$alkyl, $(C_2\text{-}C_8)$alkenyl, substituted $(C_2\text{-}C_8)$alkenyl, $(C_2\text{-}C_8)$alkynyl, substituted $(C_2\text{-}C_8)$alkynyl, $(C_1\text{-}C_3)$haloalkyl, $(C_1\text{-}C_8)$alkoxy, substituted $(C_1\text{-}C_8)$alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol.

In some embodiments of formula (I)-(Ib), $R^a$ and $R^b$ are each H.

In some embodiments of formula (Ia)-(Ib), $Y^1$ to $Y^4$ are independently selected from $CR^{10}$ and N, wherein at least three of $Y^1$ to $Y^4$ are independently $CR^{10}$.

In some embodiments of formula (Ia)-(Ib), the compound is of formula (IIa) or (IIb):

(IIa)

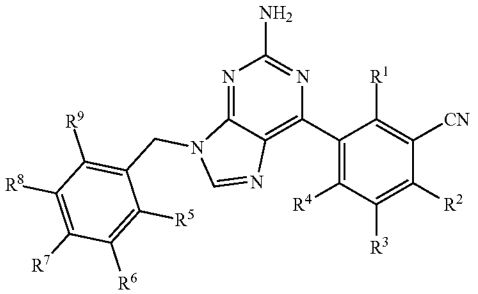

(IIb)

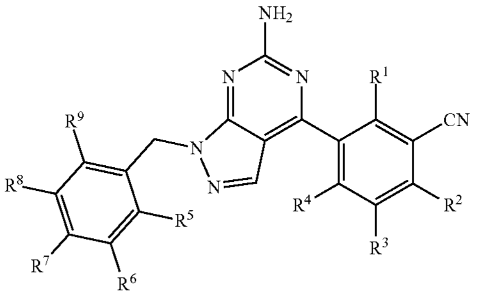

wherein:

$R^1$ to $R^9$ are independently selected from H, $(C_1\text{-}C_8)$alkyl, substituted $(C_1\text{-}C_8)$alkyl, $(C_2\text{-}C_8)$alkenyl, substituted $(C_2\text{-}C_8)$alkenyl, $(C_2\text{-}C_8)$alkynyl, substituted $(C_2\text{-}C_8)$alkynyl, $(C_1\text{-}C_3)$haloalkyl, $(C_1\text{-}C_8)$alkoxy, substituted $(C_1\text{-}C_8)$alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol;

or a solvate, a hydrate, a prodrug, and/or a stereoisomer thereof, or a pharmaceutically acceptable salt thereof.

In some embodiments of formula (IIa)-(IIb), $R^1$ to $R^9$ are independently selected from H, $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$alkoxy, —$NH_2$, substituted amino, halogen, and hydroxyl. In some embodiments of formula (IIa)-(IIb), $R^1$ to $R^9$ are independently selected from H, —$NH_2$, F, $CH_3$, and $CF_3$.

In some embodiments of formula (IIa)-(IIb), the compound is of formula (IIIa) or (IIIb):

(IIIa)

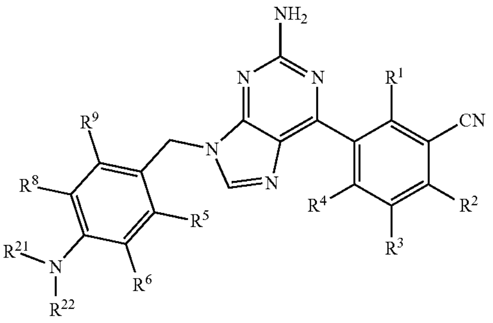

-continued (IIIb)

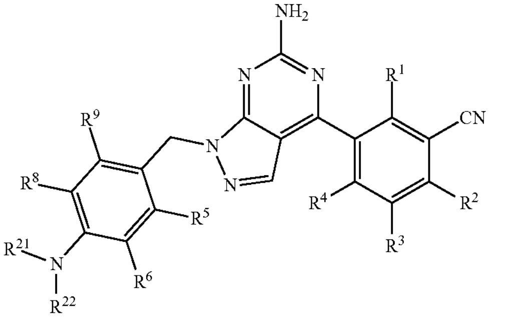

wherein:

$R^{21}$ and $R^{22}$ are independently selected from H, $(C_1-C_8)$alkyl, substituted $(C_1-C_8)$alkyl, $SO_2R^{30}$, and $COR^{30}$, wherein $R^{30}$ is $(C_1-C_8)$alkyl, or substituted $(C_1-C_8)$alkyl; or a solvate, a hydrate, a prodrug, and/or a stereoisomer thereof, or a pharmaceutically acceptable salt thereof.

In some embodiments of formula (IIIa)-(IIIb), $R^{21}$ and $R^{22}$ are each H.

In some embodiments of formula (IIIa)-(IIIb), $R^5$, $R^6$, $R^8$ and $R^9$ are independently selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl. In some embodiments of formula (IIIa)-(IIIb), $R^5$, $R^6$, $R^8$ and $R^9$ are independently selected from H, F, $CH_3$, and $CF_3$. In some embodiments of formula (IIIa)-(IIIb), $R^5$, $R^6$, $R^8$ and $R^9$ are each H.

In some embodiments of formula (IIIa)-(IIIb), $R^2$ to $R^4$ are each H, and $R^1$ is selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl. In some embodiments of formula (IIIa)-(IIIb), $R^1$ is selected from H, F, $CH_3$, and $CF_3$.

In some embodiments of formula (IIIa)-(IIIb), the compound is selected from:

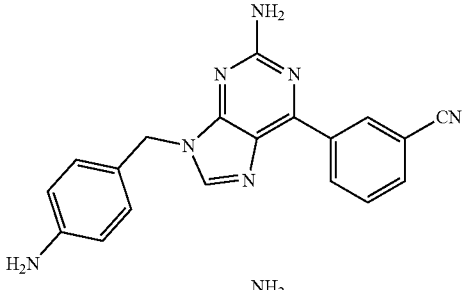

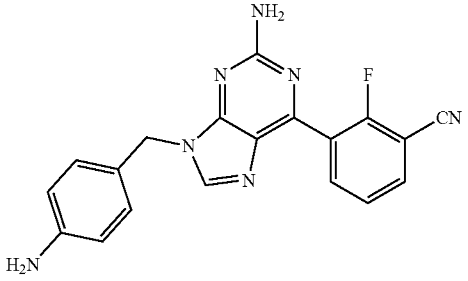

-continued

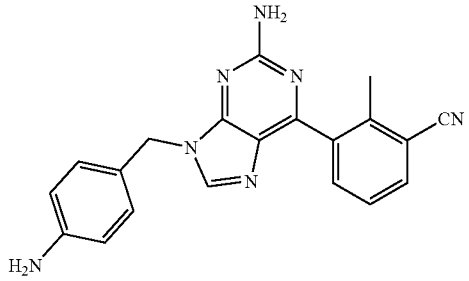

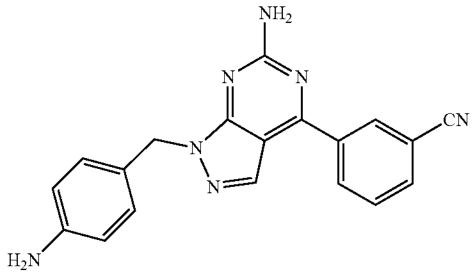

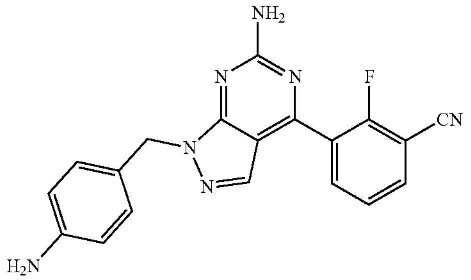

and

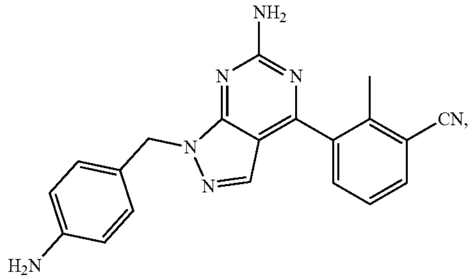

or a solvate, a hydrate, a prodrug, and/or a stereoisomer thereof, or a pharmaceutically acceptable salt thereof.

In some embodiments of formula (IIIa)-(IIIb), the compound is of formula (IVa) or (IVb):

(IVa)

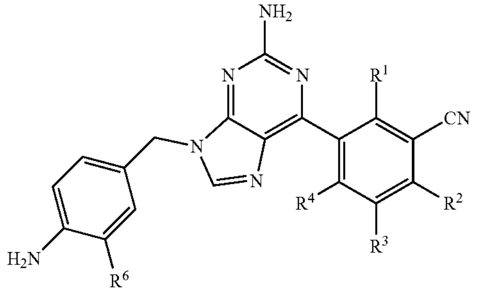

-continued (IVb)

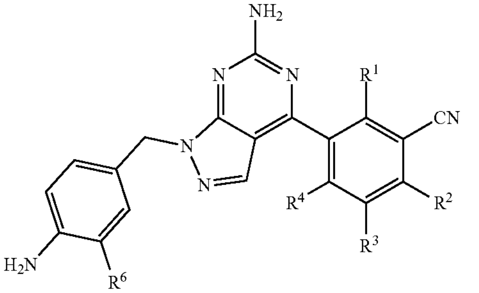

or a solvate, a hydrate, a prodrug, and/or a stereoisomer thereof, or a pharmaceutically acceptable salt thereof.

In some embodiments of formula (IVa)-(IVb), $R^6$ is selected from $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$alkoxy, halogen, and hydroxyl. In some embodiments of formula (IVa)-(IVb), $R^6$ is selected from $(C_1\text{-}C_5)$alkyl, substituted $(C_1\text{-}C_5)$alkyl, and $(C_1\text{-}C_3)$haloalkyl. In some embodiments of formula (IVa)-(IVb), $R^6$ is $CH_3$ or $CF_3$.

In some embodiments of formula (IVa)-(IVb), $R^2$ to $R^4$ are each H, and $R^1$ is selected from H, $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$alkoxy, halogen, and hydroxyl. In some embodiments of formula (IVa)-(IVb), $R^1$ is selected from H, F, $CH_3$, and $CF_3$.

In some embodiments of formula (IVa)-(IVb), the compound is selected from:

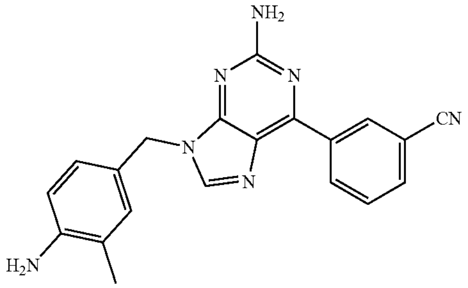

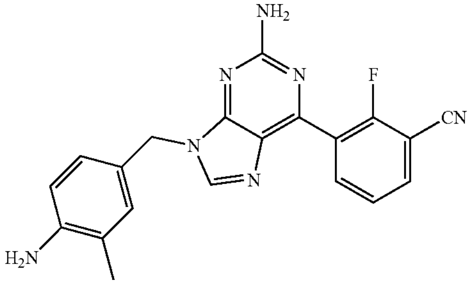

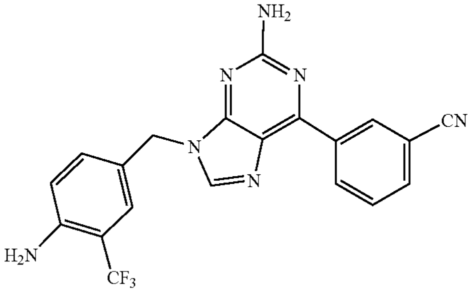

-continued

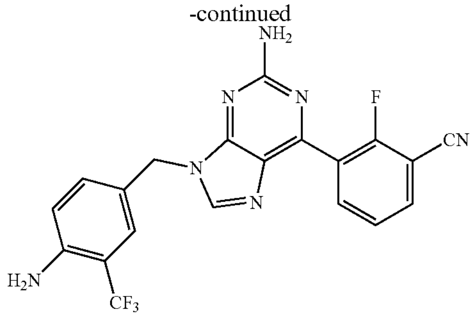

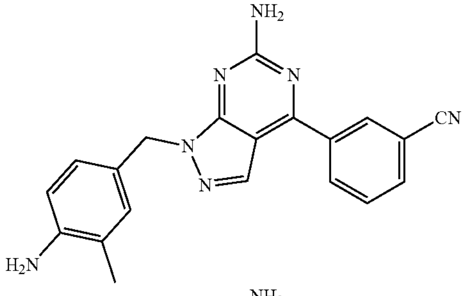

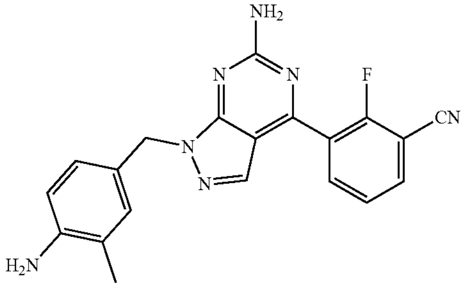

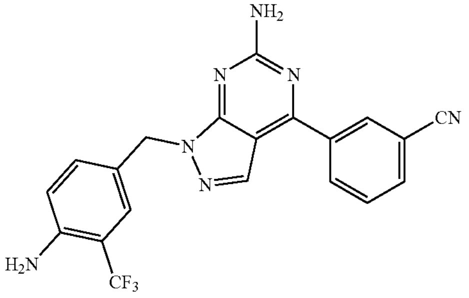

and

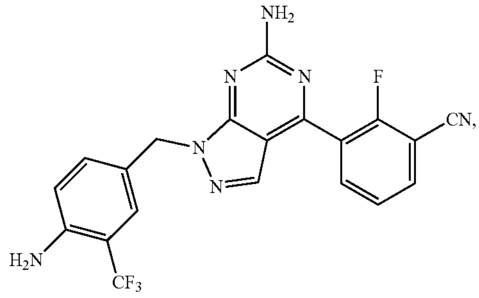

or a solvate, a hydrate, a prodrug, and/or a stereoisomer thereof, or a pharmaceutically acceptable salt thereof.

In some embodiments of formula (IIIa)-(IIIb), the compound is of formula (Va) or (Vb):

(Va)

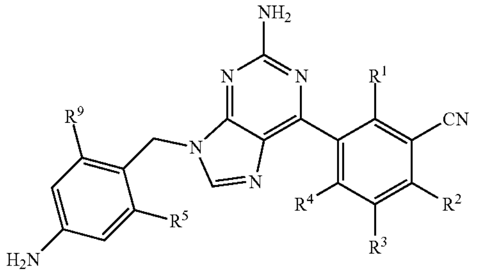

(Vb)

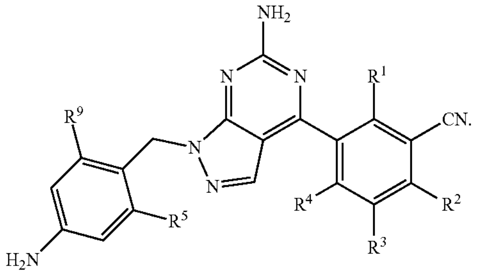

or a solvate, a hydrate, a prodrug, and/or a stereoisomer thereof, or a pharmaceutically acceptable salt thereof.

In some embodiments of formula (Va)-(Vb), $R^5$ and $R^9$ are independently selected from H, $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$alkoxy, halogen, and hydroxyl. In some embodiments of formula (Va)-(Vb), $R^5$ and $R^9$ are independently selected from H and halogen. In some embodiments of formula (Va)-(Vb), $R^5$ is F. In some embodiments of formula (Va)-(Vb), $R^9$ is F. In some embodiments of formula (Va)-(Vb), $R^5$ and $R^9$ are each F. In some embodiments of formula (Va)-(Vb), $R^5$ is H and $R^9$ is F.

In some embodiments of formula (Va)-(Vb), the compound is selected from:

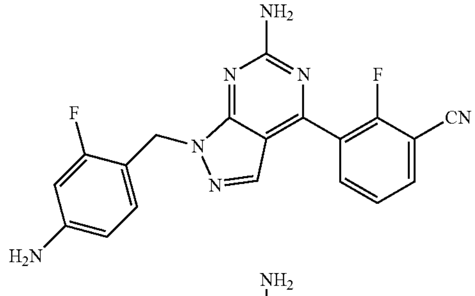

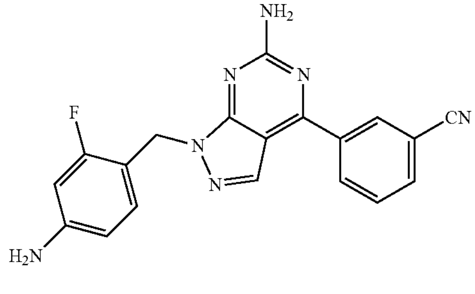

-continued

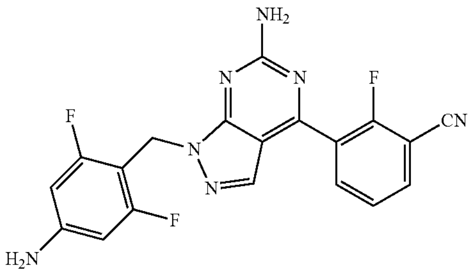

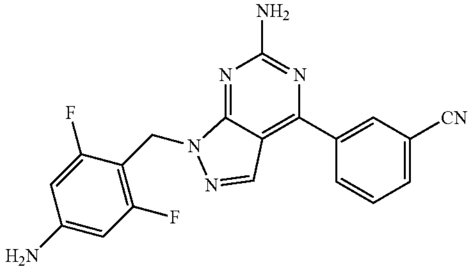

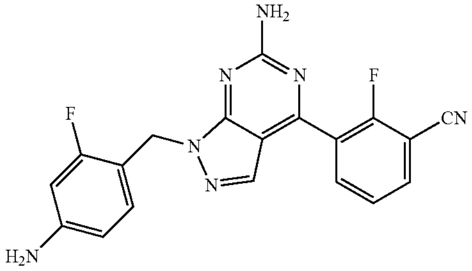

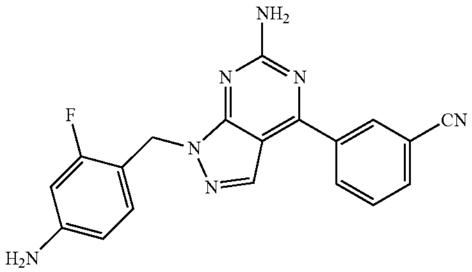

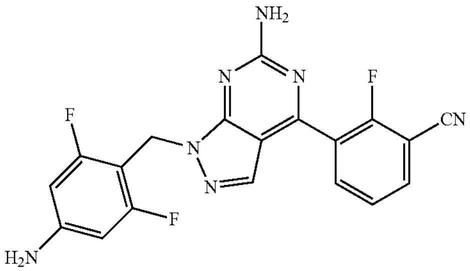

and

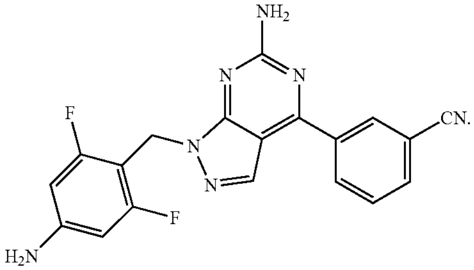

or a solvate, a hydrate, a prodrug, and/or a stereoisomer thereof, or a pharmaceutically acceptable salt thereof.

In some embodiments of formula (IIa)-(IIb), the compound is of formula (VIa) or (VIb):

(VIa)

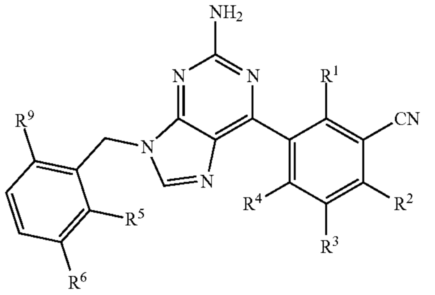

(VIb)

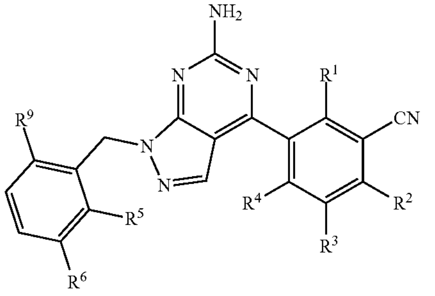

or a solvate, a hydrate, a prodrug, and/or a stereoisomer thereof, or a pharmaceutically acceptable salt thereof.

In some embodiments of formula (VIa)-(VIb), $R^5$, $R^6$ and $R^9$ are independently selected from H, $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$alkoxy, —$NH_2$, substituted amino, halogen, and hydroxyl. In some embodiments of formula (VIa)-(VIb), $R^6$ is selected from H, $(C_1\text{-}C_5)$alkyl, substituted $(C_1\text{-}C_5)$ alkyl, and $(C_1\text{-}C_3)$haloalkyl. In some embodiments of formula (VIa)-(VIb), $R^6$ is $CH_3$ or $CF_3$. In some embodiments of formula (VIa)-(VIb), $R^6$ is H.

In some embodiments of formula (VIa)-(VIb), $R^5$ and $R^9$ are independently selected from H and halogen. In some embodiments of formula (VIa)-(VIb), $R^5$ is F. In some embodiments of formula (VIa)-(VIb), $R^9$ is F. In some embodiments of formula (VIa)-(VIb), $R^5$ and $R^9$ are each F. In some embodiments of formula (VIa)-(VIb), $R^5$ is H and $R^9$ is F.

In some embodiments of formula (VIa)-(VIb), the compound is selected from:

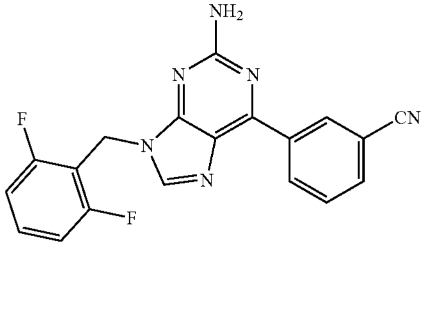

-continued

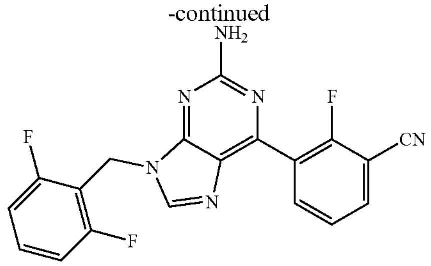

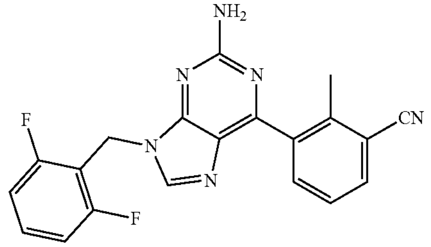

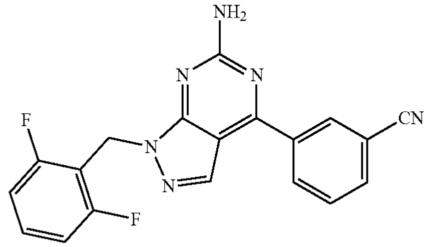

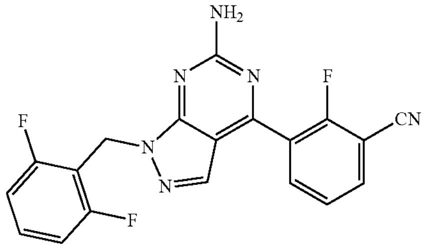

and

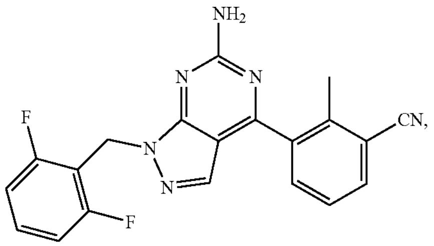

or a solvate, a hydrate, a prodrug, and/or a stereoisomer thereof, or a pharmaceutically acceptable salt thereof.

In some embodiments of formula (IIa)-(VIb), $R^1$ to $R^4$ are independently selected from H, $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$alkoxy, —$NH_2$, substituted amino, halogen, and hydroxyl. In some embodiments of formula (IIa)-(VIb), $R^1$ to $R^4$ are independently selected from H, $(C_1\text{-}C_5)$alkyl, substituted $(C_1\text{-}C_5)$alkyl, $(C_1\text{-}C_3)$haloalkyl and halogen.

In some embodiments of formula (IIa)-(VIb), $R^1$ is H. In some embodiments of formula (IIa)-(VIb), $R^1$ is selected from $(C_1\text{-}C_5)$alkyl, substituted $(C_1\text{-}C_5)$alkyl, $(C_1\text{-}C_3)$haloalkyl and halogen. In some embodiments of formula (IIa)-(VIb), $R^1$ is F, $CH_3$ or $CF_3$. In some embodiments of formula (IIa)-(VIb), $R^2$, $R^3$ or $R^4$ is selected from $(C_1\text{-}C_5)$alkyl, substituted $(C_1\text{-}C_5)$alkyl, $(C_1\text{-}C_3)$haloalkyl and halogen. In some embodiments of formula (IIa)-(VIb), $R^2$, $R^3$ and $R^4$ are each H.

In some embodiments of formula (Ia)-(Ib), the compound is of formula (VIIa) or (VIIb):

(VIIa)

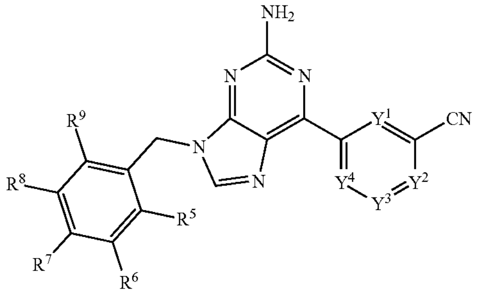

(VIIb)

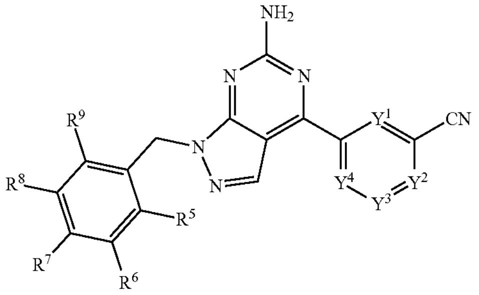

wherein:

$Y^1$ to $Y^4$ are independently selected from $CR^{10}$ and N, wherein at least three of $Y^1$ to $Y^4$ are independently $CR^{10}$;

$R^5$ to $R^9$ and each $R^{10}$ are independently selected from H, $(C_1\text{-}C_8)$alkyl, substituted $(C_1\text{-}C_8)$alkyl, $(C_2\text{-}C_8)$alkenyl, substituted $(C_2\text{-}C_8)$alkenyl, $(C_2\text{-}C_8)$alkynyl, substituted $(C_2\text{-}C_8)$alkynyl, $(C_1\text{-}C_3)$haloalkyl, $(C_1\text{-}C_8)$alkoxy, substituted $(C_1\text{-}C_8)$alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol;

or a solvate, a hydrate, a prodrug, and/or a stereoisomer thereof, or a pharmaceutically acceptable salt thereof.

In some embodiments of formula (VIIa)-(VIIb), one of $Y^1$ to $Y^4$ is N.

In some embodiments of formula (VIIa)-(VIIb), $R^5$ to $R^9$ and each $R^{10}$ are independently selected from H, $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$alkoxy, —$NH_2$, substituted amino, halogen, and hydroxyl. In some embodiments of formula (VIIa)-(VIIb), $R^5$ to $R^9$ and each $R^{10}$ are independently selected from H, —$NH_2$, F, $CH_3$, and $CF_3$.

In some embodiments of formula (VIIa)-(VIIb), the compound is of formula (VIIIa) or (VIIIb):

(VIIIa)

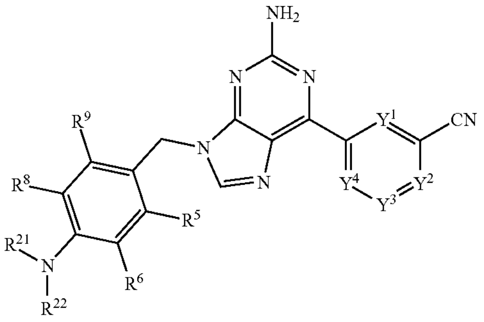

(VIIIb)

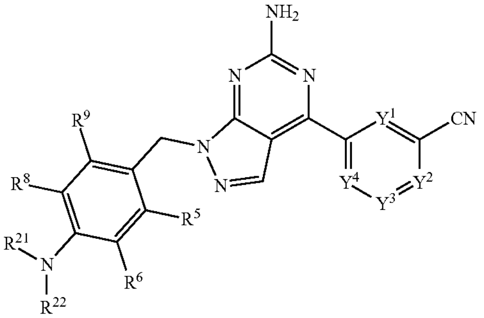

wherein:

one of $Y^1$ to $Y^4$ is N; and $R^{21}$ and $R^{22}$ are independently selected from H, $(C_1\text{-}C_8)$alkyl, substituted $(C_1\text{-}C_8)$alkyl, $SO_2R^{30}$, and $COR^{30}$, wherein $R^{30}$ is $(C_1\text{-}C_8)$alkyl, or substituted $(C_1\text{-}C_8)$alkyl;

or a solvate, a hydrate, a prodrug, and/or a stereoisomer thereof, or a pharmaceutically acceptable salt thereof.

In some embodiments of formula (VIIIa)-(VIIIb), $R^{21}$ and $R^{22}$ are each H.

In some embodiments of formula (VIIIa)-(VIIIb), $R^5$, $R^6$, $R^8$ and $R^9$ are independently selected from H, $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$alkoxy, halogen, and hydroxyl. In some embodiments of formula (VIIIa)-(VIIIb), $R^5$, $R^6$, $R^8$ and $R^9$ are independently selected from H, F, $CH_3$, and $CF_3$. In some embodiments of formula (VIIIa)-(VIIIb), $R^5$, $R^6$, $R^8$ and $R^9$ are each H.

In some embodiments of formula (VIIIa)-(VIIIb), the compound is selected from:

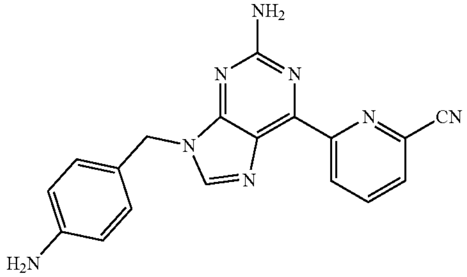

-continued

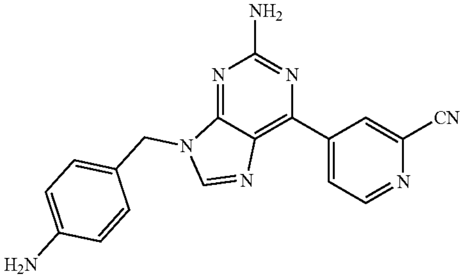

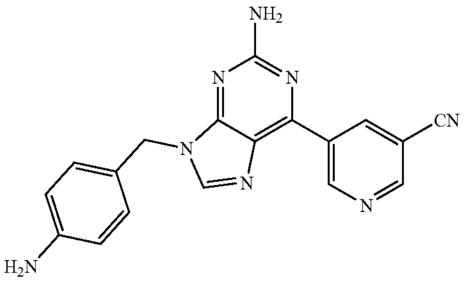

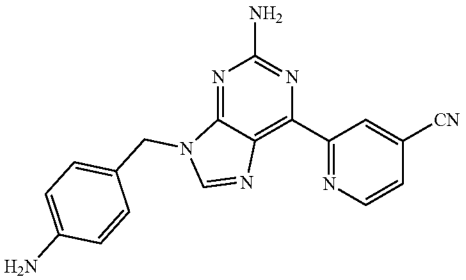 [SMILES: N#Cc1cccc(-c2nc(N)nc3c2ncn3Cc2ccc(N)cc2)c1]

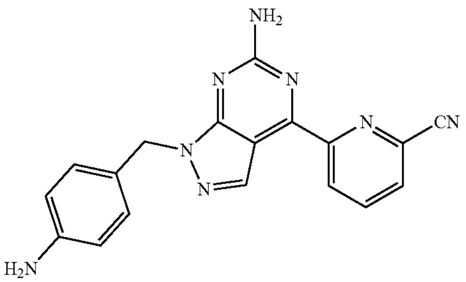

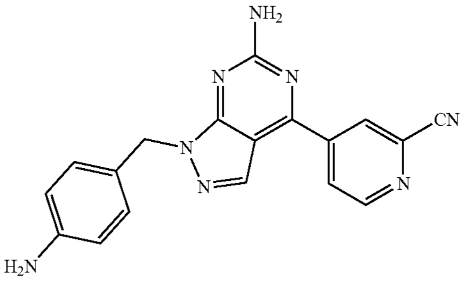 [SMILES: N#Cc1cccc(-c2nc(N)nc3c2cnn3Cc2ccc(N)cc2)c1]

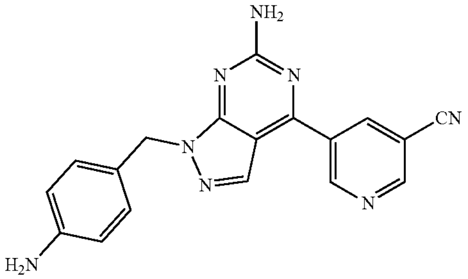

and

-continued

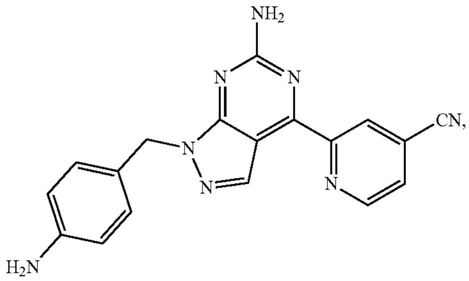

, or a solvate, a hydrate, a prodrug, and/or a stereoisomer thereof, or a pharmaceutically acceptable salt thereof.

In some embodiments of formula (VIIIa)-(VIIIb), the compound is of formula (IXa) or (IXb):

(IXa)

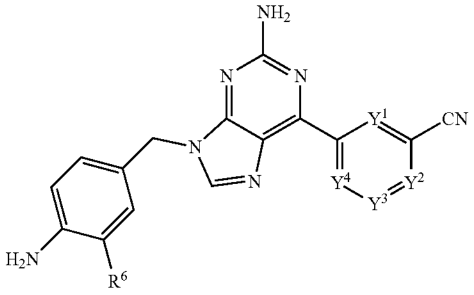

(IXb)

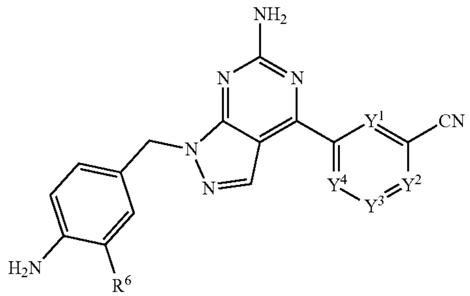

or a solvate, a hydrate, a prodrug, and/or a stereoisomer thereof, or a pharmaceutically acceptable salt thereof.

In some embodiments of formula (IXa)-(IXb), $R^6$ is selected from $(C_1$-$C_5)$alkyl, substituted $(C_1$-$C_5)$alkyl, $(C_1$-$C_3)$haloalkyl, $(C_1$-$C_5)$alkoxy, substituted $(C_1$-$C_5)$alkoxy, halogen, and hydroxyl. In some embodiments of formula (IXa)-(IXb), $R^6$ is selected from $(C_1$-$C_5)$alkyl, substituted $(C_1$-$C_5)$alkyl, and $(C_1$-$C_3)$haloalkyl. In some embodiments of formula (IXa)-(IXb), $R^6$ is $CH_3$ or $CF_3$.

In some embodiments of formula (IXa)-(IXb), the compound is selected from:
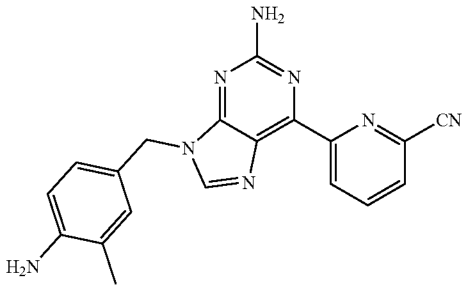
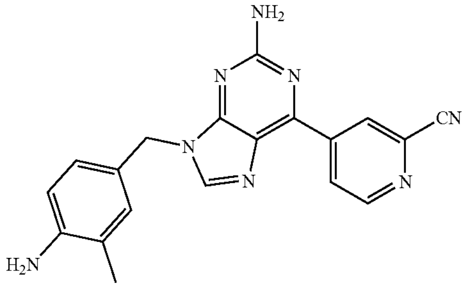
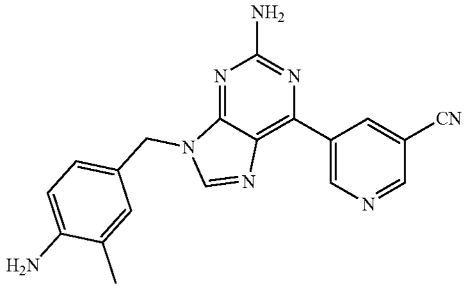
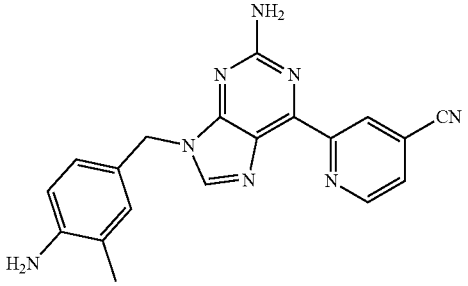
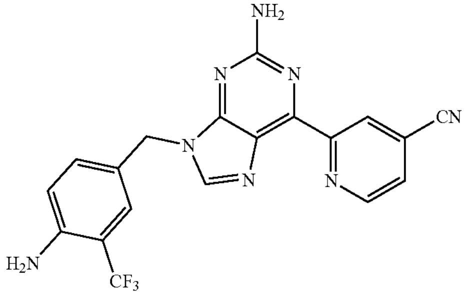
-continued
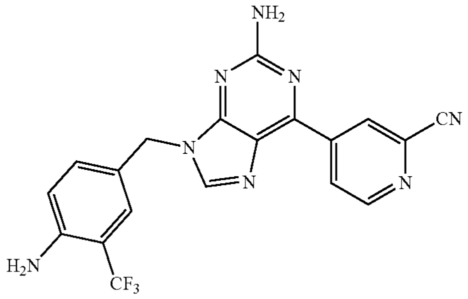
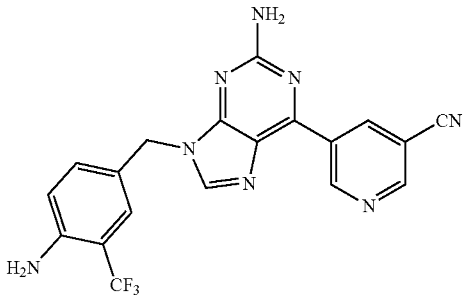
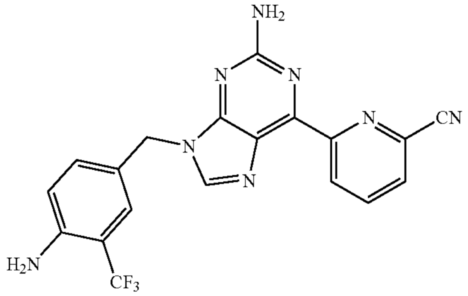
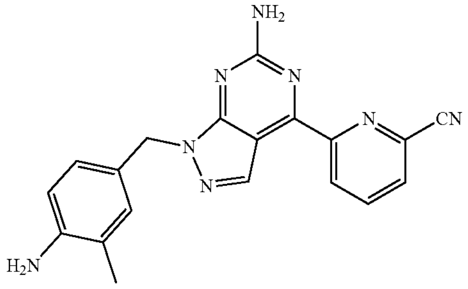
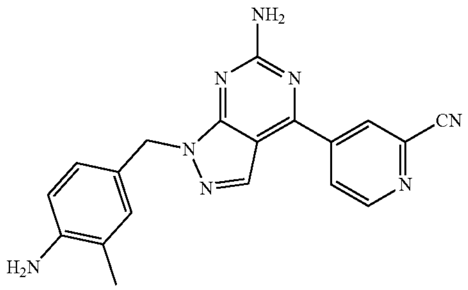

-continued

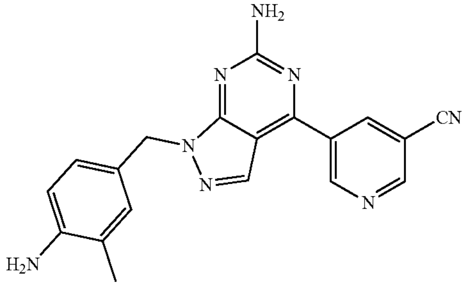

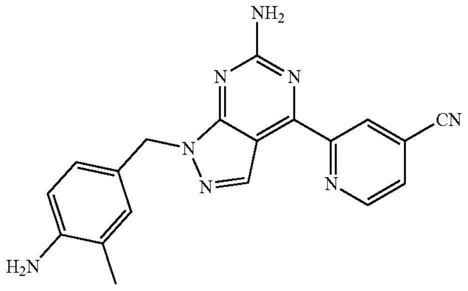

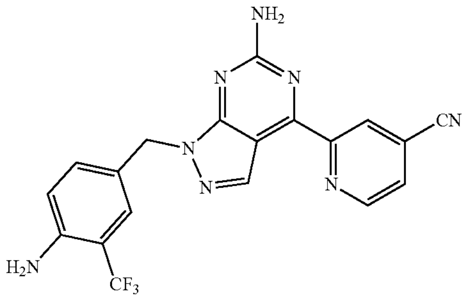

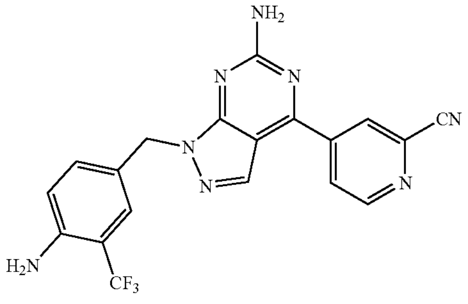

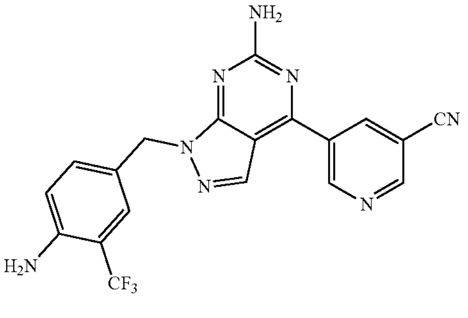

and

-continued

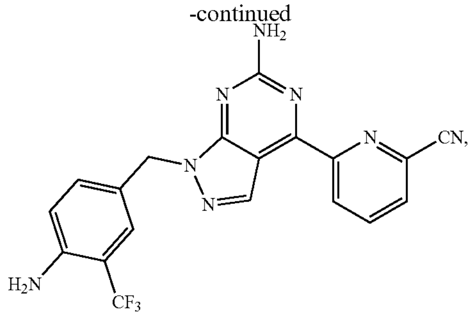

or a solvate, a hydrate, a prodrug, and/or a stereoisomer thereof, or a pharmaceutically acceptable salt thereof.

In some embodiments of formula (VIIIa)-(VIIIb), is of formula (Xa) or (Xb):

(Xa)

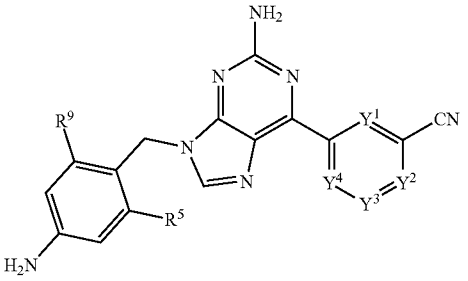

(Xb)

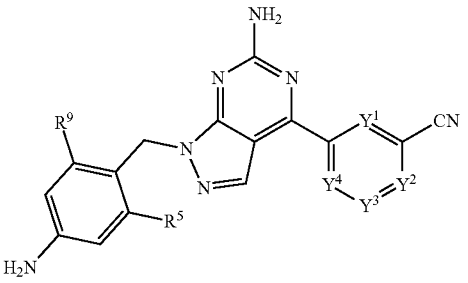

or a solvate, a hydrate, a prodrug, and/or a stereoisomer thereof, or a pharmaceutically acceptable salt thereof.

In some embodiments of formula (Xa)-(Xb), $R^5$ and $R^9$ are independently selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl. In some embodiments of formula (Xa)-(Xb), $R^5$ and $R^9$ are independently selected from H and halogen. In some embodiments of formula (Xa)-(Xb), $R^5$ is F. In some embodiments of formula (Xa)-(Xb), $R^9$ is F. In some embodiments of formula (Xa)-(Xb), $R^5$ and $R^9$ are each F. In some embodiments of formula (Xa)-(Xb), $R^5$ is H and $R^9$ is F.

In some embodiments of formula (Xa)-(Xb), the compound is selected from:
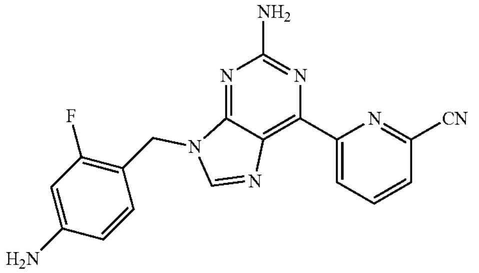
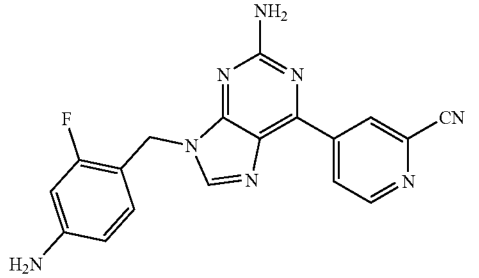
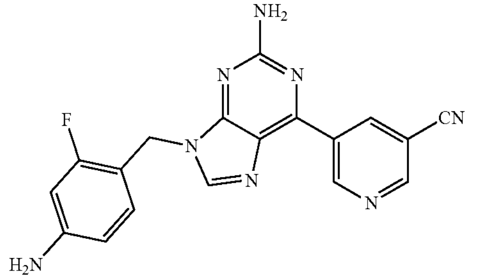
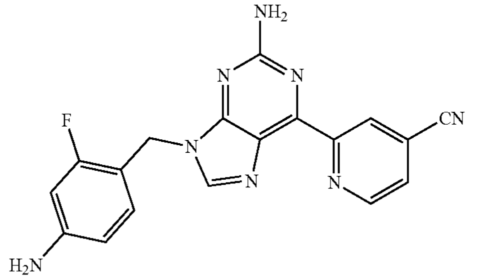
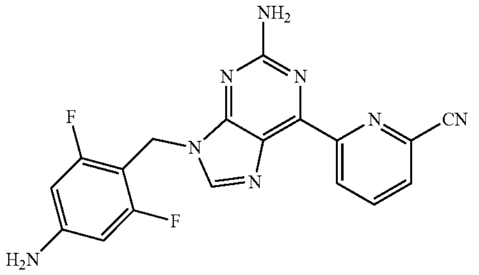
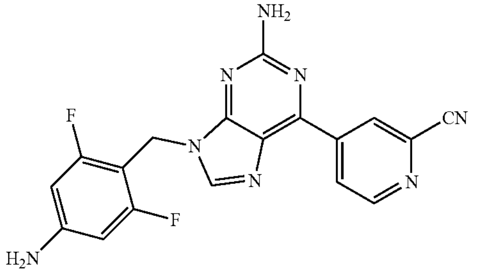
-continued
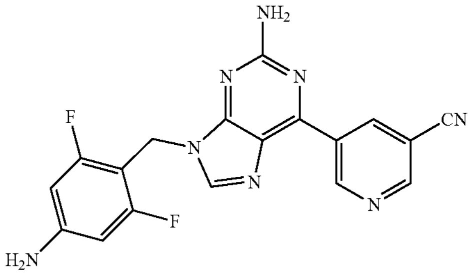
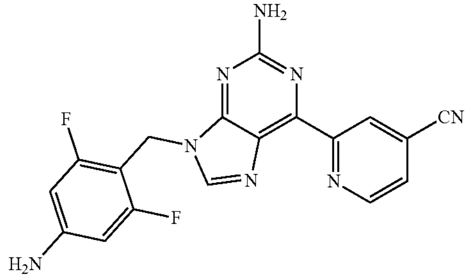
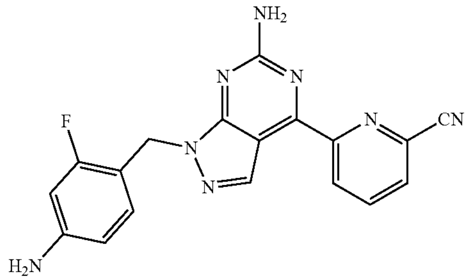
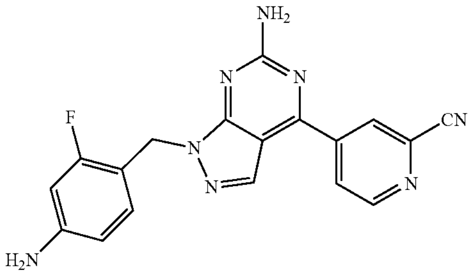
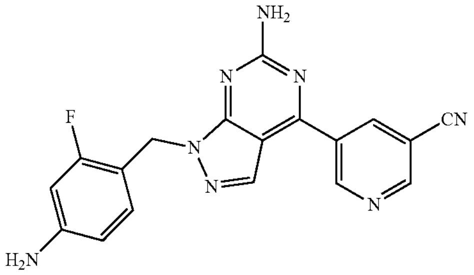
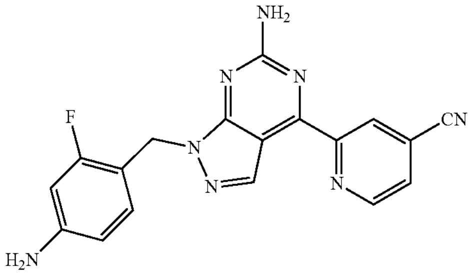

-continued

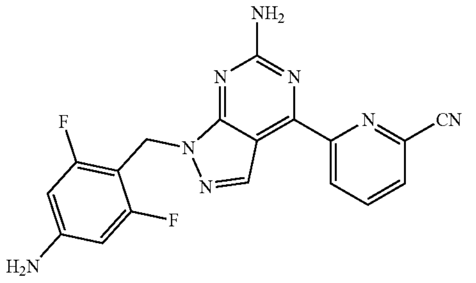

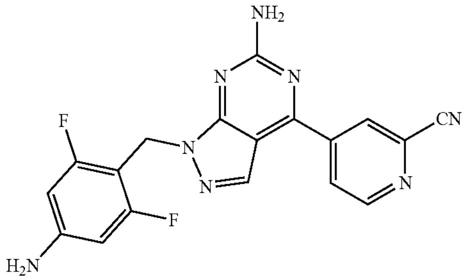

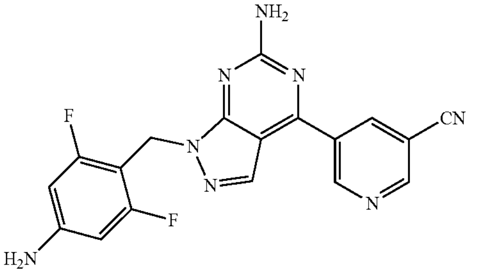

and

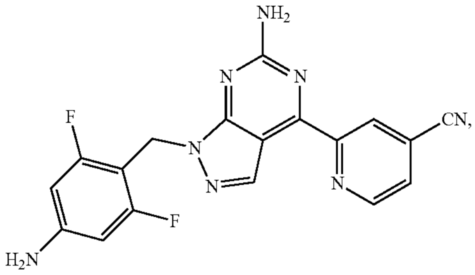

, or a solvate, a hydrate, a prodrug, and/or a stereoisomer thereof, or a pharmaceutically acceptable salt thereof.

In some embodiments of formula (VIIa)-(VIIb), the compound is of formula (XIa) or (XIb):

(XIa)

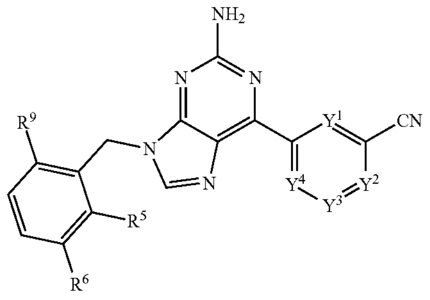

-continued (XIb)

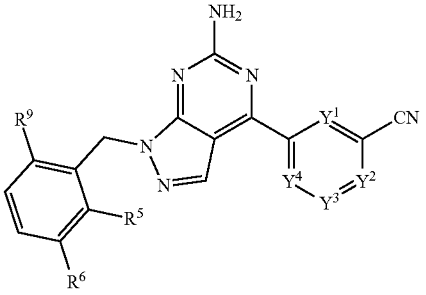

or a solvate, a hydrate, a prodrug, and/or a stereoisomer thereof, or a pharmaceutically acceptable salt thereof.

In some embodiments of formula (XIa)-(XIb), $R^5$, $R^6$ and $R^9$ are independently selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, —$NH_2$, substituted amino, halogen, and hydroxyl. In some embodiments of formula (XIa)-(XIb), $R^6$ is selected from H, $(C_1-C_5)$alkyl, substituted $(C_1-C_5)$ alkyl, and $(C_1-C_3)$haloalkyl. In some embodiments of formula (XIa)-(XIb), $R^6$ is $CH_3$ or $CF_3$. In some embodiments of formula (XIa)-(XIb), $R^6$ is H.

In some embodiments of formula (XIa)-(XIb), $R^5$ and $R^9$ are independently selected from H and halogen. In some embodiments of formula (XIa)-(XIb), $R^5$ is F. In some embodiments of formula (XIa)-(XIb), $R^9$ is F. In some embodiments of formula (XIa)-(XIb), $R^5$ and $R^9$ are each F. In some embodiments of formula (XIa)-(XIb), $R^5$ is F and $R^9$ is H.

In some embodiments of formula (XIa)-(XIb), the compound is selected from:

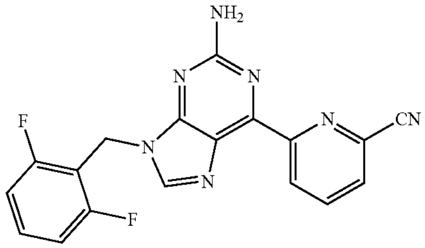

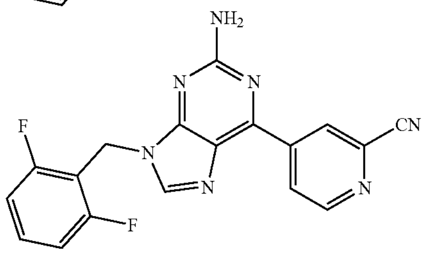

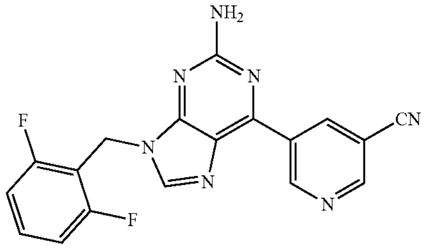

-continued

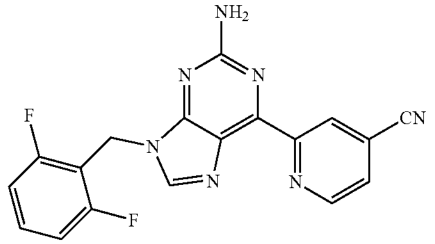

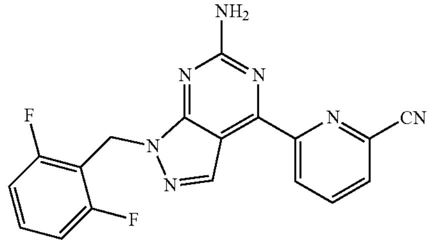

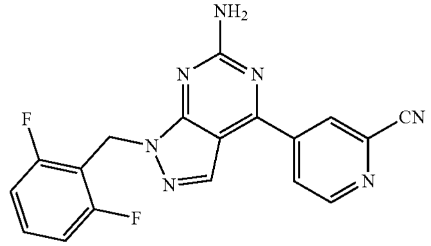

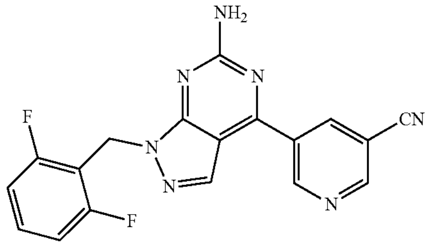

and

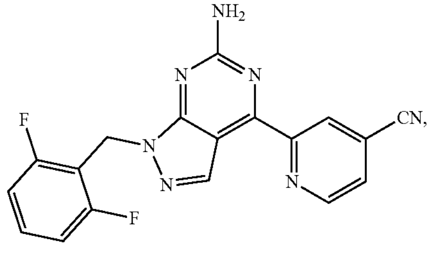

or a solvate, a hydrate, a prodrug, and/or a stereoisomer thereof, or a pharmaceutically acceptable salt thereof.

In some embodiments of formula (VIIa)-(VIIb), the compound is of formula (XIVa) or (XIVb):

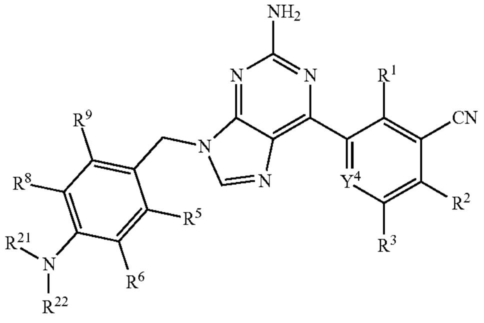

(XIVa)

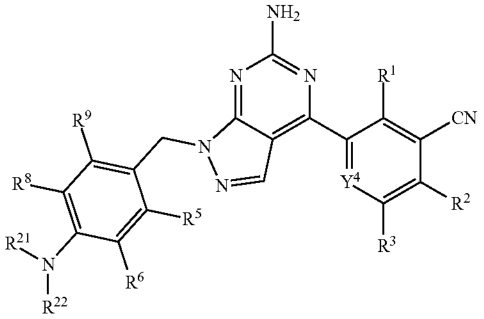

(XIVb)

wherein:

$Y^4$ is $CR^4$ or N;

$R^1$ to $R^4$ are independently selected from H, $(C_1-C_8)$alkyl, substituted $(C_1-C_8)$alkyl, $(C_2-C_8)$alkenyl, substituted $(C_2-C_8)$alkenyl, $(C_2-C_8)$alkynyl, substituted $(C_2-C_8)$alkynyl, $(C_1-C_3)$haloalkyl, $(C_1-C_8)$alkoxy, substituted $(C_1-C_8)$alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol; and $R^{21}$ and $R^{22}$ are independently selected from H, $(C_1-C_8)$alkyl, substituted $(C_1-C_8)$alkyl, $SO_2R^{30}$, and $COR^{30}$, wherein $R^{31}$ is $(C_1-C_8)$alkyl, or substituted $(C_1-C_8)$alkyl, or a solvate, a hydrate, a prodrug, and/or a stereoisomer thereof, or a pharmaceutically acceptable salt thereof.

In some embodiments of formula (XIVa)-(XIVb), $R^5$, $R^6$, $R^8$ and $R^9$ are independently selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl.

In some embodiments of formula (XIVa)-(XIVb), $R^{21}$ and $R^{22}$ are each H.

In some embodiments of formula (XIVa)-(XIVb), $R^2$ to $R^4$ are each H; and $R^1$ is selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl. In some embodiments of formula (XIVa)-(XIVb), $R^1$ is selected from H, F, $CH_3$, and $CF_3$.

In some embodiments of formula (XIVa)-(XIVb), the compound is of formula (XVa) or (XVb):

(XVa)

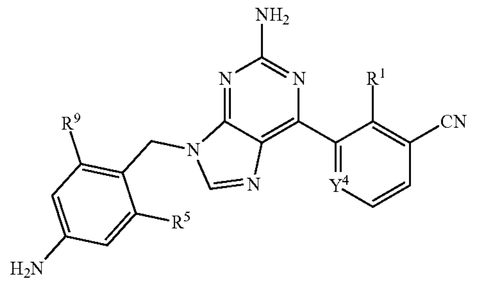

(XVb)

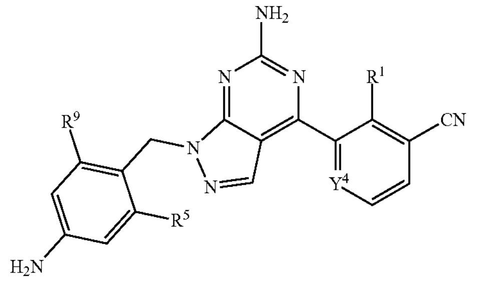

or a solvate, a hydrate, a prodrug, and/or a stereoisomer thereof, or a pharmaceutically acceptable salt thereof.

In some embodiments of formula (XVa)-(XVb), $R^5$ and $R^9$ are independently selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl. In some embodiments of formula (XVa)-(XVb), $R^5$ and $R^9$ are independently selected from H and halogen. In some embodiments of formula (XVa)-(XVb), $R^5$ is F. In some embodiments of formula (XVa)-(XVb), $R^9$ is F. In some embodiments of formula (XVa)-(XVb), $R^5$ and $R^9$ are each F. In some embodiments of formula (XVa)-(XVb), $R^5$ is H and $R^9$ is F.

In some embodiments of formula (XVa)-(XVb), $R^1$ is selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl. In some embodiments of formula (XVa)-(XVb), $R^1$ is selected from H, F, $CH_3$, and $CF_3$.

In some embodiments of formula (XVa)-(XVb), $Y^4$ is CH. In some embodiments of formula (XVa)-(XVb), $Y^4$ is N.

In some embodiments of formula (XVIa)-(XVIb), the compound is selected from:

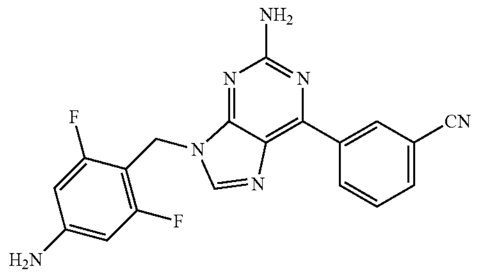

-continued

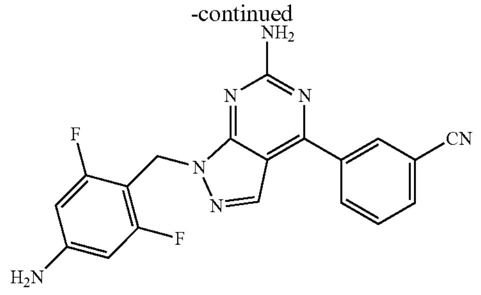

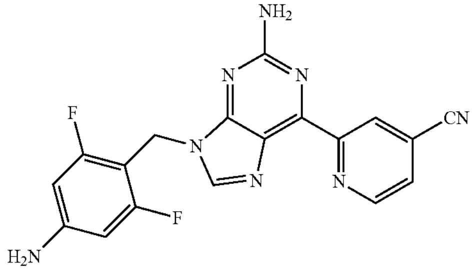

and

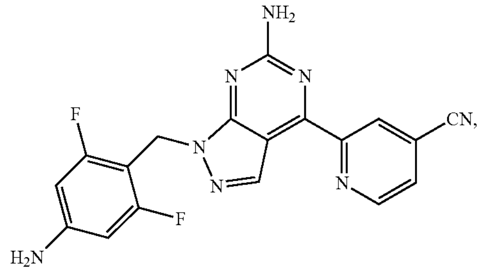

or a solvate, a hydrate, a prodrug, and/or a stereoisomer thereof, or a pharmaceutically acceptable salt thereof.

In some embodiments of formula (XIVa)-(XIVb), the compound is of formula (XVIa) or (XVIb):

(XVIa)

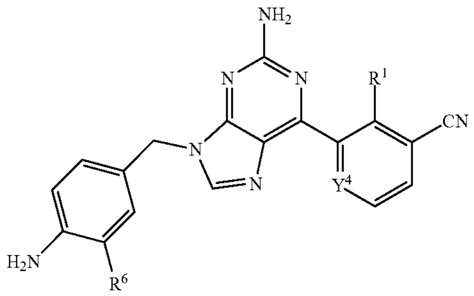

(XVIb)

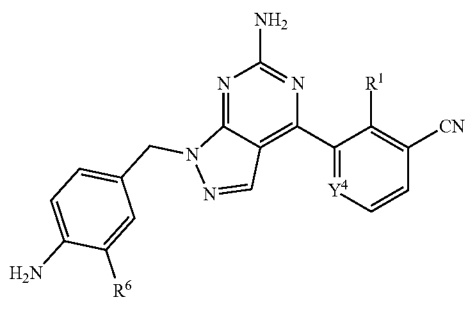

or a solvate, a hydrate, a prodrug, and/or a stereoisomer thereof, or a pharmaceutically acceptable salt thereof.

In some embodiments of formula (XVIa)-(XVIb), $R^6$ is selected from $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl. In some embodiments of formula (XVIa)-(XVIb), $R^6$ is selected from $(C_1-C_5)$alkyl, substituted $(C_1-C_5)$alkyl, and $(C_1-C_3)$haloalkyl. In some embodiments of formula (XVIa)-(XVIb), $R^6$ is $CH_3$ or $CF_3$.

In some embodiments of formula (XVIa)-(XVIb), $R^1$ is selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl. In some embodiments of formula (XVIa)-(XVIb), $R^1$ is selected from H, F, $CH_3$, and $CF_3$.

In some embodiments of formula (XVIa)-(XVIb), $Y^4$ is CH. In some embodiments of formula (XVIa)-(XVIb), $Y^4$ is N.

In some embodiments of formula (XVIa)-(XVIb), the compound is selected from:

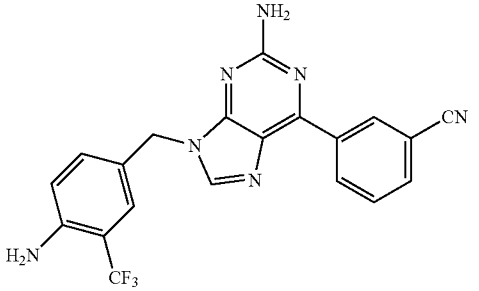

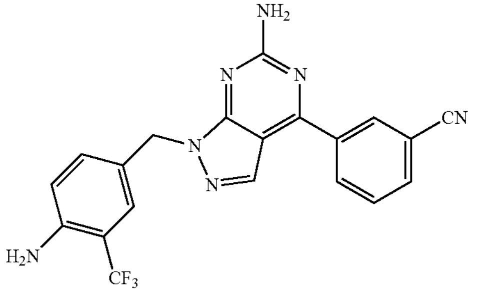

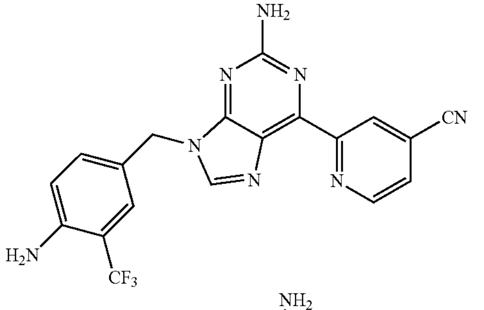

and

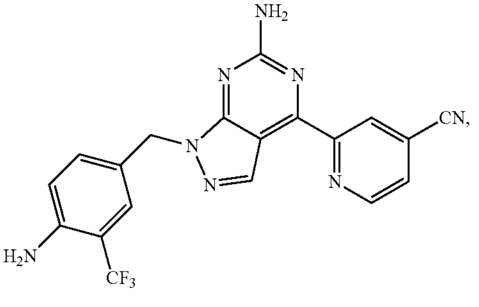

, or a solvate, a hydrate, a prodrug, and/or a stereoisomer thereof, or a pharmaceutically acceptable salt thereof.

In some embodiments of formula (I)-(Ib), the compound is of formula (XIIa) or (XIIb):

(XIIa)

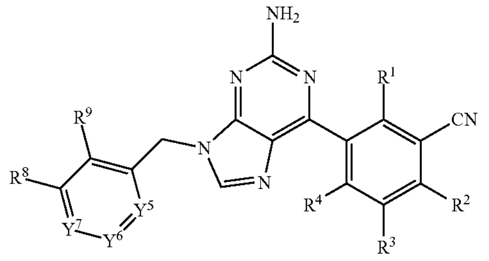

(XIIb)

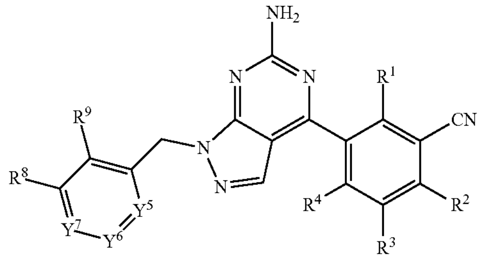

wherein:

$Y^5$ to $Y^7$ are each independently $CR^{20}$ or N, wherein one of $Y^5$ to $Y^7$ is N; and $R^1$ to $R^4$, $R^8$, $R^9$ and each $R^{20}$ are independently selected from H, $(C_1-C_8)$alkyl, substituted $(C_1-C_{85})$ alkyl, $(C_2-C_8)$alkenyl, substituted $(C_2-C_8)$alkenyl, $(C_2-C_8)$alkynyl, substituted $(C_2-C_8)$alkynyl, $(C_1-C_3)$ haloalkyl, $(C_1-C_8)$alkoxy, substituted $(C_1-C_8)$alkoxy, $-CONH_2$, substituted amido, $-NH_2$, substituted amino, $-CO_2H$, cyano, halogen, hydroxyl, $-NO_2$, $-SO_3H$, $-SO_2NH_2$, substituted sulfonamide, and thiol.

In some embodiments of formula (XIIa)-(XIIb), $Y^5$ is N. In some embodiments of formula (XIIa)-(XIIb), $Y^6$ is N. In some embodiments of formula (XIIa)-(XIIb), $Y^7$ is N.

In some embodiments of formula (XIIa)-(XIIb), $R^8$, $R^9$ and each $R^{20}$ are independently selected from H, $(C_1-C_5)$ alkyl, substituted $(C_1-C_5)$alkyl, $(C_1-C_3)$haloalkyl, $(C_1-C_5)$ alkoxy, substituted $(C_1-C_5)$alkoxy, $-NH_2$, substituted amino, halogen, and hydroxyl.

In some embodiments of formula (XIIa)-(XIIb), $R^8$, $R^9$ and each $R^{20}$ are independently selected from H, $-NH_2$, F, $CH_3$, and $CF_3$.

In some embodiments of formula (XIIa)-(XIIb), $R^1$ to $R^4$ are independently selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, $-NH_2$, substituted amino, halogen, and hydroxyl. In some embodiments of formula (XIIa)-(XIIb), $R^1$ to $R^4$ are independently selected from H, $(C_1-C_5)$alkyl, substituted $(C_1-C_5)$alkyl, $(C_1-C_3)$haloalkyl and halogen.

In some embodiments of formula (I)-(Ib), the compound is of formula (XIIIa) or (XIIIb):

(XIIIa)

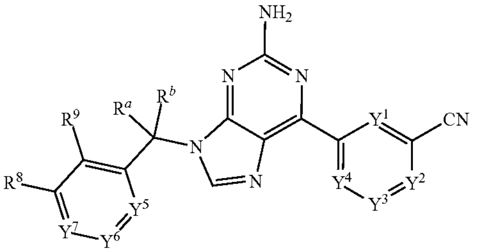

(XIIIb)

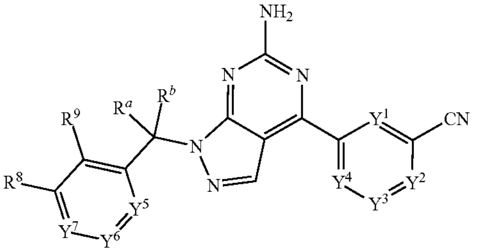

wherein:

$Y^5$ to $Y^7$ are each independently $CR^{20}$ or N, wherein one of $Y^5$ to $Y^7$ is N; and $R^8$, $R^9$, each $R^{10}$, and each $R^{20}$ are independently selected from H, $(C_1\text{-}C_8)$alkyl, substituted $(C_1\text{-}C_8)$alkyl, $(C_2\text{-}C_8)$alkenyl, substituted $(C_2\text{-}C_8)$alkenyl, $(C_2\text{-}C_8)$alkynyl, substituted $(C_2\text{-}C_8)$alkynyl, $(C_1\text{-}C_3)$haloalkyl, $(C_1\text{-}C_8)$alkoxy, substituted $(C_1\text{-}C_8)$alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol.

In some embodiments of formula (XIIIa)-(XIIIb), $Y^5$ is N. In some embodiments of formula (XIIIa)-(XIIIb), $Y^6$ is N. In some embodiments of formula (XIIIa)-(XIIIb), $Y^7$ is N.

In some embodiments of formula (XIIIa)-(XIIIb), $R^8$, $R^9$ and each $R^{20}$ are independently selected from H, $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$alkoxy, —$NH_2$, substituted amino, halogen, and hydroxyl. In some embodiments of formula (XIIIa)-(XIIIb), $R^8$, $R^9$ and each $R^{20}$ are independently selected from H, —$NH_2$, F, $CH_3$, and $CF_3$. In some embodiments of formula (XIIIa)-(XIIIb), each $R^{10}$ is independently selected from H, $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$alkoxy, —$NH_2$, substituted amino, halogen, and hydroxyl.

In some embodiments of formula (XIIIa)-(XIIIb), $Y^1$ is $CR^{10}$.

In some embodiments of formula (XIIIa)-(XIIIb), $R^{10}$ is H. In some embodiments of formula (XIIIa)-(XIIIb), $R^{10}$ is selected from $(C_1\text{-}C_5)$alkyl, substituted $(C_1\text{-}C_5)$alkyl, $(C_1\text{-}C_3)$haloalkyl and halogen. In some embodiments of formula (XIIIa)-(XIIIb), $R^{10}$ is F, $CH_3$ or $CF_3$.

In some embodiments of formula (XIIIa)-(XIIIb), $Y^1$ to $Y^4$ are each $CR^{10}$.

In some embodiments of formula (XIIIa)-(XIIIb), each $R^{10}$ is independently selected from $(C_1\text{-}C_5)$alkyl, substituted $(C_1\text{-}C_5)$alkyl, $(C_1\text{-}C_3)$haloalkyl and halogen.

In some embodiments of formula (XIIIa)-(XIIIb), $Y^1$ to $Y^4$ are each CH. In some embodiments of formula (XIIIa)-(XIIIb), one and only one of $Y^1$ to $Y^4$ is N. In some embodiments of formula (XIIIa)-(XIIIb), $Y^1$ is N. In some embodiments of formula (XIIIa)-(XIIIb), $Y^2$ is N. In some embodiments of formula (XIIIa)-(XIIIb), $Y^3$ is N. In some embodiments of formula (XIIIa)-(XIIIb), $Y^4$ is N.

In some embodiments of the embodiments described above, the compound is one that is of Formula (Ia) to (XVIa) (e.g., a purine compound), or a salt (e.g., a pharmaceutically acceptable salt) thereof. In some embodiments of the embodiments described above, the compound is of Formula (Ib) to (XVIb) (e.g., a pyrazolo-pyrimidine compound), or a salt (e.g., a pharmaceutically acceptable salt) thereof.

In some embodiments of formula (I), the compound is selected from:

3-(6-amino-1-(4-aminobenzyl)-1H-pyrazolo-[3,4-d]-pyrimidine-4-yl)-benzonitrile;

3-(6-amino-1-(4-aminobenzyl)-1H-pyrazolo-[3,4-d]-pyrimidine-4-yl)-2-methylbenzonitrile;

3-(6-amino-1-(4-aminobenzyl)-1H-pyrazolo-[3,4-d]-pyrimidine-4-yl)-2-fluorobenzonitrile;

3-(2-amino-9-(4-aminobenzyl)-9H-purin-6-yl)-benzonitrile;

3-(2-amino-9-(4-aminobenzyl)-9H-purin-6-yl)-2-fluorobenzonitrile;

3-(2-amino-9-(4-aminobenzyl)-9H-purin-6-yl)-2-methylbenzonitrile;

3-(2-amino-9-(4-amino-2, 6-difluorobenzyl)-9H-purin-6-yl)-benzonitrile;

3-(2-amino-9-(4-amino-2,6-difluorobenzyl)-9H-purin-6-yl)-2-fluorobenzonitrile;

3-(2-amino-9-(4-amino-2-fluorobenzyl)-9H-purin-6-yl)-benzonitrile;

3-(2-amino-9-(4-amino-2-fluorobenzyl)-9H-purin-6-yl)-2-fluorobenzonitrile;

3-(2-amino-9-(4-amino-3-methylbenzyl)-9H-purin-6-yl)-benzonitrile;

3-(2-amino-9-(4-amino-3-methylbenzyl)-9H-purin-6-yl)-2-fluorobenzonitrile;

3-(2-amino-9-(2,6-difluorobenzyl)-9H-purin-6-yl) benzonitrile;

3-(2-amino-9-(2,6-difluorobenzyl)-9H-purin-6-yl)-2-fluorobenzonitrile; and 3-(2-amino-9-(2,6-difluorobenzyl)-9H-purin-6-yl)-2-methylbenzonitrile.

It is understood that all variations of salts, and/or solvates, hydrates, prodrugs and/or stereoisomers of the compounds described herein e.g., of formula (I)-(XVIb), or shown in Table 1 are meant to be encompassed by the present disclosure. Accordingly, any of the compounds described herein may also be referred to as a compound of formula (I)-(XVIb) or a solvate, a hydrate, a prodrug, and/or a stereoisomer thereof, or a pharmaceutically acceptable salt thereof.

In some embodiments, the compound is represented by the structure of one of the compounds in Table 1, or a solvate, a hydrate, a prodrug, and/or a stereoisomer thereof, or a salt (e.g., a pharmaceutically acceptable salt) thereof. In some embodiments, the compound is represented by the structure of one of the compounds in Table 1 that is of Formula (Ia) (e.g., a purine compound), or a salt (e.g., a pharmaceutically acceptable salt) thereof. In some embodiments, the compound is represented by the structure of one of the compounds in Table 1 that is of Formula (Ib) (e.g., a pyrazolo-pyrimidine compound), or a salt (e.g., a pharmaceutically acceptable salt) thereof. The present disclosure is meant to encompass, a compound of any one of Table 1, or a salt thereof, and/or a solvate, a hydrate, a prodrug thereof, a single stereoisomer, a mixture of stereoisomers and/or an isotopically labelled form thereof. For example, salts of a solvate, hydrate, prodrug and/or stereoisomer form of any of the compounds described herein (e.g., of formula (I)-(XVIb)), or shown in Table 1 are meant to be encompassed by the present disclosure.

TABLE 1
Exemplary A2A and/or A1 Receptor Antagonist Compounds
| Cmpd. No. | Compounds of Formula (Ia) | Cmpd No. | Compounds of Formula (Ib) |
| --- | --- | --- | --- |
| 101 | 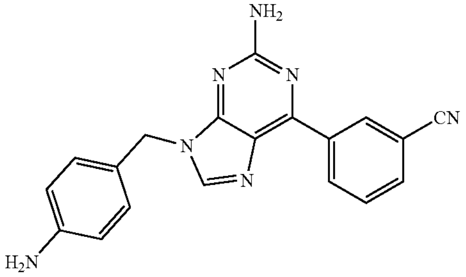 | 201 | 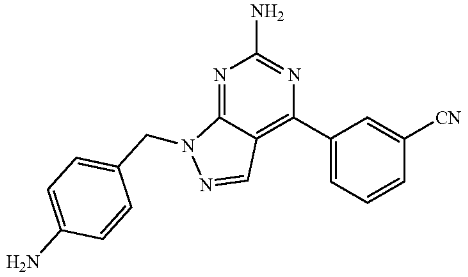 |
| 102 | 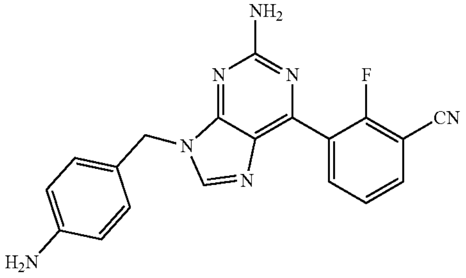 [SMILES: N#Cc1cccc(-c2nc(N)nc3c2ncn3Cc2ccc(N)cc2)c1F] | 202 | 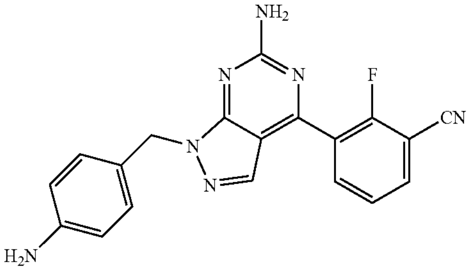 [SMILES: N#Cc1cccc(-c2nc(N)nc3c2cnn3Cc2ccc(N)cc2)c1F] |
| 103 | 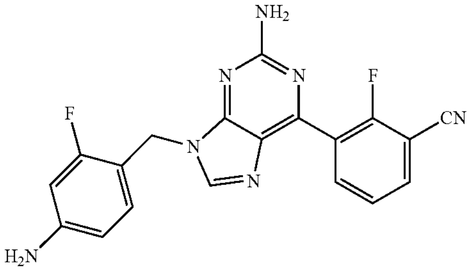 [SMILES: N#Cc1cccc(-c2nc(N)nc3c2ncn3Cc2ccc(N)cc2F)c1F] | 203 | 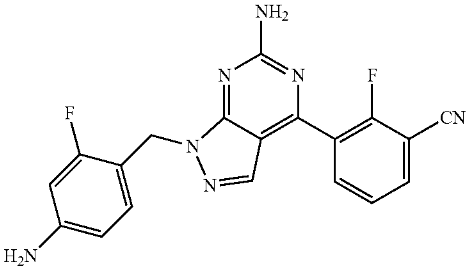 [SMILES: N#Cc1cccc(-c2nc(N)nc3c2cnn3Cc2ccc(N)cc2F)c1F] |
| 104 | 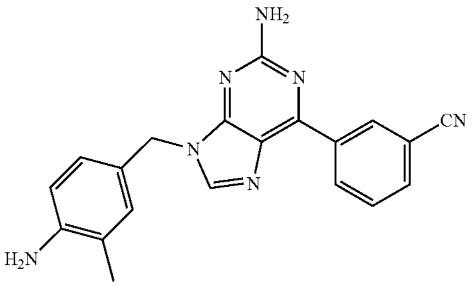 | 204 | 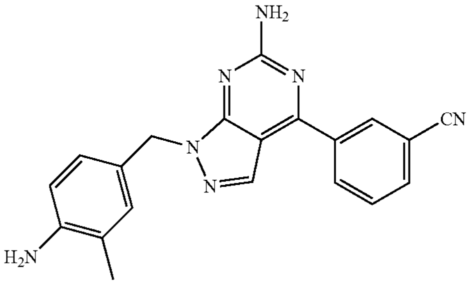 |
| 105 | 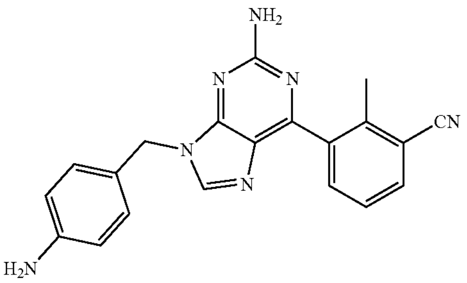 [SMILES: Cc1c(C#N)cccc1-c1nc(N)nc2c1ncn2Cc1ccc(N)cc1] | 205 | 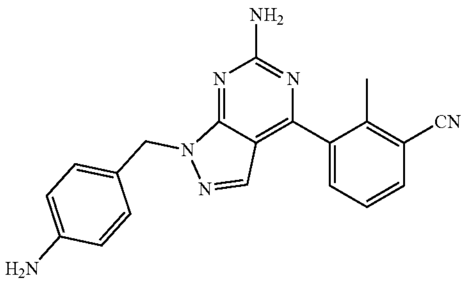 [SMILES: Cc1c(C#N)cccc1-c1nc(N)nc2c1cnn2Cc1ccc(N)cc1] |

TABLE 1-continued
| Exemplary A2A and/or A1 Receptor Antagonist Compounds | | | |
|---|---|---|---|
| Cmpd. No. | Compounds of Formula (Ia) | Cmpd No. | Compounds of Formula (Ib) |
| 106 | 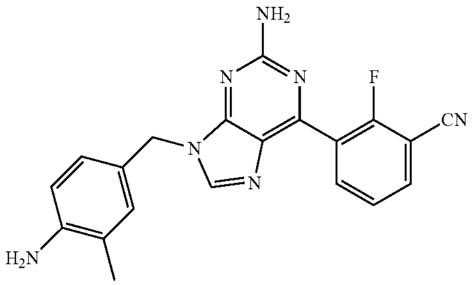 [SMILES: Cc1cc(Cn2cnc3c(-c4cccc(C#N)c4F)nc(N)nc32)ccc1N] | 206 | 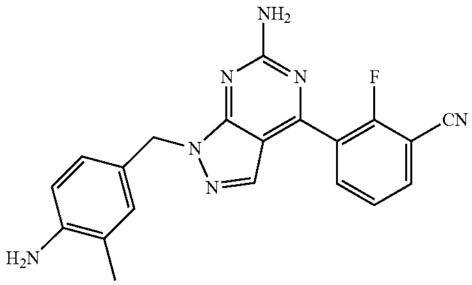 [SMILES: Cc1cc(Cn2ncc3c(-c4cccc(C#N)c4F)nc(N)nc32)ccc1N] |
| 107 | 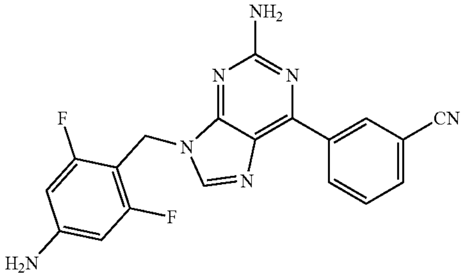 [SMILES: N#Cc1cccc(-c2nc(N)nc3c2ncn3Cc2c(F)cc(N)cc2F)c1] | 207 | 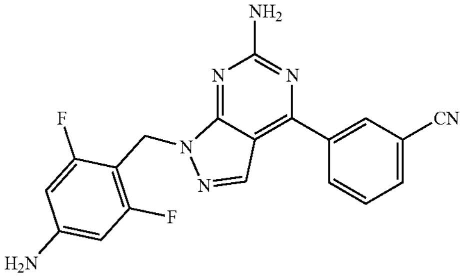 [SMILES: N#Cc1cccc(-c2nc(N)nc3c2cnn3Cc2c(F)cc(N)cc2F)c1] |
| 108 | 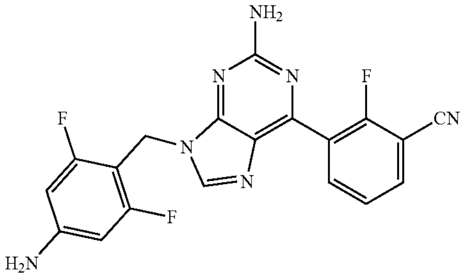 [SMILES: N#Cc1cccc(-c2nc(N)nc3c2ncn3Cc2c(F)cc(N)cc2F)c1F] | 208 | 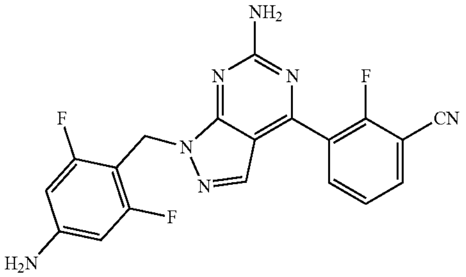 [SMILES: N#Cc1cccc(-c2nc(N)nc3c2cnn3Cc2c(F)cc(N)cc2F)c1F] |
| 109 | 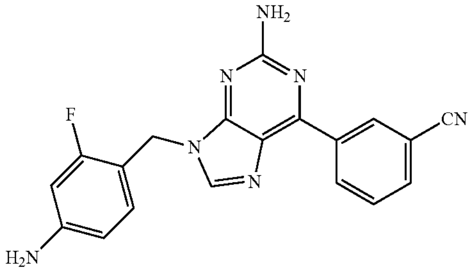 [SMILES: N#Cc1cccc(-c2nc(N)nc3c2ncn3Cc2ccc(N)cc2F)c1] | 209 | 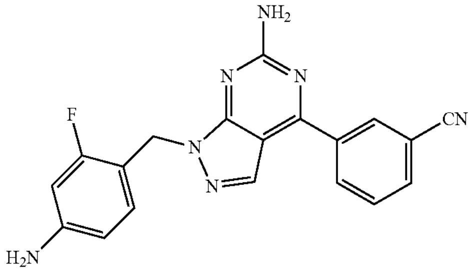 [SMILES: N#Cc1cccc(-c2nc(N)nc3c2cnn3Cc2ccc(N)cc2F)c1] |
| 110 | 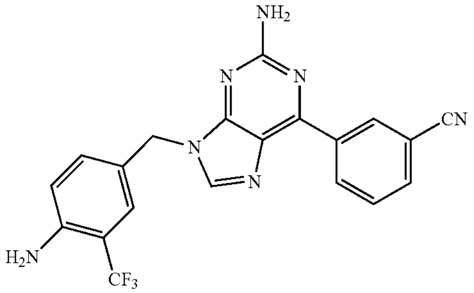 [SMILES: N#Cc1cccc(-c2nc(N)nc3c2ncn3Cc2ccc(N)c(C(F)(F)F)c2)c1] | 210 | 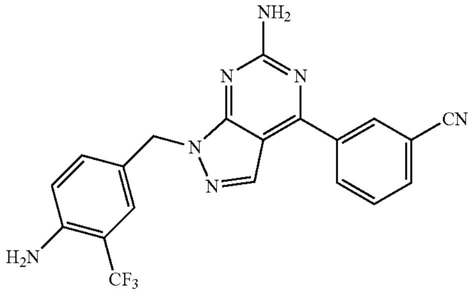 [SMILES: N#Cc1cccc(-c2nc(N)nc3c2cnn3Cc2ccc(N)c(C(F)(F)F)c2)c1] |

TABLE 1-continued
Exemplary A2A and/or A1 Receptor Antagonist Compounds
| Cmpd. No. | Compounds of Formula (Ia) | Cmpd No. | Compounds of Formula (Ib) |
|---|---|---|---|
| 111 | 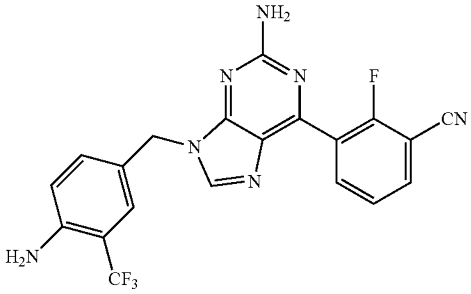 [SMILES: N#Cc1cccc(-c2nc(N)nc3c2ncn3Cc2ccc(N)c(C(F)(F)F)c2)c1F] | 211 | 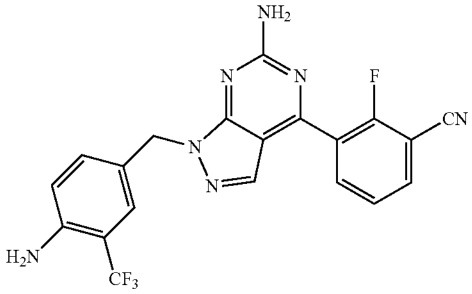 [SMILES: N#Cc1cccc(-c2nc(N)nc3c2cnn3Cc2ccc(N)c(C(F)(F)F)c2)c1F] |
| 112 | 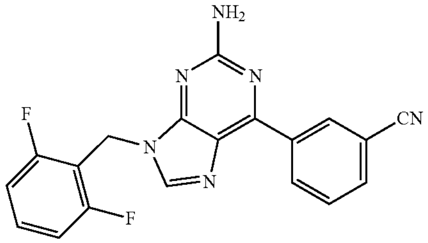 [SMILES: N#Cc1cccc(-c2nc(N)nc3c2ncn3Cc2c(F)cccc2F)c1] | 212 | 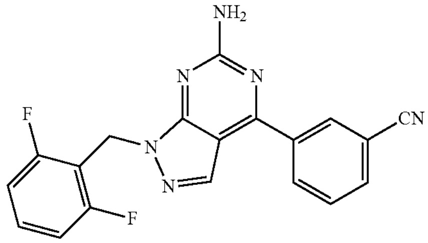 [SMILES: N#Cc1cccc(-c2nc(N)nc3c2cnn3Cc2c(F)cccc2F)c1] |
| 113 | 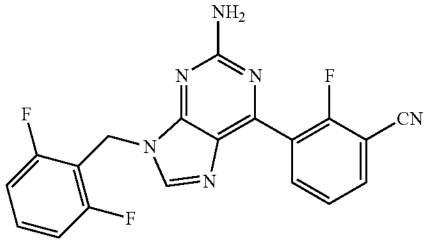 [SMILES: N#Cc1cccc(-c2nc(N)nc3c2ncn3Cc2c(F)cccc2F)c1F] | 213 | 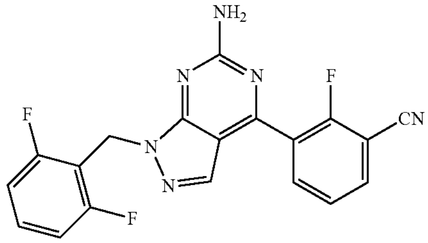 [SMILES: N#Cc1cccc(-c2nc(N)nc3c2cnn3Cc2c(F)cccc2F)c1F] |
| 114 | 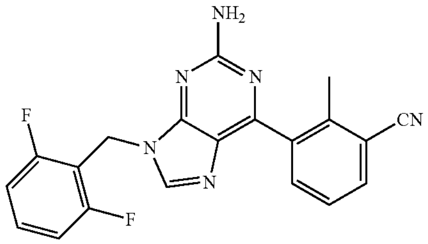 [SMILES: Cc1c(C#N)cccc1-c1nc(N)nc2c1ncn2Cc1c(F)cccc1F] | 214 | 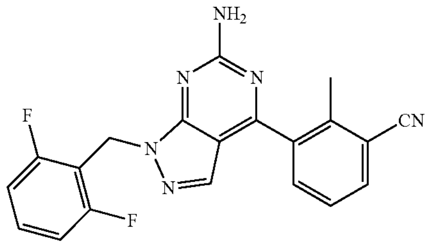 [SMILES: Cc1c(C#N)cccc1-c1nc(N)nc2c1cnn2Cc1c(F)cccc1F] |
| 115 | 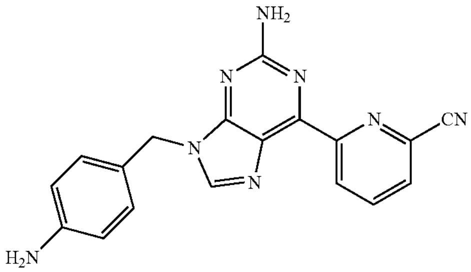 [SMILES: N#Cc1cccc(-c2nc(N)nc3c2ncn3Cc2ccc(N)cc2)n1] | 215 | 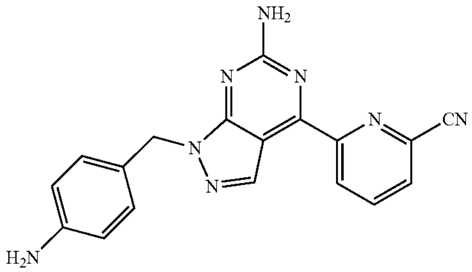 [SMILES: N#Cc1cccc(-c2nc(N)nc3c2cnn3Cc2ccc(N)cc2)n1] |

TABLE 1-continued
Exemplary A2A and/or A1 Receptor Antagonist Compounds
| Cmpd. No. | Compounds of Formula (Ia) | Cmpd No. | Compounds of Formula (Ib) |
|---|---|---|---|
| 116 | 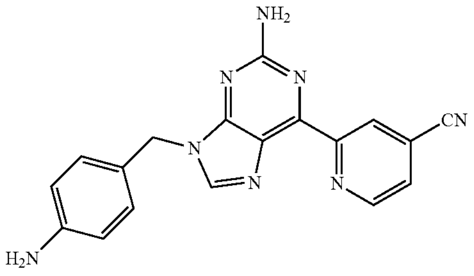 [SMILES: N#Cc1ccnc(-c2nc(N)nc3c2ncn3Cc2ccc(N)cc2)c1] | 216 | 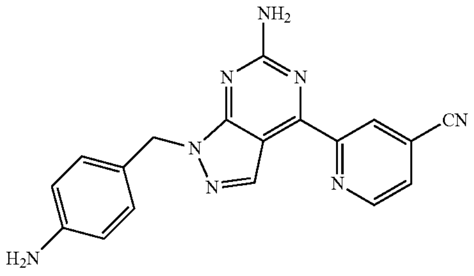 [SMILES: N#Cc1ccnc(-c2nc(N)nc3c2cnn3Cc2ccc(N)cc2)c1] |
| 117 | 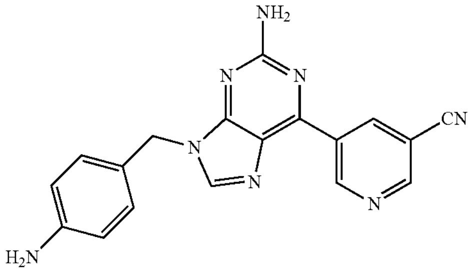 [SMILES: N#Cc1cncc(-c2nc(N)nc3c2ncn3Cc2ccc(N)cc2)c1] | 217 | 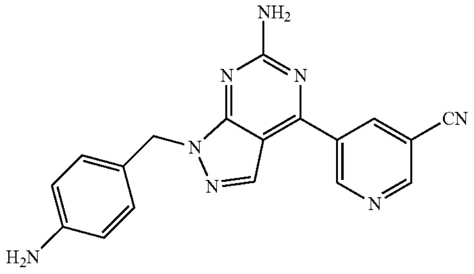 [SMILES: N#Cc1cncc(-c2nc(N)nc3c2cnn3Cc2ccc(N)cc2)c1] |
| 118 | 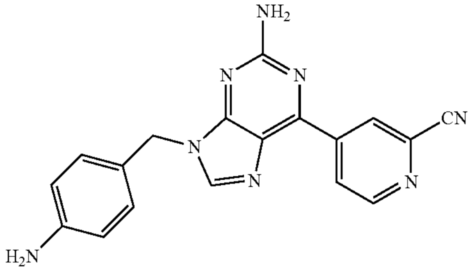 [SMILES: N#Cc1cc(-c2nc(N)nc3c2ncn3Cc2ccc(N)cc2)ccn1] | 218 | 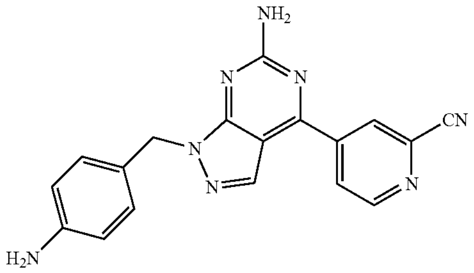 |
| 119 | 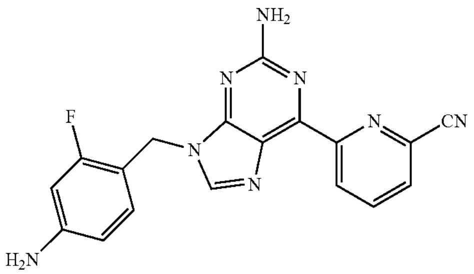 [SMILES: N#Cc1cccc(-c2nc(N)nc3c2cnn3Cc2ccc(N)cc2F)n1] | 219 | 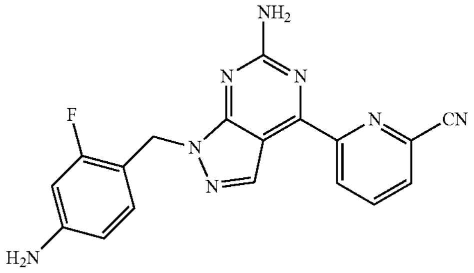 |
| 120 | 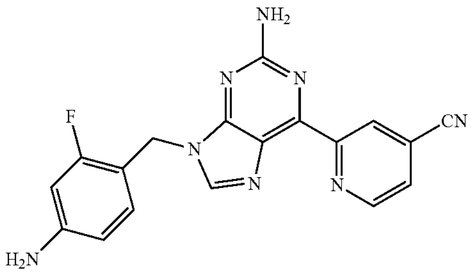 [SMILES: N#Cc1ccnc(-c2nc(N)nc3c2ncn3Cc2ccc(N)cc2F)c1] | 220 | 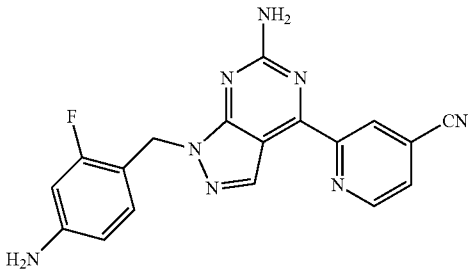 |

TABLE 1-continued
Exemplary A2A and/or A1 Receptor Antagonist Compounds
| Cmpd. No. | Compounds of Formula (Ia) | Cmpd No. | Compounds of Formula (Ib) |
|---|---|---|---|
| 121 | 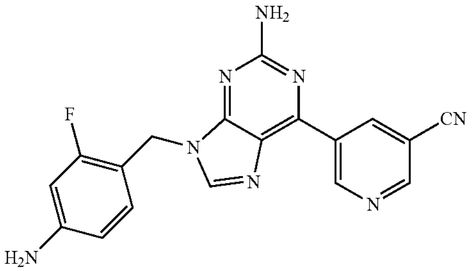 [SMILES: N#Cc1cncc(-c2nc(N)nc3c2ncn3Cc2ccc(N)cc2F)c1] | 221 | 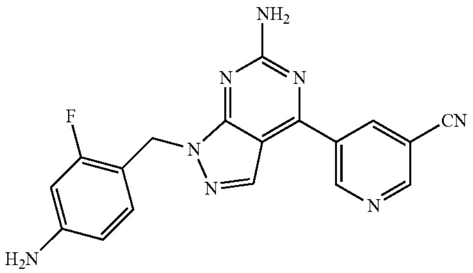 [SMILES: N#Cc1cncc(-c2nc(N)nc3c2cnn3Cc2ccc(N)cc2F)c1] |
| 122 | 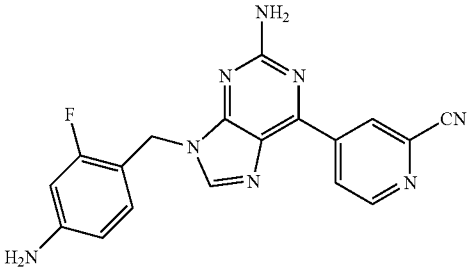 | 222 | 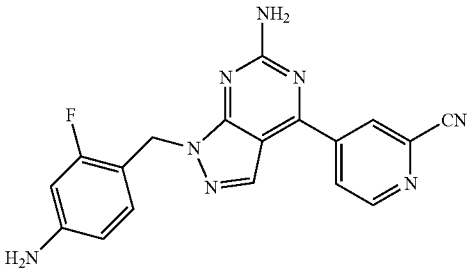 [SMILES: N#Cc1cc(-c2nc(N)nc3c2cnn3Cc2ccc(N)cc2F)ccn1] |
| 123 | 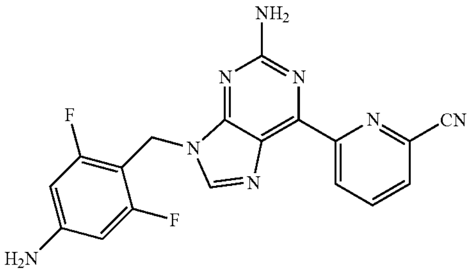 | 223 | 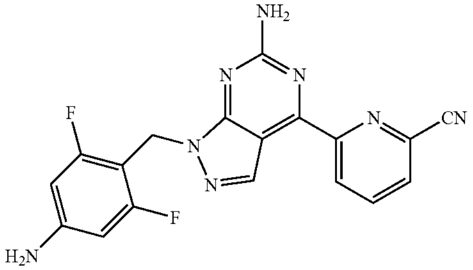 [SMILES: N#Cc1cccc(-c2nc(N)nc3c2cnn3Cc2c(F)cc(N)cc2F)n1] |
| 124 | 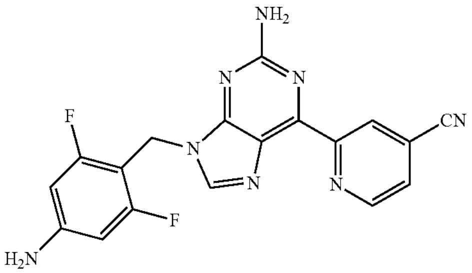 | 224 | 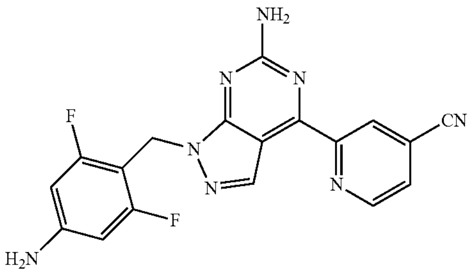 |
| 125 | 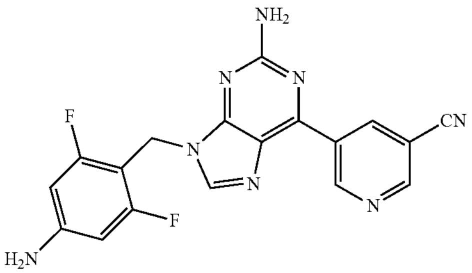 [SMILES: N#Cc1cncc(-c2nc(N)nc3c2ncn3Cc2c(F)cc(N)cc2F)c1] | 225 | 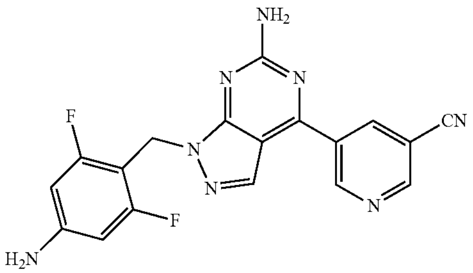 [SMILES: N#Cc1cncc(-c2nc(N)nc3c2cnn3Cc2c(F)cc(N)cc2F)c1] |

TABLE 1-continued
| Cmpd. No. | Compounds of Formula (Ia) | Cmpd No. | Compounds of Formula (Ib) |
|---|---|---|---|
| | Exemplary A2A and/or A1 Receptor Antagonist Compounds | | |
| 126 | 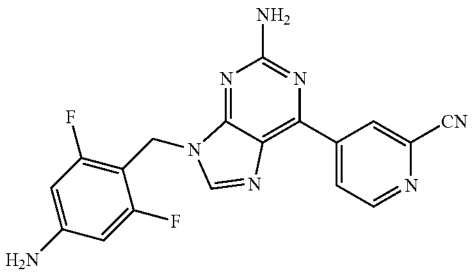 [SMILES: N#Cc1cc(-c2nc(N)nc3c2ncn3Cc2c(F)cc(N)cc2F)ccn1] | 226 | 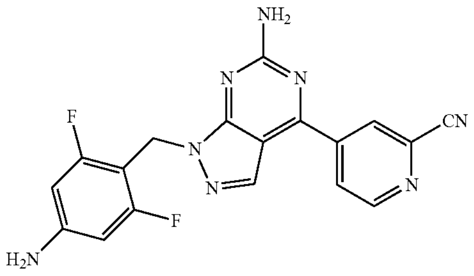 [SMILES: N#Cc1cc(-c2nc(N)nc3c2cnn3Cc2c(F)cc(N)cc2F)ccn1] |
| 127 | 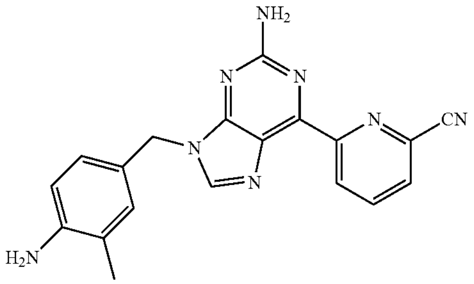 [SMILES: Cc1cc(Cn2cnc3c(-c4cccc(C#N)n4)nc(N)nc32)ccc1N] | 227 | 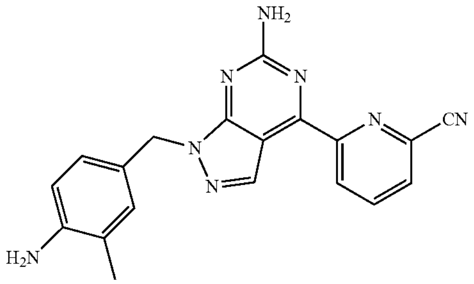 [SMILES: Cc1cc(Cn2ncc3c(-c4cccc(C#N)n4)nc(N)nc32)ccc1N] |
| 128 | 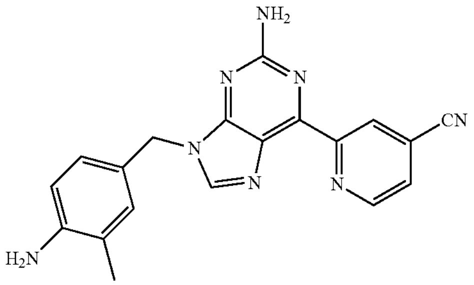 [SMILES: Cc1cc(Cn2cnc3c(-c4cc(C#N)ccn4)nc(N)nc32)ccc1N] | 228 | 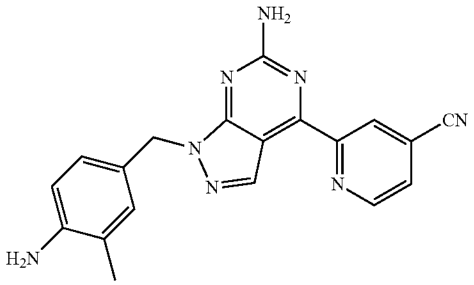 [SMILES: Cc1cc(Cn2ncc3c(-c4cc(C#N)ccn4)nc(N)nc32)ccc1N] |
| 129 | 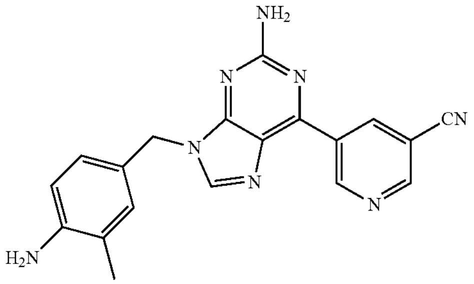 [SMILES: Cc1cc(Cn2cnc3c(-c4cncc(C#N)c4)nc(N)nc32)ccc1N] | 229 | 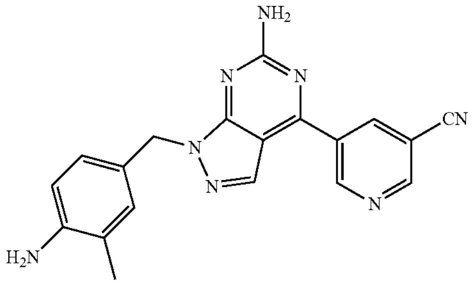 [SMILES: Cc1cc(Cn2ncc3c(-c4cncc(C#N)c4)nc(N)nc32)ccc1N] |
| 130 | 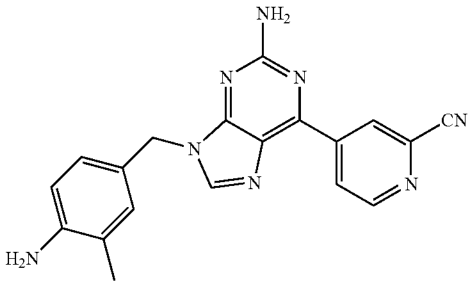 | 230 | 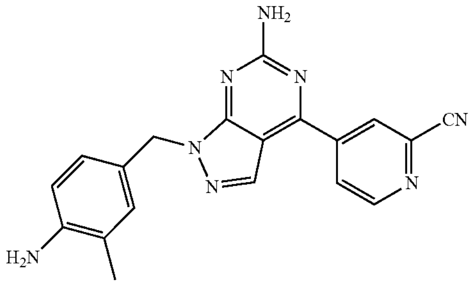 [SMILES: Cc1cc(Cn2ncc3c(-c4ccnc(C#N)c4)nc(N)nc32)ccc1N] |

TABLE 1-continued
| Cmpd. No. | Compounds of Formula (Ia) | Cmpd No. | Compounds of Formula (Ib) |
|---|---|---|---|
| | Exemplary A2A and/or A1 Receptor Antagonist Compounds | | |
| 131 | 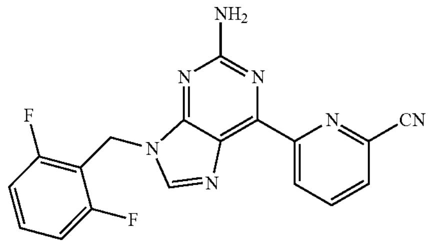 [SMILES: N#Cc1cccc(-c2nc(N)nc3c2ncn3Cc2c(F)cccc2F)n1] | 231 | 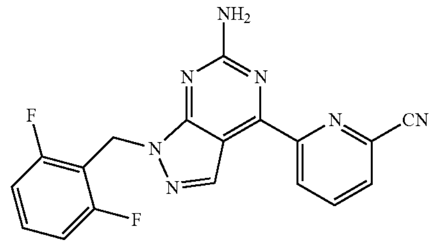 [SMILES: N#Cc1cccc(-c2nc(N)nc3c2cnn3Cc2c(F)cccc2F)n1] |
| 132 | 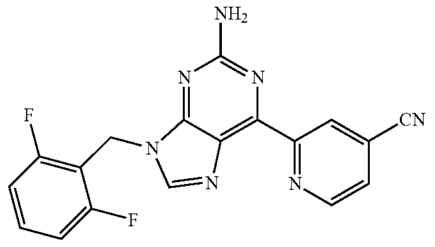 [SMILES: N#Cc1ccnc(-c2nc(N)nc3c2ncn3Cc2c(F)cccc2F)c1] | 232 | 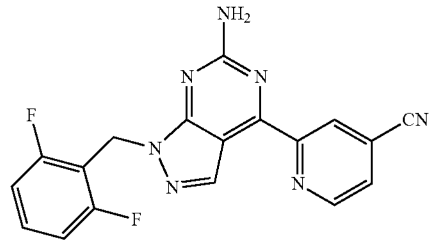 [SMILES: N#Cc1ccnc(-c2nc(N)nc3c2cnn3Cc2c(F)cccc2F)c1] |
| 133 | 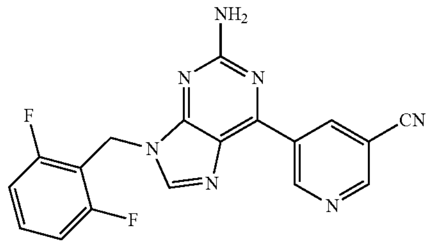 [SMILES: N#Cc1cncc(-c2nc(N)nc3c2ncn3Cc2c(F)cccc2F)c1] | 233 | 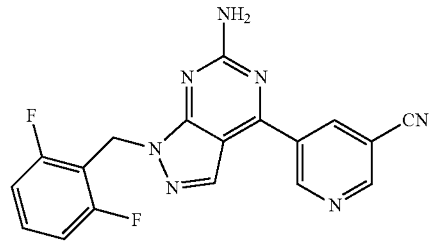 [SMILES: N#Cc1cncc(-c2nc(N)nc3c2cnn3Cc2c(F)cccc2F)c1] |
| 134 | 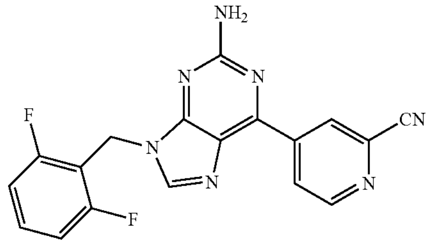 [SMILES: N#Cc1cc(-c2nc(N)nc3c2ncn3Cc2c(F)cccc2F)ccn1] | 234 | 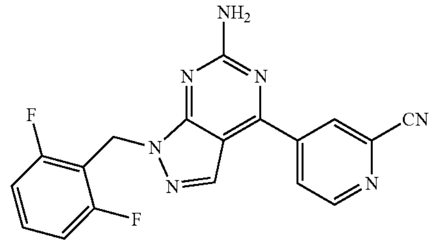 [SMILES: N#Cc1cc(-c2nc(N)nc3c2cnn3Cc2c(F)cccc2F)ccn1] |
| 135 | 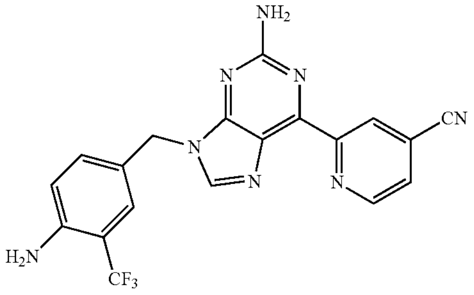 [SMILES: N#Cc1ccnc(-c2nc(N)nc3c2ncn3Cc2ccc(N)c(C(F)(F)F)c2)c1] | 235 | 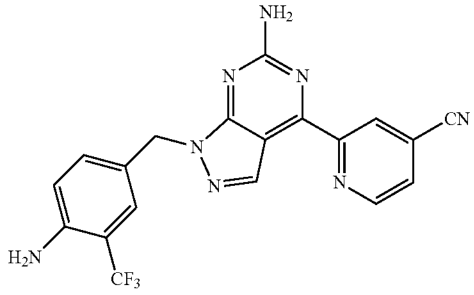 [SMILES: N#Cc1ccnc(-c2nc(N)nc3c2cnn3Cc2ccc(N)c(C(F)(F)F)c2)c1] |

TABLE 1-continued

Exemplary A2A and/or A1 Receptor Antagonist Compounds

| Cmpd. No. | Compounds of Formula (Ia) | Cmpd No. | Compounds of Formula (Ib) |
|---|---|---|---|
| 136 | 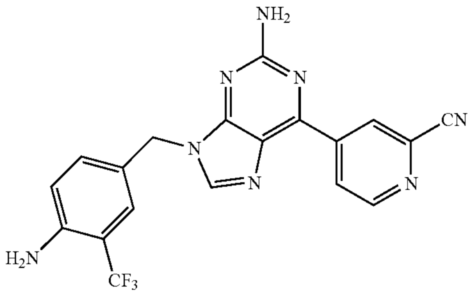 [SMILES: N#Cc1cc(-c2nc(N)nc3c2ncn3Cc2ccc(N)c(C(F)(F)F)c2)ccn1] | 236 | 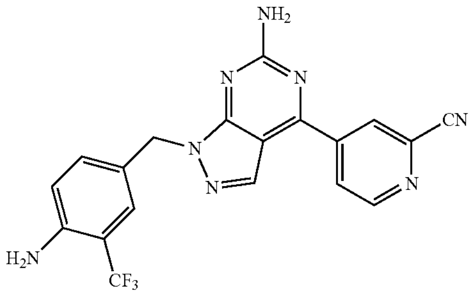 [SMILES: N#Cc1cc(-c2nc(N)nc3c2cnn3Cc2ccc(N)c(C(F)(F)F)c2)ccn1] |
| 137 | 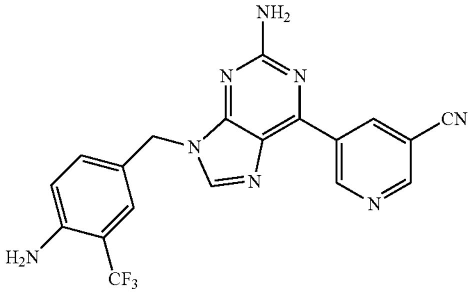 [SMILES: N#Cc1cncc(-c2nc(N)nc3c2ncn3Cc2ccc(N)c(C(F)(F)F)c2)c1] | 237 | 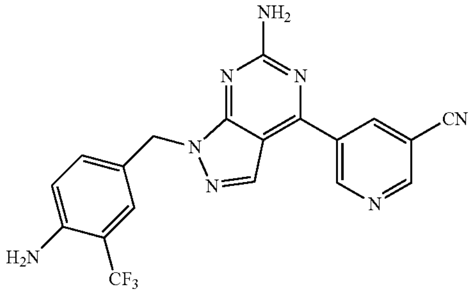 [SMILES: N#Cc1cncc(-c2nc(N)nc3c2cnn3Cc2ccc(N)c(C(F)(F)F)c2)c1] |
| 138 | 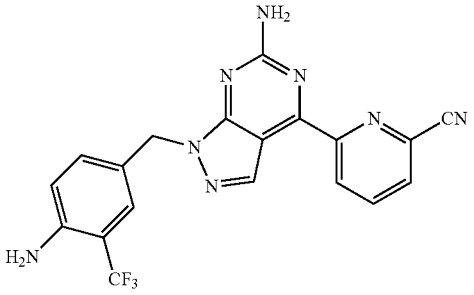 [SMILES: N#Cc1cccc(-c2nc(N)nc3c2cnn3Cc2ccc(N)c(C(F)(F)F)c2)n1] | 238 | 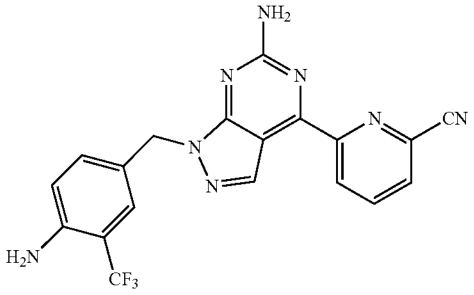 [SMILES: N#Cc1cccc(-c2nc(N)nc3c2cnn3Cc2ccc(N)c(C(F)(F)F)c2)n1] |

Isotopically Labelled Analogs

The present disclosure also encompasses isotopically-labeled compounds which are identical to those compounds as described herein, except that one or more atoms are replaced by an atom having an atomic mass or mass number different from the atomic mass or mass number usually found in nature ("isotopologues"). The compounds of the present disclosure may also contain unnatural proportions of atomic isotopes at one or more atoms that constituted such compounds. Examples of isotopes that can be incorporated into compounds described herein include isotopes of hydrogen, carbon, nitrogen, oxygen, phosphorus, fluorine and chlorine, such as $^{2}$H ("D"), $^{3}$H, $^{13}$C, $^{14}$C, $^{15}$N, $^{18}$O, $^{17}$O, $^{31}$P, $^{32}$p, $^{35}$S, $^{18}$F, and $^{36}$Cl, respectively. For example, a compound described herein can have one or more H atoms replaced with deuterium.

Generally, reference to or depiction of a certain element such as hydrogen or H is meant to include all isotopes of that element. For example, if an R group is defined to include hydrogen or H, it also includes deuterium and tritium. Compounds comprising radioisotopes such as tritium, $^{14}$C, $^{32}$P and $^{35}$S are thus within the scope of the present technology. Procedures for inserting such labels into the compounds of the present technology will be readily apparent to those skilled in the art based on the disclosure herein.

Unless otherwise stated, compounds described herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

In some embodiments, certain isotopically-labeled compounds, such as those labeled with $^{3}$H and $^{14}$C, can be useful in compound and/or substrate tissue distribution assays. Tritiated ($^{3}$H) and carbon-14 ($^{14}$C) isotopes can be particularly preferred for their ease of preparation and detectability. Further, substitution with heavier isotopes such as deuterium can afford certain therapeutic advantages resulting from greater metabolic stability, such as increased in vivo half-life or reduced dosage requirements, and hence can be preferred in some circumstances. Isotopically-labeled compounds can generally be prepared by following procedures analogous to those disclosed herein, for example, in the Examples section, by substituting an isotopically-labeled reagent for a non-isotopically-labeled reagent.

In some embodiments, the compounds disclosed in the present disclosure are deuterated analogs of any of the compounds, or a salt thereof, as described herein. A deuterated analog of a compound of formula (I)-(XVIb) is a compound where one or more hydrogen atoms are substituted with a deuterium. In some embodiments, the deuterated analog is a compound of formula (I) that includes a deuterated R, $R^a$, $R^b$, or $R^1$ to $R^{20}$ group.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)]2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Fluorinated Analogs

In some embodiments, the compounds disclosed in the present disclosure are fluorinated analogs of any of the compounds, or a salt thereof, as described herein. A fluorinated analog of a compound of formula (I)-(XVIb) is a compound where one or more hydrogen atoms or substituents are substituted with a fluorine atom. In some embodiments, the fluorinated analog is a compound of formula (I) that includes a fluorinated R, $R^a$, $R^b$, or $R^1$ to $R^{20}$ group. In some embodiments of a fluorinated analog of a compound of formula (I), the hydrogen atom of an aliphatic or an aromatic C—H bond is replaced by a fluorine atom. In some embodiments of a fluorinated analog of a compound of formula (I), at least one hydrogen of an optionally substituted aryl (e.g., phenyl) or an optionally substituted heteroaryl (e.g., pyridyl) is replaced by a fluorine atom. In some embodiments of a fluorinated analog of a compound of formula (I), a hydroxyl substituent (—OH) or an amino substituent ($—NH_2$) is replaced by a fluorine atom. In some embodiments of a fluorinated analog of a compound, the compound includes one or more substituents independently selected from —F, $—CF_3$, $—CF_2CF_3$, $—CHF_2$, $—OCF_3$, $—OCHF_2$, and $—OCF_2CF_3$.

Isomers

The term "compound", as used herein, is meant to include all stereoisomers, geometric isomers, tautomers, and isotopes of the structures depicted.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. In some embodiments, the compounds described herein have one or more chiral centers. It is understood that if an absolute stereochemistry is not expressly indicated, then each chiral center may independently be of the R-configuration or the S-configuration or a mixture thereof. Thus, compounds described herein include enriched or resolved optical isomers at any or all asymmetric atoms as are apparent from the depictions. Racemic mixtures of R-enantiomer and S-enantiomer, and enantio-enriched stereoisomeric mixtures comprising of R- and S-enantiomers, as well as the individual optical isomers can be isolated or synthesized so as to be substantially free of their enantiomeric or diastereomeric partners, and these stereoisomers are all within the scope of the present technology.

Compounds of the present disclosure containing an asymmetrically substituted atom may be isolated in optically active or racemic forms. It is well known in the art how to prepare optically active forms, such as by resolution of racemic forms, by synthesis from optically active starting materials, or through use of chiral auxiliaries.

Geometric isomers, resulting from the arrangement of substituents around a carbon-carbon double bond or arrangement of substituents around a cycloalkyl or heterocyclic ring, can also exist in the compounds of the present disclosure. Geometric isomers of olefins, C═N double bonds, or other types of double bonds may be present in the compounds described herein, and all such stable isomers are included in the present disclosure. Specifically, cis and trans geometric isomers of the compounds of the present disclosure may also exist and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Salts and Other Forms

In some embodiments, the compounds described herein are present in a salt form. In some embodiments, the compounds are provided in the form of pharmaceutically acceptable salts.

Compounds included in the present compositions that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to, chloride.

Compounds containing an amine functional group or a nitrogen-containing heteroaryl group may be basic in nature and may react with a variety of inorganic and organic acids to form the corresponding salts. The compounds could be used in the form of a pharmaceutically acceptable salt derived from inorganic acid or organic acid. In some embodiments, the pharmaceutically acceptable salt could be a salt derived from hydrochloric acid (i.e., a hydrochloride salt of a compound as described herein), or the like.

The pharmaceutically acceptable salts of the compounds of this disclosure could be produced by dissolving the compound in a water-miscible organic solvent, such as acetone, methanol, ethanol, or acetonitrile, and so on, and adding excessive amount of organic acid or inorganic acid aqueous solution and precipitating or crystalizing. Then, it is possible to obtain additional salt by evaporating the solvent or excessive acid from this mixture and then drying it or by produce salt by filtering extracted salt.

Other examples of salts include anions of the compounds of the present disclosure compounded with a suitable cation. For therapeutic use, salts of the compounds of the present disclosure can be pharmaceutically acceptable. However, salts of acids and bases that are non-pharmaceutically acceptable may also find use, for example, in the preparation or purification of a pharmaceutically acceptable compound.

Compounds included in the present compositions that are acidic in nature are capable of forming base salts with various pharmacologically acceptable cations. Examples of such salts include alkali metal or alkaline earth metal salts.

Compounds that include a basic or acidic moiety can also form pharmaceutically acceptable salts with various amino acids. The compounds of the disclosure can contain both acidic and basic groups; for example, one amino and one carboxylic acid group. In such a case, the compound can exist as an acid addition salt, a zwitterion, or a base salt.

The compounds described herein can be present in various forms including crystalline, powder and amorphous forms of those compounds, pharmaceutically acceptable salts, including, for example, polymorphs, pseudopolymorphs, solvates, hydrates, unsolvated polymorphs (including anhydrates), conformational polymorphs, and amorphous forms of the compounds, as well as mixtures thereof. It is understood that a salt form of any one of the subject compounds can be present in a crystalline, powder or amorphous form.

The compounds described herein may exist as solvates, especially hydrates, and unless otherwise specified, all such solvates and hydrates are intended. The term "solvate" could refer to the compound of the present disclosure containing a stoichiometric or non-stoichiometric solvent combined by non-covalent intermolecular force or its salt. Hydrates may form during manufacture of the compounds or compositions comprising the compounds, or hydrates may form over time due to the hygroscopic nature of the compounds.

Compounds of the present technology may exist as organic solvates as well, including dimethylformamide (DMF), ether, and alcohol solvates, among others. The identification and preparation of any particular solvate is within the skill of the ordinary artisan of synthetic organic or medicinal chemistry.

In some embodiments, the compounds described herein are present in a solvate form. In some embodiments, the compounds described herein are present in a hydrate form when the solvent component of the solvate is water.

Prodrugs

In some embodiments, the compounds described herein are present in a prodrug form. Any convenient prodrug forms of the subject compounds can be prepared, for example, according to the strategies and methods described by Rautio et al. ("Prodrugs: design and clinical applications", Nature Reviews Drug Discovery 7, 255-270 (February 2008)).

Compound Synthesis

Compounds of the present disclosure may be synthesized according to standard methods known in the art [see, e.g. Morrison and Boyd in "Organic Chemistry", $6^{th}$ edition, Prentice Hall (1992)]. Some compounds and/or intermediates of the present disclosure may be commercially available, known in the literature, or readily obtainable by those skilled in the art using standard procedures. Some compounds of the present disclosure may be synthesized using schemes, examples, or intermediates described herein. Where the synthesis of a compound, intermediate or variant thereof is not fully described, those skilled in the art can recognize that the reaction time, number of equivalents of reagents and/or temperature may be modified from reactions described herein to prepare compounds presented or intermediates or variants thereof and that different work-up and/or purification techniques may be necessary or desirable to prepare such compounds, intermediates, or variants.

Synthesized compounds may be validated for proper structure by methods known to those skilled in the art, for example by nuclear magnetic resonance (NMR) spectroscopy and/or mass spectrometry.

Pharmaceutical Compositions

Compounds of the present disclosure may be formulated in pharmaceutical compositions. The pharmaceutical composition can include one or more such A2A and/or A1 receptor antagonist compounds (e.g., as described herein) and at least one excipient (e.g., a pharmaceutically acceptable excipient).

The compounds described herein can find use in pharmaceutical compositions for administration to a subject in need thereof in a variety of therapeutic applications where inhibition or antagonism of the activity of A2A and/or A1 receptor is desirable.

Accordingly, in a second aspect, the present disclosure provides pharmaceutical compositions comprising at least one compound described herein, a pharmaceutically acceptable salt thereof, or a prodrug thereof, and at least one pharmaceutically acceptable excipient. The phrase "pharmaceutically acceptable excipient," refers any ingredient other than the inventive compounds described herein (for example, a vehicle capable of suspending or dissolving the active compound, or any other convenient pharmaceutically acceptable carriers, excipients or additives) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, dispensing, or dispersing agents, sweeteners, and waters of hydration. In some embodiments, the pharmaceutical composition comprises a compound as described herein, a pharmaceutically acceptable salt thereof, or a prodrug thereof in a therapeutically effective amount.

The pharmaceutical composition may be formulated according to any convenient methods, and may be prepared in various forms for oral administration such as tablets, pills, powders, nanoparticles, capsules, syrups, suspensions, emulsions and microemulsions, or in forms for non-oral administration such as preparations for intramuscular, intravenous or subcutaneous administration.

In a specific example, the pharmaceutical composition could contain a pharmaceutically allowed carrier, excipient, or additive. The pharmaceutical composition could be produced as medicine in the conventional method, and could be produced as various oral medicine such as tablet, pill, powder, capsule, syrup, emulsion, micro-emulsion, and so on, or could be produced as non-oral medicine such as muscular injection, vascular injection, or subcutaneous injection.

If the pharmaceutical composition is produced in the form of an oral medicine, examples of the used additive or carrier could include cellulose, silicic calcium, corn starch, lactose, sucrose, dextrose, phosphoric acid calcium, stearic acid, stearic acid magnesium, stearic acid calcium, gelatin, talc, surfactant, suspension, emulsifying agent, diluting agent, and so on. If the pharmaceutical composition of this disclosure is produced in the form of an injection, the additives or carrier could include water, saline water, glucose aqueous solution, similar sugar-soluble solution, alcohol, glycol, ether (e.g., polyethylene glycol 400), oil, fatty acid, fatty acid ester, glyceride, surfactant, suspension, emulsifying agent, and so on.

In some embodiments, the pharmaceutical compositions are formulated for parenteral administration to a subject in need thereof. In some parenteral embodiments, the pharmaceutical compositions are formulated for intravenous administration to a subject in need thereof. In some parenteral embodiments, the pharmaceutical compositions are formulated for subcutaneous administration to a subject in need thereof.

Methods of Modulating A2A and/or A1 Receptor

Aspects of the present disclosure include methods of modulating the activity of A2A and/or A1 receptor in a biological system or sample. In some embodiments, modulating the activity of A2A and/or A1 receptor refers to inhibiting an A2A and/or A1 receptor in a sample. In some embodiments, modulating the activity of A2A and/or A1 receptor refers to antagonizing the activity of an A2A and/or A1 receptor in a cell or biological system.

In some embodiments, the method includes contacting a sample with a compound of this disclosure which can modulate A2A and/or A1 receptor activity. In some embodiments, the method includes contacting a cell or biological system with a compound of this disclosure which can modulate A2A and/or A1 receptor activity.

The present disclosure provides compounds having A2A and/or A1 receptor modulating activity, e.g., A2A and/or A1 receptor inhibition and/or antagonistic activity. In some embodiments, the compound has A2A receptor inhibition and/or antagonist activity. In some embodiments, the compound has A2A and A1 receptor inhibition and/or antagonist activity. In some embodiments, the compound has A1 receptor inhibition and/or antagonist activity. The ability of the compounds to modulate A2A and/or A1 receptor activity may be characterized using a variety of assays, e.g., by an A2A and/or A1 receptor binding assay and/or an A2A receptor functional assay. For example, the experimental section describes A2A receptor binding assays. Exemplary compounds of this disclosure were assessed, and $K_i$ values determined, to show that the compounds of this disclosure can provide specific binding to human A2A receptor in an assay system. In addition, the experimental section describes A2A functional assays involving monitoring cAMP signals produced in a human recombinant A2A receptor stable cell line. Exemplary compounds of this disclosure were assessed, and values obtained, indicating that the compounds can antagonize human A2A receptor in an assay system.

Aspects of the present disclosure include methods of modulating (e.g., inhibiting or antagonizing) A2A and/or A1 receptor using a compound described herein. Such methods may include methods of modulating A2A and/or A1 receptor in biological systems by contacting such systems with compounds (e.g., compounds having structures according to Formula (I)-(XVIb) or the compounds of Table 1). Biological systems may include, but are not limited to, cells, tissues, organs, bodily fluids, organisms, non-mammalian subjects, and mammalian subjects (e.g., humans). Biological systems may include subjects (e.g., human subjects).

In some embodiments, the method of inhibiting or antagonizing A2A and/or A1 receptor comprises contacting a biological system or sample comprising A2A and/or A1 receptor with an effective amount of any of the compounds or a pharmaceutically acceptable salt thereof as described herein, or a pharmaceutical composition as described herein to inhibit or antagonize the A2A and/or A1 receptor. In certain embodiments, the biological system or sample is in vitro. In another embodiment, the biological system or sample is in vivo. In some embodiments, the sample is a cell sample. In some embodiments, the A2A and/or A1 receptor is cell membrane bound.

The compounds of this disclosure may antagonize an A2A receptor, e.g., as assessed by a human A2A functional assay, e.g., as described in Example 3. The A2A receptor antagonist compounds according to such methods may have values (e.g., as assessed by the cAMP assay of Example 3) of 10 μM or less, such as 2 μM or less, 1 μM or less, 500 nM or less, 300 nM or less, 100 nM or less, 30 nM or less, or 10 nM or less.

Biological systems may include subjects (e.g., human subjects). The A2A receptor antagonist compounds according to such methods may have Ki values (e.g., as assessed by the binding assay of Example 2) of 1 μM or less, such as 500 nM or less, 300 nM or less, 100 nM or less, 30 nM or less, 10 nM or less, 3 nM or less, or 1 nM or less.

In some embodiments, the compound is an A2A receptor antagonist that exhibits a desirable level of inhibition activity at A1 receptor. In some embodiments, the compound is a dual antagonist of the A2A receptor and the A1 receptor. In some embodiments, a desirable level of A1 receptor inhibition activity refers to compound having a Ki value at a human A1 receptor in a cell model (e.g., as assessed in Example 4.1) that is 1 mM or lower, such as 300 μM or lower, 100 μM or lower, 30 μM or lower, 10 μM or lower, 3 μM or lower, or 1 μM or lower. In some embodiments, the compound of this disclosure exhibits inhibition activity for A2A receptor and A1 receptor. Example 4, Table 5, of the experimental section, provides A2A and A1 receptor inhibition data which indicates compounds of this disclosure can have potent activity as dual antagonists. In such cases, the compounds can find use in treatment of CNS and neurodegenerative diseases (e.g., a compound of formula (Ib) to (XVIb)).

Therapeutic Indications

Aspects of the present disclosure include methods of treating a subject for a therapeutic indication of interest using compounds and/or compositions disclosed herein. The term "therapeutic indication" refers to any symptom, condition, disorder, or disease that may be alleviated, stabilized, improved, cured, or otherwise addressed in a subject by some form of treatment or other therapeutic intervention (e.g., through A2A and/or A1 receptor antagonist administration). Therapeutic indications associated with modulation of A2A and/or A1 receptor biological activity and/or dysfunction are referred to herein as "adenosine receptor-related indications." In some embodiments, methods of the present disclosure may include treating adenosine receptor-related indications by administering an effective amount of compounds and/or compositions disclosed herein (e.g., A2A and/or A1 receptor antagonist compounds) to a subject.

The term "to treat" or "treatment" refers to inhibiting an illness, for example inhibiting an illness, condition, or disability in an subject that experiences the pathology or symptoms of the illness, condition, or disorder, namely preventing additional occurrence of pathology and/or symptoms, or improving the illness, for example improving the illness, condition or disorder in the subject that experiences or exhibits the pathology or symptoms of the illness, condition, or disorder, namely reversing the pathology and/or symptoms, for example reducing the severity of the illness. In the context of the present disclosure insofar as it relates to any of the other conditions recited herein below, the terms "treat," "treatment," and the like mean to relieve or alleviate at least one symptom associated with such condition, or to slow or reverse the progression or anticipated progression of such condition.

The term "to prevention" or "prevention" refers to preventing an illness, for example preventing an illness, condition or disorder in an entity that has not experienced or exhibited the pathology or symptoms of the illness even though the entity may have a tendency for the illness, condition or disorder.

The terms "individual", "patient", "subject" and "entity" are used interchangeably and refer to a human person or non-human animal that requires treatment of a disease. More specifically, what is referred to is a mammal such as a human, nonhuman primate, mouse, dog, cat, horse, cow, rabbit, rat, or other mammal.

Cancer and Immuno-Oncology

The present disclosure provides a method of treating or preventing cancer in a subject using the subject compounds as therapeutic agents, and compositions including the compounds. Any cancer for which an A2A receptor antagonist are thought to be useful by those of ordinary skill in the art are contemplated as cancers treatable by this embodiment, either as a monotherapy or in combination with other therapeutic agents discussed below.

The illness subject to prevention or treatment by the aforementioned pharmaceutical composition, which is "cancer," refers collectively to the illness caused by cells wherein cells have aggressive characteristics such as dividing and growing by ignoring normal growth limit, invasive characteristics whereby cells invade the surrounding tissues, and metastatic characteristics whereby cells spread to other areas of the body. In some embodiments, the cancer is a solid tumor cancer. Cancers which are the object of prevention or therapy using the compounds and pharmaceutical compositions of this disclosure include, but are not limited to, lung cancer, breast cancer, prostate cancer, ovarian cancer, solenoma, cervical cancer, bladder cancer, head and neck cancer, renal cell carcinoma, cancer of the esophagus, pancreatic cancer, brain cancer, liver cancer, leukemia, lymphoma, melanoma, multiple myeloma, Ewing's sarcoma, osteosarcoma, colorectal neoplasm, cholangiocarcinoma, choriocarcinoma, mouth cancer, neuroblastoma, skin cancer, testicular cancer, stromal tumor, germ cell tumor, and thyroid cancer.

In some embodiments, the cancer is cancer of the kidney, breast, lung, or liver. In some embodiments, the cancer is a solid tumor cancer. In some embodiments, the liver cancer is hepatocellular carcinoma (HCC). In some embodiments, the lung cancer is non-small cell lung carcinoma (NSCLC). In some embodiments, the cancer is a solid tumor cancer.

In some embodiments, the method further comprises identifying a subject suffering from or having cancer.

The compounds of this disclosure can be administered alone or in combination with one or more additional agents described herein. Accordingly, aspects of the methods include co-administering to the subject an effective amount of a compound or composition of this disclosure and an effective amount of an additional active agent. The compound and additional active agent can be administered concurrently or sequentially.

In some embodiments of the methods, the additional active agent is an anticancer agent selected from anti-angiogenesis agent, anti-inflammatory agent, immune checkpoint inhibitor, poly ADP ribose polymerase (PARP) inhibitor, chemotherapeutic agent, and immunity anticancer agent.

Given the immunosuppressive role of adenosine, the administration of an A2A receptor antagonist of this disclosure (e.g., compounds of formula (Ia) to (XVIa)) can enhance the efficacy of an immunotherapy, such as an immune checkpoint inhibitor therapy. In some embodiments, the additional active agent is an immune checkpoint inhibitor selected from CTLA-4 inhibitor, PD-1 inhibitors, and PD-L1 inhibitor.

In some embodiments, the immune checkpoint inhibitor is an antibody or antibody fragment. In some embodiments, the additional therapeutic agent is an anti-PD-1 antibody. In another embodiment, the additional therapeutic agent is an anti-PD-L1 antibody. In some embodiments, the additional therapeutic agent is selected from pembrolizumab, nivolumab, atezolizumab, durvalumab, and avelumab.

Inflammatory Disease

The present disclosure provides a method of treating or preventing an inflammatory disease in a subject using the subject compounds as therapeutic agents, and compositions including the compounds. Any inflammatory diseases for which an A2A receptor antagonist are thought to be useful by those of ordinary skill in the art are contemplated as diseases treatable using compounds of this disclosure, either as a monotherapy or in combination with other therapeutic agents (e.g., as described herein).

In some embodiments, the method includes administering to a subject having an inflammatory disease a therapeutically effective amount of an A2A and/or A1 receptor antagonist compound (e.g., as described herein). In some embodiments, the inflammatory disease is a chronic inflammatory disease, such as rheumatoid arthritis (RA). In some embodiments, the inflammatory disease is an acute inflammatory disease.

In some embodiments, the method further comprises identifying a subject suffering from or at risk of an inflammatory disease.

In some embodiments, the method further comprises identifying an underlying disease or condition associated with the inflammatory disease.

CNS and Neurodegenerative Diseases

The present disclosure provides a method of treating or preventing central nervous system (CNS) or neurodegenerative diseases or disorders in a subject using the compounds of this disclosure as therapeutic agents, or pharmaceutical compositions including the compounds. In some embodiments, the CNS disease is referred to as a neurodegenerative disease or disorder of the CNS. CNS and neurodegenerative diseases, which are the object of prevention or therapy using the compounds and pharmaceutical compositions of this disclosure, are diseases that include, but are not limited to, Parkinson's disease (PD), Alzheimer's disease (AD), amyotrophic lateral sclerosis (ALS), multiple sclerosis, Huntington's disease (HD), depression, schizophrenia, and epilepsy.

In some embodiments, method is a method of treating or preventing Parkinson's disease, and includes administering to a subject having, or at risk of Parkinson's disease an effective amount of a compound of this disclosure. In some cases, the compound is one having dual inhibition activity at both A2A receptor and A1 receptor (e.g., a compound of formula (Ib to XVIb).

In some embodiments, the method further comprises identifying a subject suffering from, or at risk of, a CNS or neurodegenerative disease.

In some embodiments, the method further comprises identifying an underlying disease or condition associated with the CNS or neurodegenerative disease.

The amount of the aforementioned pharmaceutical composition administered is the effective amount to treat or prevent illness for an entity or patient, and could be administered orally or non-orally according to the purpose. When administered orally, the amount administered based on the active component is 0.01 to 1,000 mg per 1 kg of body weight, more specifically 0.1 to 300 mg per 1 kg. When administered non-orally, 0.01 to 100 mg based on the active component is administered per 1 kg of body weight per day, and more specifically 0.1 to 50 mg is administered once or several times. The amount administered for a specific entity or patient can be determined based on many related factors including the patient's weight, age, sex, health status, diet, time of administration, method of administration, severity of the illness, and so on, must be understood to be able to be increased or decreased appropriately by the specialist, and the aforementioned amount of administration does not limit the scope of the present disclosure in any way. A medical doctor or veterinarian with ordinary level of knowledge in the related technological field may determine and prescribe effective amount of the pharmaceutical composition. For example, a medical doctor or veterinarian may start with the amount of the compound under the present disclosure used in a pharmaceutical composition that is lower than the amount required to achieve the desired treatment effect, and may increase the amount administered gradually until the desired effect is achieved.

The compounds and compositions of this disclosure may be administered alone, in combination with a compound according to another example of the present disclosure, or in simultaneous, separate or sequential concomitant administration with at least one other therapeutic agent, for example with other pharmaceutical active ingredients described herein.

In a specific example, a pharmaceutical composition of this disclosure includes within its scope at least one of the compounds in accordance with a specific example of the effective treatment amount as effective component, or a pharmaceutical composition that is contained in combination with a pharmaceutical carrier. Arbitrarily, the compound in accordance with an embodiment of the present disclosure could be administered independently, in combination with a compound in accordance with another specific example, or simultaneously with one or more other treatment medications, for example simultaneously with an anticancer medicine (e.g., as described herein) or with an active pharmaceutical material, separately, or consecutively in conjunction.

Definitions

Unless defined otherwise, all technical and scientific terms used herein have the same meaning as commonly understood by one of ordinary skill in the art to which this disclosure pertains.

It is understood that the definitions provided herein are not intended to be mutually exclusive. Accordingly, some chemical moieties may fall within the definition of more than one term.

The term "$C_x$-$C_y$" when used in conjunction with a chemical moiety, such as alkyl, alkenyl, or alkynyl is meant to include groups that contain from x to y carbons in the chain. For example, the term "$C_1$-$C_6$ alkyl" refers to substituted or unsubstituted saturated hydrocarbon groups, including straight-chain alkyl and branched-chain alkyl groups that contain from 1 to 6 carbons. In some embodiments, the term "($C_x$-$C_y$)alkylene" refers to a substituted or unsubstituted alkylene chain with from x to y carbons in the alkylene chain. For example "($C_x$-$C_y$)alkylene may be selected from methylene, ethylene, propylene, butylene, pentylene, and hexylene, any one of which is optionally substituted.

The term "alkyl" refers to an unbranched or branched saturated hydrocarbon chain. In some embodiments, alkyl as used herein has 1 to 20 carbon atoms (($C_1$-$C_{20}$)alkyl), 1 to 10 carbon atoms (($C_1$-$C_{10}$)alkyl), 1 to 8 carbon atoms (($C_1$-$C_8$)alkyl), 1 to 6 carbon atoms (($C_1$-$C_6$)alkyl), 1 to 5 carbon atoms (($C_1$-$C_5$)alkyl) or 1 to 3 carbon atoms (($C_1$-$C_5$)alkyl). Examples include, but are not limited to, methyl, ethyl, n-propyl, isopropyl, n-butyl, sec-butyl, tert-butyl, n-pentyl, 2-pentyl, isopentyl, neopentyl, n-hexyl, 2-hexyl, 3-hexyl, and 3-methyl pentyl. When an alkyl residue having a specific number of carbons is named, all geometric isomers having that number of carbons may be encompassed. For example, "butyl" can include n-butyl, sec-butyl, isobutyl and t-butyl, and "propyl" can include n-propyl and isopropyl. Unless stated otherwise specifically in the specification, an alkyl chain is optionally substituted by one or more substituents such as those substituents described herein.

The term "alkoxy" refers to an unbranched or branched alkyl group attached to an oxygen atom (alkyl-O—). In some embodiments, alkoxy as used herein has 1 to 20 carbon atoms (($C_1$-$C_{20}$)alkoxy), 1 to 10 carbon atoms (($C_1$-$C_{10}$) alkoxy), 1 to 8 carbon atoms (($C_1$-$C_8$)alkoxy), 1 to 6 carbon atoms (($C_1$-$C_6$)alkoxy), 1 to 5 carbon atoms (($C_1$-$C_5$)alkoxy) or 1 to 3 carbon atoms (($C_1$-$C_5$)alkoxy). Examples include, but are not limited to, methoxy, ethoxy, n-propoxy, and butoxy. When an alkoxy residue having a specific number of carbons is named, all geometric isomers having that number of carbons may be encompassed, such as isopropoxy, isobutoxy, and t-butoxy. Unless stated otherwise specifically in the specification, an alkoxy chain is optionally substituted by one or more substituents such as those substituents described herein.

The term "alkylene" refers to a straight divalent hydrocarbon chain linking the rest of the molecule to a radical group, consisting solely of carbon and hydrogen, containing no unsaturation, and preferably having from 1 to 20 carbon atoms (($C_1$-$C_{20}$)alkylene), 1 to 10 carbon atoms (($C_1$-$C_{10}$) alkylene), 1 to 6 carbon atoms (($C_1$-$C_6$)alkylene), or 1 to 5 carbon atoms (($C_1$-$C_5$)alkylene). Examples include, but are not limited to, methylene, ethylene, propylene, butylene, and the like. The alkylene chain is attached to the rest of the molecule through a single bond and to the radical group through a single bond. The points of attachment of the alkylene chain to the rest of the molecule and to the radical group are through the terminal carbons respectively. Unless stated otherwise specifically in the specification, an alkylene chain is optionally substituted by one or more substituents such as those substituents described herein. Examples include, methylene ($—CH_2—$), ethylene ($—CH_2CH_2—$), propylene ($—CH_2CH_2CH_2—$), 2-methylpropylene ($—CH_2—CH(CH_3)—CH_2—$), hexylene ($—(CH_2)_6—$) and the like.

The term "alkenyl" refers to an aliphatic hydrocarbon group containing at least one carbon-carbon double bond including straight-chain, branched-chain and cyclic alkenyl groups. In some embodiments, the alkenyl group has 2-10 carbon atoms (a $C_{2-10}$ alkenyl). In another embodiment, the alkenyl group has 2-4 carbon atoms in the chain (a $C_{2-4}$ alkenyl). Exemplary alkenyl groups include, but are not limited to, ethenyl, propenyl, n-butenyl, i-butenyl, 3-methylbut-2-enyl, 3-methylbut-1-enyl, n-pentenyl, heptenyl, octenyl, cyclohexyl-butenyl, decenyl, and the like, and their isomers. An alkylalkenyl is an alkyl group as defined herein bonded to an alkenyl group as defined herein. The alkenyl group can be unsubstituted or substituted through available carbon atoms with one or more groups defined hereinabove for alkyl The term “alkynyl” refers to straight or branched monovalent hydrocarbyl groups having from 2 to 6 carbon atoms and preferably 2 to 3 carbon atoms and having at least 1 and preferably from 1 to 2 sites of acetylenic (C≡C—) unsaturation. Examples of such alkynyl groups include, but are not limited to, acetylenyl (C≡CH), propargyl ($CH_2C≡CH$), 1-propynyl, 1-butynyl, and 1-pentynyl.

The term “amino-alkyl” refers to a group formed by combining an alkyl and an amino group. Examples include —$NHCH_3$, —$NHCH_2CH_3$—$NHCH(CH_3)_2$, —$N(CH_3)_2$, —$NCH_3(CH_2CH_3)$—$NCH_3(CH(CH_3)_2)$ and similar groups, but are not restricted to these.

The term “aryl” refers to a monocyclic or polycyclic group having at least one hydrocarbon aromatic ring, wherein all of the ring atoms of the at least one hydrocarbon aromatic ring are carbon. Aryl may include groups with a single aromatic ring (e.g., phenyl) and multiple fused aromatic rings (e.g., naphthyl, anthryl). Aryl may further include groups with one or more aromatic hydrocarbon rings fused to one or more non-aromatic hydrocarbon rings (e.g., fluorenyl; 2,3-dihydro-1H-indene; 1,2,3,4-tetrahydronaphthalene). In certain embodiments, aryl includes groups with an aromatic hydrocarbon ring fused to a non-aromatic ring, wherein the non-aromatic ring comprises at least one ring heteroatom independently selected from the group consisting of N, O, and S. For example, in some embodiments, aryl includes groups with a phenyl ring fused to a non-aromatic ring, wherein the non-aromatic ring comprises at least one ring heteroatom independently selected from the group consisting of N, O, and S (e.g., chromane; thiochromane; 2,3-dihydrobenzofuran; indoline). In some embodiments, aryl as used herein has from 6 to 14 carbon atoms (($C_6$-$C_{14}$) aryl), or 6 to 10 carbon atoms (($C_6$-$C_{10}$)aryl). Where the aryl includes fused rings, the aryl may connect to one or more substituents or moieties of the formulae described herein through any atom of the fused ring for which valency permits.

The term “cycloalkyl” refers to a monocyclic or polycyclic saturated hydrocarbon. In some embodiments, cycloalkyl has 3 to 20 carbon atoms (($C_3$-$C_{20}$)cycloalkyl), 3 to 8 carbon atoms (($C_3$-$C_8$)cycloalkyl), 3 to 6 carbon atoms (($C_3$-$C_6$)cycloalkyl), or 3 to 5 carbon atoms (($C_3$-$C_5$)cycloalkyl). In some embodiments, cycloalkyl has 3 to 8 carbon atoms having single or multiple cyclic rings including fused, bridged, and spiro ring systems. Examples of suitable cycloalkyl groups include, but are not limited to, adamantyl, cyclopropyl, cyclobutyl, cyclopentyl, cyclooctyl, octahydropentalenyl, octahydro-1H-indene, decahydronaphthalene, cubane, bicyclo[3.1.0]hexane, and bicyclo[1.1.1]pentane, and the like.

The term “carbocycle” refers to a saturated, unsaturated or aromatic ring system in which each atom of the ring system is carbon. Carbocycle includes 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In an exemplary embodiment, an aromatic ring, e.g., phenyl, may be fused to a saturated or unsaturated ring, e.g., cyclohexane, cyclopentane, or cyclohexene. A bicyclic carbocycle includes any combination of saturated, unsaturated and aromatic bicyclic rings, as valence permits. A bicyclic carbocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. Exemplary carbocycles include cyclopentyl, cyclohexyl, cyclohexenyl, adamantyl, phenyl, indanyl, and naphthyl.

The term “haloalkyl” refers to a mono haloalkyl or a polyhaloalkyl group that can be further substituted or unsubstituted. The terms halogen and alkyl are as stated herein.

The term “heterocycle” refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. A bicyclic heterocycle includes any combination of saturated, unsaturated and aromatic bicyclic rings, as valence permits. In an exemplary embodiment, an aromatic ring, e.g., pyridyl, may be fused to a saturated or unsaturated ring, e.g., cyclohexane, cyclopentane, morpholine, piperidine or cyclohexene. A bicyclic heterocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems.

The term “heteroaryl” refers to a monocyclic or bicyclic or higher aromatic group that could be substituted or unsubstituted containing at least one heteroatom (e.g., a heteroatom selected from B, N, O, S, P(═O), Si, and P. In some embodiments, the term refers to an aromatic group of from 4 to 10 carbon atoms and 1 to 4 heteroatoms selected from the group consisting of oxygen, nitrogen and sulfur within the ring. Such heteroaryl groups can have a single ring (i.e., pyridinyl or furyl) or multiple condensed rings (i.e., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N oxide (N→O), sulfinyl, or sulfonyl moieties. Examples of monocyclic heteroaryl include pyrazolyl, pyrrolyl, thiazolyl, oxazolyl, thiophenyl, furanyl, imidazolyl, isoxazolyl, triazolyl, thiadiazolyl, tetrazolyl, oxadiazolyl, pyridinyl, pyridazinyl, pyrimidinyl, pyrazinyl, thiazolyl, and similar groups, but are not limited to the aforementioned. Examples of bicyclic heteroaryl include indolyl, benzothiophenyl, benzofuranyl, benzimidazolyl, benzoxazolyl, benzisoxazolyl, benzothiazoleil, benzothiadiazole, benzotriazolyl, quinolinyl, isoquinolinyl, purinyl, furopyridinyl, oxocromen, dioxoisoindolin, pyrazolopyridinyl, pyrazolo [1,5-a]pyridinyl, and similar groups, but are not restricted to the aforementioned. Preferred heteroaryls include 5 or 6 membered heteroaryls such as pyridinyl, pyrrolyl, indolyl, thiophenyl, and furanyl.

The term “heterocycloalkyl” refers to substituted or unsubstituted monocyclic alkyl containing one or more hetero atoms selected from B, N, O, S, P(═O), Si and P. Examples include piperidinyl, piperazinyl, morpholinyl, pyrrolidinyl, thiomorpholinyl, imidazolidinyl, tetrahydrofurfuryl, and similar groups, but are not restricted to the aforementioned.

The term “heteroalkyl” refers to an alkyl substituent in which one or more of the carbon atoms and any attached hydrogen atoms are independently replaced with the same or different heteroatomic group. For example, 1, 2, or 3 carbon atoms may be independently replaced with the same or different heteroatomic substituent.

The term “substituted” refers to moieties having substituents replacing a hydrogen on one or more carbons or substitutable heteroatoms, e.g., NH or $NH_2$, of a compound.

It will be understood that "substitution" or "substituted with" includes the implicit proviso that such substitution is in accordance with permitted valence of the substituted atom and the substituent, and that the substitution results in a stable compound. For example, stable compounds include, but is not limited to, compounds which do not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. The term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

It will be understood by those skilled in the art that substituents can themselves be substituted, if appropriate. Unless specifically stated as "unsubstituted," references to chemical moieties herein are understood to include substituted variants and unsubstituted variants. For example, reference to a "heteroaryl" group or moiety implicitly includes both substituted and unsubstituted variants, unless specified otherwise.

When referring to compound features, the phrase "optionally substituted" may be used interchangeably with the phrase "unsubstituted or substituted" and refers to when a non-hydrogen substituent may or may not be present on a given atom or group, and, thus, the description includes structures where a non-hydrogen substituent is present and structures where a non-hydrogen substituent is not present. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible and/or inherently unstable.

It will also be understood by those skilled in the art that when "optionally substituted" is used, any part of the following term can be substituted.

The terms "linker", "linkage" and "linking group" are used interchangeably and refer to a linking moiety that covalently connects two or more substituents. A linking moiety may connect two groups where the linker may be linear, branched, cyclic or a single atom. In some embodiments, the linker is divalent. In some embodiments, the linker is a branched linker. In some embodiments, the two or more substituents that are covalently connected by the linking moiety are optionally substituted alkyl or alkoxy groups. In some embodiments, the linkers are selected from $—CO_2—$, —O—, —OCO—, —CONH—, —NHCO—, and —NH—.

In some embodiments, substituents may include any substituents described herein, for example: halogen, hydroxy, oxo (=O), thioxo (=S), cyano (—CN), nitro ($—NO_2$), imino (=N—H), oximo (=N—OH), hydrazino ($=N—NH_2$), $—R^b—OR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^bN(R^a)S(O)_tR^a$ (where t is 1 or 2), $—R^b—S(O)_tR^a$ (where t is 1 or 2), $—R^b—S(O)_tOR^a$ (where t is 1 or 2), and $—R^b—S(O)_tN(R^a)_2$ (where t is 1 or 2). In another exemplary embodiment, substituents include alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl, any of which may be optionally substituted by alkyl, alkenyl, alkynyl, halogen, haloalkyl, haloalkenyl, haloalkynyl, oxo, thioxo, cyano, nitro, imino, oximo, hydrazine, $—R^bOR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)_tR^a$ (where t is 1 or 2), $—R^b—S(O)_tR^a$ (where t is 1 or 2), $—R^b—S(O)OR^a$ (where t is 1 or 2) and $—R^b—S(O)_tN(R^a)_2$ (where t is 1 or 2); and wherein each $R^a$, $R^b$, and $R^c$ are independently selected from hydrogen, alkyl, cycloalkyl, cycloalkylalkyl, aryl, aralkyl, heterocycloalkyl, heterocycloalkylalkyl, heteroaryl, and heteroarylalkyl; and wherein each $R^a$, $R^b$, and $R^c$, valence permitting, may be optionally substituted with alkyl, alkenyl, alkynyl, halogen, haloalkyl, haloalkenyl, haloalkynyl, oxo, thioxo, cyano, nitro, imino, oximo, hydrazine, $—R^bOR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)_tR^a$ (where t is 1 or 2), $—R^b—S(O)_tR^a$ (where t is 1 or 2), $—R^b—S(O)OR^a$ (where t is 1 or 2) and $—R^b—S(O)_tN(R^a)_2$ (where t is 1 or 2).

The term "isomers" or "three-dimensional isomers" refers to two or more compounds comprising the same numbers and types of atoms, groups or components, but with different structural arrangement and connectivity of the atoms. The term can refer to compounds that are identical in terms of chemical equation or molecular equation but are different optically or three-dimensionally, or their salts, and specifically could be partially three-dimensional isomers, enantiomers, geometrical isomers, or shape isomers.

The term "tautomer" refers to one of two or more structural isomers which readily convert from one isomeric form to another and which exist in equilibrium.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposeable mirror images of one another.

Individual enantiomers and diastereomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns, or (4) kinetic resolution using stereoselective chemical or enzymatic reagents. Racemic mixtures also can be resolved into their respective enantiomers by well-known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. See, for example, Carreira and Kvaerno, Classics in Stereoselective Synthesis, Wiley-VCH: Weinheim, 2009.

The symbol=denotes a bond that may be a single, double or triple bond as described herein. Substituents around a carbon-carbon double bond are designated as being in the "Z" or "E" configuration, where the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituent on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compound wherein the substituents are disposed on both the same and opposite sides of the plane of the ring are designated "cis/trans."

Singular articles such as "a," "an" and "the" and similar referents in the context of describing the elements are to be construed to cover both the singular and the plural, unless otherwise indicated herein or clearly contradicted by context. Recitation of ranges of values herein are merely intended to serve as a shorthand method of referring individually to each separate value falling within the range, including the upper and lower bounds of the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (i.e., "such as") provided herein, is intended merely to better illuminate the embodiments and does not pose a limitation on the scope of the claims unless otherwise stated.

In some embodiments, where the use of the term "about" is before a quantitative value, the present disclosure also includes the specific quantitative value itself, unless specifically stated otherwise. As used herein, the term "about" refers to a ±10% variation from the nominal value unless otherwise indicated or inferred. Where a percentage is provided with respect to an amount of a component or material in a composition, the percentage should be understood to be a percentage based on weight, unless otherwise stated or understood from the context.

Where a molecular weight is provided and not an absolute value, for example, of a polymer, then the molecular weight should be understood to be an average molecule weight, unless otherwise stated or understood from the context.

It should be understood that the order of steps or order for performing certain actions is immaterial so long as the present disclosure remain operable. Moreover, two or more steps or actions can be conducted simultaneously.

A dash ("-") symbol that is not between two letters or symbols refers to a point of bonding or attachment for a substituent. For example, —$NH_2$ is attached through the nitrogen atom.

The term "pharmaceutically acceptable salt" refers to a salt which is acceptable for administration to a subject. It is understood that such salts, with counter ions, will have acceptable mammalian safety for a given dosage regime. Such salts can also be derived from pharmaceutically acceptable inorganic or organic bases and from pharmaceutically acceptable inorganic or organic acids, and may comprise organic and inorganic counter ions. The neutral forms of the compounds described herein may be converted to the corresponding salt forms by contacting the compound with a base or acid and isolating the resulting salts.

The terms "pharmaceutically acceptable excipient," "pharmaceutically acceptable diluent," "pharmaceutically acceptable carrier," and "pharmaceutically acceptable adjuvant" are used interchangeably and refer to an excipient, diluent, carrier, or adjuvant that is useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. The phrase "pharmaceutically acceptable excipient" includes both one and more than one such excipient, diluent, carrier, and/or adjuvant.

The term "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (i.e., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intratracheal, intramuscular, subcutaneous, and the like.

EXEMPLARY EMBODIMENTS

As described herein, the text refers to various embodiments of the present compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present technology.

Notwithstanding the appended claims, aspects of the present disclosure are illustrated by the following clauses.

Clause 1. A compound of formula (Ia) or (Ib):

(Ia)

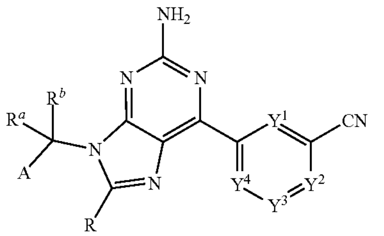

(Ib)

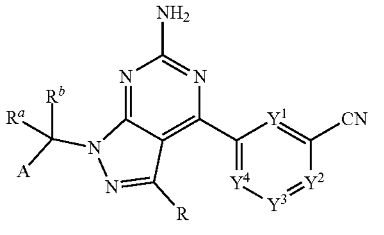

wherein:

R is H, $(C_1-C_3)$alkyl, or substituted $(C_1-C_3)$alkyl;

$Y^1$ to $Y^4$ are independently selected from $CR^{10}$ and N, wherein at least two of $Y^1$ to $Y^4$ are independently $CR^{10}$;

each $R^{10}$ is independently selected from H, $(C_1-C_8)$alkyl, substituted $(C_1-C_8)$alkyl, $(C_2-C_8)$alkenyl, substituted $(C_2-C_8)$alkenyl, $(C_2-C_8)$alkynyl, substituted $(C_2-C_8)$ alkynyl, $(C_1-C_3)$haloalkyl, $(C_1-C_8)$alkoxy, substituted $(C_1-C_8)$alkoxy, $—CONH_2$, substituted amido, $—NH_2$, substituted amino, $—CO_2H$, cyano, halogen, hydroxyl, $—NO_2$, $—SO_3H$, $—SO_2NH_2$, substituted sulfonamide, and thiol;

$R^a$ and $R^b$ are each independently selected from H, F, $(C_1-C_3)$alkyl, and substituted $(C_1-C_3)$alkyl, or $R^a$ and $R^b$ are cyclically linked and together with the carbon atom to which they are attached form a cyclopropyl or substituted cyclopropyl; and A is phenyl, substituted phenyl, pyridyl or substituted pyridyl;

or a solvate, a hydrate, a prodrug, and/or a stereoisomer thereof, or a pharmaceutically acceptable salt thereof.

Clause 2. The compound of clause 1, wherein A is phenyl or phenyl substituted with one, two or three $R^{20}$ groups, each $R^{20}$ is independently selected from $(C_1-C_8)$alkyl, substituted $(C_1-C_8)$alkyl, $(C_2-C_8)$alkenyl, substituted $(C_2-C_8)$alkenyl, $(C_2-C_8)$alkynyl, substituted $(C_2-C_8)$ alkynyl, $(C_1-C_3)$haloalkyl, $(C_1-C_8)$alkoxy, substituted $(C_1-C_8)$alkoxy, $—CONH_2$, substituted amido, $—NH_2$, substituted amino, $—CO_2H$, cyano, halogen, hydroxyl, $—NO_2$, $—SO_3H$, $—SO_2NH_2$, substituted sulfonamide, and thiol.

Clause 3. The compound of clause 1, wherein A is pyridyl or pyridyl substituted with one, two or three $R^{20}$ groups, each $R^{20}$ is independently selected from $(C_1-C_8)$alkyl, substituted $(C_1-C_8)$alkyl, $(C_2-C_8)$alkenyl, substituted $(C_2-C_8)$alkenyl, $(C_2-C_8)$alkynyl, substituted $(C_2-C_8)$alkynyl, $(C_1-C_3)$haloalkyl, $(C_1-C_8)$alkoxy, substituted $(C_1-C_8)$alkoxy, $—CONH_2$, substituted amido, $—NH_2$, substituted amino, $—CO_2H$, cyano, halogen, hydroxyl, $—NO_2$, $—SO_3H$, $—SO_2NH_2$, substituted sulfonamide, and thiol.

Clause 4. The compound of any one of clauses 1-3, wherein R is H.

Clause 5. The compound of any one of clauses 1-4, wherein $R^a$ and $R^b$ are each H.

Clause 6. The compound of clause 2, wherein the compound is of formula (IIa) or (IIb):

(IIa)

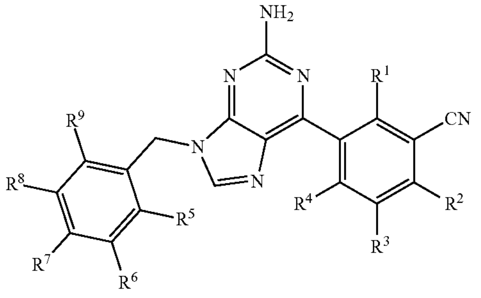

-continued (IIb)

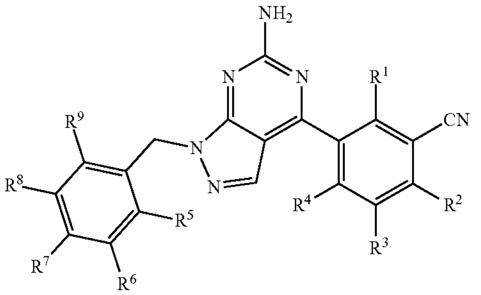

wherein:

$R^1$ to $R^9$ are independently selected from H, $(C_1-C_8)$alkyl, substituted $(C_1-C_8)$alkyl, $(C_2-C_8)$alkenyl, substituted $(C_2-C_8)$alkenyl, $(C_2-C_8)$alkynyl, substituted $(C_2-C_8)$ alkynyl, $(C_1-C_3)$haloalkyl, $(C_1-C_8)$alkoxy, substituted $(C_1-C_8)$alkoxy, $—CONH_2$, substituted amido, $—NH_2$, substituted amino, $—CO_2H$, cyano, halogen, hydroxyl, $—NO_2$, $—SO_3H$, $—SO_2NH_2$, substituted sulfonamide, and thiol.

Clause 7. The compound of clause 6, wherein $R^1$ to $R^9$ are independently selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, $—NH_2$, substituted amino, halogen, and hydroxyl.

Clause 8. The compound of clause 7, wherein $R^1$ to $R^9$ are independently selected from H, $—NH_2$, F, $CH_3$, and $CF_3$.

Clause 9. The compound of clause 6, wherein the compound is of formula (IIIa) or (IIIb):

(IIIa)

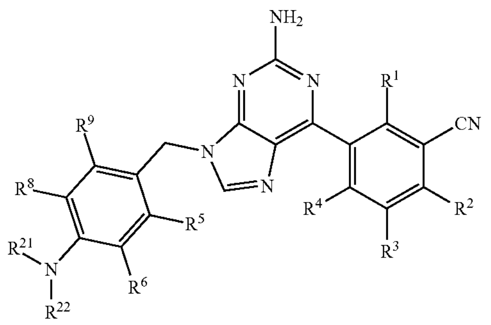

(IIIb)

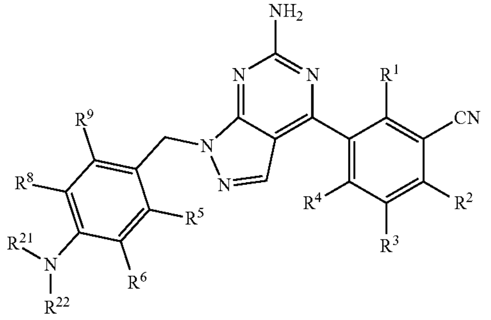

wherein:

$R^{21}$ and $R^{22}$ are independently selected from H, $(C_1-C_8)$alkyl, substituted $(C_1-C_8)$alkyl, $SO_2R^{30}$, and $COR^{30}$, wherein $R^{30}$ is $(C_1-C_8)$alkyl, or substituted $(C_1-C_8)$alkyl.

Clause 10. The compound of clause 9, wherein $R^{21}$ and $R^{22}$ are each H.

Clause 11. The compound of clause 9 or 10, wherein $R^5$, $R^6$, $R^8$ and $R^9$ are independently selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl.

Clause 12. The compound of clause 11, wherein $R^5$, $R^6$, $R^8$ and $R^9$ are independently selected from H, F, $CH_3$, and $CF_3$.

Clause 13. The compound of clause 12, wherein $R^5$, $R^6$, $R^8$ and $R^9$ are each H.

Clause 14. The compound of any one of clauses 9 to 13, wherein: $R^2$ to $R^4$ are each H; and $R^1$ is selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl.

Clause 15. The compound of clause 14, wherein $R^1$ is selected from H, F, $CH_3$, and $CF_3$.

Clause 16. The compound of clause 15, wherein the compound is selected from:

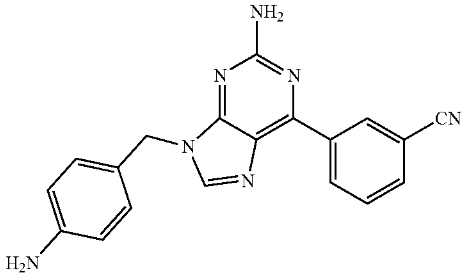

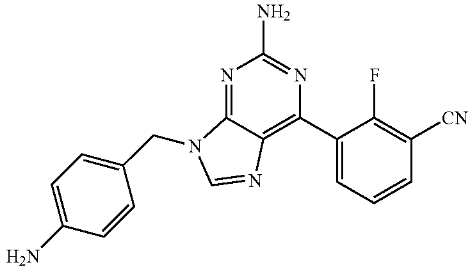

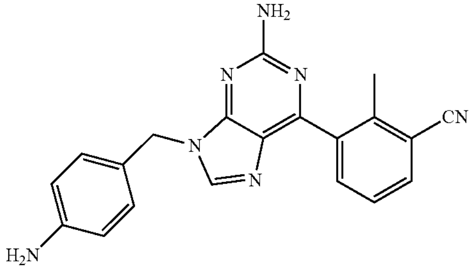

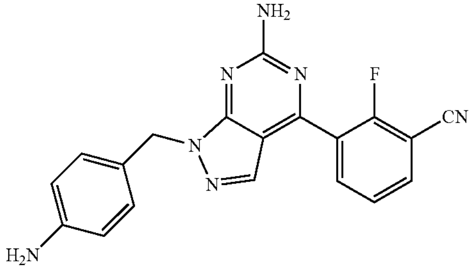

-continued

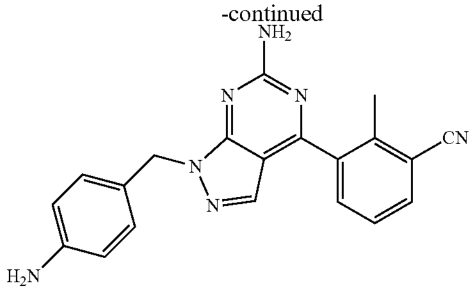

and

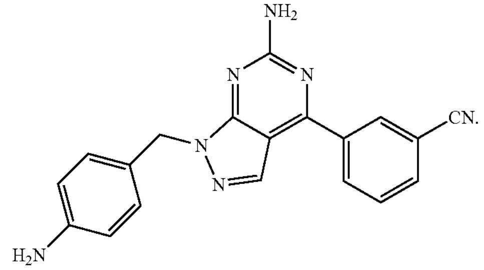

Clause 17. The compound of clause 9, wherein the compound is of formula (IVa) or (IVb):

(IVa)

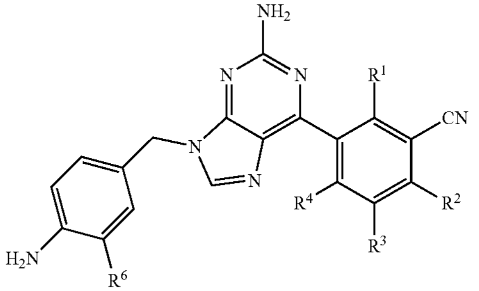

(IVb)

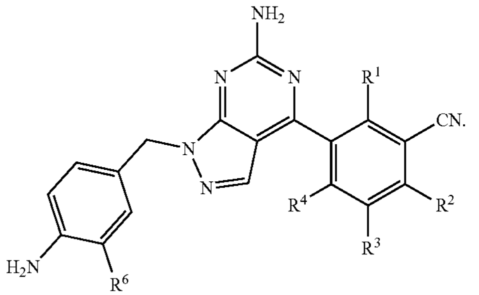

Clause 18. The compound of clause 17, wherein $R^6$ is selected from $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl.

Clause 19. The compound of clause 18, wherein $R^6$ is selected from $(C_1-C_5)$alkyl, substituted $(C_1-C_5)$alkyl, and $(C_1-C_3)$haloalkyl.

Clause 20. The compound of clause 19, wherein $R^6$ is $CH_3$ or $CF_3$.

Clause 21. The compound of any one of clauses 17 to 20, wherein: $R^2$ to $R^4$ are each H; and $R^1$ is selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl.

Clause 22. The compound of clause 21, wherein $R^1$ is selected from H, F, $CH_3$, and $CF_3$.

Clause 23. The compound of any one of clauses 17 to 22, wherein the compound is selected from:
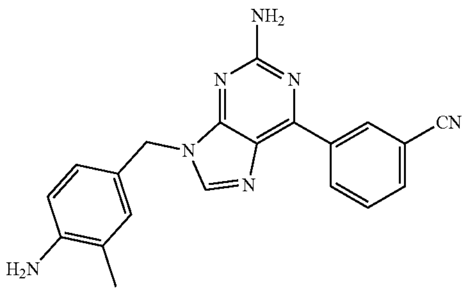
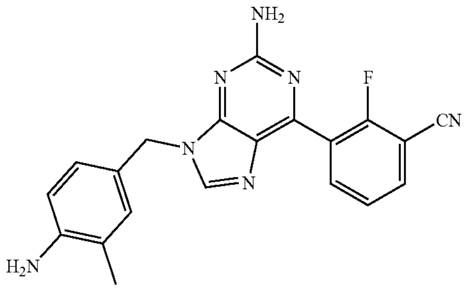
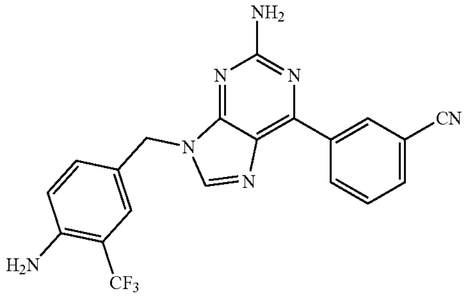
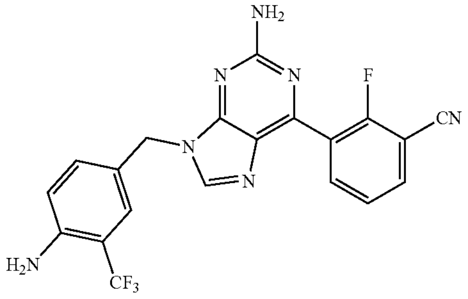
-continued
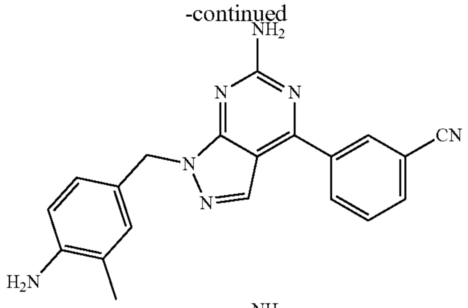
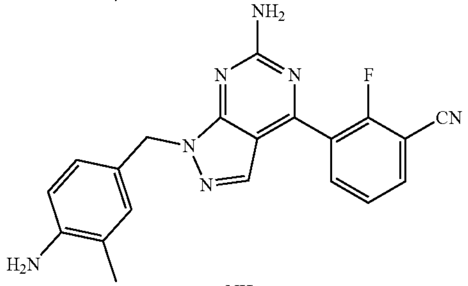
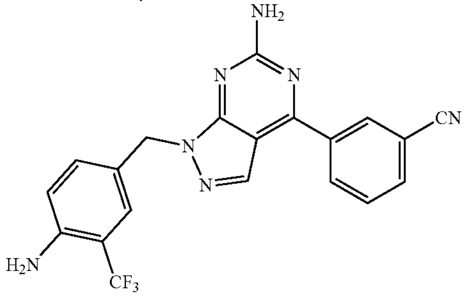
and
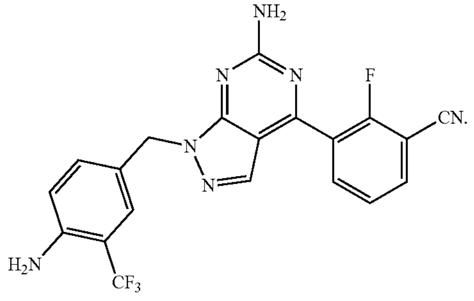
Clause 24. The compound of clause 9, wherein the compound is of formula (Va) or (Vb):
(Va)
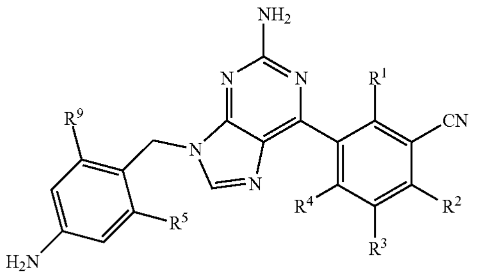

-continued (Vb)

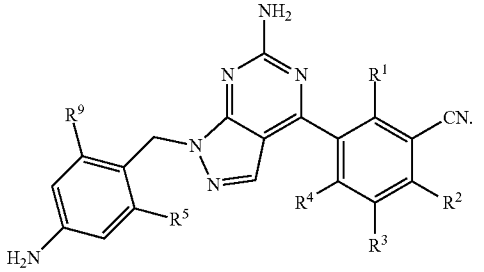

Clause 25. The compound of clause 24, wherein $R^5$ and $R^9$ are independently selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl.

Clause 26. The compound of clause 25, wherein $R^5$ and $R^9$ are independently selected from H and halogen.

Clause 27. The compound of clause 26, wherein $R^5$ is F.

Clause 28. The compound of clause 26 or 27, wherein $R^9$ is F.

Clause 29. The compound of clause 26, wherein the compound is selected from:

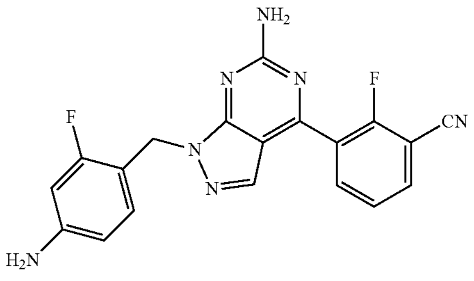

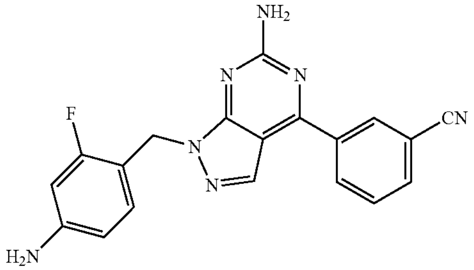

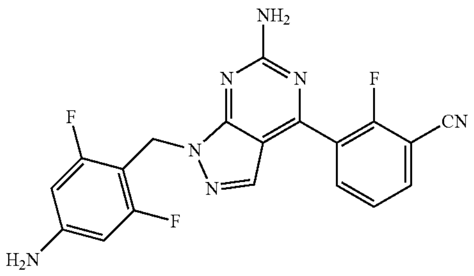

-continued

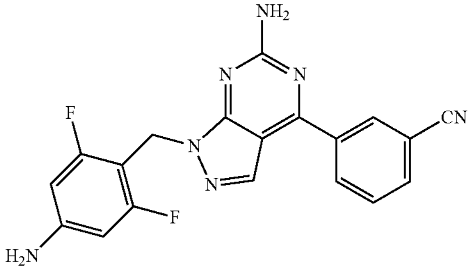

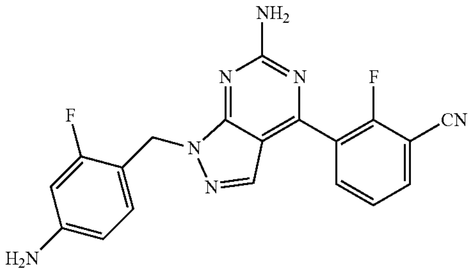

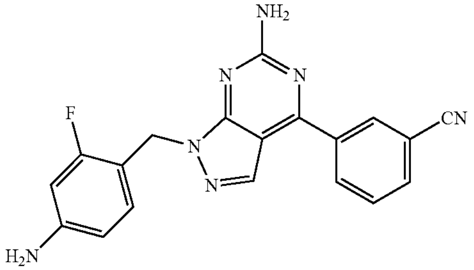

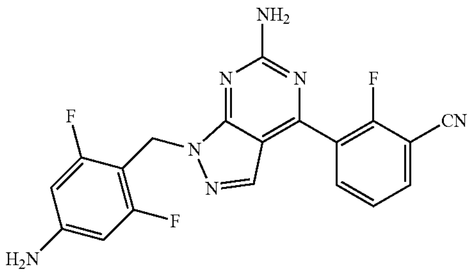

and

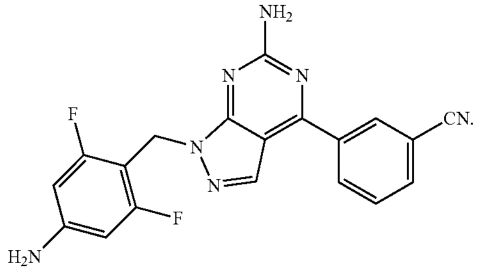

Clause 30. The compound of clause 6, wherein the compound is of formula (VIa) or (VIb):

(VIa)

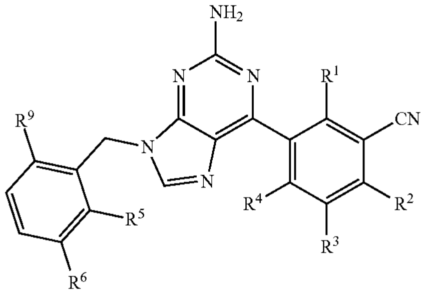

(VIb)

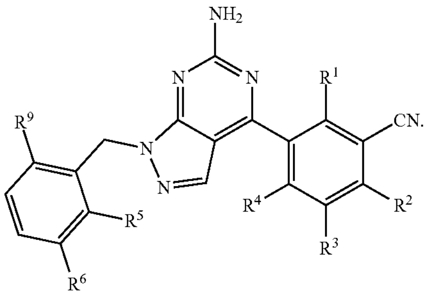

Clause 31. The compound of clause 30, wherein $R^5$, $R^6$ and $R^9$ are independently selected from H, $(C_1\text{-}C_5)$ alkyl, substituted $(C_1\text{-}C_5)$alkyl, $(C_1\text{-}C_3)$haloalkyl, $(C_1\text{-}C_5)$alkoxy, substituted $(C_1\text{-}C_5)$alkoxy, —$NH_2$, substituted amino, halogen, and hydroxyl.

Clause 32. The compound of clause 30 or 31, wherein $R^6$ is selected from H, $(C_1\text{-}C_5)$alkyl, substituted $(C_1\text{-}C_5)$ alkyl, and $(C_1\text{-}C_3)$haloalkyl.

Clause 33. The compound of clause 32, wherein $R^6$ is $CH_3$ or $CF_3$.

Clause 34. The compound of clause 32, wherein $R^6$ is H.

Clause 35. The compound of any one of clauses 30 to 34, wherein $R^5$ and $R^9$ are independently selected from H and halogen.

Clause 36. The compound of clause 35, wherein $R^5$ is F.

Clause 37. The compound of clause 35 or 36, wherein $R^9$ is F.

Clause 38. The compound of clause 35, wherein the compound is selected from:

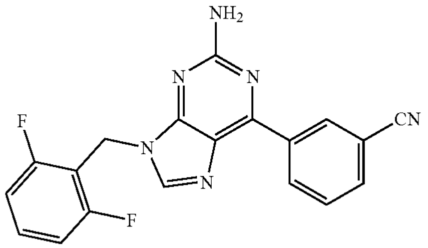

-continued

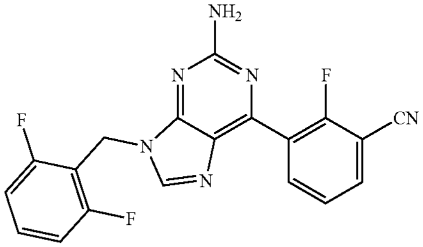

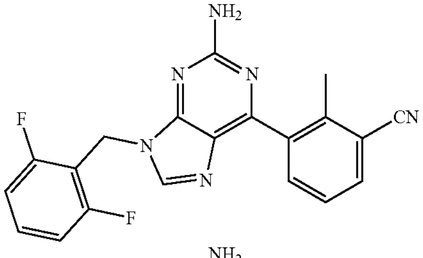

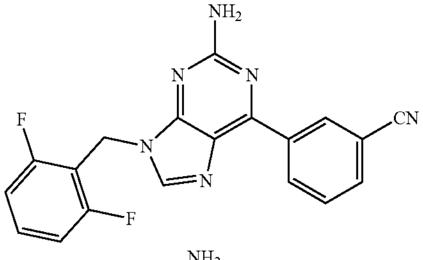

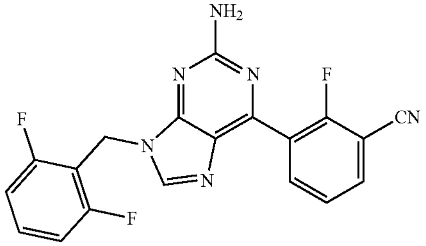

and

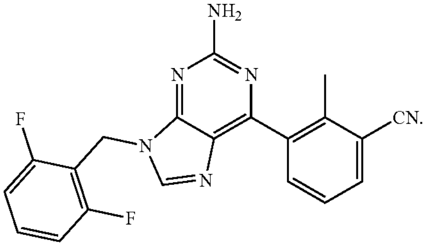

Clause 39. The compound of any one of clauses 1-38, wherein each $R^{10}$ or $R^1$ to $R^4$ are independently selected from H, $(C_1\text{-}C_5)$alkyl, substituted $(C_1\text{-}C_5)$alkyl, $(C_1\text{—}C_3)$haloalkyl, $(C_1\text{-}C_5)$alkoxy, substituted $(C_1\text{-}C_5)$ alkoxy, —$NH_2$, substituted amino, halogen, and hydroxyl.

Clause 40. The compound of clause 39, wherein each $R^{10}$ or $R^1$ to $R^4$ are independently selected from H, $(C_1\text{-}C_5)$alkyl, substituted $(C_1\text{-}C_5)$alkyl, $(C_1\text{-}C_3)$haloalkyl and halogen.

Clause 41. The compound of any one of clauses 6-40, wherein $R^1$ is H.

Clause 42. The compound of any one of clauses 6-40, wherein $R^1$ is selected from $(C_1\text{-}C_5)$alkyl, substituted $(C_1\text{-}C_5)$alkyl, $(C_1\text{-}C_3)$haloalkyl and halogen.

Clause 43. The compound of clause 42, wherein $R^1$ is F, $CH_3$ or $CF_3$.

Clause 44. The compound of any one of clauses 6-43, wherein $R^2$ to $R^4$ are each H.

Clause 45. The compound of clause 1 or 2, wherein the compound is of formula (VIIa) or (VIIb):

(VIIa)

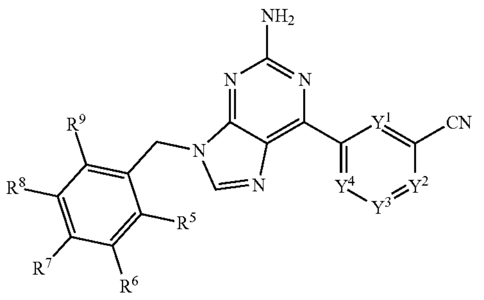

(VIIb)

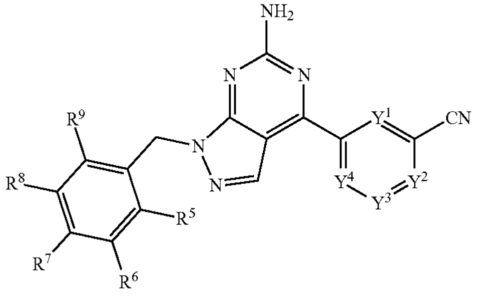

wherein:

$R^5$ to $R^9$ and each $R^{10}$ are independently selected from H, $(C_1\text{-}C_8)$alkyl, substituted $(C_1\text{-}C_8)$alkyl, $(C_2\text{-}C_8)$alkenyl, substituted $(C_2\text{-}C_8)$alkenyl, $(C_2\text{-}C_8)$alkynyl, substituted $(C_2\text{-}C_8)$alkynyl, $(C_1\text{-}C_3)$haloalkyl, $(C_1\text{-}C_8)$alkoxy, substituted $(C_1\text{-}C_8)$alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol.

Clause 46. The compound of clause 45, wherein one of $Y^1$ to $Y^4$ is N.

Clause 47. The compound of clause 46, wherein $R^5$ to $R^9$ and each $R^{10}$ are independently selected from H, $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$alkoxy, —$NH_2$, substituted amino, halogen, and hydroxyl.

Clause 48. The compound of clause 47, wherein $R^5$ to $R^9$ and each $R^{10}$ are independently selected from H, —$NH_2$, F, $CH_3$, and $CF_3$.

Clause 49. The compound of clause 46, wherein the compound is of formula (VIIIa) or (VIIIb):

(VIIIa)

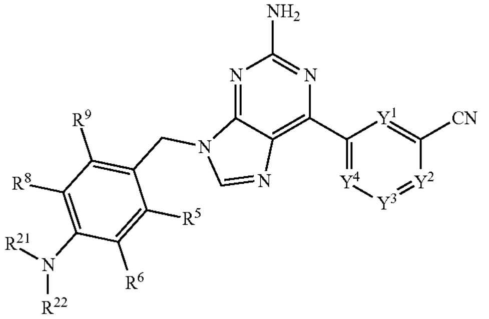

-continued (VIIIb)

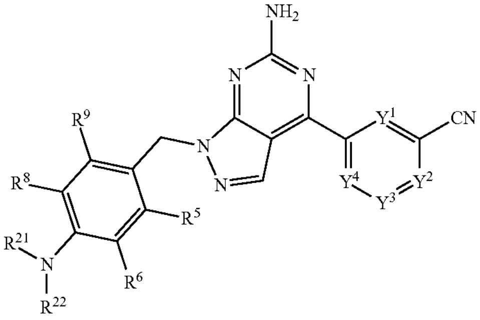

wherein:

$R^{21}$ and $R^{22}$ are independently selected from H, $(C_1\text{-}C_8)$alkyl, substituted $(C_1\text{-}C_8)$alkyl, $SO_2R^{30}$, and $COR^{30}$, wherein $R^{30}$ is $(C_1\text{-}C_8)$alkyl, or substituted $(C_1\text{-}C_8)$alkyl.

Clause 50. The compound of clause 49, wherein $R^{21}$ and $R^{22}$ are each H.

Clause 51. The compound of clause 49 or 50, wherein $R^5$, $R^6$, $R^8$ and $R^9$ are independently selected from H, $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$alkoxy, halogen, and hydroxyl.

Clause 52. The compound of clause 51, wherein $R^5$, $R^6$, $R^8$ and $R^9$ are independently selected from H, F, $CH_3$, and $CF_3$.

Clause 53. The compound of clause 52, wherein $R^5$, $R^6$, $R^8$ and $R^9$ are each H.

Clause 54. The compound of clause 53, wherein the compound is selected from:

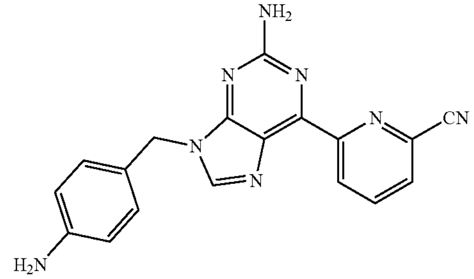

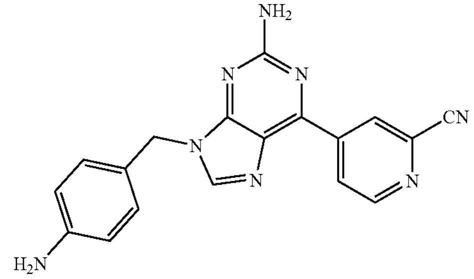

-continued

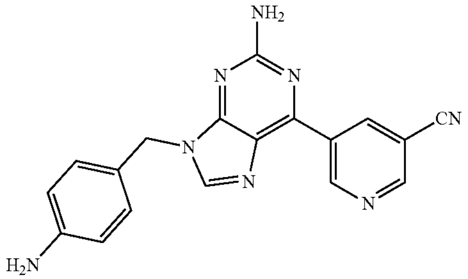

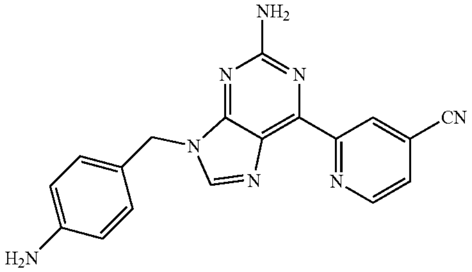

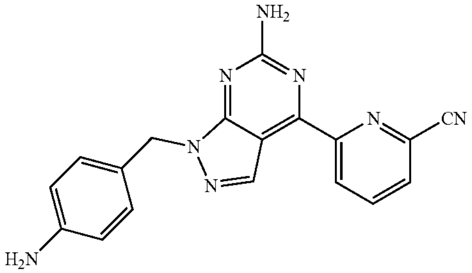

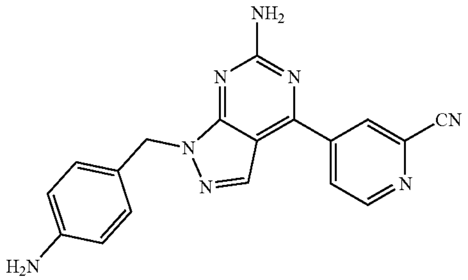

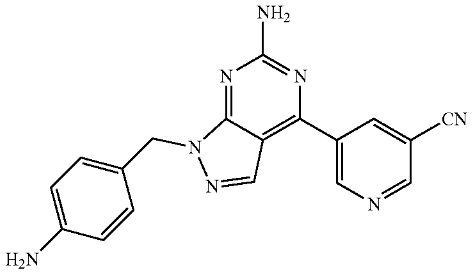

and

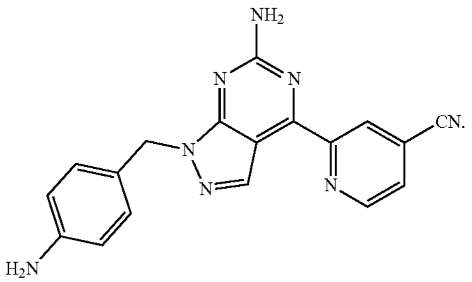

Clause 55. The compound of clause 49, wherein the compound is of formula (IXa) or (IXb):

(IXa)

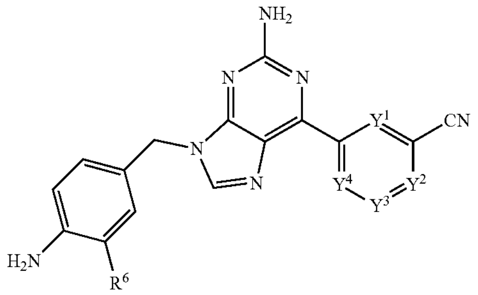

(IXb)

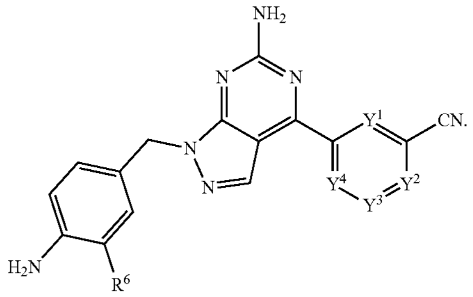

Clause 56. The compound of clause 55, wherein $R^6$ is selected from $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$ alkoxy, halogen, and hydroxyl.

Clause 57. The compound of clause 56, wherein $R^6$ is selected from $(C_1\text{-}C_5)$alkyl, substituted $(C_1\text{-}C_5)$alkyl, and $(C_1\text{-}C_3)$haloalkyl.

Clause 58. The compound of clause 57, wherein $R^6$ is $CH_3$ or $CF_3$.

Clause 59. The compound of clause 58, wherein the compound is selected from:

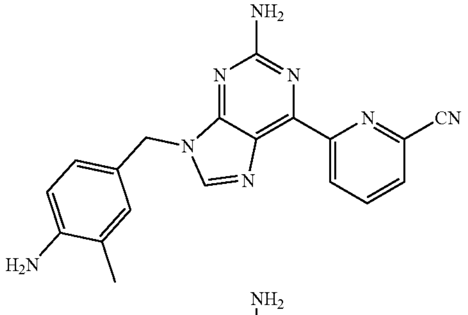

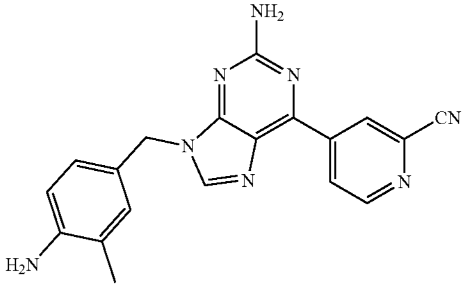

-continued
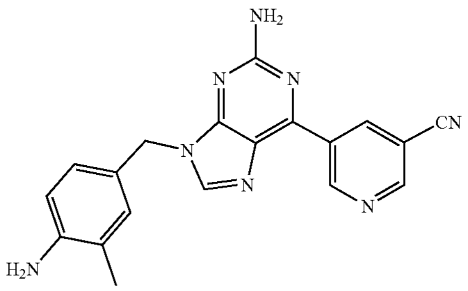
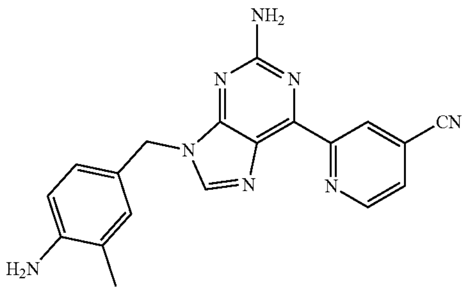
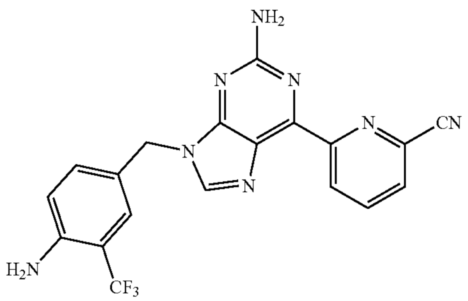
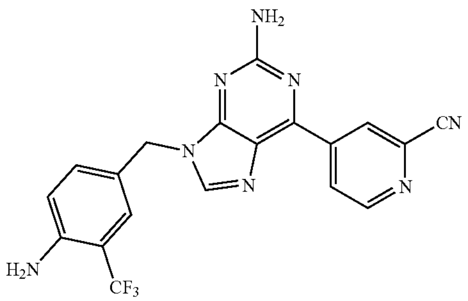
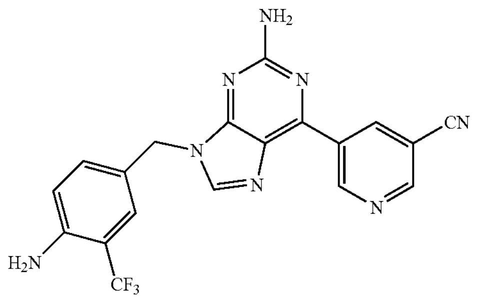
-continued
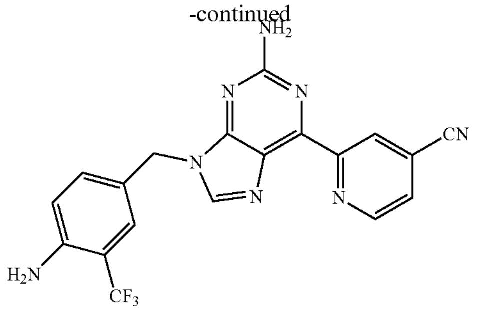
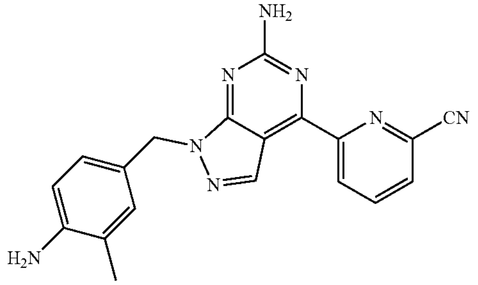
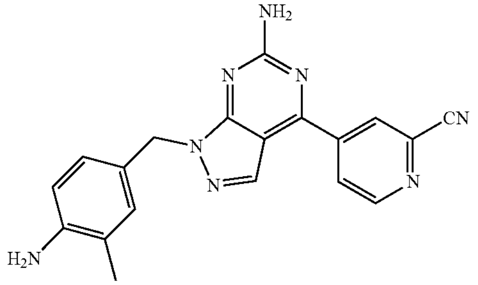
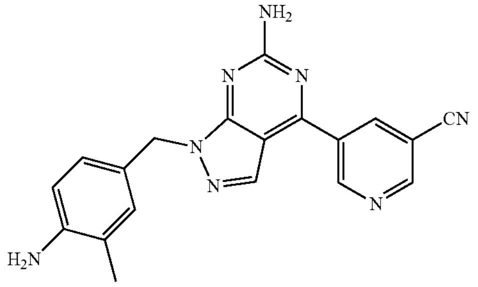
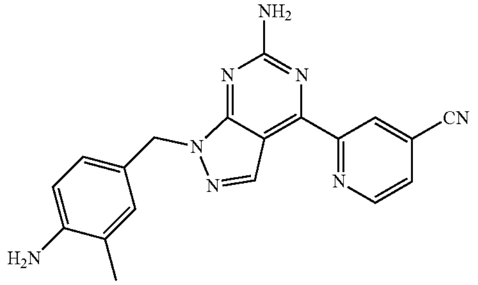
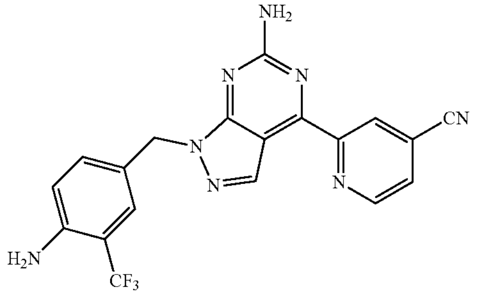

-continued

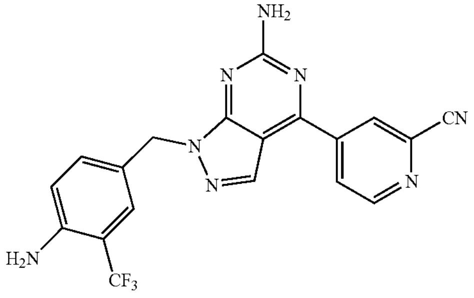

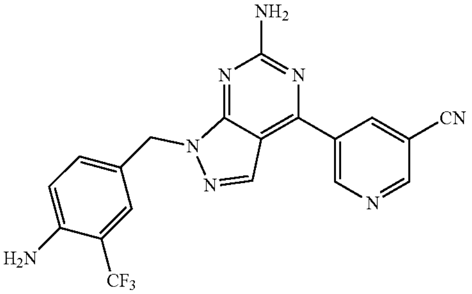

and

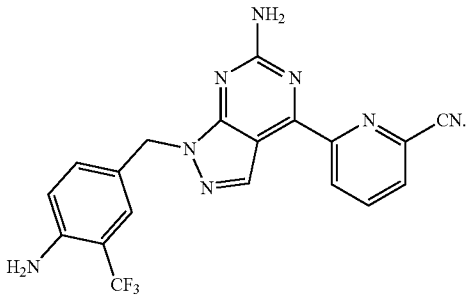

Clause 60. The compound of clause 49, wherein the compound is of formula (Xa) or (Xb):

(Xa)

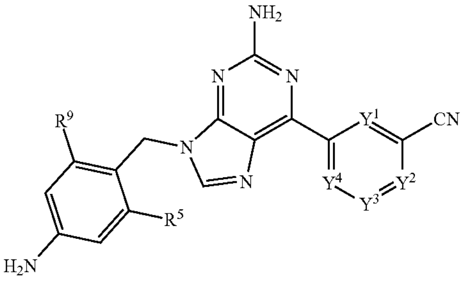

(Xb)

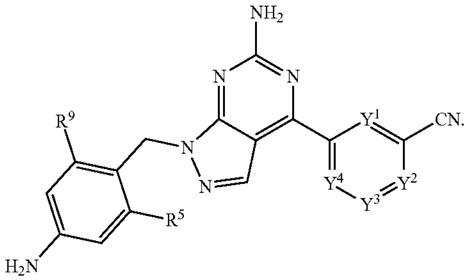

Clause 61. The compound of clause 60, wherein R and R are independently selected from H, ($C_1$-$C_5$)alkyl, substituted ($C_1$-$C_5$)alkyl, ($C_1$-$C_3$)haloalkyl, ($C_1$-$C_5$)alkoxy, substituted ($C_1$-$C_5$)alkoxy, halogen, and hydroxyl.

Clause 62. The compound of clause 61, wherein $R^5$ and $R^9$ are independently selected from H and halogen.

Clause 63. The compound of clause 62, wherein $R^5$ is F.

Clause 64. The compound of clause 62 or 63, wherein $R^9$ is F.

Clause 65. The compound of clause 62, wherein the compound is selected from:

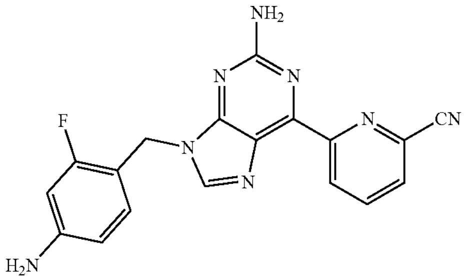

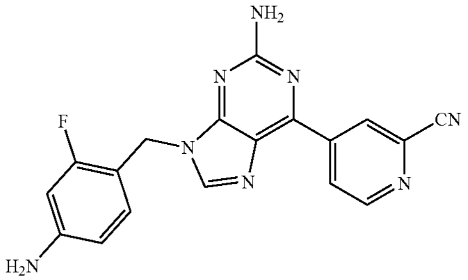

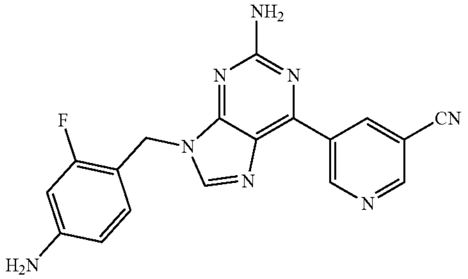

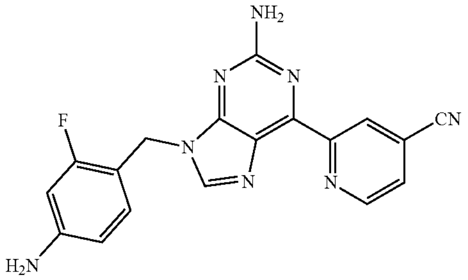

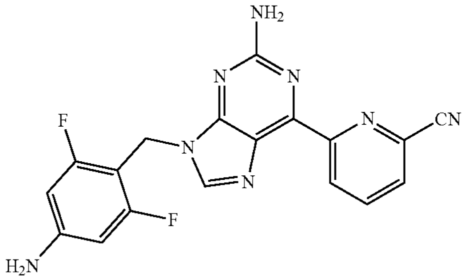

-continued
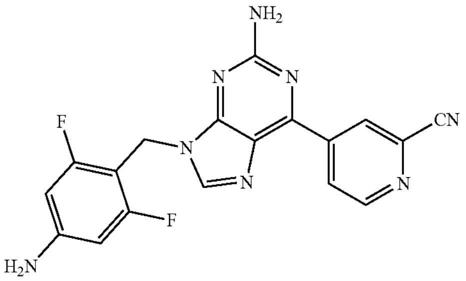
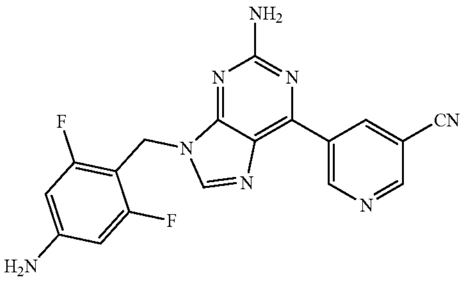
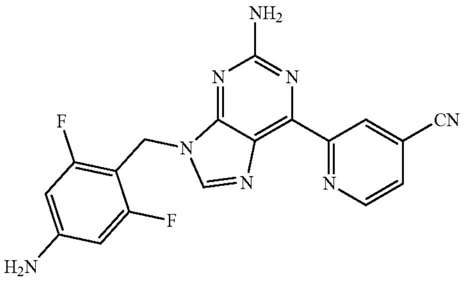
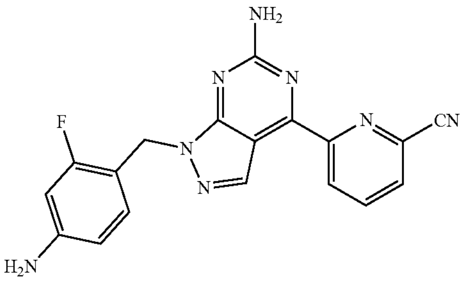
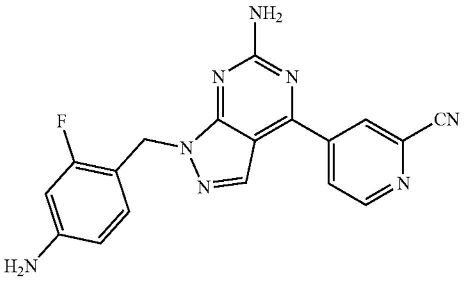
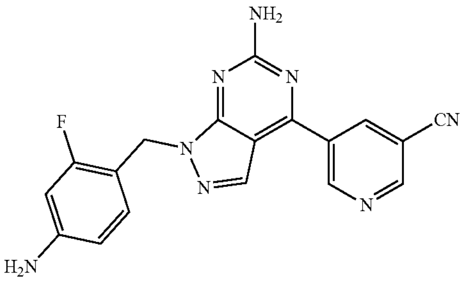
-continued
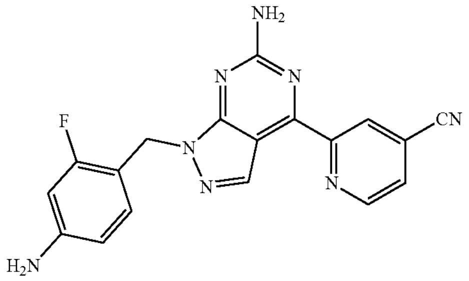
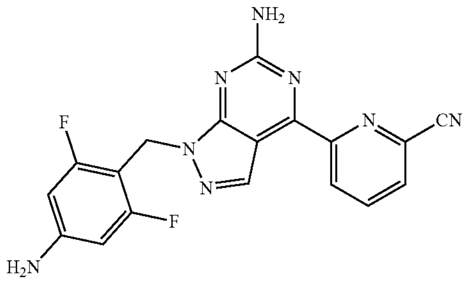
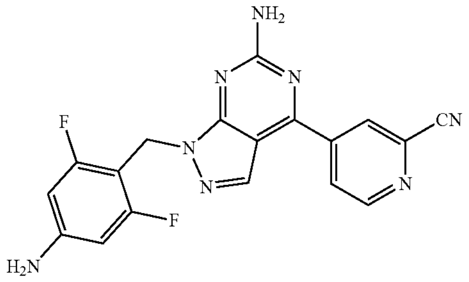
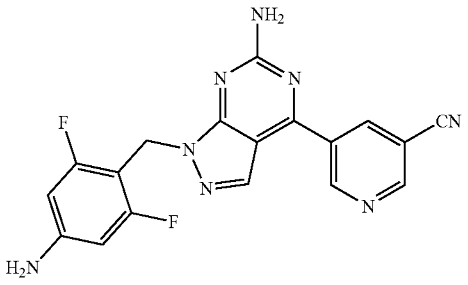
and
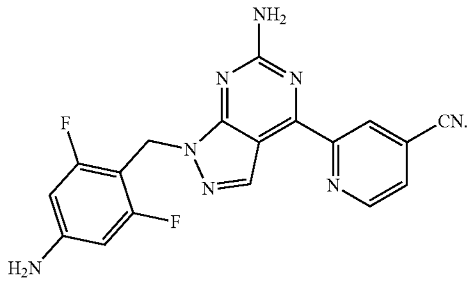

Clause 66. The compound of clause 46, wherein the compound is of formula (XIa) or (XIb):

(XIa)

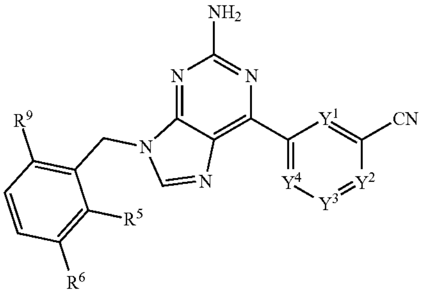

(XIb)

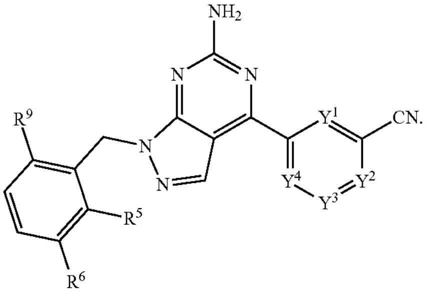

Clause 67. The compound of clause 66, wherein $R^5$, $R^6$ and $R^9$ are independently selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, —$NH_2$, substituted amino, halogen, and hydroxyl.

Clause 68. The compound of clause 66 or 67, wherein $R^6$ is selected from H, $(C_1-C_5)$alkyl, substituted $(C_1-C_5)$alkyl, and $(C_1-C_3)$haloalkyl.

Clause 69. The compound of clause 68, wherein $R^6$ is $CH_3$ or $CF_3$.

Clause 70. The compound of clause 68, wherein $R^6$ is H.

Clause 71. The compound of any one of clauses 66 to 70, wherein $R^5$ and $R^9$ are independently selected from H and halogen.

Clause 72. The compound of clause 71, wherein $R^5$ is F.

Clause 73. The compound of clause 71 or 72, wherein $R^9$ is F.

Clause 74. The compound of clause 71, wherein the compound is selected from:

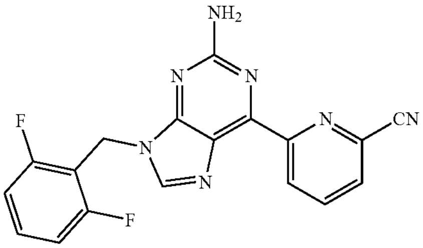

-continued

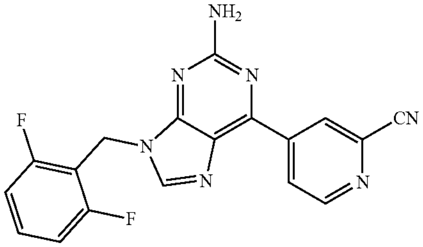

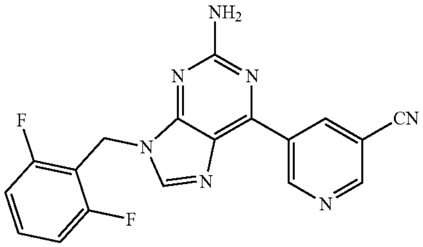

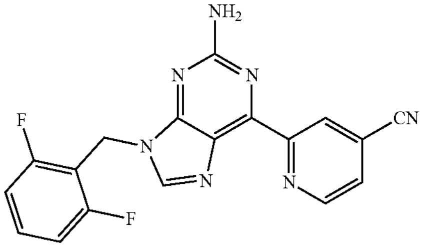

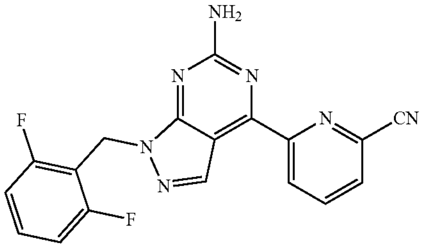

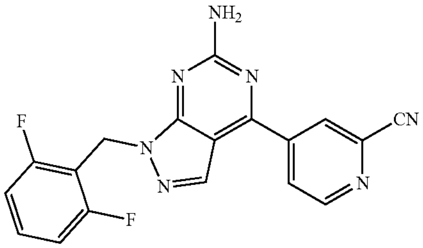

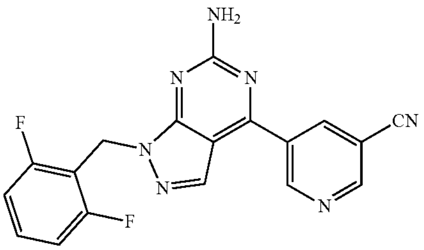

and

-continued

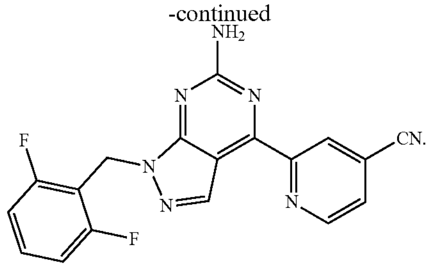

Clause 75. The compound of cause 45, wherein the compound is of formula (XIVa) or (XIVb):

(XIVa)

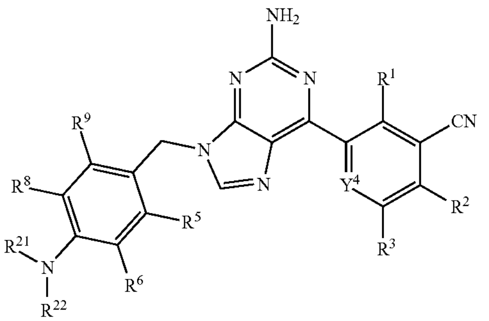

(XIVb)

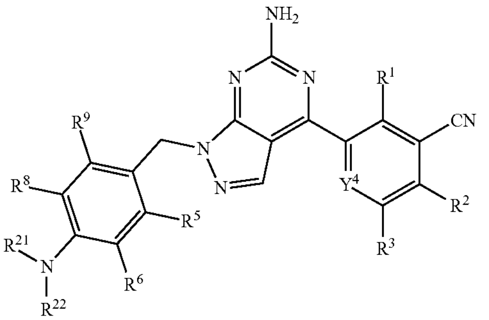

wherein:

$Y^4$ is $CR^4$ or N;

$R^1$ to $R^4$ are independently selected from H, $(C_1-C_8)$ alkyl, substituted $(C_1-C_8)$alkyl, $(C_2-C_8)$alkenyl, substituted $(C_2-C_8)$alkenyl, $(C_2-C_8)$alkynyl, substituted $(C_2-C_8)$alkynyl, $(C_1-C_3)$haloalkyl, $(C_1-C_8)$alkoxy, substituted $(C_1-C_8)$alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol; and $R^{21}$ and $R^{22}$ are independently selected from H, $(C_1-C_8)$alkyl, substituted $(C_1-C_8)$alkyl, $SO_2R^{30}$, and $COR^{31}$, wherein $R^{31}$ is $(C_1-C_8)$alkyl, and substituted $(C_1-C_8)$alkyl.

Clause 76. The compound of clause 75, wherein $R^5$, $R^6$, $R^8$ and $R^9$ are independently selected from H, $(C_1-C_5)$ alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl.

Clause 77. The compound of clause 75 or 76, wherein $R^{21}$ and $R^{22}$ are each H.

Clause 78. The compound of any one of clauses 75 to 77, wherein: $R^2$ to $R^4$ are each H; and $R^1$ is selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl.

Clause 79. The compound of clause 78, wherein $R^1$ is selected from H, F, $CH_3$, and $CF_3$.

Clause 80. The compound of clause 75, wherein the compound is of formula (XVa) or (XVb):

(XVa)

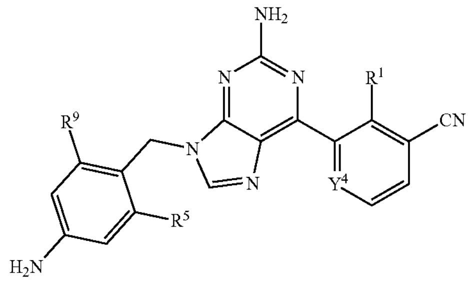

(XVb)

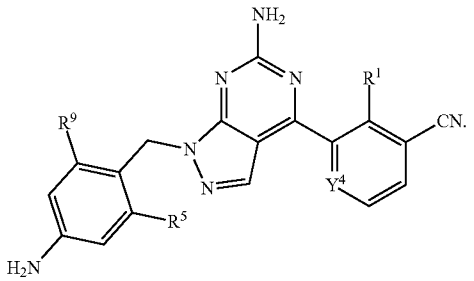

Clause 81. The compound of clause 80, wherein $R^5$ and $R^9$ are independently selected from H, $(C_1-C_5)$alkyl, substituted $(C_1-C_5)$alkyl, $(C_1-C_3)$haloalkyl, $(C_1-C_5)$ alkoxy, substituted $(C_1-C_5)$alkoxy, halogen, and hydroxyl.

Clause 82. The compound of clause 81, wherein $R^5$ and $R^9$ are independently selected from H and halogen.

Clause 83. The compound of clause 82, wherein $R^5$ is F.

Clause 84. The compound of clause 82 or 83, wherein $R^9$ is F.

Clause 85. The compound of clause 75, wherein the compound is of formula (XVIa) or (XVIb):

(XVIa)

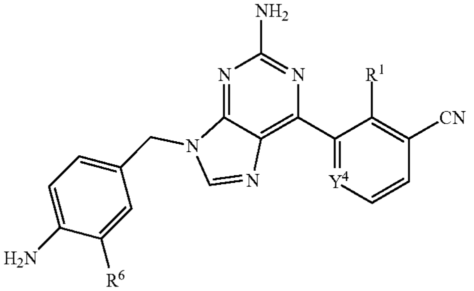

-continued (XVIb)

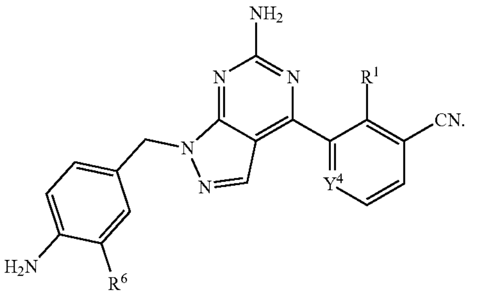

Clause 86. The compound of clause 85, wherein $R^6$ is selected from $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$ alkoxy, halogen, and hydroxyl.

Clause 87. The compound of clause 86, wherein $R^6$ is selected from $(C_1\text{-}C_5)$alkyl, substituted $(C_1\text{-}C_5)$alkyl, and $(C_1\text{-}C_3)$haloalkyl.

Clause 88. The compound of clause 87, wherein $R^6$ is $CH_3$ or $CF_3$.

Clause 89. The compound of any one of clauses 80 to 88, wherein $R^1$ is selected from H, $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$alkoxy, halogen, and hydroxyl.

Clause 90. The compound of clause 89, wherein $R^1$ is selected from H, F, $CH_3$, and $CF_3$.

Clause 91. The compound of any one of clauses 75 to 90, wherein $Y^4$ is CH.

Clause 92. The compound of any one of clauses 75 to 90, wherein $Y^4$ is N.

Clause 93. The compound of clause 75, 80 or 85, wherein the compound is selected from:

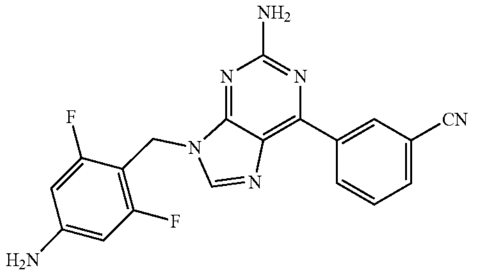

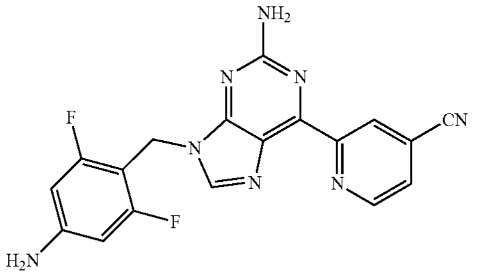

-continued

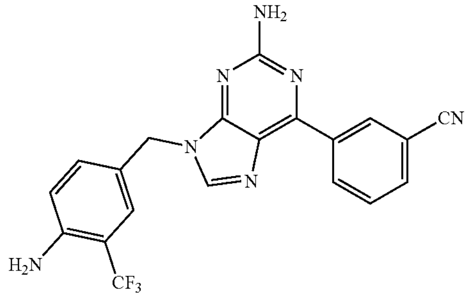

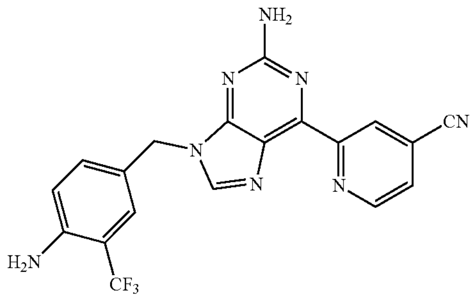

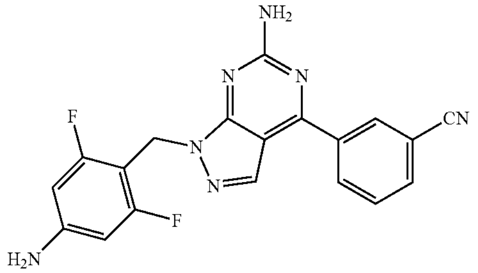

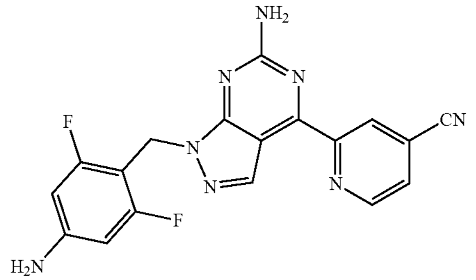

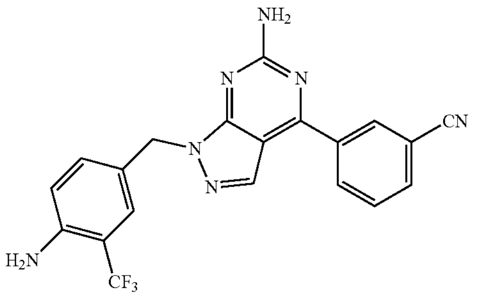

and

-continued

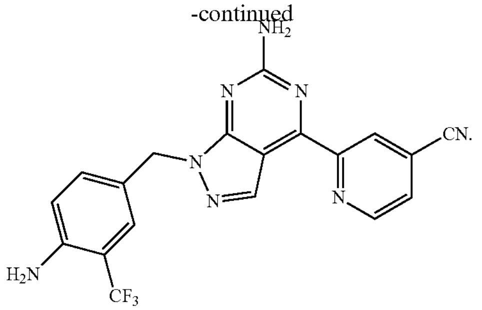

Clause 94. The compound of clause 1, wherein the compound is a compound of Table 1, or a solvate, a hydrate, a prodrug, and/or a stereoisomer thereof, or a pharmaceutically acceptable salt thereof Clause 95. A pharmaceutical composition comprising a compound or a solvate, a hydrate, a prodrug, and/or a stereoisomer thereof, or a pharmaceutically acceptable salt thereof according to any one of clauses 1-94; and a pharmaceutically acceptable excipient.

Clause 96. A compound for use in inhibiting or antagonizing an adenosine A2A and/or A1 receptor, wherein the compound is a compound or a solvate, a hydrate, a prodrug, and/or a stereoisomer thereof, or a pharmaceutically acceptable salt thereof according to any one of clauses 1-94.

Clause 97. A pharmaceutical composition for use in inhibiting or antagonizing an adenosine A2A and/or A1 receptor, wherein the pharmaceutical composition is according to clause 95.

Clause 98. A method of inhibiting an adenosine A2A and/or A1 receptor, the method comprising: contacting a sample comprising the adenosine A2A and/or A1 receptor with an effective amount of a compound or a solvate, a hydrate, a prodrug, and/or a stereoisomer thereof, or a pharmaceutically acceptable salt thereof according to any one of clauses 1-94 to inhibit the adenosine A2A and/or A1 receptor.

Clause 99. The method of clause 98, wherein the sample is in vitro.

Clause 100. A method of antagonizing an adenosine A2A and/or A1 receptor, the method comprising: contacting a cell comprising the adenosine A2A and/or A1 receptor with an effective amount of a compound or a solvate, a hydrate, a prodrug, and/or a stereoisomer thereof, or a pharmaceutically acceptable salt thereof according to any one of clauses 1-94 to antagonize the adenosine A2A and/or A1 receptor.

Clause 101. The method of clause 100, wherein the cell in comprised in a cellular sample in vitro.

Clause 102. The method of clause 100, wherein the cell is comprised in a biological system in vivo.

Clause 103. A method of treating cancer, comprising administering to a subject having cancer a therapeutically effective amount of an A2A and/or A1 receptor antagonist compound or a solvate, a hydrate, a prodrug, and/or a stereoisomer thereof, or a pharmaceutically acceptable salt thereof according to any one of clauses 1 to 94.

Clause 104. The method of clause 103, wherein the cancer is a solid tumor cancer.

Clause 105. The method of clause 103, wherein the cancer is selected from lung cancer, breast cancer, prostate cancer, ovarian cancer, solenoma, cervical cancer, bladder cancer, head and neck cancer, renal cell carcinoma, cancer of the esophagus, pancreatic cancer, brain cancer, liver cancer, leukemia, lymphoma, melanoma, multiple myeloma, Ewing's sarcoma, osteosarcoma, colorectal neoplasm, cholangiocarcinoma, choriocarcinoma, mouth cancer, neuroblastoma, skin cancer, testicular cancer, stromal tumor, germ cell tumor, and thyroid cancer.

Clause 106. The method of clause 105, wherein the cancer is liver cancer that is hepatocellular carcinoma (HCC), Clause 107. The method of clause 105, wherein the cancer is lung cancer that is non-small cell lung carcinoma (NSCLC).

Clause 108. The method of any one of clauses 103 to 107, further comprising co-administering to the subject an additional active agent.

Clause 109. The method of clause 108, wherein the additional active agent is selected from anti-angiogenesis agent, anti-inflammatory agent, immune checkpoint inhibitor, PARP inhibitor, chemotherapeutic agent, and immunity anticancer agent.

Clause 110. The method of clause 109, wherein the additional active agent is an immune checkpoint inhibitor selected from CTLA-4 inhibitor, PD-1 inhibitors, and PD-L1 inhibitor.

Clause 111. The method of clause 110, wherein the immune checkpoint inhibitor is an antibody or antibody fragment.

Clause 112. A method of treating an inflammatory disease, comprising administering to a subject having an inflammatory disease a therapeutically effective amount of an A2A and/or A1 receptor antagonist compound or a solvate, a hydrate, a prodrug, and/or a stereoisomer thereof, or a pharmaceutically acceptable salt thereof according to any one of clauses 1 to 94.

Clause 113. The method of clause 112, wherein the inflammatory disease is a chronic inflammatory disease.

Clause 114. The method of clause 112, wherein the inflammatory disease is an acute inflammatory disease.

Clause 115. A method of treating a central nervous system disease, comprising administering to a subject having or at risk from a central nervous system disease a therapeutically effective amount of an A2A and/or A1 receptor antagonist compound or a solvate, a hydrate, a prodrug, and/or a stereoisomer thereof, or a pharmaceutically acceptable salt thereof according to any one of clauses 1 to 94.

Clause 116. The method of clause 115, wherein the central nervous system disease is selected from Parkinson's disease, Alzheimer's disease, amyotrophic lateral sclerosis, multiple sclerosis, Huntington's disease, depression, schizophrenia, and epilepsy.

Clause 117. The method of clause 116, wherein the central nervous system disease is Parkinson's disease.

Clause 118. A compound or pharmaceutical composition for use in treating a disease selected from cancer, inflammatory disease and central nervous system disease, wherein the compound is according to any one of clauses 1-94, and the pharmaceutical composition is according to clause 95.

Clause 119. Use of a compound according to any one of clauses 1-94, or pharmaceutical composition according to clause 95 in the manufacture of a medicament for treating a disease selected from cancer, inflammatory disease and central nervous system disease.

Clause 120. A compound of the formula:

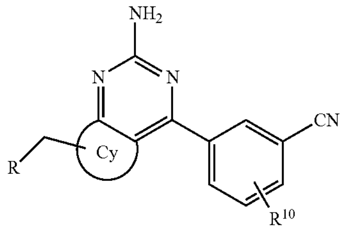

or a solvate, a three-dimensional isomer, or a pharmaceutically acceptable salt thereof, wherein:

Cy is a fused five membered heterocycle ring (e.g., heteroaryl or heterocycloalkyl ring) that contains at least one hetero atom selected from nitrogen, oxygen, and sulfur, R is the phenyl group substituted by $R^{11}$, $R^{12}$, and/or $R^{13}$, $R^{11}$, $R^{12}$, and/or $R^{13}$ are each independently halogen, hydroxyl group, thiol group, carbonyl group, amide group, nitro group, amino group, substituted or unsubstituted $(C_1\text{-}C_5)$alkyl group, substituted or unsubstituted $(C_2\text{-}C_5)$alkenyl group, substituted or unsubstituted $(C_2\text{-}C_5)$alkynyl group, substituted or unsubstituted $(C_1\text{-}C_3)$haloalkyl group, and substituted or unsubstituted $(C_1\text{-}C_3)$aminoalkyl group or substituted or unsubstituted $(C_1\text{-}C_5)$alkoxy group, and $R^{10}$ is one or more groups independently selected from hydrogen, halogen, hydroxyl group, thiol group, substituted or unsubstituted $(C_1\text{-}C_5)$alkyl group, substituted or unsubstituted $(C_2\text{-}C_5)$alkenyl group, substituted or unsubstituted $(C_2\text{-}C_5)$alkynyl group, substituted or unsubstituted $(C_1\text{-}C_3)$haloalkyl group, substituted or unsubstituted $(C_1\text{-}C_5)$alkoxy group, or cyano.

Clause 121. The compound of clause 120 or a solvate, a three-dimensional isomer or pharmaceutically acceptable salt, wherein: Cy contains at least one hetero atom selected from nitrogen, oxygen, and sulfur, and forms a five-membered heteroaryl ring fused with the atoms in the pyrimidine ring, and R is a phenyl group substituted with $R^{11}$, $R^{12}$, and/or $R^{13}$ that are each independently selected from hydrogen, halogen, amino group, hydroxyl group, thiol group, $(C_1\text{-}C_5)$alkyl group, $(C_2\text{-}C_5)$alkenyl group, $(C_2\text{-}C_5)$alkynyl group, $(C_1\text{-}C_3)$haloalkyl group, $(C_1\text{-}C_3)$aminoalkyl group, or $(C_1\text{-}C_5)$alkoxy group, and each $R^{10}$ is independently selected from hydrogen, halogen, hydroxyl group, thiol group, $(C_1\text{-}C_5)$alkyl group, $(C_2\text{-}C_5)$alkenyl group, $(C_2\text{-}C_5)$alkynyl group, $(C_1\text{-}C_3)$haloalkyl group, $(C_1\text{-}C_5)$ alkoxy group, and cyano.

Clause 122. The compound of clause 120 or a solvate, a three-dimensional isomer or pharmaceutically acceptable salt, wherein: Cy contains at least one nitrogen atom, and forms a five-membered heteroaryl ring fused with the atoms of the pyrimidine ring, R is of the structure

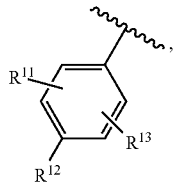

and is linked to a nitrogen atom of the Cy ring, and $R^{11}$, $R^{12}$, and/or $R^{13}$ are each independently selected from hydrogen, halogen, amino group, $(C_1\text{-}C_5)$alkyl group, $(C_2\text{-}C_5)$alkenyl group, $(C_2\text{-}C_5)$alkynyl group, $(C_1\text{-}C_3)$ haloalkyl group, $(C_1\text{-}C_3)$aminoalkyl group, or $(C_1\text{-}C_5)$ alkoxy group, and each $R^{10}$ is independently selected from hydrogen, halogen, hydroxyl group, thiol group, $(C_1\text{-}C_5)$alkyl group, $(C_2\text{-}C_5)$alkenyl group, $(C_2\text{-}C_5)$ alkynyl group, $(C_1\text{-}C_3)$haloalkyl group, $(C_1\text{-}C_5)$alkoxy group, and cyano.

Clause 123. The compound of clause 120 or a solvate, a three-dimensional isomer or pharmaceutically acceptable salt, wherein:

Cy contains at least one nitrogen atom, and forms a five-membered heteroaryl ring with the atoms of the pyrimidine ring, R is

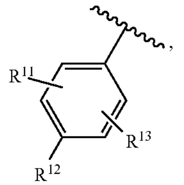

and is linked to a nitrogen atom of the Cy ring, $R^{11}$ and $R^{13}$ are each independently hydrogen, halogen, $(C_1\text{-}C_5)$alkyl group, $(C_2\text{-}C_5)$alkenyl group, $(C_2\text{-}C_5)$ alkynyl group, $(C_1\text{-}C_3)$haloalkyl group, or $(C_1\text{-}C_5)$ alkoxy group, $R^{12}$ is hydrogen or amino group, and each $R^{10}$ is independently selected from hydrogen, halogen, $(C_1\text{-}C_5)$alkyl group, $(C_2\text{-}C_5)$alkenyl group, $(C_2\text{-}C_5)$alkynyl group, $(C_1\text{-}C_3)$haloalkyl group, $(C_1\text{-}C_5)$alkoxy group, and cyano.

Clause 124. The compound of clause 123 or a solvate, a three-dimensional isomer or pharmaceutically acceptable salt, wherein: $R^{11}$ and $R^{13}$ are each independently hydrogen, halogen, $(C_1\text{-}C_5)$alkyl group, $(C_2\text{-}C_5)$alkenyl group, $(C_2\text{-}C_5)$alkynyl group, $(C_1\text{-}C_3)$haloalkyl group, or $(C_1\text{-}C_5)$alkoxy group, $R^{12}$ is hydrogen or amino group, and $R^{10}$ is hydrogen, halogen, $(C_1\text{-}C_5)$alkyl group, $(C_2\text{-}C_5)$alkenyl group, $(C_2\text{-}C_5)$alkynyl group, $(C_1\text{-}C_3)$haloalkyl group, or $(C_1\text{-}C_5)$alkoxy group, or cyano.

Clause 125. The compound of clause 124 or a solvate, a three-dimensional isomer or pharmaceutically acceptable salt, wherein: $R^{11}$ and $R^{13}$ are each hydrogen, halogen, $C_1\text{-}C_5$ alkyl group, or $C_1\text{-}C_3$ haloalkyl group, $R^{12}$ is hydrogen or amino group, and $R^{10}$ is hydrogen, halogen, $C_1\text{-}C_5$ alkyl group, or cyano group.

Clause 126. The compound of clause 120 or a solvate, a three-dimensional isomer or pharmaceutically acceptable salt, wherein:

Cy forms pyrazolopyrimidine or purine with the pyrimidine combined with Cy,

R is

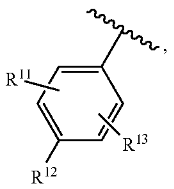

and combines with Cy's nitrogen atoms, $R^{11}$ and $R^{13}$ are each hydrogen, halogen, $C_1$-$C_5$ alkyl group, $C_2$-$C_5$ alkenyl group, $C_2$-$C_5$ alkynyl group, $C_1$-$C_3$ haloalkyl group, or $C_1$-$C_5$ alkoxy group, $R_2$ is hydrogen or amino group, and $R^{10}$ is hydrogen, halogen, $C_1$-$C_5$ alkyl group, $C_2$-$C_5$ alkenyl group, $C_2$-$C_5$ alkynyl group, $C_1$-$C_3$ haloalkyl group, $C_1$-$C_5$ alkoxy group, or cyano group.

Clause 127. The compound of clause 126 or a solvate, a three-dimensional isomer or pharmaceutically acceptable salt, wherein:

$R^{11}$ and $R^{13}$ are each hydrogen, halogen, $C_1$-$C_5$ alkyl group, $C_2$-$C_5$ alkenyl group, $C_2$-$C_5$ alkynyl group, $C_1$-$C_3$ haloalkyl group, or $C_1$-$C_5$ alkoxy group, $R_2$ is hydrogen or amino group, and $R^{10}$ is hydrogen, halogen, $C_1$-$C_8$alkyl group, $C_2$-$C_5$ alkenyl, $C_2$-$C_5$ alkynyl, $C_1$-$C_3$ haloalkyl group, $C_1$-$C_5$ alkoxy or cyano.

Clause 128. The compound of clause 120, or a solvate, a three-dimensional isomer or pharmaceutically acceptable salt thereof, wherein the compound is selected from the group consisting of:

3-(6-amino-1-(4-aminobenzyl)-1H-pyrazolo-[3,4-d]-pyrimidine-4-yl)-benzonitrile;

3-(6-amino-1-(4-aminobenzyl)-1H-pyrazolo-[3,4-d]-pyrimidine-4-yl)-2-methylbenzonitrile;

3-(6-amino-1-(4-aminobenzyl)-1H-pyrazolo-[3,4-d]-pyrimidine-4-yl)-2-fluorobenzonitrile;

3-(2-amino-9-(4-aminobenzyl)-9H-purin-6-yl)-benzonitrile;

3-(2-amino-9-(4-aminobenzyl)-9H-purin-6-yl)-2-fluorobenzonitrile;

3-(2-amino-9-(4-aminobenzyl)-9H-purin-6-yl)-2-methylbenzonitrile;

3-(2-amino-9-(4-amino-2,6-difluorobenzyl)-9H-purin-6-yl)-benzonitrile;

3-(2-amino-9-(4-amino-2,6-difluorobenzyl)-9H-purin-6-yl)-2-fluorobenzonitrile;

3-(2-amino-9-(4-amino-2-fluorobenzyl)-9H-purin-6-yl)-benzonitrile;

3-(2-amino-9-(4-amino-2-fluorobenzyl)-9H-purin-6-yl)-2-fluorobenzonitrile;

3-(2-amino-9-(4-amino-3-methylbenzyl)-9H-purin-6-yl)-benzonitrile;

3-(2-amino-9-(4-amino-3-methylbenzyl)-9H-purin-6-yl)-2-fluorobenzonitrile;

3-(2-amino-9-(2,6-difluorobenzyl)-9H-purin-6-yl)-benzonitrile;

3-(2-amino-9-(2,6-difluorobenzyl)-9H-purin-6-yl)-2-fluorobenzonitrile; and 3-(2-amino-9-(2,6-difluorobenzyl)-9H-purin-6-yl)-2-methylbenzonitrile.

Clause 129. A pharmaceutical composition to prevent or treat cancer comprising an effective amount of a compound of any one of clauses 119 to 127, or a solvate, a three-dimensional isomer, or a pharmaceutically acceptable salt thereof Clause 130. The pharmaceutical composition according to clause 129, wherein the composition has antagonistic effects on the adenosine A2A receptor.

Clause 131. The pharmaceutical composition according to clause 129, wherein the cancer is lung cancer, breast cancer, prostate cancer, ovarian cancer, solenoma, cervical cancer, bladder cancer, head and neck cancer, renal cell carcinoma, cancer of the esophagus, pancreatic cancer, brain cancer, liver cancer, leukemia, lymphoma, melanoma, multiple myeloma, Ewing's sarcoma, osteosarcoma, colorectal neoplasm, cholangiocarcinoma, choriocarcinoma, mouth cancer, neuroblastoma, skin cancer, testicular cancer, stromal tumor, germ cell tumor, or thyroid cancer.

Clause 132. The pharmaceutical composition according to clause 129, wherein the composition is administered simultaneously with, separately, or consecutively with another anticancer medication.

Clause 133. The pharmaceutical composition according to clause 129, wherein the composition is produced in a pharmaceutically allowed form that is tablet, pill, powder, capsule, syrup, emulsion, or micro-emulsion.

EXAMPLES

The following examples are offered to illustrate the present disclosure and are not to be construed in any way as limiting the scope of the present technology. Any methods that are functionally equivalent are within the scope of the present technology. Various modifications of the present technology in addition to those described herein will become apparent to those skilled in the art from the foregoing description. Such modifications fall within the scope of the appended claims.

Unless otherwise stated, all temperatures are in degrees Celsius. Efforts have been made to ensure accuracy with respect to numbers used (e.g., amounts, temperatures, etc.), but some experimental errors and deviation should be allowed for.

If an abbreviation is not defined, it has its generally accepted meaning.

General Synthetic Methods

Final compounds were confirmed by high-performance liquid chromatography/mass spectrometry (HPLC/MS) analysis and determined to be >90% pure by weight. $^1H$ nuclear magnetic resonance (NMR) spectra were recorded in $CDCl_3$ (residual internal standard $CHCl_3$=δ 7.26), dimethyl sulfoxide (DMSO)-$d_6$ (residual internal standard $CD_3SOCD_2H$=δ 2.50), methanol-$d_4$ (residual internal standard $CD_2HOD$=δ 3.30), or acetone-$d_6$ (residual internal standard $CD_3COCD_2H$=δ 2.05). The chemical shifts (6) reported are given in parts per million (ppm) and the coupling constants (J) are in Hertz (Hz). The spin multiplicities are reported as s=singlet, bs=broad singlet, bm=broad multiplet, d=doublet, t=triplet, q=quartet, p=pentuplet, dd=doublet of doublet, ddd=doublet of doublet of doublet, dt=doublet of triplet, td=triplet of doublet, tt=triplet of triplet, and m=multiplet.

HPLC-MS analysis was carried out with gradient elution. Medium pressure liquid chromatography (MPLC) was performed with silica gel columns in both the normal phase and reverse phase.

Example 1: Preparation of Compounds

The compounds of this disclosure are produced by adapting well known chemical conversions in accordance with the method illustrated by Scheme 1 or 2 below. The synthesis of several exemplary compounds of Table 1 is described below in examples 1.1 to 1.69. Several other compounds of Table 1 were prepared by adapting the methods described herein and assessed according to the biological assays described in Examples 2-4.

General Scheme 1

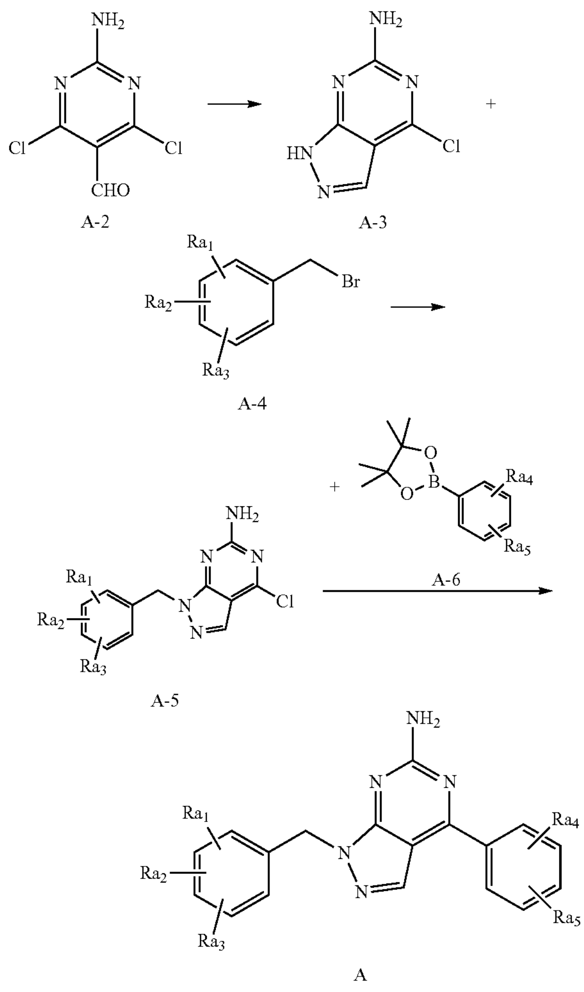

A-2 A-3 A-4 A-6 A-5 A

Exemplary synthetic methods for Scheme 1 are described in detail below.

To describe in more detail by referring to the aforementioned scheme 1, it is possible to produce the compound indicated by the aforementioned scheme 1 through a series of processes that includes the first stage in which the A-2 compound is dissolved in a solvent of tetrahydrofuran and $H_2O$, and in which the compound of scheme A-3 is produced by subjecting the solution to chain reaction with hydrazine monohydrate for 24 hours at 25° C. to 60° C., the second stage in which the A-3 compound is dissolved in the N,N-dimethylformamide solvent, and then subjecting the solution to nucleophilic substitution reaction with the compound of scheme A-4 for 24 hours at 25° C. to 60° C. under the condition in which potassium carbonate or cesium carbonate is provided to produce the scheme A-5 compound; and the third stage in which the A-5 compound is dissolved in 1,4-dioxane and distilled water, and in which the solution is subject to Suzuki coupling reaction with the compound of scheme A-6 for two hours to 24 hours at 100° C. to 115° C. to produce the A compound under the condition in which 3-(4,4,5,5-tetramethyl-1,3,2-dioxaborolane-2-yl) benzonitrile and its derivative, and tetrakis (triphenylphosphine) palladium and sodium carbonate are provided, or in which the solution is subject to the Suzuki coupling reaction under the same conditions and in which the solution is dissolved in ethanol solvent, and in which the solution is subject to reduction reaction under the conditions of tin (II) chloride dihydrate and acid. Here, the aforementioned scheme 1's $R_{a1}$, $R_{a2}$, $R_{a3}$, $R_{a4}$, and $R_{a5}$ can correspond to the substituents of the formula described herein, e.g., formula (IIb)'s $R^1$ to $R^9$, and cyano group.

General Scheme 2

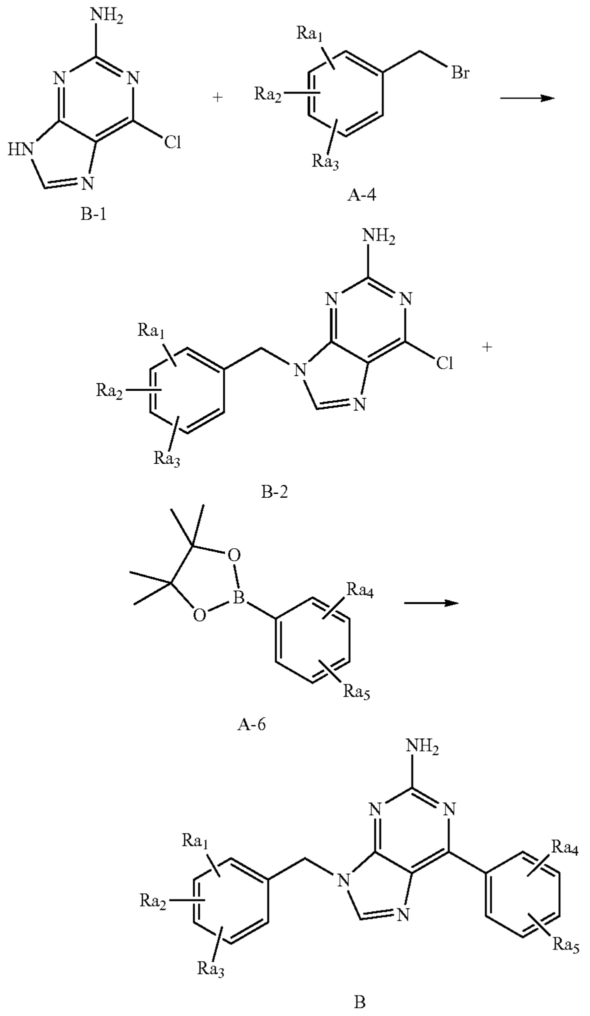

B-1 A-4 B-2 A-6 B

Exemplary synthetic methods for Scheme 2 are described in detail below.

It is possible to produce compounds according to the schemes above through a series of processes that includes the first stage in which the B-1 compound is dissolved in N,N-dimethylformamide solvent, and in which the B-2 compound is produced by subjecting the solution to nucleophilic substitution reaction with the compound of scheme A-4 for 24 h at 25° C. to 60° C. under the condition in which potassium carbonate or cesium carbonate is provided, and the second stage in which the B-2 compound is dissolved a solvent of 1,4-dioxane and distilled water, and in which the solution is subject to Suzuki coupling reaction with the compound of scheme A-6 for two hours to 24 h at 100° C. to 115° C. to produce compound B under the condition in which 3-(4,4,5,5-tetramethyl-1,3,2-dioxaborolane-2-yl) benzonitrile and its derivative, tetrakis (triphenylphosphine) palladium, and sodium carbonate are provided, or in which the solution is subject to the Suzuki coupling reaction under the same conditions and in which the solution is dissolved in ethanol solvent, and in which the solution is subject to reduction reaction under the conditions of tin (II) chloride dihydrate and acid. Here, the aforementioned scheme 2's $R_{a1}$, $R_{a2}$, $R_{a3}$, $R_{a4}$, and $R_{a5}$ can correspond to the substituents of the formula described herein, e.g., formula (IIa)'s $R^1$ to $R^9$, and cyano groups.

Example 1.1: Production of 3-(6-amino-1-(4-aminobenzyl)-1H-pyrazolo [3,4-d]pyrimidine-4-yl) benzonitrile (Compound 201)

1.1.1. Production of 4-chloro-(4-nitrobenzyl)-1H-pyrazolo [3,4-d]pyrimidine-6-amine

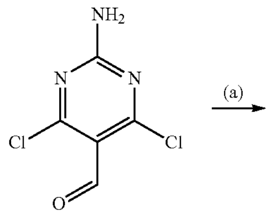

S1

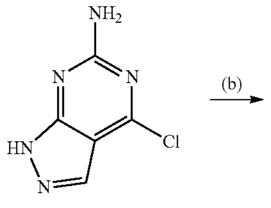

S2

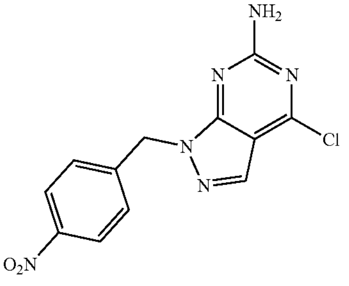

S3

Reagents and Conditions: (a) hydrazine, TEA, THF:$H_2O$ (3:1), r.t. to 50° C., 3 h, quant; (b) 4-nitrobenzyl bromide, $K_2CO_3$, DMF, 0° C. to r.t., 12 h, 58%.

Stage 1: Production of 4-chloro-1H-pyrazolo [3,4-d]pyrimidine-6-amine 2-amino-4,6-dichloropyrimidine-5-carbaldehyde (S1, 4 g, 20.83 mmol) was melted in a solvent of tetrahydrofuran (THF) and $H_2O$, and to this hydrazine monohydrate (0.78 ml, 24.99 mmol) and triethylamine (TEA, 3.51 ml, 24.99 mmol) were added. Afterwards, the aforementioned reaction mixture was heated at 50° C. and agitated for 3 hours, and concentrated. Then, the aforementioned concentrate was cleaned with distilled water to obtain an intermediate compound (S2, 3.45 g, 100%). $^1$H-NMR (DMSO-$d_6$, 400 MHz): δ 13.25 (s, 1H), 8.02 (s, 1H), 7.14 (s, 2H).

Stage 2: Production of 4-chloro-1-(4-nitrobenzyl)-1H-pyrazolo [3,4-d]pyrimidine-6-amine The intermediate compound produced in the aforementioned stage 1 (S2, 3.0 g, 18.12 mmol) was dissolved in dimethylformamide (DMF), and 4-nitro benzyl bromide (3.92 g, 18.12 mmol) and potassium carbonate ($K_2CO_3$, 3.75 g, 27.18 mmol) was added to this. Then, this was agitated in room temperature for 12 hours. The aforementioned reaction mixture was diluted with ethyl acetate (EA), and was cleaned with distilled. Then, it was dried with magnesium sulfate and then filtered and concentrated. Then, the aforementioned concentrate was refined with silica gen chromatography to obtain the desired compound (S3, 3.2 g, 58%). $^1$H-NMR (DMSO-$d_6$, 400 MHz): δ 8.19 (d, 2H), 8.09 (s, 1H), 7.40-7.38 (m, 4H), 5.56 (s, 2H).

1.1.2. Production of 3-(6-amino-1-(4-aminobenzyl)-1H-pyrazolo [3,4-d]pyrimidine-4-yl) benzonitrile (Compound 201)

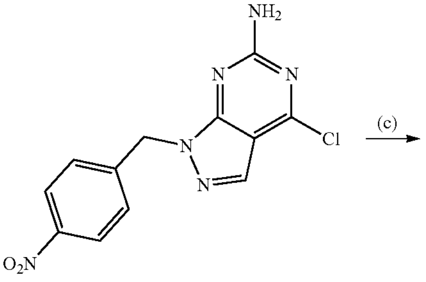

S3

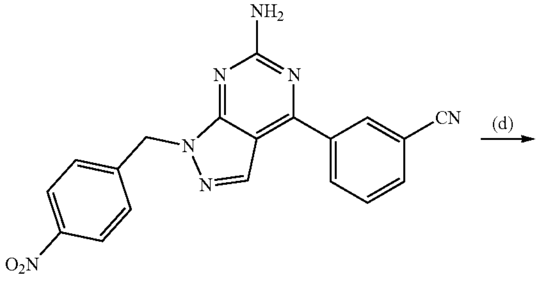

S4

-continued

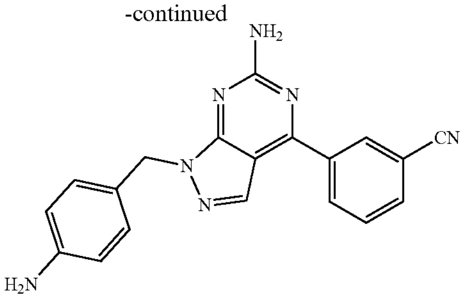

201

Reagents and Conditions: (c) 3-(4,4,5,5-tetramethyl-1,3,2-dioxaborolan-2-yl)benzonitrile, $Pd(PPh_3)_4$, $Na_2CO_3$, dioxane:$H_2O$ (8:1), r.t. to 105° C., 12 h, 70%; (d) $SnCl_2 \cdot 2H_2O$, conc. HCl, EtOH, r.t. to 50° C., 3 h, 45%.

Stage 1: Production of 3-(6-amino-1-(4-nitrobenzyl)-1H-pyrazolo [3,4-d]pyrimidine-4-yl) benzonitrile The compound of the aforementioned example 1-1 (S3, 1.0 g, 3.28 mmol) was dissolved in the solvent of 1,4-dioxane and $H_2O$, and 3-(4,4,5,5-tetramethyl-1,3,2-dioxaborolan-2-yl) benzonitrile (1.12 g, 4.92 mmol), tetrakis (triphenylphosphine) palladium ((0) ($Pd(PPh_3)_4$, 758 mg, 0.65 mmol), and sodium carbonate ($Na_2CO_3$, 695 mg, 6.56 mmol) were added to this. Afterwards, the aforementioned reaction mixture was agitated for 12 hours at the 105° C. using a sealed tube, and then was diluted with dichloromethane (DCM), and then this was cleaned with distilled water. Afterwards, this was dried with magnesium sulfate and then filtered and concentrated, and the aforementioned concentrate was cleaned with ethyl acetate/hexane (EA/Hex) to obtain an intermediate compound (S4, 852 mg, 70%). $^1$H-NMR (DMSO-$d_6$, 400 MHz): δ 8.54 (s, 1H), 8.51-8.49 (m, 2H), 8.08 (dd, 1H), 7.80 (t, 1H), 7.42 (d, 2H), 7.15 (s, 2H), 5.62 (s, 2H).

Stage 2: Production of 3-(6-amino-1-(4-aminobenzyl)-1H-pyrazolo [3,4-d]pyrimidine-4-yl) benzonitrile The intermediate compound produced in the aforementioned stage 1 (S4, 400 mg, 1.07 mmol) was dissolved in ethanol (EtOH), and then tin (II) chloride dihydrate ($SnCl_2$ $2H_2O$, 730 mg, 3.23 mmol) and Conc. HCl (aq) (1.8 mL, 21.54 mmol) were added to this. Afterwards, the aforementioned reaction mixture was agitated for 3 hours at 50° C., and then was diluted with dichloromethane (DCM), and was cleaned with distilled water. Afterwards, this was dried with magnesium sulfate, and then dried, filtered, and concentrated. Then, the aforementioned concentrate was refined with silica gen chromatography to obtain the desired compound (201, 161 mg, 45%). $^1$H-NMR (DMSO-$d_6$, 400 MHz): δ 8.50 (s, 1H), 8.48-8.45 (m, 1H), 8.35 (s, 1H), 8.07-8.04 (m, 1H), 7.79 (t, 1H), 7.07 (s, 2H), 6.95 (d, 2H), 6.47 (d, 2H), 5.23 (s, 2H), 5.04 (s, 2H).

Example 1.2: Production of 3-(6-amino-1-(4-aminobenzyl)-1H-pyrazolo [3,4-d]pyrimidine-4-yl)-2-methylbenzonitrile (Compound 205)

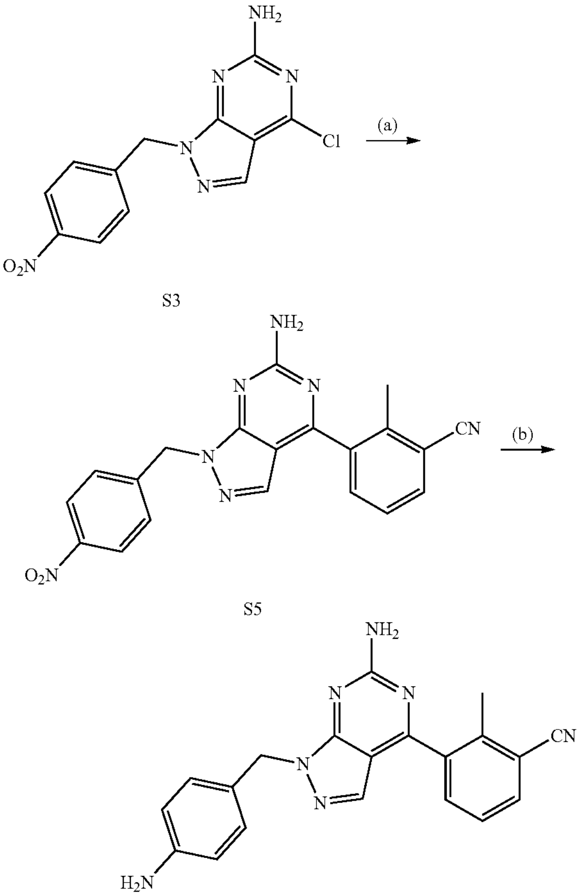

S3

S5

205

Reagents and Conditions: (a) 2-methyl-3-(4,4,5,5-tetramethyl-1,3,2-dioxaborolan-2-yl)benzonitrile, $Pd(PPh_3)_4$, $Na_2CO_3$, dioxane:$H_2O$ (8:1), r.t. to 105° C., 12 h, 81%; (b) $SnCl_2 \cdot 2H_2O$, conc HCl, EtOH, r.t. to 50° C., 3 h, 74%.

Stage 1: Production of 3-(6-amino-1-(4-nitrobenzyl)-1H-pyrazolo [3,4-d]pyrimidine-4-yl)-2-methylbenzonitrile In stage 1 of the aforementioned example 1.1.2, except for using 2-methyl-3-(4,4,5,5-tetramethyl-1,3,2-dioxiborolan-2-yl) benzonitrile (120 mg, 0.49 mmol) instead of 3-(4,4,5,5-tetramethyl-1,3,2-dioxaborolane-2-yl) benzonitrile (1.12 g, 4.92 mmol), the same process as stage 1 of the aforementioned example 1.1.2 was carried out to obtain an intermediate compound (S5, 103 mg, 81%). $^1$H-NMR (DMSO-$d_6$, 400 MHz): δ 8.21 (d, 2H), 7.97 (d, 1H), 7.90 (s, 1H), 7.82 (d, 1H), 7.56 (t, 1H), 7.46 (d, 2H), 7.13 (s, 2H), 5.59 (s, 2H), 2.52 (s, 3H)

Stage 2: Production of 3-(6-amino-1-(4-aminobenzyl)-1H-pyrazolo [3,4-d]pyrimidine-4-yl)-2-methylbenzonitrile In stage 2 of the aforementioned example 1.1.2, except for changing the amount of tin (II) chloride dihydrate ($SnCl_2 \cdot 2H_2O$, 180 mg, 0.80 mmol), and Conc. HCl (aq) (0.45 ml, 5.34 mmol), the same process as stage 2 of the aforementioned example 1.1.2 was performed on the intermediate compound of the aforementioned stage 1 (S5,103 mg, 0.26 mmol), to obtain a desired compound (205.71 mg, 74%). $^1$H-NMR (DMSO-$d_6$, 400 MHz): δ 7.95 (d, 1H), 7.79 (d, 1H), 7.77 (s, 1H), 7.54 (t, 1H), 7.05 (s, 2H), 6.98 (d, 2H), 6.48 (d, 2H), 5.21 (s, 2H), 5.04 (s, 2H), 2.49 (s, 3H).

Example 1.3: Production of 3-(6-amino-1-(4-aminobenzyl)-1H-pyrazolo [3,4-d]pyrimidine-4-yl)-2-fluorobenzonitrile (Compound 202)

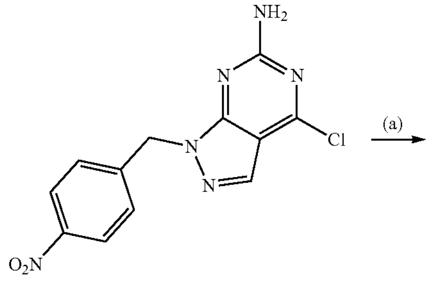

S3

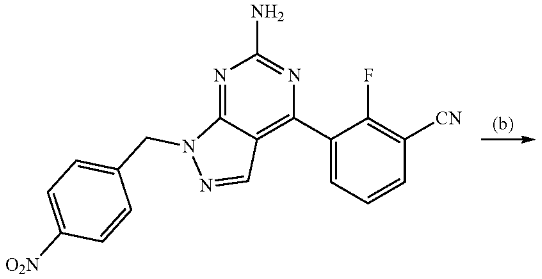

S6

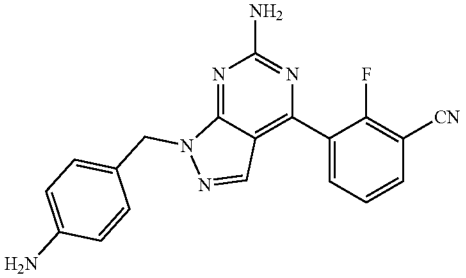

202

Reagents and Conditions: (a) 2-fluoro-3-(4,4,5,5-tetramethyl-1,3,2-dioxaborolan-2-yl)benzonitrile, $Pd(PPh_3)_4$, $Na_2CO_3$, dioxane:$H_2O$ (8:1), r.t. to 105° C., 12 h, 90%; (b) $SnCl_2 \cdot 2H_2O$, conc. HCl, EtOH, r.t. to 50° C., 3 h, 92%.

Stage 1: Production of 3-(6-amino-1-(4-nitrobenzyl)-1H-pyrazolo [3,4-d]pyrimidine-4-yl)-2-fluorobenzonitrile The same process as stage 1 of the aforementioned example 1.1.2 was performed except that 2-fluoro-3-(4,4,5,5-tetramethyl-1,3,2-dioxaborolan-2-yl) benzonitrile (1.21 g, 4.92 mmol) was used instead of 3-(4,4,5,5-tetramethyl-1,3,2-dioxaborolan-2-yl) benzonitrile (1.12 g, 4.92 mmol) in stage 1 of the aforementioned example 1.1.2, and except that the amount of tetrakis (triphenylphosphine) palladium (0)

($Pd(PPh_3)_4$, 758 mg, 0.65 mmol), and the amount of sodium carbonate ($Na_2CO_3$, 695 mg, 6.56 mmol) were changed, to obtain an intermediate compound (S6, 1.15 g, 90%). $^1$H-NMR (DMSO-$d_6$, 400 MHz): δ 8.22-8.15 (m, 4H), 8.10 (d, 1H), 7.61 (t, 1H), 7.43 (d, 2H), 7.21 (s, 2H), 5.60 (s, 2H).

Stage 2: Production of 3-(6-amino-1-4(4-aminobenzyl)-1H-pyrazolo [3,4-d]pyrimidine-4-yl)-2-fluorobenzonitrile The same process as stage 2 of the aforementioned example 1.1.2 was performed for the intermediate compound of the aforementioned stage 1 (S6, 144 mg, 0.37 mmol) except that the amount of tin (II) chloride dihydrate ($SnCl_2 \cdot 2H_2O$, 250 mg, 1.11 mmol), Conc. HCl (aq) (0.62 ml, 7.40 mmol) in stage 2 of the aforementioned example 1.1.2 was changed to obtain the desired compound (202, 131 mg, 92%). $^1$H-NMR (DMSO-$d_6$, 400 MHz): δ 8.14 (t, 2H) 7.96 (d, 1H), 7.11 (s, 2H), 6.96 (d, 2H), 6.48 (d, 2H), 5.22 (s, 2H), 5.04 (s, 2H).

Example 1.4: Production of 3-(2-amino-9-(4-aminobenzyl)-9H-purin-6-yl) benzonitrile (Compound 101)

1.4.1. Production of 6-chloro-9 (4-nitrobenzyl)-9H-purin-2-amine

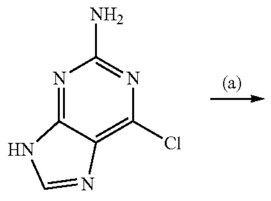

S12

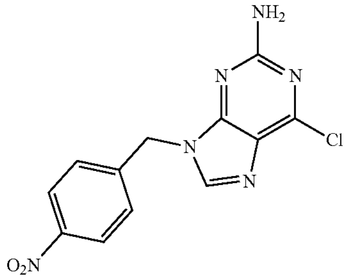

S8

Reagent and condition: (a) 4-nitro benzyl bromide, $K_2CO_3$, DMF, rt.

6-chloro-9H-purin-2-amine (S12, 3 g, 18.12 mmol) was dissolved in N,N-dimethylformamide (DMF) and 4-nitro benzyl bromide (4.1 g, 19.30 mmol) and potassium carbonate ($K_2CO_3$, 3.76 g, 27.18 mmol) were added. Then, the mixture was agitated in room temperature. Afterwards, the aforementioned reaction mixture was diluted in dichloromethane (DCM), and was cleaned with distilled water. Then, this was dried with magnesium sulfate, filtered, and concentrated, and the aforementioned concentrate was refined with silica gel chromatography to obtain an intermediate compound (S8, 395 mg, 42%). $^1$H-NMR (DMSO-$d_6$, 400 MHz): δ 8.27 (s, 1H), 8.22-8.20 (m, 2H), 7.47-7.45 (m, 2H), 6.96 (s, 2H), 5.46 (s, 2H).

1.4.2. Production of 3-(2-amino-9-(4-aminobenzyl)-9H-purin-6-yl) benzonitrile

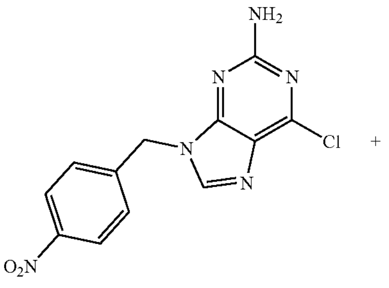

S8

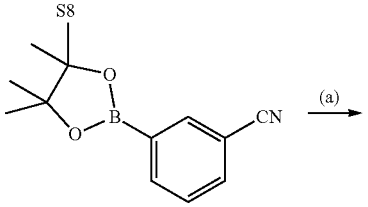

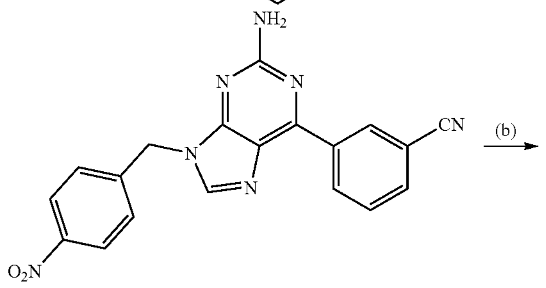

S9

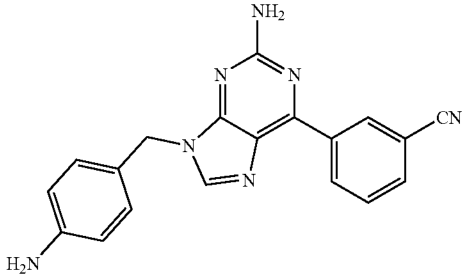

101

Reagents and conditions: (a) $Pd(PPh_3)_4$, $Na_2CO_3$ in $H_2O$, 1,4-dioxane, microwave, 105° C., 30 min; (b) $SnCl_2 \cdot 2H_2O$, Conc. HCl(aq), EtOH, 55° C., 4 h.

Stage 1: Production of 3-(2-amino-9-(4-nitrobenzyl)-9H-purin-6-yl) benzonitrile

An intermediate compound (S8, 200 mg, 0.652 mmol) was dissolved in 1,4-dioxane, 3-(4,4,5,5-tetramethyl-1,3,2-dioxaborolane-2-yl) benzonitrile (224 mg, 0.978 mmol) and tetrakis (triphenylphosphine) palladium (0) (($Pd(PPh_3)_4$, 151 mg, 0.131 mmol), and sodium carbonate ($Na_2CO_3$, 139 mg, 1.304 mmol) were added, and then the solution was heated at 105° C. using a microwave device and agitated for 30 minutes. Afterwards, the aforementioned reaction mixture was diluted with dichloromethane (DCM) and cleaned with distilled water. Afterwards, this was dried with magnesium sulfate, filtered, and concentrated, and the aforementioned concentrate was refined with silica gel chromatography to obtain an intermediate compound (S9, 395 mg, 54%). $^1$H-NMR (DMSO-$d_6$, 400 MHz): δ 9.10-9.08 (m, 1H), 9.05-9.02 (m, 1H), 8.39 (s, 1H), 8.22 (d, 2H), 8.03-8.01 (m, 1H), 7.80 (t, 1H), 7.51-7.49 (m, 2H), 6.73 (s, 2H), 5.53 (s, 2H).

Stage 2: Production of 3-(2-amino-9-(4-aminobenzyl)-9H-purin-6-yl) benzonitrile

The intermediate compound produced in the aforementioned stage 1 (S9, 244 mg, 0.624 mmol) was dissolved in ethanol (EtOH), tin (II) chloride dihydrate ($SnCl_2 \cdot 2H_2O$, 423 mg, 1.872 mmol) and Conc. HCl (aq) (1.1 mL, 12.48 mmol) were added, and the solution was agitated for 4 h at 55° C. Afterwards, the aforementioned reaction mixture was diluted with dichloromethane (DCM), and then was cleaned with distilled water. Afterwards, the solution was dried with magnesium sulfate, filtered, and concentrated, and the aforementioned concentrate was refined with silica gel chromatography to obtain the desired compound (101, 41 mg, 38%). $^1$H-NMR (DMSO-$d_6$, 400 MHz): δ 9.07 (s, 1H), 9.02 (d, 1H), 8.24 (s, 1H), 8.00 (d, 1H), 7.78 (t, 1H), 7.05-7.03 (m, 2H), 6.69 (br, 2H), 6.52-6.50 (m, 2H), 5.11 (d, 4H).

Example 1.5: Production of 3-(2-amino-9-(4-aminobenzyl)-9H-purin-6-yl)-2-fluorobenzonitrile (Compound 102)

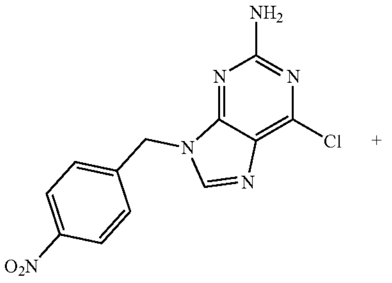

S8

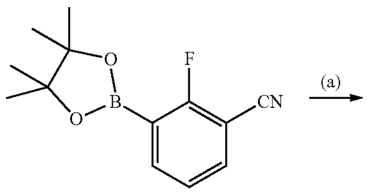

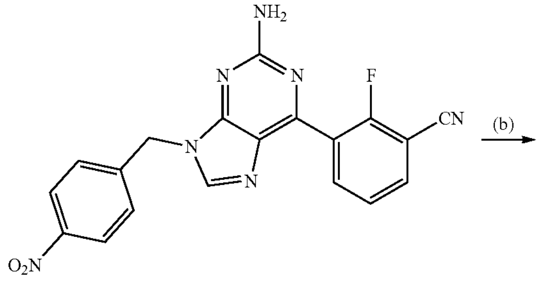

S10

-continued

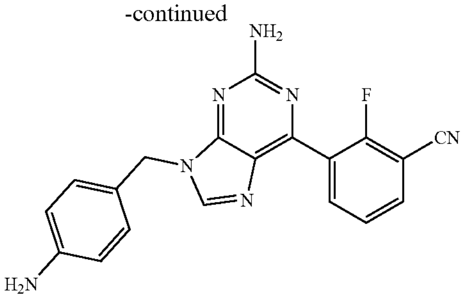

102

Reagents and conditions: (a) $Pd(PPh_3)_4$, $Na_2CO_3$ in $H_2O$, 1,4-dioxane, microwave, 105° C., 1 h; (b) $SnCl_2{\cdot}2H_2O$, Conc. HCl(aq), EtOH, 55° C., 4 h.

Stage 1: Production of 3-(2-amino-9-(4-nitrobenzyl)-9H-purin-6-yl)-2-fluorobenzonitrile The same process as stage 1 of the aforementioned example 1.1 was performed except that 2-fluoro-3-(4,4,5,5-tetramethyl-1,3,2-dioxaborolan-2-yl)benzonitrile (224 mg, 0.978 mmol) instead of 3-(4,4,5,5-tetramethyl-1,3,2-dioxaborolan-2-yl)benzonitrile (224 mg, 0.978 mmol) in stage 1 of the aforementioned example 1.1 was used, to obtain an intermediate compound (S10, 395 mg, 54%). $^1$H-NMR (DMSO-$d_6$, 400 MHz): δ 8.29 (s, 1H), 8.27-8.17 (m, 2H), 8.13-8.07 (m, 1H), 7.65-7.50 (m, 4H), 6.78 (d, 2H), 5.51 (d, 2H).

Stage 2: Production of 3-(2-amino-9-(4-aminobenzyl)-9H-purin-6-yl)-2-fluorobenzonitrile The same process as stage 2 of the aforementioned example 1.1 was performed for the intermediate compound of the aforementioned stage 1 (S10, 244 mg, 0.624 mmol), to obtain the desired compound (102, 52 mg, 48%). $^1$H-NMR (DMSO-$d_6$, 400 MHz): δ 8.22-8.13 (m, 2H), 8.13-8.07 (m, 1H), 7.57 (t, 1H), 7.05 (d, 2H), 6.73 (s, 2H), 6.51 (d, 2H), 5.11 (d, 4H).

Example 1.6: Production of 3-(2-amino-9-(4-aminobenzyl)-9H-purin-6-yl)-2-methylbenzonitrile (Compound 105)

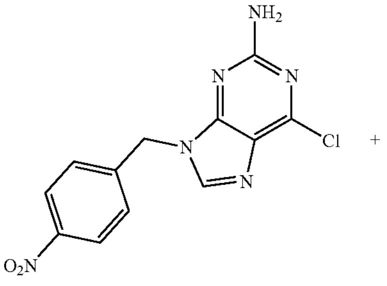

S8

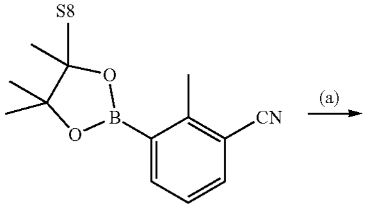

-continued

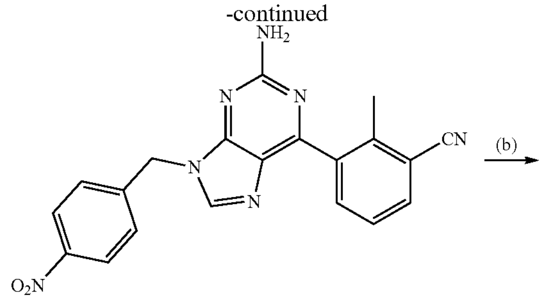

S11

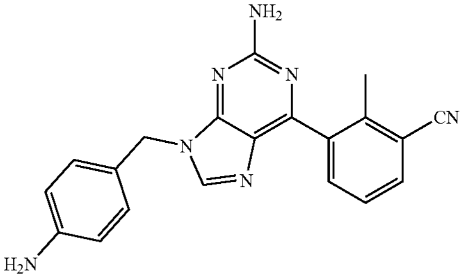

105

Reagents and conditions: (a) $Pd(PPh_3)_4$, $Na_2CO_3$ in $H_2O$, 1,4-dioxane, microwave, set T=105° C., 1 h; (b) $SnCl_2{\cdot}2H_2O$, Conc. HCl(aq), EtOH, 55° C., 4 h.

Stage 1: Production of 3-(2-amino-9-(4-nitrobenzyl)-9H-purin-6-yl)-2-methylbenzonitrile The same process as stage 1 of the aforementioned example 1.1 was performed except that 2-methyl-3-(4,4,5,5,-tetramethyl-1,3,2-dioxaborolan-2-yl) benzonitrile (224 mg, 0.978 mmol)_was used instead of 3-(4,4,5,5-tetramethyl-1,3,2-dioxaborolan-2-yl) benzonitrile (224 mg, 0.978 mmol) in stage 1 of the aforementioned example 1.1, to obtain an intermediate compound (S11, 395 mg, 54%). $^1$H-NMR (DMSO-$d_6$, 400 MHz): δ 8.27-8.22 (m, 2H), 7.83 (d, 1H), 7.88 (d, 1H), 7.65-7.52 (m, 4H), 6.71 (s, 2H), 5.50 (s, 2H).

Stage 2: Production of 3-(2-amino-9-(4-aminobenzyl)-9H-purin-6-yl)-2-methylbenzonitrile The same process as stage 2 of the aforementioned example 1.1 was performed for the intermediate compound of the aforementioned stage 1 (S11, 244 mg, 0.624 mmol), to obtain the desired compound (105, 52 mg, 48%). $^1$H-NMR (DMSO-$d_6$, 400 MHz): δ 8.10 (d, 1H), 7.91 (d, 1H), 7.83 (d, 1H), 7.51 (t, 1H), 7.06 (d, 2H), 6.66 (s, 2H), 6.55-6.46 (m, 2H), 5.10 (d, 4H), 3.32 (s, 3H).

Example 1.7: Production of 3-(2-amino-9-(4-amino-2,6-difluorobenzyl)-9H-purin-6-yl)benzonitrile (Compound 107)

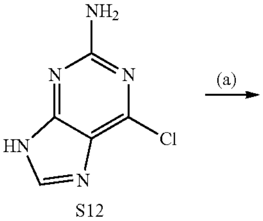

S12

-continued

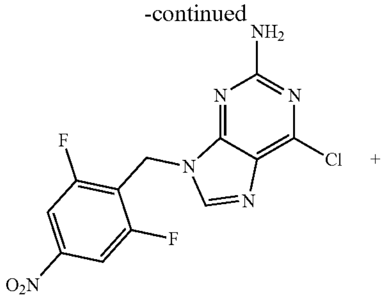

S13

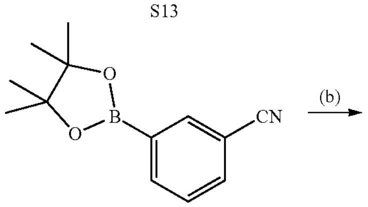

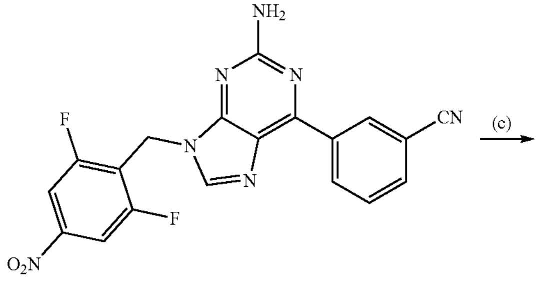

S14

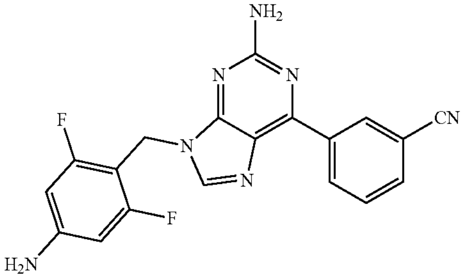

107

Reagents and conditions: (a) 2-(bromomethyl)-1,3-difluoro-5-nitrobenzene, $K_2CO_3$, DMF, rt, overnight; (b) $Pd(PPh_3)_4$, $K_2CO_3$, 1,4-dioxane, $H_2O$, 115° C., 4 h; (c) $SnCl_2{\cdot}2H_2O$, Conc. HCl(aq), EtOH, 55° C., 4 h.

Stage 1: Production of 6-chloro-9-(2,6-difluoro-4-nitrobenzyl)-9H-purin-2-amine 6-chloro-9H-purin-2-amine (S12, 500 mg, 2.95 mmol) was dissolved in dimethylformamide (DMF) and 2-(bromomethyl)-1,3-difluoro-5-nitrobenzene (817.4 mg, 3.24 mmol) and potassium carbonate ($K_2CO_3$, 611.6 mg, 4.43 mmol) was added, and the solution was agitated in room temperature for 1 day. Afterwards, the aforementioned reaction mixture was diluted with dichloromethane (DCM) and then cleaned with distilled water, and was dried with magnesium sulfate, filtered, and concentrated, and the aforementioned concentrate was refined with silica gen chromatography to obtain an intermediate compound (S13, 300 mg, 33%). $^1$H-NMR (DMSO-$d_6$, 400 MHz): δ 8.68 (s, 1H), 7.55 (d, 2H), 6.93 (s, 2H), 4.99 (s, 2H).

Stage 2: Production of 3-(2-amino-9-(2,6-difluoro-4-nitrobenzyl)-9H-purin-6-yl) benzonitrile The intermediate compound produced in the aforementioned stage 1 (S13, 150 mg, 0.44 mmol) was dissolved in 1,4-dioxane, 3-(4,4,5,5-tetramethyl-1,3,2-dioxaborolan-2-yl) benzonitrile (151 mg, 0.66 mmol), tetrakis (triphenylphosphine) palladium (0) ($Pd(PPh_3)_4$, 25.4 mg, 0.022 mmol), and potassium carbonate ($K_2CO_3$, 121.6 mg, 0.88 mmol) were added, and the salutation was heated at 115° C. and agitated for 4 h. Afterwards, the aforementioned reaction mixture was diluted with dichloromethane (DCM), and then cleaned with distilled water, and was dried with magnesium sulfate, filtered, and concentrated, and the aforementioned concentrate was refined with silica gel chromatography to obtain an intermediate compound (S14, 95.5 mg, 53.3%). $^1$H-NMR (methanol-$d_4$, 400 MHz): δ 8.98 (s, 1H), 8.93 (dd, 1H), 8.18 (s, 1H), 8.01-7.96 (m, 2H), 7.86 (dd, 1H), 7.70 (t, 1H), 5.56 (s, 2H).

Stage 3: Production of 3-(2-amino-9-(4-amino-2,6-difluorobenzyl)-9H-purin-6-yl) benzonitrile The intermediate compound produced in the aforementioned stage 2 (S14, 95.1 mg, 0.23 mmol) was dissolved in ethanol (EtOH), and tin (II) chloride dihydrate ($SnCl_2{\cdot}2H_2O$, 263.4 mg, 1.17 mmol) was added to this, and the solution was agitated for 4 h at 55° C. Afterwards, the aforementioned reaction mixture was diluted with dichloromethane (DCM), and then was cleaned with distilled water, and then was dried with magnesium sulfate, filtered, and concentrated, and the aforementioned concentrate was refined with silica gel chromatography to obtain the desired compound (107, 38.7 mg, 44.6%). $^1$H-NMR (DMSO-$d_6$, 400 MHz): δ 9.06 (s, 1H), 8.99 (dd, 1H), 8.05 (s, 1H), 7.98 (dd, 1H), 7.78 (t, 1H), 6.67 (s, 2H), 6.25-6.18 (m, 2H), 5.89 (s, 2H), 5.17 (s, 2H).

Example 1.8: Production of 3-(2-amino-9-(4-amino-2,6-difluorobenzyl)-9H-purin-6-yl)-2-fluorobenzonitrile (Compound 108)

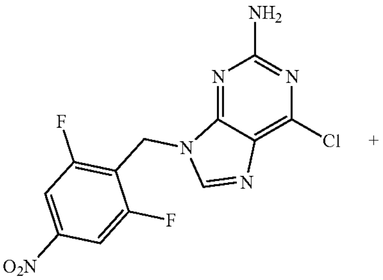

S13

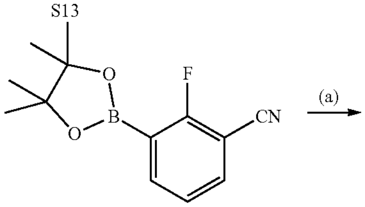

-continued

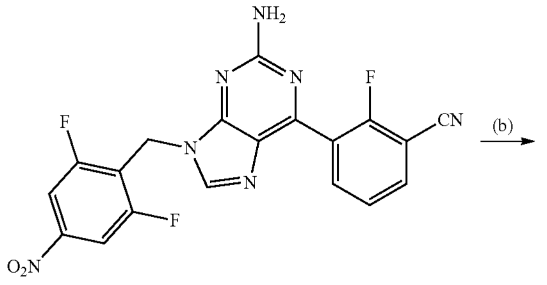

S15

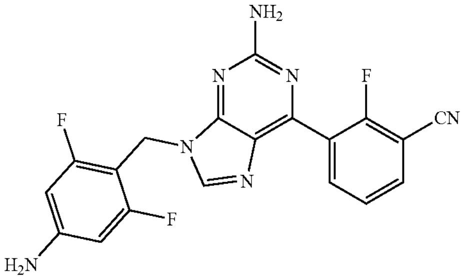

108

Reagents and conditions: (a) $Pd(PPh_3)_4$, $K_2CO_3$ 1,4-dioxane, $H_2O$, 115° C., overnight; (b) $SnCl_2 \cdot 2H_2O$, Conc. HCl(aq), EtOH, 55° C., 3 h.

Stage 1: Production of 3-(2-amino-9-(2,6-difluoro-4-nitrobenzyl)-9H-purin-6-yl)-2-fluorobenzonitrile The same process as stage 2 of the aforementioned example 1.4 was performed except that 2-fluoro-3-(4,4,5,5-tetramethyl-1,3,2-dioxaborolan-2-yl) benzonitrile (130.5 mg, 0.53 mmol) was used instead of 3-(4,4,5,5-tetramethyl-1,3,2-dioxaborolan-2-yl) benzonitrile (151 mg, 0.66 mmol) in stage 2 of the aforementioned example 1.4, and an intermediate compound (S15, 100 mg, 53.4%) was obtained. $^1$H-NMR ($CDCl_3$, 400 MHz): δ 8.15-8.13 (m, 1H), 7.90-7.87 (m, 3H), 7.75-7.74 (m, 1H), 7.40 (t, 1H), 5.54 (s, 2H), 5.12 (s, 2H).

Stage 2: Production of 3-(2-amino-9-(4-amino-2,6-difluorobenzyl)-9H-purin-6-yl)-2-fluorobenzonitrile The intermediate compound produced in the aforementioned stage 1 (S15, 100 mg, 0.24 mmol) was dissolved in ethanol (EtOH), and tin (II) chloride dihydrate ($SnCl_2 \cdot 2H_2O$, 265 mg, 1.18 mmol) was added to the solution, and the solution was agitated for 3 h at 50° C. Afterwards, the aforementioned reaction mixture was diluted with dichloromethane (DCM) and then cleaned with distilled water, and then was dried with magnesium sulfate, filtered, and concentrated, and the aforementioned concentrate was refined with silica gel chromatography to obtain the desired compound (108, 32.9 mg, 34.7%). $^1$H-NMR (methanol-$d_4$, 400 MHz): δ 8.12-8.08 (m, 1H), 7.96-7.91 (m, 2H), 7.53 (t, 1H), 6.26 (d, 2H), 5.29 (s, 2H).

Example 1.9: Production of 3-(2-amino-9-(4-amino-2-fluorobenzyl)-9H-purin-6-yl)benzonitrile (Compound 109)

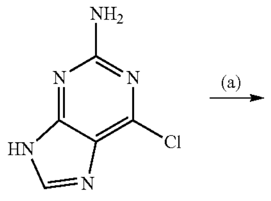

S12

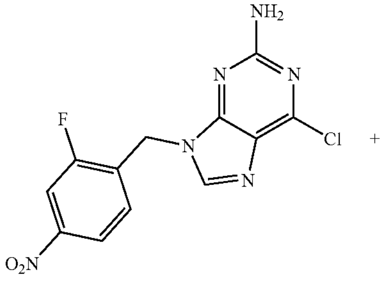

S16

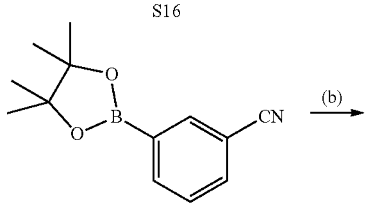

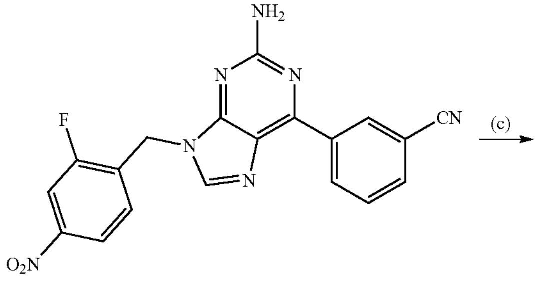

S17

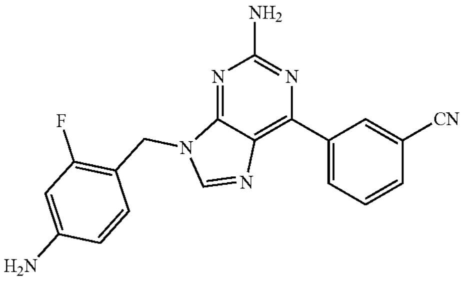

109

Reagents and conditions: (a) 1-(bromomethyl)-2-fluoro-4-nitrobenzene, $K_2CO_3$, DMF, rt, overnight; (b) $Pd(PPh_3)_4$, $K_2CO_3$, 1,4-dioxane, $H_2O$, 115° C., 5 h; (c) $SnCl_2 \cdot 2H_2O$, EtOH, 50° C., 1 h.

Stage 1: Production of the 6-chloro-9-(2-fluoro-4-nitrobenzyl)-9H-purin-2-amine 6-chloro-9H-purin-2-amine (S12, 500 mg, 2.95 mmol) was melted in dimethylformamide (DMF), and 1-(bromomethyl)-2-fluoro-4-nitrobenzene (758.2 mg, 3.24 mmol) and potassium carbonate ($K_2CO_3$, 611.6 mg, 4.43 mmol) was added to the solution, and the solution was agitated for 1 day. Afterwards, the aforementioned reaction mixture was diluted with dichloromethane (DCM) and then cleaned with distilled water, and was dried with magnesium sulfate, dried, filtered, and concentrated, and the aforementioned concentrate was refined with silica gel chromatography to obtain an intermediate compound (S16, 742 mg, 77%). $^1$H-NMR (DMSO-$d_6$, 400 MHz): δ 8.23 (s, 1H), 8.18 (dd, 1H), 8.03 (dd, 1H), 7.30 (t, 1H), 6.97 (s, 2H), 5.49 (s, 2H).

Stage 2: Production of 3-(2-amino-9-(2-fluoro-4-nitrobenzyl)-9H-purin-6-yl)-benzonitrile The intermediate compound produced in the aforementioned stage 1 (S16, 300 mg, 0.93 mmol) was melted in a solvent of 1,4-dioxane and $H_2O$, 3-(4,4,5,5-tetramethyl-1,3,2-dioxaborolan-2-yl)-benzonitrile (318.4 mg, 1.39 mmol) and tetrakis (triphenylphosphine) palladium ((0) $Pd(PPh_3)_4$, 53.7 mg, 0.05 mmol), and potassium carbonate ($K_2CO_3$, 257 mg, 1.86 mmol) were added to the solution, and the solution was heated at 115° C. and agitated for 5 h. Afterwards, the aforementioned reaction mixture was diluted with dichloromethane (DCM), was cleaned with distilled water, and then was dried with magnesium sulfate, filtered, and concentrated, and the aforementioned concentrate was refined with silica gel chromatography to obtain an intermediate compound (S17, 162 mg, 44.8%). $^1$H-NMR (DMSO-$d_6$, 400 MHz): δ 9.09 (s, 1H), 9.02 (dd, 1H), 8.35 (s, 1H), 8.19 (dd, 1H), 8.06-8.01 (m, 2H), 7.81 (t, 1H), 7.31 (t, 1H), 6.75 (s, 2H), 5.55 (s, 2H).

Stage 3: Production of 3-(2-amino-9-(4-amino-2-fluorobenzyl)-9H-purin-6-yl) benzonitrile The intermediate compound produced in the aforementioned stage 2 (S17, 89 mg, 0.23 mmol) was dissolved in ethanol (EtOH), and then tin (II) chloride dihydrate ($SnCl_2 \cdot 2H_2O$, 257 mg, 1.14 mmol) was added to the solution, and the solution was agitated for 1 h at 50° C. Afterwards, the aforementioned reaction mixture was diluted with dichloromethane (DCM), and then was cleaned with distilled water, dried with magnesium sulfate, filtered, and concentrated, and the aforementioned concentrate was refined with silica gel chromatography to obtain the desired compound (109, 19 mg, 23%). $^1$H-NMR (DMSO-$d_6$, 400 MHz): δ 9.06 (s, 1H), 9.01 (d, 1H), 8.14 (s, 1H), 8.00 (d, 1H), 7.79 (t, 1H), 6.98 (t, 1H), 6.69 (s, 2H), 6.32 (d, 2H), 5.48 (s, 2H), 5.16 (s, 2H).

Example 1.10: Production of 3-(2-amino-9-(4-amino-2-fluorobenzyl)-9H-purin-6-yl)-2-fluorobenzonitrile (Compound 103)

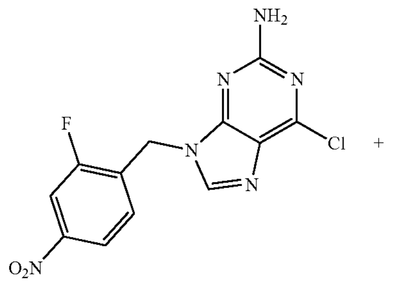

S16

-continued

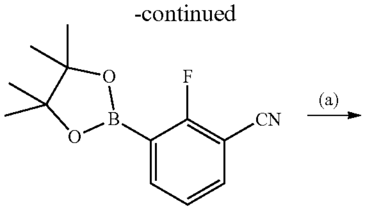

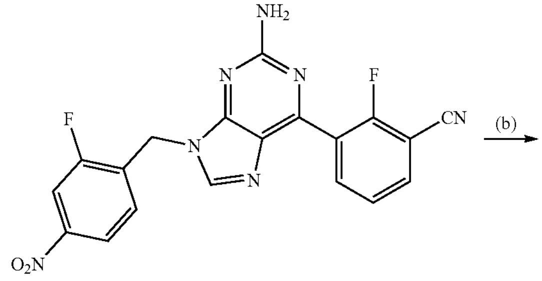

S18

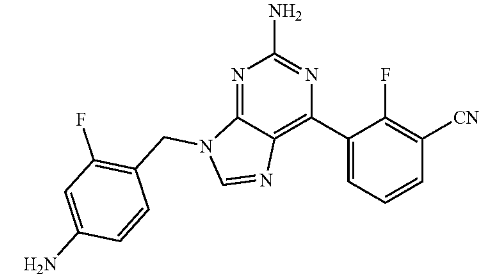

103

Reagents and conditions: (a) $Pd(PPh_3)_4$, $K_2CO_3$ 1,4-dioxane, $H_2O$, 115° C., overnight; (b) $SnCl_2 \cdot 2H_2O$, EtOH, 50° C., 3 h.

Stage 1: Production of 3-(2-amino-9-(2-fluoro-4-nitrobenzyl)-9H-purin-6-yl)-2-fluorobenzonitrile The same process as stage 2 of the aforementioned example 1.6 was performed except that 2-fluoro-3-(4,4,5,5-tetramethyl-1,3,2-dioxaborolan-2-yl) benzonitrile (138 mg, 0.56 mmol) was used instead of 3-(4,4,5,5-teramethyl-1,3,2-dioxaborolan-2-yl) benzonitrile (318 mg, 1.39 mmol) in stage 2 of the aforementioned example 1.6 to obtain an intermediate compound (S18, 80 mg, 42.7%). $^1$H-NMR (methanol-$d_4$, 400 MHz): δ 8.21 (s, 1H), 8.15-8.07 (m, 3H), 7.98-7.93 (m, 1H), 7.59-7.52 (m, 2H), 5.60 (s, 2H).

Stage 2: Production of 3-(2-amino-9-(4-amino-2-fluorobenzyl)-9H-purin-6-yl)-2-fluorobenzonitrile In stage 3 of the aforementioned example 1.6, only the amount of tin(II) chloride dihydrate ($SnCl_2 \cdot 2H_2O$, 180 mg, 0.80 mmol) was changed and the same process as stage 3 of the aforementioned example 1.6 was performed for the intermediate compound of the aforementioned stage 1 (S18, 65 mg, 0.16 mmol) to obtain the desired compound (103, 14.4 mg, 24%). $^1$H-NMR (DMSO-$d_6$, 400 MHz): δ 8.17 (t, 1H), 8.10 (t, 1H), 8.05 (s, 1H), 7.58 (t, 1H), 7.01 (t, 1H), 6.74 (s, 2H), 6.36-6.32 (m, 2H), 5.50 (s, 2H), 5.15 (s, 2H).

Example 1.11: Production of 3-(2-amino-9-(4-amino-3-methylbenzyl)-9H-purin-6-yl)benzonitrile (Compound 104)

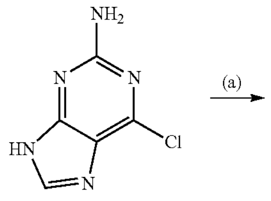

S12

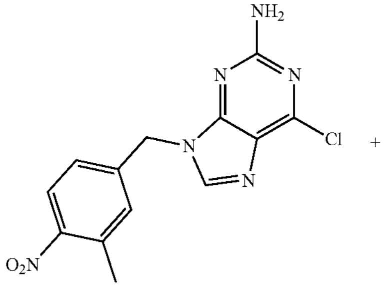

S19

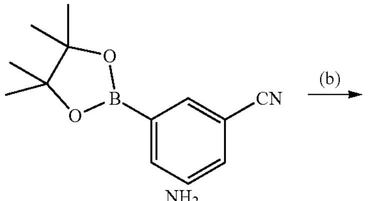

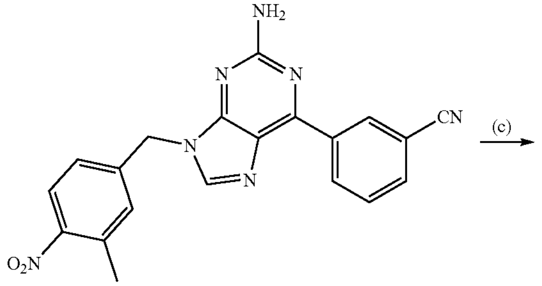

S20

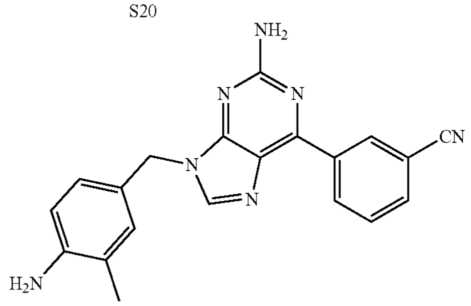

104

Reagent and condition: (a) 4-(bromomethyl)-2-methyl-1-nitrobenzene, $K_2CO_3$, DMF, rt, overnight; (b) $Pd(PPh_3)_4$, $K_2CO_3$, 1,4-dioxane, $H_2O$, 115° C., 2 h; (c) $SnCl_2 \cdot 2H_2O$, EtOH, 55° C., overnight.

Stage 1: Production of 6-chloro-9-(3-methyl-4-nitrobenzyl)-9H-purin-2-amine 6-chloro-9H-purin-2-amine (S12, 846 mg, 4.99 mmol) was dissolved in N,N-dimethylformamide (DMF), 4-(bromomethyl)-2-methyl-1-nitrobenzene (1.263 g, 5.49 mmol) and potassium carbonate ($K_2CO_3$, 1.03 g, 7.49 mmol) was added to the solution, and then the solution was agitated for 1 day at room temperature. Afterwards, the reaction mixture was diluted with dichloromethane (DCM), and was cleaned with distilled water, and then was dried with magnesium sulfate, filtered, and concentrated, and the aforementioned concentrated was refined with silica gel chromatography to obtain an intermediate compound (S19, 1.28 g, 80.5%). $^1$H-NMR ($CDCl_3$, 400 MHz): δ 7.97 (d, 1H), 7.77 (s, 1H), 7.22-7.18 (m, 2H), 5.30 (s, 2H), 2.59 (s, 3H).

Stage 2: Production of 3-(2-amino-9-(3-methyl-4-nitrobenzyl)-9H-purin-6-yl) benzonitrile The intermediate compound produced in the aforementioned stage 1 (S19, 278 mg, 0.87 mmol) was dissolved in a solvent of 1,4-dioxane and $H_2O$, and 3-(4,4,5,5-tetramethyl-1,3,2-dioxaborolan-2-yl)-benzonitrile (300 mg, 1.31 mmol) and tetrakis (triphenylphosphine) palladium (0) ((Pd $(PPh_3)_4$, 50.3 mg, 0.043 mmol), and potassium carbonate ($K_2CO_3$, 240.4 mg, 1.74 mmol) were added to the solution, and the solution was heated at 105° C. and agitated for 2 h. Afterwards, the aforementioned reaction mixture was diluted with dichloromethane (DCM), and was cleaned with distilled water, and then was dried with magnesium sulfate, filtered, and concentrated, and the aforementioned concentrate was refined with silica gel chromatography to obtain an intermediate compound (S20, 143 mg, 42.7%). $^1$H-NMR ($CDCl_3$, 400 MHz): δ 9.07 (s, 1H), 9.02 (d, 1H), 7.98 (d, 1H), 7.84 (s, 1H), 7.78 (d, 1H), 7.59-7.51 (m, 1H), 7.50-7.44 (m, 2H), 5.36 (s, 2H), 5.08 (s, 2H), 2.59 (s, 3H).

Stage 3: Production of 3-(2-amino-9-(4-amino-3-methylbenzyl)-9H-purin-6-yl) benzonitrile The intermediate compound produced in the aforementioned stage 2 (S20, 143 mg, 0.37 mmol) was dissolved with ethanol (EtOH), and tin (II) chloride dihydrate ($SnCl_2 \cdot 2H_2O$, 418.6 mg, 1.86 mmol) was added, and the solution was agitated at 55° C. for 1 day. Afterwards, the aforementioned reaction mixture was diluted with dichloromethane (DCM) and was cleaned with diluted water, and then was dried with magnesium sulfate, filtered, and concentrated, and the aforementioned concentrate was refined with silica gel chromatography to obtain the desired compound (104, 23.6 mg, 18%). $^1$H-NMR (DMSO-$d_6$, 400 MHz): δ 9.08 (s, 1H), 9.02 (d, 1H), 8.23 (s, 1H), 7.99 (d, 1H), 7.79 (t, 1H), 6.96 (s, 1H), 6.91 (d, 1H), 6.86 (s, 2H), 6.55 (d, 1H), 5.11 (s, 2H), 4.87 (s, 2H), 2.01 (s, 3H).

Example 1.12: Production of 3-(2-amino-9-(4-amino-3-methylbenzyl)-9H-purin-6-yl)-2-fluorobenzonitrile (Compound 106)

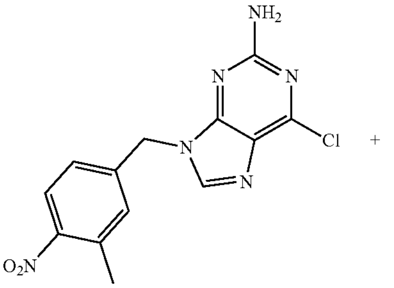

S19

-continued

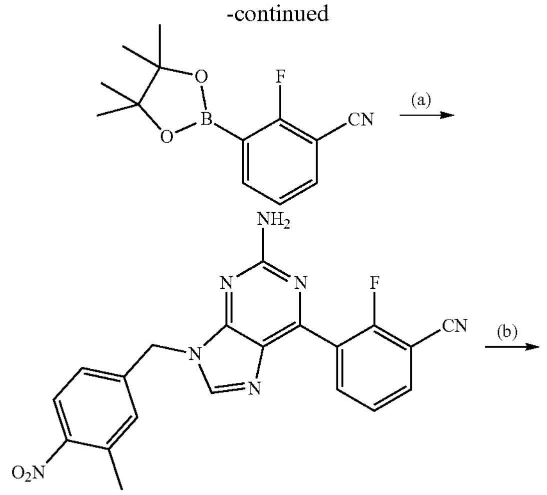

S21

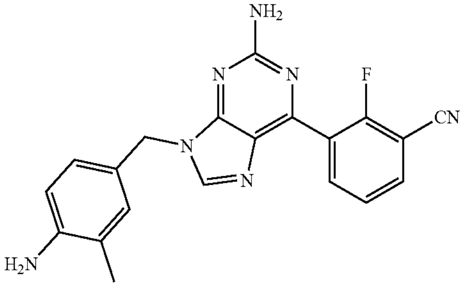

106

Reagent and condition: (a) $Pd(PPh_3)_4$, $K_2CO_3$, 1,4-dioxane, $H_2O$, 115° C., 2 h; (c) $SnCl_2 \cdot 2H_2O$, EtOH, 55° C., overnight.

Stage 1: Production of 3-(2-amino-9-(3-methyl-4-nitrobenzyl)-9H-purin-6-yl)-2-fluorobenzonitrile The intermediate compound (S19, 300 mg, 0.94 mmol) was dissolved in a solvent of 1,4-dioxane and $H_2O$, and then 2-fluoro-3-(4,4,5,5-tetramethyl-1,3,2-dioxaborolran-2-yl) benzonitrile (349 mg, 1.41 mmol) and tetrakis (triphenylphosphine) palladium (0) (($Pd(PPh_3)_4$, 54.3 mg, 0.05 mmol), and potassium carbonate ($K_2CO_3$, 260 mg, 1.88 mmol) were added to the solution, and the solution was heated at 115° C. and agitated for 2 h. Afterwards, the aforementioned reaction mixture was diluted with dichloromethane (DCM), and was cleaned with distilled water, and then was dried with magnesium sulfate, filtered, and concentrated, and the aforementioned concentrate was refined with silica gel chromatography to obtain an intermediate compound (S21, 298.2 mg, 78.6%). $^1$H-NMR ($CDCl_3$, 400 MHz): δ 8.22-8.16 (m, 1H), 7.99 (d, 1H), 7.83 (s, 1H), 7.79 (t, 1H), 7.70-7.64 (m, 1H), 7.43 (t, 1H), 7.25 (s, 1H), 5.13 (s, 2H), 2.60 (s, 3H).

Stage 2: Production of 3-(2-amino-9-(4-amino-3-methylbenzyl)-9H-purin-6-yl)-2-fluorobenzonitrile The intermediate compound produced in the aforementioned stage 1 (S21, 298.2 mg, 0.74 mmol) was dissolved in ethanol (EtOH), and then tin (II) chloride dihydrate ($SnCl_2 \cdot 2H_2O$, 835 mg, 3.7 mmol) was added to the solution, and the solution was agitated for 1 day at 55° C. Afterwards, the aforementioned reaction mixture was diluted with dichloromethane (DCM), and was cleaned with distilled water, and then was dried with magnesium sulfate, filtered, and concentrated, and the aforementioned concentrate was refined with silica gel chromatography to obtain the desired compound (106, 98 mg, 35.5%). $^1$H-NMR (DMSO-$d_6$, 400 MHz): δ 8.19-8.14 (m, 2H), 8.10-8.07 (m, 1H), 7.57 (t, 1H), 6.97 (s, 1H), 6.92 (d, 1H), 6.73 (s, 2H), 6.55 (d, 1H), 5.09 (s, 2H), 4.88 (s, 2H), 2.01 (s, 3H).

Example 1.13: Production of 3-(2-amino-9-(2,6-difluorobenzyl)-9H-purin-6-yl) benzonitrile (Compound 112)

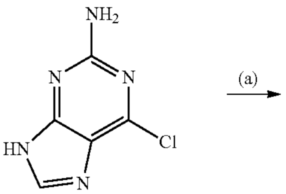

S12

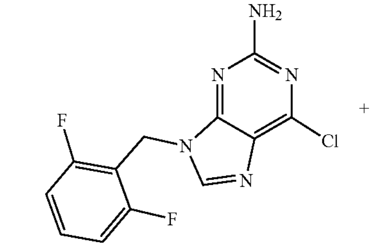

S22

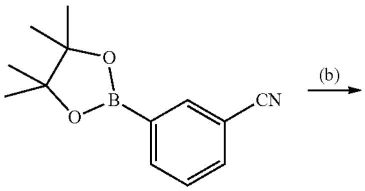

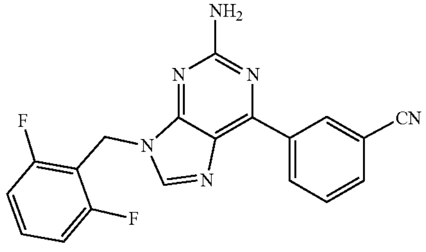

112

Reagent and condition: (a) 2,6-difluorobenzyl bromide, $K_2CO_3$, DMF, rt, 4 h; (b) $Pd(PPh_3)_4$, $K_2CO_3$, 1,4-dioxane, $H_2O$, 115° C., overnight.

Stage 1: Production of 6-chloro-9-(2,6-difluorobenzyl)-9H-purin-2-amine 6-chloro-9H-purin-2-amine (S12, 800 mg, 4.72 mmol) was dissolved in dimethylformamide (DMF), and 2,6-difluorobenzyl bromide (1.46 g, 7.08 mmol) and potassium carbonate ($K_2CO_3$, 1.95 g, 14.16 mmol) were added to the solution, and the solution was agitated for 4 h at room temperature. Afterwards, the aforementioned reaction mixture was filtered with a celite pad, and the remaining liquid was diluted with ethyl acetate (EA). Then, the solution was cleaned with diluted water and then was dried with sodium sulfate, filtered, and concentrated, and the aforementioned concentrate was refined with silica gel chromatography to obtain an intermediate compound (S22, 850 mg, 58%). $^1$H-NMR (DMSO-$d_6$, 400 MHz): δ 8.10 (s, 1H), 7.49-7.46 (m, 1H), 7.15 (t, 2H), 6.68 (s, 2H), 5.35 (s, 2H).

Stage 2: Production of 3-(2-amino-9-(2,6-difluorobenzyl)-9H-purin-6-yl) benzonitrile The intermediate compound produced in the aforementioned stage 1 (S22, 100 mg, 0.31 mmol) was dissolved in a solvent of 1,4-dioxane and $H_2O$, and 3-(4,4,5,5-tetramethyl-1,3,2-dioxabororan-2-yl) benzonitrile (85.2 mg, 0.37 mmol) and tetrakis (triphenylphosphine) palladium (0) ((Pd $(PPh_3)_4$, 18 mg, 0.02 mmol), and potassium carbonate ($K_2CO_3$, 85.7 mg, 0.62 mmol) were added to the solution, and the solution was heated at 115° C. and agitated for 1 day. Afterwards, the aforementioned reaction mixture was diluted with dichloromethane (DCM) and cleaned with distilled water, and then was dried with magnesium sulfate, filtered, and concentrated, and the aforementioned concentrate was refined with silica gel chromatography to obtain the desired compound (112, 81 mg, 89%). $^1$H-NMR ($CDCl_3$, 400 MHz): δ 9.02 (s, 1H), 8.98 (dd, 1H), 7.87 (s, 1H), 7.75 (dd, 1H), 7.61 (t, 1H), 7.39-7.32 (m, 1H), 6.97 (t, 2H), 5.39 (s, 2H), 5.07 (s, 2H).

Example 1.14: Production of 3-(2-amino-9-(2,6-difluorobenzyl)-9H-purin-6-yl)-2-fluorobenzonitrile (Compound 113)

S22

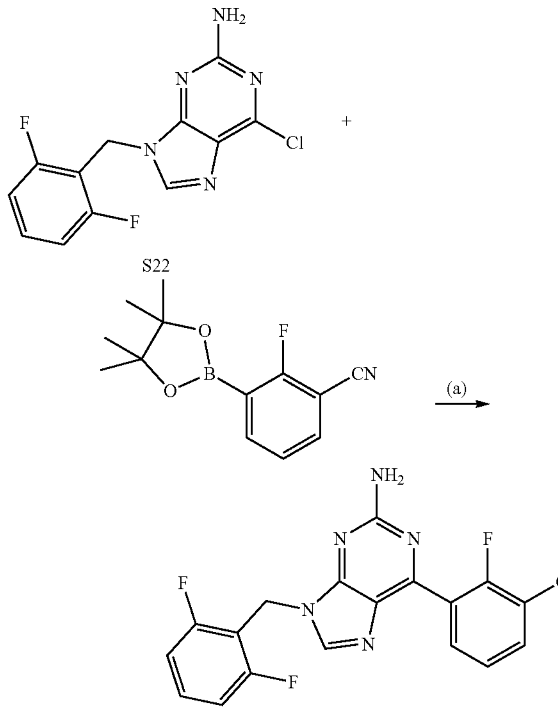

113

Reagent and condition: (a) $Pd(PPh_3)_4$, $K_2CO_3$, 1,4-dioxane, $H_2O$, 115° C., overnight.

The intermediate compound produced in stage 1 of the aforementioned example 1.13 (S22, 50 mg, 0.17 mmol) was dissolved in a solvent of 1,4-dioxane and $H_2O$, and 2-fluoro-3-(4,4,5,5-tetramethyl-1,3,2-dioxaborolan-2-yl) benzonitrile (49.4 mg, 0.20 mmol), tetrakis (triphenylphosphine) palladium (0) (($Pd(PPh_3)_4$, 8.7 mg, 0.008 mmol), and potassium carbonate ($K_2CO_3$, 47 mg, 0.34 mmol) were added to the solution, and the solution was heated at 115° C. and agitated for 1 day. Afterwards, the aforementioned reaction mixture was diluted with dichloromethane (DCM), and was cleaned with diluted water, and then was dried with magnesium sulfate, filtered, and concentrated, and the aforementioned concentrate was refined with silica gel chromatography to obtain the desired compound (113, 45 mg, 70%). $^1$H-NMR (DMSO-$d_6$, 400 MHz): δ 8.18-8.11 (m, 1H), 8.10-8.08 (m, 2H), 7.57 (t, 1H), 7.51-7.46 (m, 1H), 7.16 (t, 2H), 6.73 (s, 2H), 5.39 (s, 2H).

Example 1.15: Production of 3-(2-amino-9-(2,6-difluorobenzyl)-9H-purin-6-yl)-2-methylbenzonitrile (Compound 114)

S22

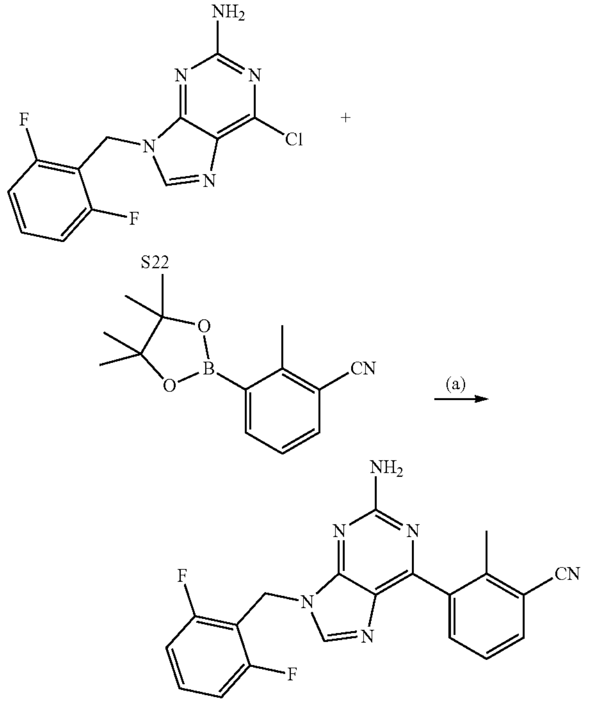

114

Reagent and condition: (a) $Pd(PPh_3)_4$, $K_2CO_3$, 1,4-dioxane, $H_2O$, 115° C., 4 h.

The intermediate compound produced in stage 1 of the aforementioned example 1.13 (S22, 50 mg, 0.17 mmol) was dissolved in a solvent of 1,4-dioxane and $H_2O$, and 2-methyl-3-(4,4,5,5-tetramethyl-1,3,2-dioxaborolan-2-yl) benzonitrile (48.6 mg, 0.20 mmol) and tetrakis (triphenylphosphine) palladium (0) (($Pd(PPh_3)_4$, 8.7 mg, 0.008 mmol), and potassium carbonate ($K_2CO_3$, 47 mg, 0.34 mmol) were added, and the solution was heated at 115° C. and agitated for 4 h. Afterwards, the reaction mixture was diluted with dichloromethane (DCM), and was cleaned with distilled water, and then was dried with magnesium sulfate, filtered, and concentrated, and the aforementioned concentrate was refined with silica gel chromatography to obtain the desired compound (114, 47.6 mg, 74%). $^1$H-NMR (Methanol-$d_4$, 400 MHz): δ 8.07 (s, 1H), 7.83 (dd, 1H), 7.77 (dd, 1H), 7.54-7.46 (m, 2H), 7.07 (t, 2H), 5.50 (s, 2H), 2.51 (s, 3H).

Example 1.16: Production of 3-[2-amino-9-[[4-amino-3-(trifluoromethyl)phenyl]methyl]purin-6-yl]benzonitrile (Compound 110)

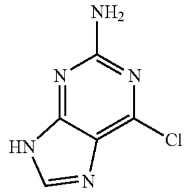

S12

+

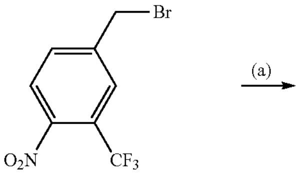

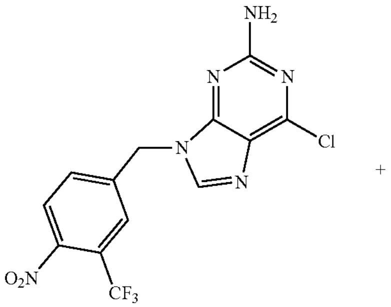

S23

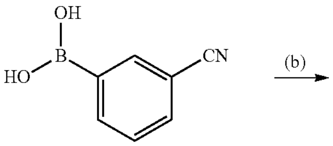

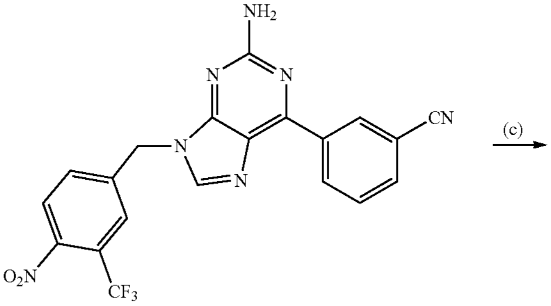

S24

-continued

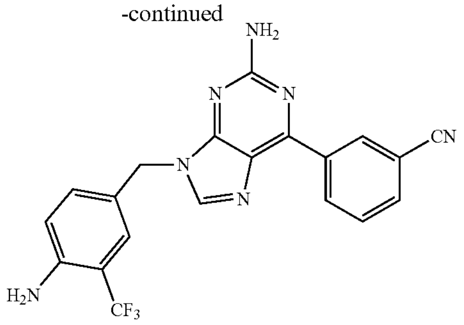

110

Reagents and condition: (a) $K_2CO_3$, DMAc, 25° C., 3 h; (b) Pd(dppf)$Cl_2$, $K_2CO_3$, dioxane/$H_2O$, 110° C., 15 h; (c) Fe, $NH_4Cl$, EtOH/$H_2O$, 80° C., 2 h.

Stage 1: Production of 6-chloro-9-[[4-nitro-3-(trifluoromethyl)phenyl]methyl]purin-2-amine To the solution of 4-(bromomethyl)-1-nitro-2-(trifluoromethyl)benzene (3 g, 10.56 mmol) in DMAc (50 mL) were added intermediate S12, 6-chloro-9H-purin-2-amine (1.79 g, 10.56 mmol) and $K_2CO_3$ (2.92 g, 21.12 mmol). Then the mixture was stirred at 25° C. for 3 h. After that the mixture was added water (80 mL) and extracted with ethyl acetate (80 mL×3). Combined the organic phase to wash by brines (150 mL×2), dry over anhydrous sodium sulfate, filter and concentrate in vacuum to give a residue. The residue was purified by flash silica gel chromatography (80 g SepaFlash® Silica Flash Column, Eluent of 20~100% Ethyl acetate/Petroleum ether gradient @60 mL/min). Compound S23, 6-chloro-9-[[4-nitro-3-(trifluoromethyl)phenyl]methyl]purin-2-amine (2.5 g, 6.62 mmol, 63% yield, 98.7% purity) was obtained as a yellow solid. $^1H$ NMR (400 MHz, DMSO-$d_6$): δ 8.27 (s, 1H), 8.12 (d, J=8.3 Hz, 1H), 8.05 (s, 1H), 7.67 (dd, J=8.3 Hz, 1H), 6.97 (s, 2H), 5.50 (s, 2H). MS: m/z=373.0 (M+1, ESI+).

Stage 2: Production of 3-[2-amino-9-[[4-nitro-3-(trifluoromethyl)phenyl]methyl]purin-6-yl]benzonitrile To the solution of compound S23, 6-chloro-9-[[4-nitro-3-(trifluoromethyl)phenyl]methyl]purin-2-amine (2.5 g, 6.71 mmol, 1 eq) in dioxane (40 mL) and water (10 mL) were added (3-cyanophenyl)boronic acid (1.97 g, 13.42 mmol, 2 eq), Pd(dppf)$Cl_2$ (490 mg, 670.80 μmol, 0.1 eq) and $K_2CO_3$ (1.85 g, 13.42 mmol, 2 eq). Then the mixture was stirred at 110° C. for 15 h. The mixture was concentrated in vacuum to give a residue. The residue was purified by flash silica gel chromatography (40 g SepaFlash® Silica Flash Column, Eluent of 20~60% Ethyl acetate/Petroleum ether gradient @50 mL/min). Compound S24, 3-[2-amino-9-[[4-nitro-3-(trifluoromethyl)phenyl]methyl]purin-6-yl]benzonitrile (2.3 g, 4.56 mmol, 68% yield, 87% purity) was obtained as a yellow solid. $^1H$ NMR (400 MHz, DMSO-$d_6$): δ 9.08 (t, J=1.5 Hz, 1H), 9.02 (td, J=1.4, 8.0 Hz, 1H), 8.38 (s, 1H), 8.13 (d, J=8.4 Hz, 1H), 8.08 (d, J=1.2 Hz, 1H), 8.01 (td, J=1.3, 7.8 Hz, 1H), 7.79 (t, J=7.8 Hz, 1H), 7.71 (dd, J=1.5, 8.4 Hz, 1H), 6.73 (s, 2H), 5.56 (s, 2H). MS: m/z=440.0 (M+1, ESI+).

Stage 3: Production of 3-[2-amino-9-[[4-amino-3-(trifluoromethyl) phenyl]methyl]purin-6-yl]benzonitrile To the solution of 3-[2-amino-9-[[4-nitro-3-(trifluoromethyl)phenyl]methyl]purin-6-yl]benzonitrile (2.3 g, 4.55 mmol, 87% purity, 1 eq) in ethanol (30 mL) and water (6 mL) were added iron dust (1.27 g, 22.77 mmol, 5 eq) and $NH_4Cl$ (1.95 g, 36.44 mmol, 8 eq). Then the mixture was stirred at 80° C. for 2 h. The reaction mixture was filtered and the filtrate was concentrated in vacuum. To the mixture was added water (80 mL) and extracted with ethyl acetate (80 mL×3). Combined the organic phase to filter and concentrate in vacuum to give a residue. The residue was purified by prep-HPLC (column: Welch Ultimate XB-CN 250*70*10 μm; mobile phase: [Hexane-EtOH (0.1% ammonia hydroxide)]; B %: 30%-70%, 15 min) to give a product. The product was purified by re-crystallization from THF (20 mL) at 70° C. to give crude product. The crude product was purified by prep-HPLC (column: Welch Ultimate XB-SiOH 250*50*10 μm; mobile phase: [Hexane-EtOH (0.1% ammonia hydroxide)]; B %: 5%-45%, 15 min). Compound 110 or 3-[2-amino-9-[[4-amino-3-(trifluoromethyl) phenyl]methyl] purin-6-yl]benzonitrile (602.34 mg, 1.44 mmol, 32% yield, 97.62% purity) was obtained as a yellow solid. $^1H$ NMR (400 MHz, DMSO-$d_6$) δ=9.07 (s, 1H), 9.01 (br d, J=7.9 Hz, 1H), 8.30 (s, 1H), 8.00 (br d, J=7.7 Hz, 1H), 7.78 (t, J=7.9 Hz, 1H), 7.41 (s, 1H), 7.29 (br d, J=8.6 Hz, 1H), 6.79 (d, J=8.6 Hz, 1H), 6.71 (s, 2H), 5.65 (s, 2H), 5.19 (s, 2H). HRMS-TOF: 410.1347

Example 1.17: Production of 3-[2-amino-9-[[4-amino-3-(trifluoromethyl)phenyl]methyl]purin-6-yl] 2-fluorobenzonitrile (Compound 111)

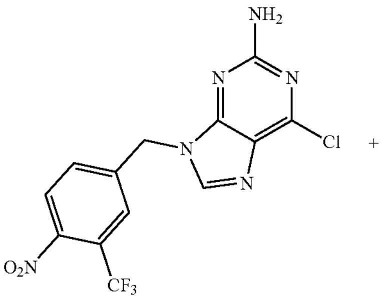

S19

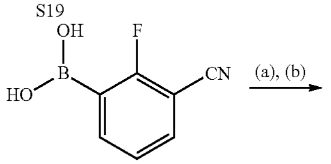

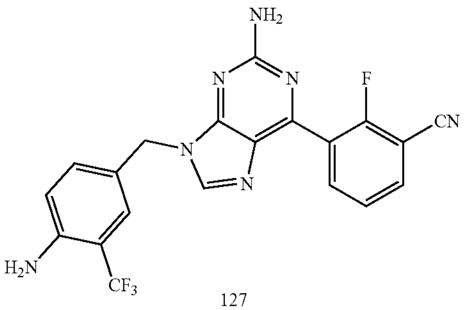

127

Reagents and condition: (a) $Pd(PPh_3)_4$, $K_2CO_3$, dioxane/$H_2O$, 110° C., 15 h; (b) Fe, $NH_4C_1$, EtOH/$H_2O$, 60° C., 1 h.

Stage 1: Production of 3-[2-amino-9-[[4-nitro-3-(trifluoromethyl)phenyl]methyl]purin-6-yl]-2-fluorobenzonitrile A mixture of (3-cyano-2-fluorophenyl)boronic acid (265 mg, 1.61 mmol, 1.5 eq), intermediate compound S23 or 6-chloro-9-[[4-nitro-3-(trifluoromethyl) phenyl]methyl]purin-2-amine (400 mg, 1.07 mmol), $Pd(PPh_3)_4$ (124 mg, 107.00 μmol) and $K_2CO_3$ (296 mg, 2.14 mmol) in dioxane (10 mL) and water (1 mL) was degassed and purged with nitrogen for three times, and then the mixture was stirred at 100° C. for 15 h under nitrogen atmosphere. The reaction mixture was concentrated under reduced pressure to remove dioxane and water to give a residue. The residue was purified by flash silica gel chromatography (ISCO®; 12 g SepaFlash® Silica Flash Column, Eluent of 0~100% Ethyl acetate/Petroleum ether gradient @35 mL/min). Intermediate compound 3-[2-amino-9-[[4-nitro-3-(trifluoromethyl) phenyl]methyl]purin-6-yl]-2-fluorobenzonitrile (200 mg, 437.31 μmol, 41% yield) was obtained as a yellow solid. MS: m/z=440.3 (M+1, ESI+).

Stage 2: Production of 3-[2-amino-9-[[4-amino-3-(trifluoromethyl)phenyl]methyl]purin-6-yl]2-fluorobenzonitrile To a solution of 3-[2-amino-9-[[4-nitro-3-(trifluoromethyl)phenyl]methyl]purin-6-yl]-2-fluorobenzonitrile (300 mg, 655.97 μmol, 1 eq) in ethanol (15 mL) and water (5 mL) was added $NH_4Cl$ (292 mg, 5.25 mmol, 8 eq) and iron dust (183 mg, 3.28 mmol, 5 eq). The mixture was stirred at 60° C. for 1 h. The reaction mixture was concentrated under reduced pressure to remove ethanol to give a residue. The residue was purified by prep-HPLC (column: Phenomenex luna C18 150*25 mm*10 μm; mobile phase: [water (0.225% FA)-ACN]; B %: 40%-70%, 10 min). Compound 111 or 3-[2-amino-9-[[4-amino-3-(trifluoromethyl)phenyl]methyl] purin-6-yl]benzonitrile (75.32 mg, 175.81 μmol, 27% yield, 99.75% purity) was obtained as a white solid. $^1H$ NMR (400 MHz, DMSO-$d_6$): δ 8.21 (s, 1H), 8.17 (t, 1H), 8.09 (t, 1H), 7.57 (t, 1H), 7.41 (s, 1H), 7.30 (br d, 1H), 6.80 (d, 1H), 6.75 (s, 2H), 5.65 (s, 2H), 5.17 (s, 2H). HRMS-TOF: 428.1244.

Example 1.18: Production of 6-[2-amino-9-[(4-aminophenyl)methyl]purin-6-yl]pyridine-2-carbonitrile (Compound 115)

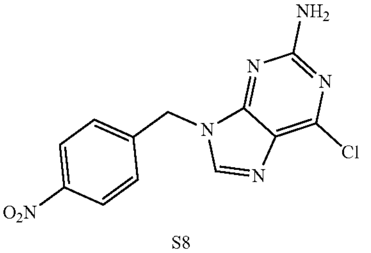

S8

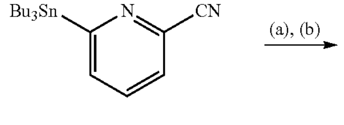

-continued

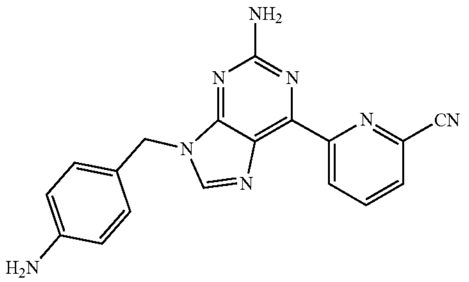

115

Reagents and condition: (a) XPhos-Pd-G3, THF, 90° C., 15 h; (b) Fe, $NH_4Cl$, THF/$H_2O$, 80° C., 2 h.

Stage 1: Production of 6-[2-amino-9-[(4-nitrophenyl)methyl]purin-6-yl]pyridine-2-carbonitrile To the solution of intermediate compound S8, 6-chloro-9-[(4-nitrophenyl)methyl]purin-2-amine (800 mg, 2.63 mmol, 1 eq) in THF (20 mL) were added 6-tributylstannylpyridine-2-carbonitrile (2.06 g, 5.25 mmol, 2 eq) and XPhos-Pd-G3 (222 mg, 262.56 μmol, 0.1 eq). Then the mixture was stirred at 90° C. for 15 h. To the mixture was added water (30 mL) and extracted with ethyl acetate (30 mL×3). Combined the organic phase to dry over anhydrous sodium sulfate, filter and concentrate in vacuum to give a residue. The residue was purified by flash silica gel chromatography (12 g Sepa Flash® Silica Flash Column, Eluent of 0~100% Ethyl acetate/Petroleum ether gradient @35 mL/min). Compound 6-[2-amino-9-[(4-nitrophenyl)methyl]purin-6-yl]pyridine-2-carbonitrile (167 mg, 372.27 μmol, 14% yield, 83% purity) was obtained as a yellow solid. $^1H$ NMR (400 MHz, DMSO-$d_6$): δ 8.91 (dd, J=0.9, 8.1 Hz, 1H), 8.37 (s, 1H), 8.31-8.25 (m, 1H), 8.22 (d, J=8.7 Hz, 2H), 8.18 (dd, J=0.9, 7.6 Hz, 1H), 7.50 (d, J=8.7 Hz, 2H), 6.85 (br s, 1H), 5.53 (s, 2H). MS: m/z=373.1 (M+1, ESI+).

Stage 2: Production of 6-[2-amino-9-[(4-aminophenyl)methyl]purin-6-yl]pyridine-2-carbonitrile To the solution of 6-[2-amino-9-[(4-nitrophenyl)methyl]purin-6-yl]pyridine-2-carbonitrile (160 mg, 429.72 μmol, 1 eq) in water (3 mL) and THF (9 mL) were added $NH_4C_1$ (184 mg, 3.44 mmol, 8 eq) and iron dust (120 mg, 2.15 mmol, 5 eq). Then the mixture was stirred at 80° C. for 2 h. The reaction mixture was filtered and the filtrate was added saturated $NaHCO_3$ solution (30 mL) and extracted with ethyl acetate (80 mL×3). Combined the organic phase to dry over anhydrous sodium sulfate, filter and concentrate in vacuum to give a residue. The residue was purified by prep-HPLC (column: Waters Xbridge C18 150*50 mm*10 μm; mobile phase: [water (10 mM $NH_4HCO_3$)-ACN]; B %: 5%-41%, 10 min). Compound 115 or 6-[2-amino-9-[(4-aminophenyl)methyl]purin-6-yl]pyridine-2-carbonitrile (18.59 mg, 53.55 μmol, 12% yield, 95.94% purity) was obtained as a yellow solid. $^1H$ NMR (400 MHz, DMSO-$d_6$) δ=8.92 (br d, J=7.9 Hz, 1H), 8.34-8.22 (m, 2H), 8.16 (br d, J=7.5 Hz, 1H), 7.05 (br d, J=8.0 Hz, 2H), 6.81 (br s, 2H), 6.52 (br d, J=8.0 Hz, 2H), 5.13 (br d, J=7.3 Hz, 4H). HRMS-TOF: 343.1415.

Example 1.19: Production of 6-[2-amino-9-[(4-amino-2-fluorophenyl)methyl]purin-6-yl]pyrindine-2-carbonitrile (Compound 119)

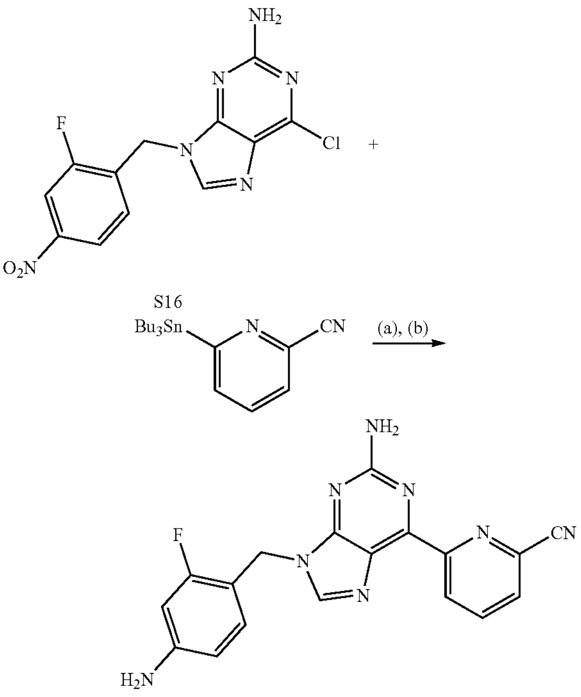

119

Reagents and condition: (a) XPhos-Pd-G3, THF, 90° C., 15 h; (b) Fe, $NH_4Cl$, THF/$H_2O$, 80° C., 1.5 h.

Stage 1: Production of 6-[2-amino-9-[(2-fluoro-4-nitro-phenyl)methyl]purin-6-yl]pyridine-2-carbonitrile To a mixture of intermediate compound S16 or 6-chloro-9-[(2-fluoro-4-nitro-phenyl)methyl]purin-2-amine (0.8 g, 2.48 mmol, 1 eq) in THF (10 mL) were added 6-tributylstannylpyridine-2-carbonitrile (1.8 g, 4.58 mmol, 1.85 eq) and XPhos-Pd-G3 (210 mg, 247.92 μmol, 0.1 eq). Then the mixture was stirred at 90° C. for 15 h. To the mixture was added saturated aqueous potassium fluoride solution (30 mL) and extracted with ethyl acetate (30 mL×3). Combined the organic phase was and concentrated in vacuum to give a residue. The residue was purified by flash silica gel chromatography (25 g Sepa Flash® Silica Flash Column, Eluent of 0~100% Ethyl acetate/Petroleum ether gradient 50 mL/min). Compound 6-[2-amino-9-[(2-fluoro-4-nitro-phenyl)methyl]purin-6-yl]pyridine-2-carbonitrile (260 mg, 652.78 μmol, 26% yield, 98.0% purity) was obtained as a yellow solid. $^1H$ NMR (400 MHz, DMSO-$d_6$) δ=8.90 (d, J=7.9 Hz, 1H), 8.33 (s, 1H), 8.28 (t, J=7.9 Hz, 1H), 8.21-8.15 (m, 2H), 8.05 (dd, J=1.8, 8.5 Hz, 1H), 7.33 (t, J=8.1 Hz, 1H), 6.84 (br s, 2H), 5.55 (s, 2H). MS: m/z=391.0 (M+1, ESI+).

Stage 2: Production of 6-[2-amino-9-[(4-amino-2-fluorophenyl)methyl]purin-6-yl]pyridine-2-carbonitrile To the solution of 6-[2-amino-9-[(2-fluoro-4-nitro-phenyl)methyl]purin-6-yl]pyridine-2-carbonitrile (150 mg, 384.29 μmol, 1 eq) in water (1.5 mL) and THF (6 mL) were added iron powder (107 mg, 1.92 mmol, 5 eq) and $NH_4Cl$ (164 mg, 3.07 mmol, 8 eq). Then the mixture was stirred at 80° C. for 1.5 h. The reaction mixture was filtered. To the filtrate was added saturated $NaHCO_3$ solution (30 mL) and extracted with ethyl acetate (30 mL×2). Combined the organic phase was dried over anhydrous $Na_2SO_4$, filtered and concentrated in vacuum to give a residue. The residue was purified by prep-HPLC (column: Phenomenex Gemini NX-C18 (75*30 mm*3 μm); mobile phase: [water (0.05% ammonia hydroxide v/v)-ACN]; B %: 13%-40%, 7 min). Compound 119 or 6-[2-amino-9-[(4-amino-2-fluoro-phenyl) methyl]purin-6-yl]pyridine-2-carbonitrile (21.61 mg, 58.63 μmol, 15% yield, 98.70% purity) was obtained as a yellow solid. $^1H$ NMR (400 MHz, DMSO-$d_6$) δ=8.91 (dd, J=1.0, 8.0 Hz, 1H), 8.30-8.24 (m, 1H), 8.16 (d, J=7.8 Hz, 1H), 8.14 (s, 1H), 6.99 (t, J=8.5 Hz, 1H), 6.81 (s, 2H), 6.41-6.28 (m, 2H), 5.49 (br s, 2H), 5.18 (s, 2H). HRMS-TOF: 361.1321.

Example 1.20: Production of 6-[2-amino-9-[(4-amino-2,6-difluoro-phenyl)methyl]purin-6-yl]pyridine-2-carbonitrile (Compound 123)

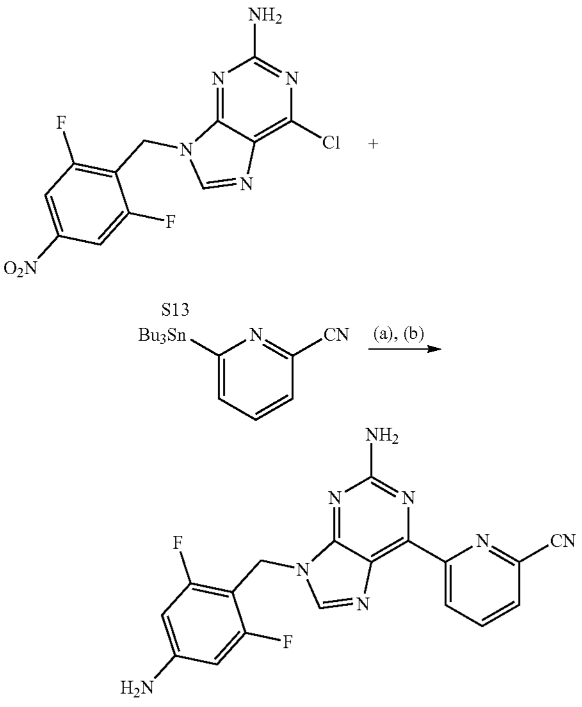

123

Reagents and condition: (a) XPhos-Pd-G3, THF, 90° C., 15 h; (b) Fe, $NH_4C_1$, THF/$H_2O$, 80° C., 1.5 h.

Stage 1: Production of 6-[2-amino-9-[(2,6-difluoro-4-nitro-phenyl)methyl]purin-6-yl]pyridine-2-carbonitrile A mixture of intermediate compound S13 or 6-chloro-9-[(2,6-difluoro-4-nitro-phenyl)methyl]purin-2-amine (1 g, 2.94 mmol, 1 eq), 6-tributylstannylpyridine-2-carbonitrile (2.31 g, 5.87 mmol, 2 eq) and XPhos-Pd-G3 (250 mg, 293.54 μmol, 0.1 eq) in THF (15 mL) was degassed by nitrogen and then heated to 90° C. for 15 h. To the mixture was added water (30 mL) and extracted with ethyl acetate (30 mL×3). Combined the organic phase was dried over anhydrous sodium sulfate, filtered and concentrated in vacuum to give a residue. The residue was purified by column chromatography ($SiO_2$, Petroleum ether/Ethyl acetate=50/1 to 0/1). Compound 6-[2-amino-9-[(2,6-difluoro-4-nitro-phenyl)methyl]purin-6-yl]pyridine-2-carbonitrile (500 mg, 1.05 mmol, 36% yield, 85% purity) was obtained as a yellow solid. $^1H$ NMR (400 MHz, DMSO-$d_6$) δ=8.86 (d, J=8.0 Hz, 1H), 8.31-8.23 (m, 2H), 8.15 (d, J=7.6 Hz, 1H), 8.09 (d, J=7.4 Hz, 2H), 6.76 (br s, 2H), 5.52 (s, 2H) MS: m/z=409.1 (M+1, ESI+).

Stage 2: Production of 6-[2-amino-9-[(4-amino-2,6-difluoro-phenyl)methyl]purin-6-yl]pyridine-2-carbonitrile To the solution of 6-[2-amino-9-[(2,6-difluoro-4-nitro-phenyl)methyl]purin-6-yl]pyridine-2-carbonitrile (200 mg, 489.81 μmol, 1 eq) in THF (8 mL) and water (2 mL) were added iron dust (137 mg, 2.45 mmol, 5 eq) and $NH_4Cl$ (210 mg, 3.92 mmol, 8 eq). Then the mixture was stirred at 80° C. for 1.5 h. The reaction mixture was filtered and the filtrate was added saturated $NaHCO_3$ aqueous solution (30 mL) and extracted with ethyl acetate (80 mL×3). Combined the organic phase to dry over anhydrous sodium sulfate, filter and concentrate in vacuum to give a residue. The residue was purified by prep-HPLC (column: Waters Xbridge 150*25 mm*5 μm; mobile phase: [water (10 mM $NH_4HCO_3$)-ACN]; B %: 18%-38%, 9 min). Compound 123 or 6-[2-amino-9-[(4-amino-2,6-difluoro-phenyl)methyl]purin-6-yl]pyridine-2-carbonitrile (31.07 mg, 79.80 μmol, 16% yield, 99.33% purity) was obtained as a white solid. $^1H$ NMR (400 MHz, DMSO-$d_6$) δ=8.88 (dd, J=1.1, 8.1 Hz, 1H), 8.29-8.22 (m, 1H), 8.15 (dd, J=1.0, 7.8 Hz, 1H), 8.03 (s, 1H), 6.77 (s, 2H), 6.22 (d, J=10.5 Hz, 2H), 5.88 (s, 2H), 5.17 (s, 2H). HRMS-TOF: 379.1235.

Example 1.21: Production of 6-[2-amino-9-[(2,6-difluorophenyl)methyl]purin-6-yl]pyridine-2-carbonitrile (Compound 131)

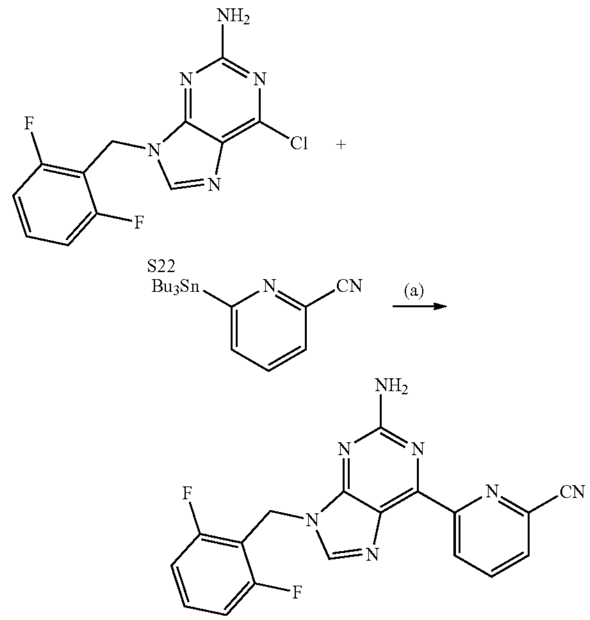

131

Reagents and condition: (a) XPhos-Pd-G3, THF, 90° C., 15 h.

To the solution of intermediate compound S22 or 6-chloro-9-[(2,6-difluorophenyl)methyl]purin-2-amine (200 mg, 676.42 μmol, 1 eq) and 6-tributylstannylpyridine-2-carbonitrile (266 mg, 676.42 μmol, 1 eq) in THF (10 mL) was added XPhos-Pd-G3 (57.26 mg, 67.64 μmol, 0.1 eq). Then the mixture was stirred at 90° C. for 15 h. To the mixture was added potassium fluoride aqueous solution (30 mL) and extracted with ethyl acetate (30 mL×3). Combined the organic phase was dried over anhydrous $Na_2SO_4$, filtered and concentrated in vacuum to give a residue. The residue was purified by flash silica gel chromatography (12 g Sepa Flash® Silica Flash Column, Eluent of 0~100% Ethyl acetate/Petroleum ether gradient @35 mL/min). Compound 133 or 6-[2-amino-9-[(2,6-difluorophenyl)methyl]purin-6-yl]pyridine-2-carbonitrile (40.26 mg, 110.81 μmol, 16% yield, 96.84% purity) was obtained as a yellow solid. $^1H$ NMR (400 MHz, DMSO-$d_6$) δ=8.87 (dd, J=1.0, 8.1 Hz, 1H), 8.29-8.22 (m, 1H), 8.18 (s, 1H), 8.15 (dd, J=1.0, 7.7 Hz, 1H), 7.58-7.39 (m, 1H), 7.16 (t, J=8.1 Hz, 2H), 6.77 (s, 2H), 5.42 (s, 2H). HRMS-TOF: 364.1121.

Example 1.22: Production of 6-[2-amino-9-[(4-amino-3-methyl-phenyl)methyl]purin-6-yl]pyridine-2-carbonitrile (Compound 127)

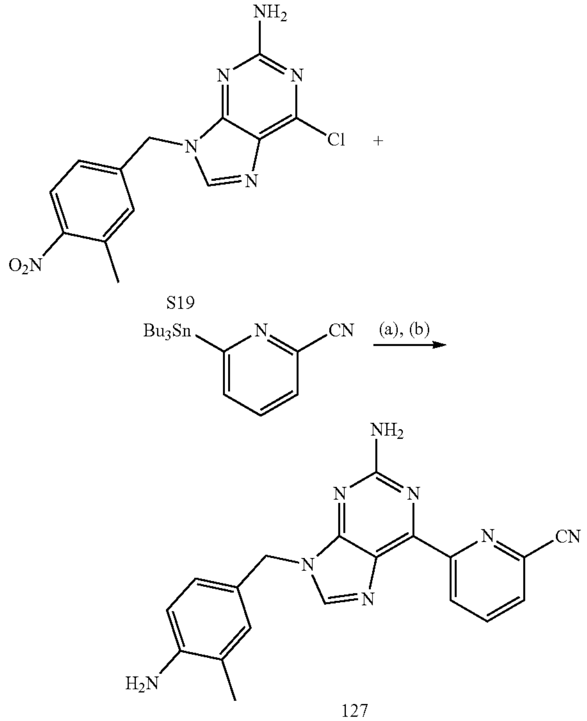

S19

127

Reagents and condition: (a) XPhos-Pd-G3, THF, 90° C., 15 h; (b) Fe, $NH_4C_1$, THF/$H_2O$, 80° C., 1 h.

Stage 1: Production of 6-[2-amino-9-[(3-methyl-4-nitro-phenyl)methyl]purin-6-yl]pyridine-2-carbonitrile A mixture of intermediate compound S19 or 6-chloro-9-[(3-methyl-4-nitro-phenyl)methyl]purin-2-amine (0.8 g, 2.51 mmol, 1 eq), 6-tributylstannylpyridine-2-carbonitrile (1.80 g, 4.58 mmol, 1.82 eq) and XPhos-Pd-G3 (212 mg, 251.01 μmol, 0.1 eq) in THF (10 mL) was de-gassed and then heated to 90° C. for 15 h under nitrogen. To the mixture was added saturated potassium fluoride aqueous solution (30 mL) and extracted with ethyl acetate (30 mL×2). The combined organic phase was dried over anhydrous $Na_2SO_4$, filtered and concentrated in vacuum to give a residue. The residue was purified by flash silica gel chromatography (25 g Sepa Flash® Silica Flash Column, Eluent of 0~100% Ethyl acetate/Petroleum ether gradient @50 mL/min). Compound 6-[2-amino-9-[(3-methyl-4-nitro-phenyl)methyl]purin-6-yl]pyridine-2-carbonitrile (350 mg, 900.89 μmol, 35% yield, 99.45% purity) was obtained as a yellow solid. $^1H$ NMR (400 MHz, DMSO-$d_6$) δ=8.91 (dd, J=0.8, 8.0 Hz, 1H), 8.36 (s, 1H), 8.32-8.24 (m, 1H), 8.17 (dd, J=0.9, 7.7 Hz, 1H), 7.98 (d, J=8.4 Hz, 1H), 7.41 (s, 1H), 7.28 (br d, J=8.4 Hz, 1H), 6.83 (s, 2H), 5.45 (s, 2H). MS: m/z=387.1 (M+1, ESI+).

Stage 2: Production of 6-[2-amino-9-[(4-amino-3-methyl-phenyl)methyl]purin-6-yl]pyridine-2-carbonitrile To the solution of 6-[2-amino-9-[(3-methyl-4-nitro-phenyl)methyl]purin-6-yl]pyridine-2-carbonitrile (150 mg, 388.23 μmol, 1 eq) in water (1 mL) and THF (4 mL) were added iron dust (108 mg, 1.94 mmol, 5 eq) and $NH_4Cl$ (166 mg, 3.11 mmol, 8 eq). Then the mixture was stirred at 80° C. for 1 h. The reaction mixture was filtered. To the filtrate was added saturated $NaHCO_3$ solution (80 mL) and extracted with ethyl acetate (80 mL×3). The combined organic phase was dried over anhydrous $Na_2SO_4$, filtered and concentrated in vacuum to give a residue. The residue was purified by prep-HPLC (column: Phenomenex Gemini NX-C18 (75*30 mm*3 μm); mobile phase: [water (10 mM $NH_4HCO_3$)-ACN]; B %: 10%-40%, 8 min). Compound 127 or 6-[2-amino-9-[(4-amino-3-methyl-phenyl)methyl]purin-6-yl]pyridine-2-carbonitrile (37.55 mg, 101.86 μmol, 26% yield, >99% purity) was obtained as a yellow solid. $^1H$ NMR (400 MHz, DMSO-$d_6$) δ=8.90 (dd, J=1.0, 8.1 Hz, 1H), 8.28-8.23 (m, 1H), 8.22 (s, 1H), 8.15 (dd, J=1.1, 7.7 Hz, 1H), 6.95 (s, 1H), 6.91 (dd, J=1.9, 8.1 Hz, 1H), 6.79 (s, 2H), 6.55 (d, J=8.1 Hz, 1H), 5.11 (s, 2H), 4.89-4.83 (m, 2H), 2.01 (s, 3H). HRMS-TOF: 357.1571.

Example 1.23: Production of 2-[2-amino-9-[(4-aminophenyl)methyl]purin-6-yl]pyridine-4-carbonitrile (Compound 116)

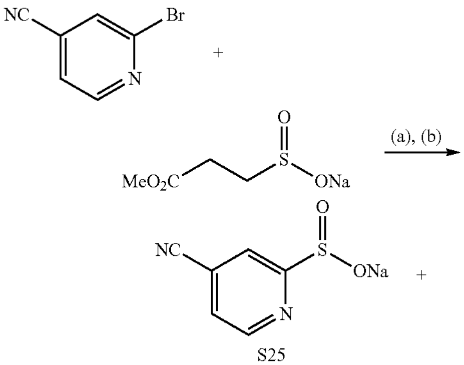

S25

-continued

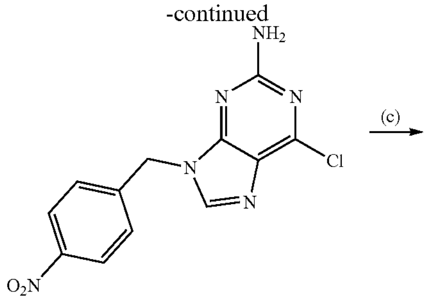

S8

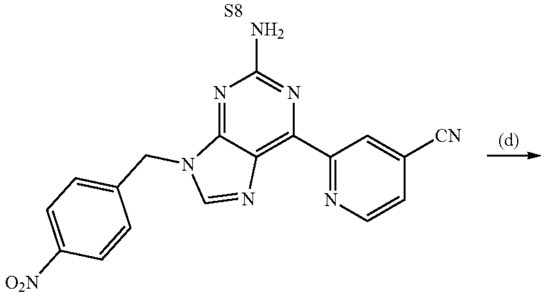

S26

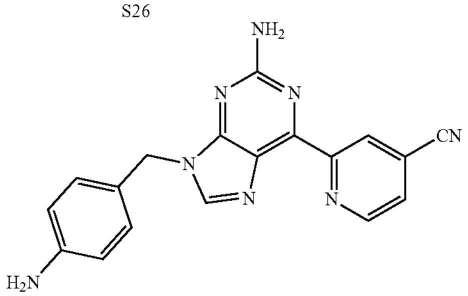

116

Reagents and condition: (a) CuI, DMSO, 110° C., 15 h; (b) NaOMe, MeOH, 25° C., 0.5 h; (c) $Pd(OAc)_2$, $Cy_3P$, $K_2CO_3$, Dioxane, 130° C., 10 h, MW; (d) Fe, $NH_4C_1$, $EtOH/H_2O$, 60° C., 1 h.

Stage 1: Production of methyl 3-((4-cyanopyridin-2-yl)sulfonyl)propanoate

A mixture of 2-bromopyridine-4-carbonitrile (4.4 g, 24.04 mmol, 1 eq), sodium 3-methoxy-3-oxo-propane-1-sulfinate (5.02 g, 28.85 mmol, 1.2 eq), CuI (5.49 g, 28.85 mmol, 1.2 eq) in DMSO (50 mL) was degassed and purged with nitrogen for three times, and then the mixture was stirred at 110° C. for 15 h under nitrogen atmosphere. The mixture was then cooled to room temperature, diluted with ethyl acetate (50 mL) and filtered through a pad of silica. The filtrate was washed by water (2×20 mL), brine (20 mL), dried over anhydrous sodium sulfate, filtered through a pad of silica and concentrated under reduced pressure. The residue was purified by flash silica gel chromatography (ISCO®; 20 g Sepa Flash® Silica Flash Column, Eluent of 0~100% Ethyl acetate/Petroleum ether gradient @35 mL/min). Compound methyl 3-[(4-cyano-2-pyridyl)sulfonyl]propanoate (3 g, 11.80 mmol, 49% yield) was obtained as a white solid. MS: m/z=254.9 (M+1, ESI+).

Stage 2: Production of (4-cyano-2-pyridyl)sulfinyloxysodium

To a solution of methyl 3-[(4-cyano-2-pyridyl)sulfonyl]propanoate (1.1 g, 4.33 mmol, 1 eq) in methanol (10 mL) was added sodium methoxide (233 mg, 4.33 mmol, 1 eq). The mixture was stirred at 25° C. for 0.5 h. The reaction mixture was concentrated under reduced pressure to remove methanol to give a residue. The crude product of intermediate compound S25 or (4-cyano-2-pyridyl)sulfinyloxysodium (700 mg, crude) was obtained as a yellow solid and used into the next step without further purification. MS: m/z=167.0 (M+1, ESI+).

Stage 3: Production of 2-[2-amino-9-[(4-nitrophenyl)methyl]purin-6-yl]pyridine-4-carbonitrile A mixture of intermediate compound S25 or (4-cyano-2-pyridyl)sulfinyloxy sodium (374 mg, 1.97 mmol, 1.2 eq), intermediate compound S8 or 6-chloro-9-[(4-nitrophenyl)methyl]purin-2-amine (500 mg, 1.64 mmol, 1 eq), tricyclohexylphosphine (92 mg, 328.20 μmol, 0.2 eq), $K_2CO_3$ (453 mg, 3.28 mmol, 2 eq) and $Pd(OAc)_2$ (36 mg, 164.10 μmol, 0.1 eq) were taken up into a microwave tube in dioxane (2 mL). The sealed tube was heated at 130° C. for 10 h under microwave. The reaction mixture was concentrated under reduced pressure to remove dioxane to give a residue. The residue was purified by flash silica gel chromatography (ISCO®; 20 g Sepa Flash® Silica Flash Column, Eluent of 0~100% Ethyl acetate/Petroleum ether gradient @40 mL/min). Compound 2-[2-amino-9-[(4-nitrophenyl)methyl]purin-6-yl]pyridine-4-carbonitrile (360 mg, 734.81 μmol, 45% yield, 76% purity) was obtained as a yellow solid. MS: m/z=373.1 (M+1, ESI+).

Stage 4: Production of 2-[2-amino-9-[(4-aminophenyl)methyl]purin-6-yl]pyridine-4-carbonitrile To a solution of intermediate compound S26 or 2-[2-amino-9-[(4-nitrophenyl)methyl]purin-6-yl]pyridine-4-carbonitrile (150 mg, 402.86 μmol, 1 eq) and $NH_4Cl$ (172 mg, 3.22 mmol, 8 eq) in ethanol (9 mL) and water (3 mL) was added iron dust (112 mg, 2.01 mmol, 5 eq). The mixture was stirred at 60° C. for 1 h. The reaction mixture was concentrated under reduced pressure to remove ethanol and water to give a residue. The residue was purified by prep-HPLC (column: Phenomenex luna C18 150*25 mm*10 μm; mobile phase: [water (0.225% FA)-ACN]; B %: 5%-25%, 10 min). Compound 116 or 2-[2-amino-9-[(4-aminophenyl)methyl]purin-6-yl]pyridine-4-carbonitrile (22.85 mg, 64.35 μmol, 16% yield, 96.90% purity, 0.2 FA) was obtained as a yellow solid. $^1H$ NMR (400 MHz, DMSO-$d_6$) δ=9.01 (dd, 1H), 8.94 (s, 1H), 8.22 (s, 1H), 7.98 (dd, 1H), 7.04 (d, 2H), 6.74 (s, 2H), 6.51 (d, 2H), 5.13 (s. 4H). HRMS-TOF: 343.1415.

Example 1.24: Production 2-[2-amino-9-[(4-amino-2-fluoro-phenyl)methyl]purin-6-yl]pyridine-4-carbonitrile (Compound 120)

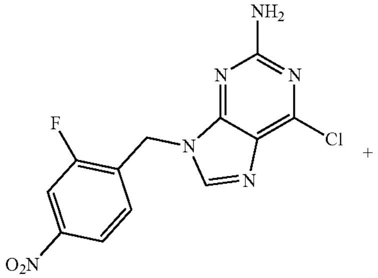

S16

-continued

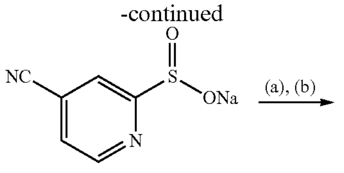

S25

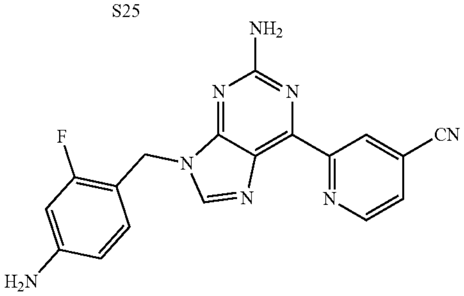

120

Reagents and condition: (a) $Pd(OAc)_2$, $Cy_3P$, $K_2CO_3$, dioxane, 130° C., 10 h, MW; (b) Fe, $NH_4Cl$, $EtOH/H_2O$, 60° C., 1 h.

Stage 1: Production of 2-[2-amino-9-[(2-fluoro-4-nitro-phenyl)methyl]purin-6-yl]pyridine-4-carbonitrile A mixture of intermediate compound S25 or (4-cyano-2-pyridyl)sulfinyloxy sodium (424 mg, 2.23 mmol, 1.2 eq), intermediate compound S16 or 6-chloro-9-[(2-fluoro-4-nitro-phenyl)methyl]purin-2-amine (600 mg, 1.86 mmol, 1 eq), tricyclohexylphosphine (104 mg, 371.88 μmol, 0.2 eq), $K_2CO_3$ (513 mg, 3.72 mmol, 2 eq) and palladium acetate (42 mg, 185.94 μmol, 0.1 eq) were taken up into a microwave tube in dioxane (4 mL). The sealed tube was heated at 130° C. for 10 h under microwave. The reaction mixture was concentrated under reduced pressure to remove dioxane to give a residue. The residue was purified by flash silica gel chromatography (ISCO®; 20 g Sepa Flash® Silica Flash Column, Eluent of 0~100% Ethyl acetate/Petroleum ether gradient @35 mL/min). Compound 2-[2-amino-9-[(2-fluoro-4-nitro-phenyl)methyl]purin-6-yl]pyridine-4-carbonitrile (300 mg, 768.58 μmol, 41% yield) was obtained as a white solid. MS: m/z=391.1 (M+1, ESI+)

Stage 2: Production of 2-[2-amino-9-[(4-amino-2-fluoro-phenyl)methyl]purin-6-yl]pyridine-4-carbonitrile To a solution of 2-[2-amino-9-[(2-fluoro-4-nitro-phenyl)methyl]purin-6-yl]pyridine-4-carbonitrile (150 mg, 230.57 μmol, 1 eq) and $NH_4Cl$ (98 mg, 1.84 mmol, 8 eq) in ethanol (15 mL) and water (5 mL) was added iron powder (64 mg, 1.15 mmol, 5 eq). The mixture was stirred at 60° C. for 1 h. The reaction mixture was filtered and concentrated under reduced pressure to give a residue. The residue was purified by prep-HPLC (column: Waters Xbridge 150*25 mm*5 μm; mobile phase: [water (10 mM $NH_4HCO_3$)-ACN]; B %: 10%-40%, 9 min) to give the product with 87% purity. Then it was purified by prep-HPLC (column: Waters Xbridge C18 150*50 mm*10 μm; mobile phase: [water (10 mM $NH_4HCO_3$)-ACN]; B %: 8%-38%, 10 min) again. Finally the compound 120 or 2-[2-amino-9-[(4-amino-2-fluoro-phenyl)methyl]purin-6-yl]pyridine-4-carbonitrile (9.83 mg, 26.40 μmol, 11% yield, 97.25% purity) was obtained as a white solid. $^1H$ NMR (400 MHz, DMSO-$d_6$) δ=9.02 (d, 1H), 8.89 (s, 1H), 8.13 (s, 1H), 7.99 (d, 1H), 6.98 (t, 1H), 6.75 (s, 2H), 6.33 (d, 2H), 5.48 (s, 2H), 5.17 (s 2H). HRMS-TOF: 361.1319.

Example 1.25: Production 2-[2-amino-9-[(4-amino-2,6-difluoro-phenyl)methyl]purin-6-yl]pyridine-4-carbonitrile (Compound 124)

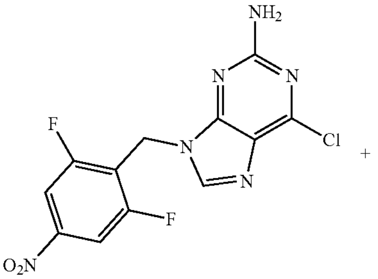

S13

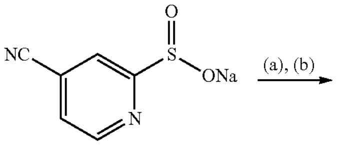

S25

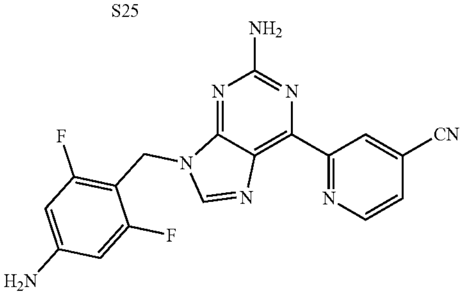

124

Reagents and condition: (a) $Pd(OAc)_2$, $Cy_3P$, $K_2CO_3$, dioxane, 130° C., 10 h, MW; (b) Fe, $NH_4Cl$, $EtOH/H_2O$, 60° C., 1 h.

Stage 1: 2-[2-amino-9-[(2, 6-difluoro-4-nitro-phenyl)methyl]purin-6-yl]pyridine-4-carbonitrile (4-cyano-2-pyridyl)sulfinyloxysodium (419 mg, 2.20 mmol, 1.5 eq), 6-chloro-9-[(2,6-difluoro-4-nitro-phenyl)methyl]purin-2-amine (500 mg, 1.47 mmol, 1 eq), tricyclohexylphosphine (123 mg, 440.31 mol, 0.3 eq), $K_2CO_3$ (405 mg, 2.94 mmol, 2 eq) and palladium acetate (50 mg, 223.09 μmol, 0.15 eq) were taken up into a microwave tube in dioxane (10 mL). The sealed tube was heated at 130° C. for 10 h under microwave. The reaction mixture was concentrated under reduced pressure to remove dioxane to give a residue. The residue was purified by prep-HPLC (column: Phenomenex Luna C18 150*25 mm*10 μm; mobile phase: [water (0.225% FA)-ACN]; B %: 23%-53%, 10 min). Compound 2-[2-amino-9-[(2, 6-difluoro-4-nitro-phenyl)methyl]purin-6-yl]pyridine-4-carbonitrile (120 mg, 293.89 μmol, 20% yield) was obtained as a white solid. $^1H$ NMR (400 MHz, DMSO-$d_6$) δ=9.02 (d, 1H), 8.85 (s, 1H), 8.28 (s, 1H), 8.11-8.07 (m, 2H), 7.99 (d, 1H), 6.72 (s, 2H), 5.52 (s, 2H). MS: m/z=409.1 (M+1, ESI+)

Stage 2: 2-[2-amino-9-[(4-amino-2,6-difluoro-phenyl)methyl]purin-6-yl]pyridine-4-carbonitrile To a solution of 2-[2-amino-9-[(2,6-difluoro-4-nitro-phenyl)methyl]purin-6-yl]pyridine-4-carbonitrile (100 mg, 244.91 mol, 1 eq) and $NH_4Cl$ (104 mg, 1.96 mmol, 8 eq) in ethanol (9 mL) and water (3 mL) was added iron dust (68 mg, 1.22 mmol, 5 eq). The mixture was stirred at 60° C. for 1 h. The reaction mixture was filtered and concentrated under reduced pressure to give a residue. The residue was purified by prep-HPLC (column: Phenomenex luna C18 150*25 mm*10 μm; mobile phase: [water (0.225% FA)-ACN]; B %: 13%-43%, 10 min) to afford the product with 90% purity. It was purified by second prep-HPLC (column: Waters Xbridge 150*25 mm*5 μm; mobile phase: [water (10 mM $NH_4HCO_3$)-ACN]; B %: 22%-52%, 9 min). Compound 2-[2-amino-9-[(4-amino-2,6-difluoro-phenyl)methyl]purin-6-yl]pyridine-4-carbonitrile (34.57 mg, 89.87 μmol, 37% yield, 97.96% purity) was obtained as a white solid. $^1H$ NMR (400 MHz, DMSO-$d_6$) δ=9.01 (dd, 1H), 8.87 (s, 1H), 8.03 (s, 1H), 7.99 (dd, 1H), 6.72 (s, 2H), 6.22 (d, 2H), 5.88 (s, 2H), 5.17 (s, 2H). HRMS (TOF): 379.1229.

Example 1.26: Production 2-[2-amino-9-[(4-amino-2,6-difluoro-phenyl)methyl]purin-6-yl]pyridine-4-carbonitrile (Compound 132)

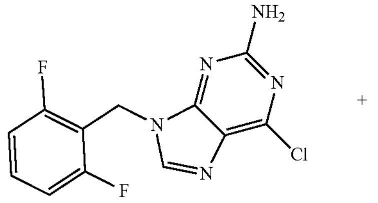

S22

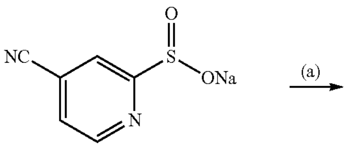

S25

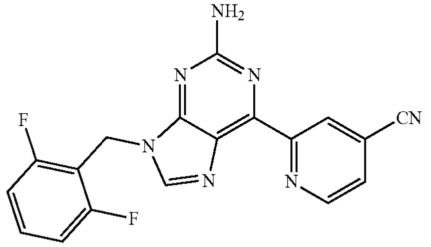

132

Reagents and condition: (a) $Pd(OAc)_2$, $Cy_3P$, $K_2CO_3$, dioxane, 130° C., 10 h, MW.

A mixture of intermediate compound S25 or (4-cyano-2-pyridyl)sulfinyloxy sodium (231 mg, 1.22 mmol, 1.2 eq), intermediate compound S22 or 6-chloro-9-[(2,6-difluorophenyl) methyl]purin-2-amine (300 mg, 1.01 mmol, 1 eq), palladium acetate (22 mg, 101.46 μmol, 0.1 eq), tricyclohexylphosphine (56 mg, 202.93 μmol, 0.2 eq) and $K_2CO_3$ (280 mg, 2.03 mmol, 2 eq) in dioxane (6 mL) was degassed and purged with nitrogen for three times, and then the mixture was stirred at 130° C. for 10 h under microwave condition. The mixture was concentrated under reduced pressure to remove dioxane to give a residue. The residue was purified by prep-HPLC (column: Phenomenex Gemini-NX C18 75*30 mm*3 μm; mobile phase: [water (0.05% ammonia hydroxide v/v)-ACN]; B %: 15%-45%, 7 min). Compound 132 or 2-[2-amino-9-[(2,6-difluorophenyl) methyl]purin-6-yl]pyridine-4-carbonitrile (49.39 mg, 130.41 μmol, 13% yield, 93.37% purity) was obtained as a yellow solid. $^1H$ NMR (400 MHz, DMSO-d6) δ=9.01 (dd, 1H), 8.87 (s, 1H), 8.18 (s, 1H), 7.99 (dd, 1H), 7.54-7.43 (m, 1H), 7.21-7.12 (m, 2H), 6.73 (s, 2H), 5.41 (s, 2H). HRMS-TOF: 364.1121.

Example 1.27: Production 2-[2-amino-9-[(4-amino-3-methyl-phenyl)methyl]purin-6-yl]pyridine-4-carbonitrile (Compound 128)

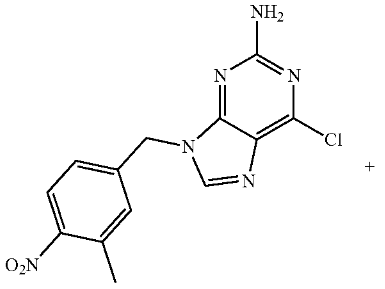

S19

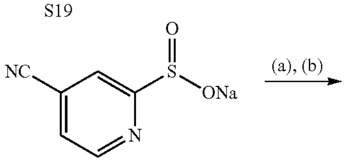

S25

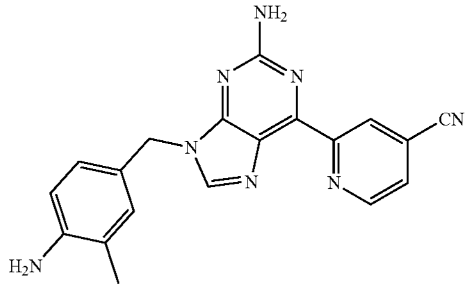

128

Reagents and condition: (a) $Pd(OAc)_2$, $Cy_3P$, $K_2CO_3$, dioxane, 130° C., 10 h, MW; (b) Fe, $NH_4Cl$, EtOH/$H_2O$, 60° C., 1 h.

Stage 1: Production of 2-[2-amino-9-[(3-methyl-4-nitro-phenyl)methyl]purin-6-yl]pyridine-4-carbonitrile A mixture of intermediate compound S25 or sodium 4-cyanopyridine-2-sulfinate (357 mg, 1.88 mmol, 1.2 eq), intermediate compound S19 or 6-chloro-9-[(3-methyl-4-nitro-phenyl)methyl]purin-2-amine (500 mg, 1.57 mmol, 1 eq), palladium acetate (35 mg, 157.00 μmol, 0.1 eq), tricyclohexylphosphine (87 mg, 314.00 μmol, 0.2 eq) and $K_2CO_3$ (433 mg, 3.14 mmol, 2 eq) in dioxane (2 mL) was degassed and purged with nitrogen for three times, and then the mixture was stirred at 130° C. for 10 h under microwave condition. The reaction mixture was concentrated under reduced pressure to remove dioxane to give a residue. The residue was purified by flash silica gel chromatography (ISCO®; 20 g Sepa Flash® Silica Flash Column, Eluent of 0~10% Ethyl acetate/Petroleum ether gradient @30 mL/min). Compound 2-[2-amino-9-[(3-methyl-4-nitro-phenyl)methyl]purin-6-yl]pyridine-4-carbonitrile (300 mg, 535.76 μmol, 34% yield, 69% purity) was obtained as a yellow solid. MS: m/z=387.3 (M+1, ESI+).

Stage 2: Production of 2-[2-amino-9-[(4-amino-3-methyl-phenyl)methyl]purin-6-yl]pyridine-4-carbonitrile To a solution of 2-[2-amino-9-[(3-methyl-4-nitro-phenyl)methyl]purin-6-yl]pyridine-4-carbonitrile (150 mg, 388.23 μmol, 1 eq) and $NH_4Cl$ (7 M, 444 μL, 8 eq) in water (5 mL) and ethanol (15 mL) was added iron powder (108 mg, 1.94 mmol, 5 eq). The mixture was stirred at 60° C. for 1 h. The reaction mixture was concentrated under reduced pressure to remove ethanol and water to give a residue. The residue was purified by prep-HPLC (column: Phenomenex luna C18 150*25 mm*10 μm; mobile phase: [water (0.225% FA)-ACN]; B %: 8%-28%, 9 min). Compound 128 or 2-[2-amino-9-[(4-amino-3-methyl-phenyl)methyl]purin-6-yl]pyridine-4-carbonitrile (21.82 mg, 58.15 μmol, 15% yield, 96.70% purity) was obtained as a yellow solid. $^1H$ NMR (400 MHz, DMSO-$d_6$) δ=9.02 (d, 1H), 8.90 (s, 1H), 8.23 (s, 1H), 7.99 (d, 1H), 6.95 (s, 1H), 6.93-6.90 (m, 1H), 6.75 (s, 2H), 6.55 (d, 1H), 5.12 (s, 2H), 4.87 (s, 2H), 2.06 (s, 3H). HRMS-TOF: 357.1569.

Example 1.28: Production 2-[2-amino-9-[[4-amino-3-(trifluoromethyl)phenyl]methyl]purin-6-yl]pyridine-4-carbonitrile (Compound 135)

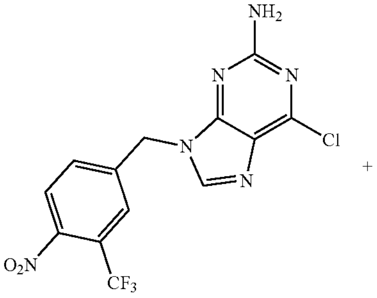

S9

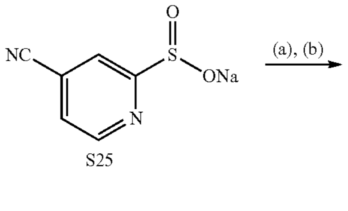

S25

-continued

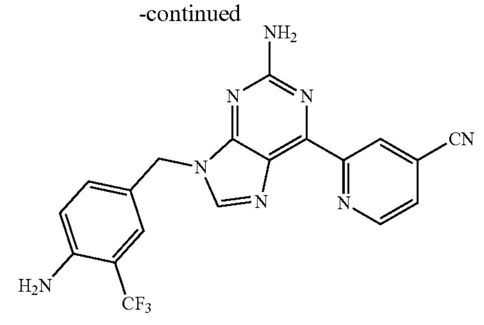

135

Reagents and condition: (a) $Pd(OAc)_2$, $Cy_3P$, $K_2CO_3$, dioxane, 130° C., 10 h, MW; (b) Fe, $NH_4Cl$, EtOH/$H_2O$, 60° C., 1 h.

Stage 1: Production of 2-[2-amino-9-[[4-nitro-3-(trifluoromethyl)phenyl]methyl]purin-6-yl]pyridine-4-carbonitrile A mixture of intermediate compound S25 or sodium 4-cyanopyridine-2-sulfinate (230 mg, 1.21 mmol, 1.5 eq), intermediate compound S23 or 6-chloro-9-[[4-nitro-3-(trifluoromethyl)phenyl]methyl]purin-2-amine (300 mg, 804.96 μmol, 1 eq), potassium carbonate (222 mg, 1.61 mmol, 2 eq) and $Cy_3P$—Pd-G3 (52 mg, 80.50 μmol, 0.1 eq) in dioxane (5 mL) was degassed and purged with nitrogen for three times, and then the mixture was stirred at 120° C. for 16 h under nitrogen atmosphere. The reaction mixture was concentrated under reduced pressure to remove dioxane to give a residue. The residue was purified by prep-HPLC (column: Shim-pack C18 150*25*10 μm; mobile phase: [water (0.225% FA)-ACN]; B %: 34%-54%, 10 min). Compound 135 or 2-[2-amino-9-[[4-nitro-3-(trifluoromethyl)phenyl]methyl]purin-6-yl]pyridine-4-carbonitrile (300 mg, 647.23 μmol, 80% yield, 95% purity) was obtained as a white solid. $^1H$ NMR (400 MHz, DMSO-$d_6$) δ=9.04 (dd, J=0.7, 4.9 Hz, 1H), 8.90 (s, 1H), 8.37 (s, 1H), 8.13 (s, 1H), 8.08 (s, 1H), 8.01 (dd, J=1.5, 5.0 Hz, 1H), 7.71 (dd, J=1.2, 8.4 Hz, 1H), 6.80 (s, 2H), 5.57 (s, 2H).

Stage 2: Production of 2-[2-amino-9-[[4-amino-3-(trifluoromethyl)phenyl]methyl]purin-6-yl]pyridine-4-carbonitrile To a solution of 2-[2-amino-9-[[4-nitro-3-(trifluoromethyl)phenyl]methyl]purin-6-yl]pyridine-4-carbonitrile (300 mg, 681.29 μmol, 1 eq) in ethanol (15 mL) and water (5 mL) were added iron dust (190 mg, 3.41 mmol, 5 eq) and $NH_4Cl$ (292 mg, 5.45 mmol, 8 eq). The mixture was stirred at 60° C. for 1 h. The reaction mixture was filtered and concentrated under reduced pressure to give a residue. The residue was purified by prep-HPLC (column: Shim-pack C18 150*25*10 μm; mobile phase: [water (0.225% FA)-ACN]; B %: 17%-47%, 10 min). Compound 135 or 2-[2-amino-9-[[4-amino-3-(trifluoromethyl)phenyl]methyl]purin-6-yl]pyridine-4-carbonitrile (40.01 mg, 96.51 μmol, 14% yield, 98.98% purity) was obtained as a yellow solid. $^1H$ NMR (400 MHz, DMSO-$d_6$) δ=9.02 (d, 1H), 8.89 (s, 1H), 8.29 (s, 1H), 7.99 (dd, 1H), 7.40 (d, 1H), 7.29 (dd, 1H), 6.82-6.74 (m, 3H), 5.64 (s, 2H), 5.20 (s, 2H) HRMS-TOF: 411.1281.

Example 1.29: Production 5-[2-amino-9-[(4-aminophenyl)methyl]purin-6-yl]pyridine-3-carbonitrile (Compound 117)

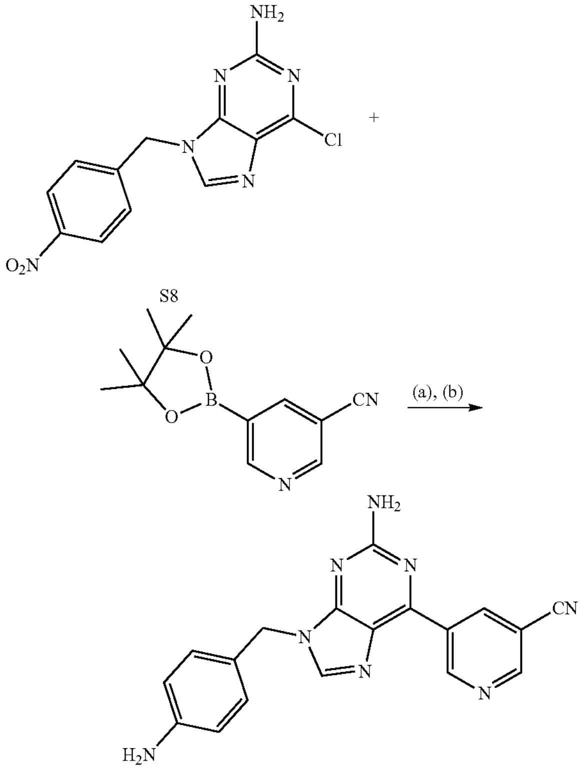

117

Reagents an condition: a Pd(pddf)$Cl_2$, $K_2CO_3$, dioxane $H_2O$, 110° C., 15 h; (b) Fe, $NH_4Cl$, EtOH/$H_2O$, 80° C., 1 h.

Stage 1: Production of 5-[2-amino-9-[(4-nitrophenyl)methyl]purin-6-yl]pyridine-3-carbonitrile A mixture of intermediate compound S8 or 6-chloro-9-[(4-nitrophenyl)methyl]purin-2-amine (200 mg, 656.40 μmol, 1 eq), 5-(4,4,5,5-tetramethyl-1,3,2-dioxaborolan-2-yl) pyridine-3-carbonitrile (181 mg, 787.68 μmol, 1.2 eq), Pd(dppf)$Cl_2$ (48 mg, 65.64 μmol, 0.1 eq) and $K_2CO_3$ (181 mg, 1.31 mmol, 2 eq) in dioxane (10 mL) and water (0.5 mL) was de-gassed and then heated to 110° C. for 15 h under nitrogen. To the mixture was added water (130 mL) and extracted with ethyl acetate (130 mL×2). Combined the organic phase was dried over anhydrous sodium sulfate, filtered and concentrated in vacuum to give a residue. The residue was purified by prep-TLC ($SiO_2$, PE:EA=1:1). Compound 5-[2-amino-9-[(4-nitrophenyl)methyl]purin-6-yl] pyridine-3-carbonitrile (150 mg, 330.34 μmol, 50% yield, 82% purity) was obtained as yellow solid. MS: m/z=373 (M+1, ESI+).

Stage 2: Production of 5-[2-amino-9-[(4-aminophenyl)methyl]purin-6-yl]pyridine-3-carbonitrile To the solution of 5-[2-amino-9-[(4-nitrophenyl)methyl] purin-6-yl]pyridine-3-carbonitrile (150 mg, 330.34 μmol, 1 eq) in ethanol (9 mL) and water (3 mL) were added iron powder (92 mg, 1.65 mmol, 5 eq) and $NH_4Cl$ (141 mg, 2.64 mmol, 8 eq). Then the mixture was stirred at 80° C. for 1 h. The reaction mixture was filtered and the filtrate was concentrated in vacuum. Then to the mixture was added water (50 mL) and extracted with ethyl acetate (80 mL×3). Combined the organic phases to dry over anhydrous sodium sulfate, filter and concentrate in vacuum to give a residue. The residue was purified by prep-HPLC (column: Waters Xbridge 150*25 mm*5 μm; mobile phase: [water (0.05% ammonia hydroxide v/v)-ACN]; B %: 14%-44%, 10 min). Compound 117 or 5-[2-amino-9-[(4-aminophenyl)methyl] purin-6-yl]pyridine-3-carbonitrile (20.59 mg, 58.88 μmol, 18% yield, 98.45% purity) was obtained as a yellow solid. $^1H$ NMR (400 MHz, DMSO-$d_6$) δ=10.01 (d, J=1.8 Hz, 1H), 9.30 (s, 1H), 9.16 (d, J=1.8 Hz, 1H), 8.29 (s, 1H), 7.05 (br d, J=8.3 Hz, 2H), 6.77 (s, 2H), 6.52 (d, J=8.3 Hz, 2H), 5.14 (s, 2H), 5.11 (s, 2H). HRMS-TOF: 343.1410.

Example 1.30: Production 5-[2-amino-9-[(4-amino-2-fluoro-phenyl)methyl]purin-6-yl]pyridine-3-carbonitrile (Compound 121)

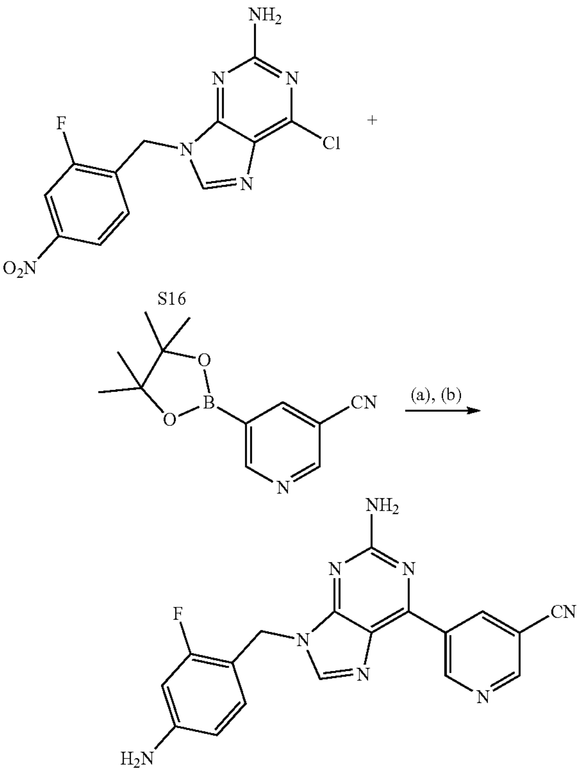

121

Reagents and condition: (a) Pd(dppf)$Cl_2$, $K_2CO_3$, dioxane/$H_2O$, 110° C., 15 h; (b) Fe, $NH_4Cl$, EtOH/$H_2O$, 80° C., 1 h.

Stage 1: Production of 5-[2-amino-9-[(2-fluoro-4-nitro-phenyl)methyl]purin-6-yl]pyridine-3-carbonitrile A mixture of intermediate compound S16 or 6-chloro-9-[(2-fluoro-4-nitro-phenyl)methyl]purin-2-amine (300 mg, 929.71 μmol, 1 eq), 5-(4,4,5,5-tetramethyl-1,3,2-dioxaborolan-2-yl)pyridine-3-carbonitrile (320 mg, 1.39 mmol, 1.5 eq), $K_2CO_3$ (257 mg, 1.86 mmol, 2 eq) and Pd(dppf)$Cl_2$ (68 mg, 92.97 μmol, 0.1 eq) in dioxane (10 mL) and water (0.5 mL) was de-gassed and then heated to 110° C. for 15 h under nitrogen. To the mixture was added water (30 mL) and then extracted with ethyl acetate (30 mL×3). Combined the organic phase to wash with brines (50 mL×2), dry over anhydrous $Na_2SO_4$, filter and concentrate in vacuum to give a residue. The residue was purified by flash silica gel chromatography (20 g Sepa Flash® Silica Flash Column, Eluent of 0~80% Ethyl acetate/Petroleum ether gradient @35 mL/min). Compound 121 or 5-[2-amino-9-[(2-fluoro-4-nitro-phenyl)methyl]purin-6-yl]pyridine-3-carbonitrile (200 mg, 502.14 μmol, 54% yield, 98% purity) was obtained as a yellow solid. MS: m/z=391.2 (M+1, ESI+).

Stage 2: Production of 5-[2-amino-9-[(4-amino-2-fluoro-phenyl)methyl]purin-6-yl]pyridine-3-carbonitrile To the solution of 5-[2-amino-9-[(2-fluoro-4-nitro-phenyl)methyl]purin-6-yl]pyridine-3-carbonitrile (200 mg, 512.39 μmol, 1 eq) and $NH_4Cl$ (220 mg, 4.10 mmol, 8 eq) in ethanol (9 mL) and water (3 mL) was added iron powder (143 mg, 2.56 mmol, 5 eq). Then the mixture was stirred at 80° C. for 1 h. The mixture was concentrated in vacuum to give a residue. To the residue was added water (30 mL) and extracted with ethyl acetate (30 mL×3). Combined the organic phase and dried over anhydrous $Na_2SO_4$, filtered and concentrated in vacuum to give a residue. The crude product was triturated with methanol (10 mL) and THF (1 mL) at 60° C. for 30 min. Compound 121 or 5-[2-amino-9-[(4-amino-2-fluoro-phenyl)methyl]purin-6-yl]pyridine-3-carbonitrile (60 mg, 166.51 μmol, 32% yield, 95.08% purity) was obtained as yellow solid. $^1H$ NMR (400 MHz, DMSO-$d_6$) δ=10.01 (d, J=2.0 Hz, 1H), 9.30 (t, J=2.1 Hz, 1H), 9.17 (d, J=2.0 Hz, 1H), 8.20 (s, 1H), 6.99 (t, J=8.4 Hz, 1H), 6.79 (s, 2H), 6.44-6.28 (m, 2H), 5.50 (s, 2H), 5.18 (s, 2H). HRMS-TOF: 361.1319.

Example 1.31: Production 5-[2-amino-9-[(4-amino-2,6-difluoro-phenyl)methyl]purin-6-yl]pyridine-3-carbonitrile (Compound 125)

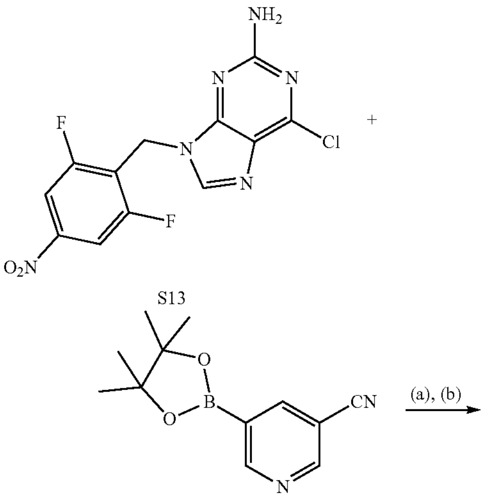

S13

-continued

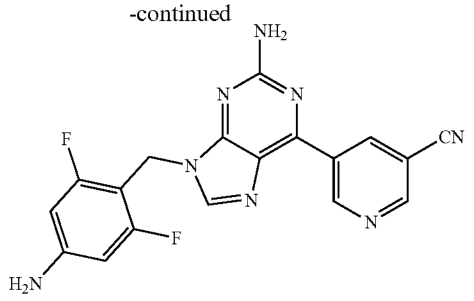

125

Reagents and condition: (a) Pd(dppf)$Cl_2$, $K_2CO_3$, dioxane/$H_2O$, 110° C., 2 h; (b) Fe, $NH_4Cl$, EtOH/$H_2O$, 80° C., 1 h.

Stage 1: Production of 5-[2-amino-9-[(2,6-difluoro-4-nitro-phenyl)methyl]purin-6-yl]pyridine-3-carbonitrile A mixture of intermediate compound S13 or 6-chloro-9-[(2,6-difluoro-4-nitro-phenyl)methyl]purin-2-amine (200 mg, 587.07 μmol, 1 eq), 5-(4,4,5,5-tetramethyl-1,3,2-dioxaborolan-2-yl)pyridine-3-carbonitrile (270 mg, 1.17 mmol, 2 eq), Pd(dppf)$Cl_2$ (43 mg, 58.71 μmol, 0.1 eq) and $K_2CO_3$ (162 mg, 1.17 mmol, 2 eq) were taken up into a microwave tube in dioxane (10 mL) and water (2 mL). The sealed tube was heated at 110° C. for 2 h under microwave condition. After that the mixture was added water (130 mL) and extracted with ethyl acetate (130 mL×2). Combined the organic phases to dry over anhydrous $Na_2SO_4$, filter and concentrate in vacuum to give a residue. The residue was purified by flash silica gel chromatography (ISCO®; 20 g Sepa Flash® Silica Flash Column, Eluent of 0~100% Ethyl acetate/Petroleum ether gradient @40 mL/min). Compound 125 or 5-[2-amino-9-[(2,6-difluoro-4-nitro-phenyl)methyl]purin-6-yl]pyridine-3-carbonitrile (200 mg, 426.14 μmol, 72% yield, 87% purity) was obtained as a yellow solid. MS: m/z=408.9 (M+1, ESI+).

Stage 2: Production of 5-[2-amino-9-[(4-amino-2,6-difluoro-phenyl)methyl]purin-6-yl]pyridine-3-carbonitrile To the solution of 5-[2-amino-9-[(2,6-difluoro-4-nitro-phenyl)methyl]purin-6-yl]pyridine-3-carbonitrile (200 mg, 489.81 μmol, 1 eq) in ethanol (8 mL) and water (2 mL) were added iron powder (137 mg, 2.45 mmol, 5 eq) and $NH_4Cl$ (210 mg, 3.92 mmol, 8 eq). Then the mixture was stirred at 80° C. for 1 h. After that the reaction mixture was filtered and the filtrate was concentrated in vacuum, then the residue was added water (50 mL) and extracted with ethyl acetate (50 mL×3). Combined the organic phases to dry over anhydrous $Na_2SO_4$, filter and concentrate in vacuum to give a residue. The residue was purified by prep-HPLC (column: Waters Vinridis Silica 2-EP OBD 50*150 mm*5 μm; mobile phase: [Heptane-EtOH (0.1% $NH_3 \cdot H_2O$)]; B %: 5%-45%, 10 min). Compound 125 or 5-[2-amino-9-[(4-amino-2,6-difluoro-phenyl)methyl]purin-6-yl]pyridine-3-carbonitrile (16.22 mg, 40.31 μmol, 8% yield, 96.64% purity) was obtained as a yellow solid. $^1H$ NMR (400 MHz, DMSO-$d_6$) δ=9.99 (d, J=2.0 Hz, 1H), 9.28 (t, J=2.1 Hz, 1H), 9.15 (d, J=2.1 Hz, 1H), 8.09 (s, 1H), 6.74 (s, 2H), 6.22 (d, J=10.4 Hz, 2H), 5.88 (s, 2H), 5.17 (s, 2H). HRMS-TOF: 379.1229.

Example 1.32: Production 5-[2-amino-9-[(2,6-difluorophenyl)methyl]purin-6-yl]pyridine-3-carbonitrile (Compound 133)

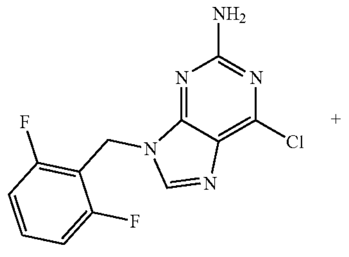

S22

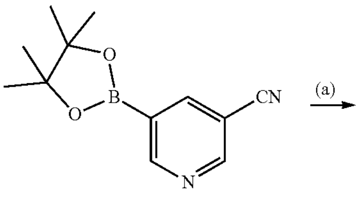

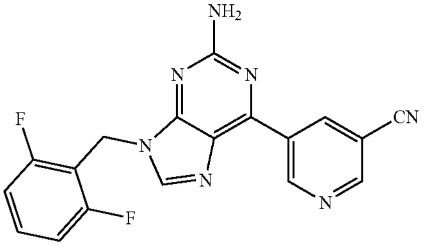

133

Reagents and condition: (a) Pd(dppf)$Cl_2$, $K_2CO_3$, dioxane/$H_2O$, 110° C., 15 h.

A mixture of intermediate compound S22 or 6-chloro-9-[(2,6-difluorophenyl)methyl]purin-2-amine (150 mg, 507.31 μmol, 1 eq), 5-(4,4,5,5-tetramethyl-1,3,2-dioxaborolan-2-yl)pyridine-3-carbonitrile (140 mg, 608.78 μmol, 1.2 eq), Pd(dppf)$Cl_2$ (37 mg, 50.73 μmol, 0.1 eq) and $K_2CO_3$ (140 mg, 1.01 mmol, 2 eq) in dioxane (10 mL) and water (1 mL) was de-gassed and then heated to 110° C. for 15 h under nitrogen. The mixture was concentrated in vacuum to give a residue. The residue was purified by prep-HPLC (column: Xtimate C18 150*40 mm*10 μm; mobile phase: [water (0.05% ammonia hydroxide v/v)-ACN]; B %: 30%-60%, 10 min). Compound 133 or 5-[2-amino-9-[(2,6-difluorophenyl)methyl]purin-6-yl]pyridine-3-carbonitrile (60.03 mg, 161.42 μmol, 32% yield, 96.75% purity) was obtained as a yellow solid. $^1$H NMR (400 MHz, DMSO-$d_6$) δ=9.98 (d, J=1.7 Hz, 1H), 9.27 (s, 1H), 9.16 (d, J=1.7 Hz, 1H), 8.24 (s, 1H), 7.55-7.42 (m, 1H), 7.16 (t, J=8.1 Hz, 2H), 6.74 (s, 2H), 5.42 (s, 2H). HRMS-TOF: 364.1121.

Example 1.33: Production 5-[2-amino-9-[(4-amino-3-methyl-phenyl)methyl]purin-6-yl]pyridine-3-carbonitrile (Compound 129)

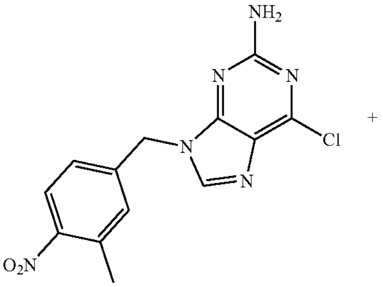

S19

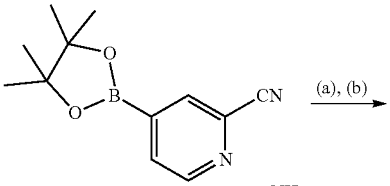

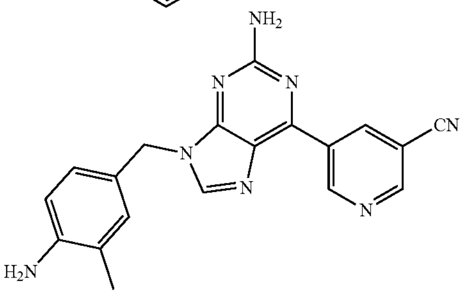

129

Reagents and condition: (a) Pd(dppf)$Cl_2$, $K_2CO_3$, dioxane/$H_2O$, 110° C., 15 h. (b) Fe, $NH_4Cl$, EtOH/$H_2O$, 80° C., 1 h.

Stage 1: Production of 5-[2-amino-9-[(3-methyl-4-nitro-phenyl)methyl]purin-6-yl]pyridine-3-carbonitrile A mixture of intermediate compound S19 or 6-chloro-9-[(3-methyl-4-nitro-phenyl)methyl]purin-2-amine (300 mg, 941.27 μmol, 1 eq), 5-(4,4,5,5-tetramethyl-1,3,2-dioxaborolan-2-yl)pyridine-3-carbonitrile (325 mg, 1.41 mmol, 1.5 eq), Pd(dppf)$Cl_2$ (69 mg, 94.13 μmol, 0.1 eq) and $K_2CO_3$ (260 mg, 1.88 mmol, 2 eq) in dioxane (10 mL) and water (0.5 mL) was de-gassed and then heated to 110° C. for 15 h under nitrogen. After that the mixture was added water (80 mL) and extracted with ethyl acetate (80 mL×3). Combined the organic phase to dry over anhydrous $Na_2SO_4$, filter and concentrate in vacuum to give a residue. The residue was purified by flash silica gel chromatography (12 g Sepa Flash® Silica Flash Column, Eluent of 0~80% Ethyl acetate/Petroleum ether gradient @30 mL/min). Compound 5-[2-amino-9-[(3-methyl-4-nitro-phenyl)methyl]purin-6-yl]pyridine-3-carbonitrile (300 mg, 750.84 μmol, 79% yield, 96.7% purity) was obtained as a yellow solid. $^1$H NMR (400 MHz, DMSO-$d_6$) δ=10.02 (d, J=2.0 Hz, 1H), 9.31 (t, J=2.1 Hz, 1H), 9.17 (d, J=2.0 Hz, 1H), 8.41 (s, 1H), 7.97 (d, J=8.4 Hz, 1H), 7.41 (s, 1H), 7.28 (dd, J=1.5, 8.4 Hz, 1H), 6.80 (s, 2H), 5.45 (s, 2H), 2.49 (br s, 3H). MS: m/z=387 (M+1, ESI+).

Stage 2: Production of 5-[2-amino-9-[(4-amino-3-methyl-phenyl)methyl]purin-6-yl]pyridine-3-carbonitrile To the solution of 5-[2-amino-9-[(3-methyl-4-nitro-phenyl)methyl]purin-6-yl]pyridine-3-carbonitrile (300 mg, 722.1 μmol, 1 eq) in ethanol (9 mL) and water (3 mL) were added iron powder (202 mg, 3.61 mmol, 5 eq) and $NH_4Cl$ (310 mg, 5.78 mmol, 8 eq). Then the mixture was stirred at 80° C. for 1 h. The reaction mixture was filtered and the filtrate was concentrated in vacuum. Then the residue was added water (50 mL) and extracted with ethyl acetate (50 mL×3). The combined organic phase was dried over anhydrous $Na_2SO_4$, filtered and concentrated in vacuum to give a residue. The crude product was triturated with methanol (8 mL) at 25° C. for 30 min, then filtered and the solid was dried under reduced pressure. Compound 129 or 5-[2-amino-9-[(4-amino-3-methyl-phenyl)methyl]purin-6-yl]pyridine-3-carbonitrile (36.5 mg, 99.14 μmol, 13% yield, 96.26% purity) was obtained as a yellow solid. $^1H$ NMR (400 MHz, DMSO-$d_6$) δ=10.01 (d, J=2.0 Hz, 1H), 9.29 (t, J=2.0 Hz, 1H), 9.15 (d, J=2.0 Hz, 1H), 8.28 (s, 1H), 6.96 (s, 1H), 6.92 (dd, J=1.7, 8.1 Hz, 1H), 6.76 (s, 2H), 6.56 (d, J=8.1 Hz, 1H), 5.12 (s, 2H), 2.01 (s, 3H). HRMS-TOF: 357.1555.

Example 1.34: Production 4-[2-amino-9-[(4-aminophenyl)methyl]purin-6-yl]pyridine-2-carbonitrile (Compound 118)

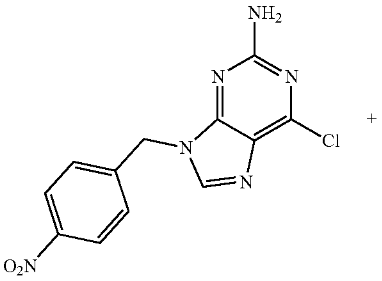

S8

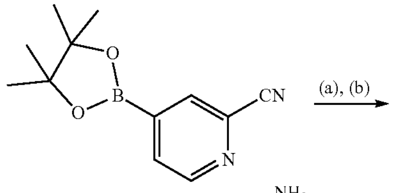

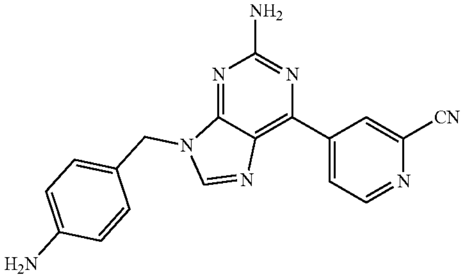

118

Reagents and condition: (a) Pd(dppf)$Cl_2$, $K_2CO_3$, dioxane/$H_2O$, 110° C., 2 h, MW. (b) Fe, $NH_4Cl$, EtOH/$H_2O$, 80° C., 1 h.

Stage 1: Production of 4-[2-amino-9-[(4-nitrophenyl)methyl]purin-6-yl]pyridine-2-carbonitrile A mixture of intermediate compound S8 or 6-chloro-9-[(4-nitrophenyl)methyl]purin-2-amine (200 mg, 656.40 μmol, 1 eq), 4-(4,4,5,5-tetramethyl-1,3,2-dioxaborolan-2-yl)pyridine-2-carbonitrile (755 mg, 3.28 mmol, 5 eq), $K_2CO_3$ (181 mg, 1.31 mmol, 2 eq) and Pd(dppf)$Cl_2$ (48 mg, 65.64 μmol, 0.1 eq) were taken up into a microwave tube in dioxane (10 mL) and water (2 mL). The sealed tube was heated at 110° C. for 2 h under microwave condition. After that, to the mixture was added water (130 mL) and extracted with ethyl acetate (130 mL×3). The combined organic phase was dried over anhydrous sodium sulfate, filtered and concentrated in vacuum to give a residue. The residue was purified by flash silica gel chromatography (12 g Sepa Flash® Silica Flash Column, Eluent of 0~80% Ethyl acetate/Petroleum ether gradient @35 mL/min). Compound 4-[2-amino-9-[(4-nitrophenyl)methyl]purin-6-yl]pyridine-2-carbonitrile (200 mg, 504.92 μmol, 77% yield, 94% purity) was obtained as yellow solid. MS: m/z=373.1 (M+1, ESI+).

Stage 2: Production of 4-[2-amino-9-[(4-aminophenyl)methyl]purin-6-yl]pyridine-2-carbonitrile To the solution of 4-[2-amino-9-[(4-nitrophenyl)methyl]purin-6-yl]pyridine-2-carbonitrile (200 mg, 537.14 μmol, 1 eq) and $NH_4Cl$ (230 mg, 4.30 mmol, 8 eq) in ethanol (8 mL) and water (2 mL) was added iron powder (150 mg, 2.69 mmol, 5 eq). Then the mixture was stirred at 80° C. for 1 h. The reaction mixture was filtered and the filtrate was concentrated in vacuum, then the residue was added water (50 mL) and extracted with ethyl acetate (50 mL×3). Combined the organic phases to concentrate in vacuum to give a residue. The residue was purified by prep-HPLC (column: Waters Vinridis Silica 2-EP OBD 50*150 mm*5 μm; mobile phase: [Heptane-EtOH (0.1% NH3H2O)]; B %: 5%-45%, 10 min). Compound 118 or 4-[2-amino-9-[(4-aminophenyl)methyl]purin-6-yl]pyridine-2-carbonitrile (38.42 mg, 107.37 μmol, 20% yield, 92.28% purity) was obtained as a yellow solid. $^1H$ NMR (400 MHz, DMSO-$d_6$) δ=9.05 (s, 1H), 8.98 (d, J=5.3 Hz, 1H), 8.89 (dd, J=1.4, 5.2 Hz, 1H), 8.33 (s, 1H), 7.05 (br d, J=8.3 Hz, 2H), 6.82 (s, 2H), 6.52 (d, J=8.4 Hz, 2H), 5.14 (s, 2H), 5.11 (s, 2H). HRMS-TOF: 343.1413.

Example 1.35: Production 4-[2-amino-9-[(4-amino-2-fluoro-phenyl)methyl]purin-6-yl]pyridine-2-carbonitrile (Compound 122)

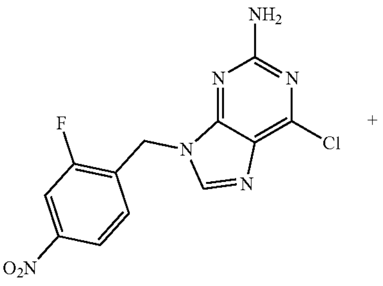

S16

-continued

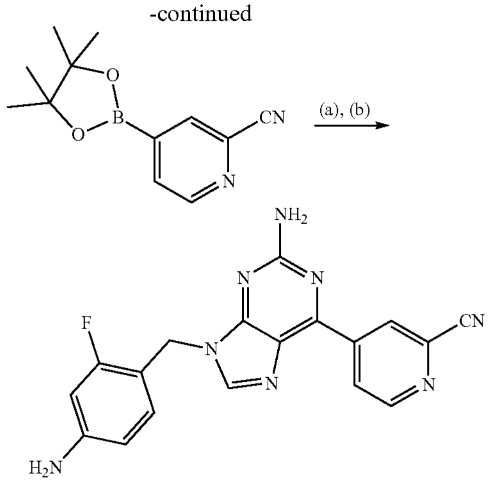

122

Reagents and condition: (a) Pd(dppf)$Cl_2$, $K_2CO_3$, dioxane/$H_2O$, 110° C., 2 h, MW. (b) Fe, $NH_4Cl$, THF/$H_2O$, 80° C., 1 h.

Stage 1: Production of 4-[2-amino-9-[(2-fluoro-4-nitro-phenyl)methyl]purin-6-yl]pyridine-2-carbonitrile A mixture of intermediate compound S16 or 6-chloro-9-[(2-fluoro-4-nitro-phenyl)methyl]purin-2-amine (300 mg, 929.71 μmol, 1 eq), 4-(4,4,5,5-tetramethyl-1,3,2-dioxaborolan-2-yl)pyridine-2-carbonitrile (428 mg, 1.86 mmol, 2 eq), $K_2CO_3$ (257 mg, 1.86 mmol, 2 eq) and Pd(dppf)$Cl_2$ (68 mg, 92.97 μmol, 0.1 eq) were taken up into a microwave tube in dioxane (8 mL) and water (2 mL). The sealed tube was heated at 110° C. for 2 h under microwave condition. The mixture was concentrated in vacuum to give a residue. The residue was purified by flash silica gel chromatography (12 g Sepa Flash® Silica Flash Column, Eluent of 0~50% Ethyl acetate/Petroleum ether gradient @60 mL/min). Compound 4-[2-amino-9-[(2-fluoro-4-nitro-phenyl)methyl]purin-6-yl] pyridine-2-carbonitrile (200 mg, 478.83 μmol, 52% yield, 93.45% purity) was obtained as a yellow solid. $^1$H NMR (400 MHz, DMSO-$d_6$) δ=9.04 (s, 1H), 8.99 (d, J=4.6 Hz, 1H), 8.88 (dd, J=1.5, 5.1 Hz, 1H), 8.41 (s, 1H), 8.18 (dd, J=2.1, 9.9 Hz, 1H), 8.04 (dd, J=1.9, 8.6 Hz, 1H), 7.35 (t, J=8.0 Hz, 1H), 6.86 (s, 2H), 5.56 (s, 2H). MS: m/z=391.1 (M+1, ESI+).

Stage 2: Production of 4-[2-amino-9-[(4-amino-2-fluoro-phenyl)methyl]purin-6-yl]pyridine-2-carbonitrile To the solution of 4-[2-amino-9-[(2-fluoro-4-nitro-phenyl)methyl]purin-6-yl]pyridine-2-carbonitrile (200 mg, 512.39 μmol, 1 eq) in ethanol (9 mL) and water (3 mL) were added iron powder (143 mg, 2.56 mmol, 5 eq) and $NH_4Cl$ (219 mg, 4.10 mmol, 8 eq). Then the mixture was stirred at 80° C. for 1 h. The reaction mixture was filtered and the filtrate was concentrated in vacuum. To the residue was added water (80 mL) and extracted with ethyl acetate (80 mL×3). Combined the organic phase was washed with brines (100 mL×2), dried over anhydrous $Na_2SO_4$, filtered and concentrated in vacuum to give a residue. The residue was purified by prep-HPLC (column: Phenomenex Gemini NX-C18 (75*30 mm*3 μm); mobile phase: [water (10 mM $NH_4HCO_3$)-ACN]; B %: 18%-48%, 8 min). Compound 122 or 4-[2-amino-9-[(4-amino-2-fluoro-phenyl)methyl]purin-6-yl]pyridine-2-carbonitrile (20.14 mg, 54.73 μmol, 11% yield, 98.80% purity) was obtained as a yellow solid. $^1$H NMR (400 MHz, DMSO-$d_6$) δ=9.04 (s, 1H), 8.97 (d, J=5.1 Hz, 1H), 8.87 (dd, J=1.5, 5.1 Hz, 1H), 8.22 (s, 1H), 6.99 (t, J=8.5 Hz, 1H), 6.81 (s, 2H), 6.34 (s, 1H), 6.32 (br d, J=1.2 Hz, 1H), 5.48 (s, 2H), 5.18 (s, 2H). HRMS-TOF: 361.1317.

Example 1.36: Production 4-[2-amino-9-[(4-amino-2,6-difluoro-phenyl)methyl]purin-6-yl]pyridine-2-carbonitrile (Compound 126)

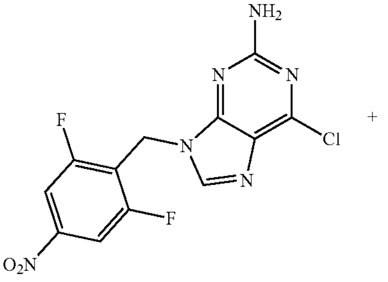

S13

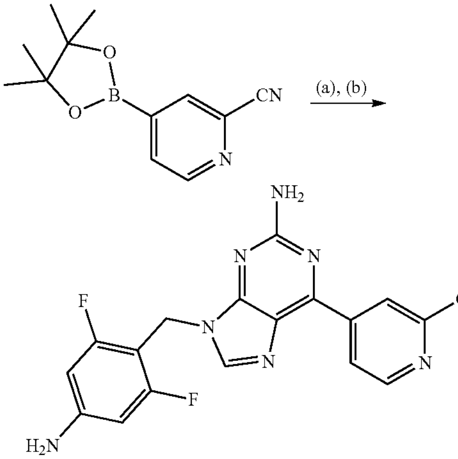

126

Reagents and condition: (a) Pd(dppf)$Cl_2$, $K_2CO_3$, dioxane/$H_2O$, 110° C., 2 h. (b) Fe, $NH_4Cl$, THF/$H_2O$, 80° C., 0.5 h.

Stage 1: Production of 4-[2-amino-9-[(2,6-difluoro-4-nitro-phenyl)methyl]purin-6-yl]pyridine-2-carbonitrile To a solution of intermediate compound S13 or 6-chloro-9-[(2,6-difluoro-4-nitro-phenyl)methyl]purin-2-amine (160 mg, 469.66 μmol, 1 eq), 4-(4,4,5,5-tetramethyl-1,3,2-dioxaborolan-2-yl) pyridine-2-carbonitrile (540 mg, 2.35 mmol, 5 eq) in dioxane (14 mL) and water (1.4 mL) were added $K_2CO_3$ (130 mg, 939.32 μmol, 2 eq) and Pd(dppf)$Cl_2$ (34 mg, 46.97 μmol, 0.1 eq). The mixture was stirred at 110° C. for 2 h. The mixture was added water (30 mL) and extracted by ethyl acetate (30 mL×3), the combined organic phase was dried over anhydrous $Na_2SO_4$, filtered and concentrated in vacuum to give a residue. The residue was purified by flash silica gel chromatography (ISCO®; 12 g Sepa Flash® Silica Flash Column, Eluent of 0~42% Ethyl acetate/Petroleum ether gradient @40 mL/min). Compound 4-[2-amino-9-[(2, 6-difluoro-4-nitro-phenyl)methyl]purin-6-yl]pyridine-2-carbonitrile (75 mg, 174.50 μmol, 37% yield, 95% purity) was obtained as a yellow solid. $^1$H NMR (400 MHz, DMSO-$d_6$) δ=9.02-9.00 (m, 1H), 8.97 (dd, J=0.6, 5.1 Hz, 1H), 8.85 (dd, J=1.6, 5.1 Hz, 1H), 8.38 (s, 1H), 8.10 (d, J=7.5 Hz, 2H), 6.79 (s, 2H), 5.53 (s, 2H). MS: m/z=409.1 (M+1, ESI+)

Stage 2: Production of 4-[2-amino-9-[(4-amino-2,6-difluoro-phenyl)methyl]purin-6-yl]pyridine-2-carbonitrile To a solution of 4-[2-amino-9-[(2,6-difluoro-4-nitro-phenyl)methyl]purin-6-yl]pyridine-2-carbonitrile (92 mg, 225.31 μmol, 1 eq) in ethanol (8 mL) and water (2 mL) were added iron dust (63 mg, 1.13 mmol, 5 eq) and $NH_4Cl$ (96 mg, 1.80 mmol, 8 eq). The mixture was stirred at 80° C. for 0.5 h. The mixture was filtered and the filtrate was concentrated in vacuum to give a residue. The residue was added water (40 mL) and extracted with ethyl acetate (30 mL×3). The combined organic layers were concentrated under reduced pressure to give a residue. The residue was purified by prep-HPLC (column: Welch Ultimate XB-CN 250*25*0 μm; mobile phase: [Heptane-EtOH (0.1% $NH_3{\cdot}H_2O$)]; B %: 25%-65%, 15 min). Compound 126 or 4-[2-amino-9-[(4-amino-2,6-difluoro-phenyl)methyl]purin-6-yl]pyridine-2-carbonitrile (38 mg, 99.43 μmol, 44% yield, 97.67% purity) was obtained as a yellow solid. $^1$H NMR (400 MHz, DMSO-$d_6$) δ=9.03 (dd, J=0.8, 1.6 Hz, 1H), 8.97 (dd, J=0.9, 5.1 Hz, 1H), 8.86 (dd, J=1.6, 5.1 Hz, 1H), 8.13 (s, 1H), 6.79 (s, 2H), 6.21 (d, J=10.5 Hz, 2H), 5.88 (s, 2H), 5.18 (s, 2H). HRMS-TOF: 379.1231.

Example 1.37: Production 4-[2-amino-9-[(2,6-difluorophenyl)methyl]purin-6-yl]pyridine-2-carbonitrile (Compound 134)

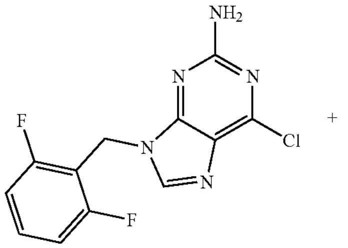

S22

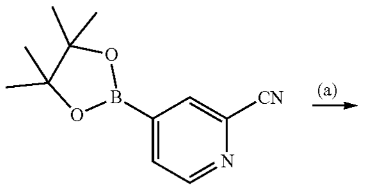

-continued

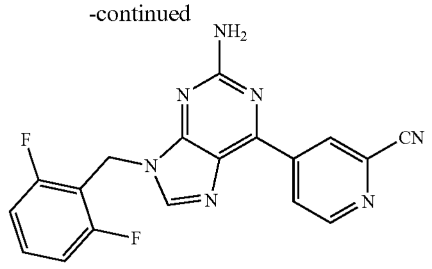

134

Reagents and condition: (a) Pd(dppf)$Cl_2$, $K_2CO_3$, dioxane/$H_2O$, 110° C., 15 h.

A mixture of intermediate compound S22 or 6-chloro-9-[(2,6-difluorophenyl)methyl]purin-2-amine (100 mg, 338.21 μmol, 1 eq), 4-(4,4,5,5-tetramethyl-1,3,2-dioxaborolan-2-yl)pyridine-2-carbonitrile (117 mg, 507.31 μmol, 1.5 eq), $K_2CO_3$ (94 mg, 676.42 μmol, 2 eq) and Pd(dppf)$Cl_2$ (25 mg, 33.82 μmol, 0.1 eq) in dioxane (5 mL) and water (0.5 mL) was de-gassed and then heated to 110° C. for 15 h under nitrogen. To the mixture was added water (20 mL) and extracted with ethyl acetate (30 mL×3). The combined organic phase was dried over anhydrous sodium sulfate, filtered and concentrated in vacuum to give a residue. The residue was purified by flash silica gel chromatography (4 g SepaFlash® Silica Flash Column, Eluent of 0~100% Ethyl acetate/Petroleum ether gradient @30 mL/min) to give impure product. The impure product was purified by prep-HPLC (column: Xtimate C18 150*40 mm*10 μm; mobile phase: [water (0.05% ammonia hydroxide v/v)-ACN]; B %: 30%-60%, 10 min). Compound 134 or 4-[2-amino-9-[(2,6-difluorophenyl)methyl]purin-6-yl]pyridine-2-carbonitrile (18.9 mg, 50.98 μmol, 15% yield, 98.03% purity) was obtained as a yellow solid. $^1$H NMR (400 MHz, DMSO-$d_6$) δ=9.03 (s, 1H), 8.98 (dd, J=0.6, 5.1 Hz, 1H), 8.86 (dd, J=1.6, 5.1 Hz, 1H), 8.29 (s, 1H), 7.54-7.43 (m, 1H), 7.17 (t, J=8.1 Hz, 2H), 6.80 (s, 2H), 5.44 (s, 2H). HRMS-TOF: 364.1120.

Example 1.38: Production 4-[2-amino-9-[(4-amino-3-methyl-phenyl)methyl]purin-6-yl]pyridine-2-carbonitrile (Compound 130)

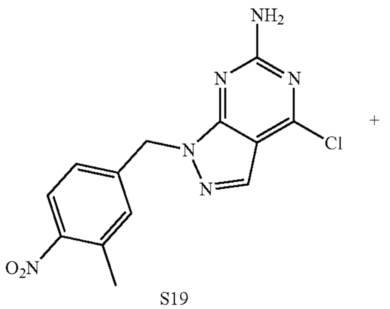

S19

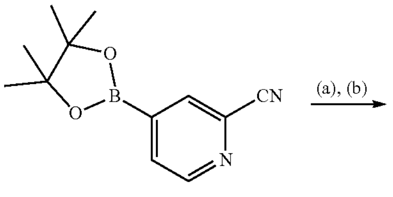

-continued

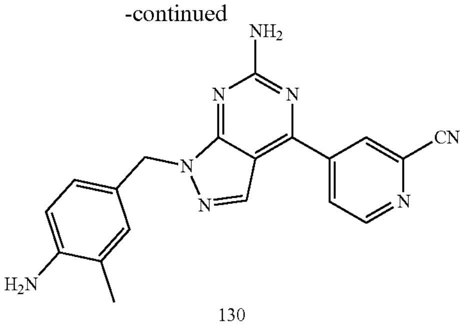

130

Reagents and condition: (a) $Pd(dppf)Cl_2$, $K_2CO_3$, dioxane/$H_2O$, 110° C., 2 h, MW. (b) Fe, $NH_4Cl$, THF/$H_2O$, 80° C., 1 h.

Stage 1: Production of 4-[2-amino-9-[(3-methyl-4-nitro-phenyl)methyl]purin-6-yl]pyridine-2-carbonitrile A mixture of intermediate compound S19 or 6-chloro-9-[(3-methyl-4-nitro-phenyl)methyl]purin-2-amine (100 mg, 313.76 μmol, 1 eq), 4-(4,4,5,5-tetramethyl-1,3,2-dioxaborolan-2-yl)pyridine-2-carbonitrile (144 mg, 627.51 μmol, 2 eq), $Pd(dppf)Cl_2$ (23 mg, 31.38 μmol, 0.1 eq) and $K_2CO_3$ (87 mg, 627.51 μmol, 2 eq) in dioxane (3 mL) and water (0.3 mL) was degassed and purged with nitrogen for three times, and then the mixture was stirred under microwave irradiation at 110° C. for 2 h. The mixture was added water (30 mL) and extracted with ethyl acetate (30 mL×3). The combined organic phase was dried over anhydrous $Na_2SO_4$, filtered and concentrated in vacuum to give a residue. The residue was purified by flash silica gel chromatography (ISCO®; 12 g Sepa Flash® Silica Flash Column, Eluent of 0~80% Ethyl acetate/Petroleum ether gradient @35 mL/min). Compound 4-[2-amino-9-[(3-methyl-4-nitro-phenyl)methyl]purin-6-yl]pyridine-2-carbonitrile (104 mg, 242.26 μmol, 77% yield, 90% purity) was obtained as a yellow solid. $^1H$ NMR (400 MHz, DMSO-$d_6$) δ=9.05 (s, 1H), 8.99 (d, J=5.1 Hz, 1H), 8.89 (dd, J=1.6, 5.1 Hz, 1H), 8.44 (s, 1H), 7.97 (d, J=8.4 Hz, 1H), 7.41 (s, 1H), 7.28 (dd, J=1.4, 8.5 Hz, 1H), 6.85 (s, 2H), 5.45 (s, 2H), 2.51 (s, 3H). MS: m/z=387.1 (M+1, ESI+)

Stage 2: Production of 4-[2-amino-9-[(4-amino-3-methyl-phenyl)methyl]purin-6-yl]pyridine-2-carbonitrile To a solution of 4-[2-amino-9-[(3-methyl-4-nitro-phenyl)methyl]purin-6-yl]pyridine-2-carbonitrile (200 mg, 517.64 μmol, 1 eq) in ethanol (6 mL) and water (2 mL) were added iron dust (145 mg, 2.59 mmol, 5 eq) and $NH_4Cl$ (221 mg, 4.14 mmol, 8 eq). The mixture was stirred at 80° C. for 1 h. The mixture was filtered and the filtrate was concentrated in vacuum to give a residue. The residue was added water (40 mL) and extracted with ethyl acetate (30 mL×3). The combined organic layers were concentrated under reduced pressure to give a residue. The crude product was triturated with THF at 70° C. for 30 min. Compound 130 or 4-[2-amino-9-[(4-amino-3-methyl-phenyl) methyl]purin-6-yl]pyridine-2-carbonitrile (62 mg, 167.01 μmol, 32% yield, 96.73% purity) was obtained as a yellow solid. $^1H$ NMR (400 MHz, DMSO-$d_6$) δ=9.04 (s, 1H), 8.97 (d, J=5.1 Hz, 1H), 8.87 (dd, J=1.5, 5.1 Hz, 1H), 8.32 (s, 1H), 6.99-6.88 (m, 2H), 6.85 (s, 2H), 6.54 (d, J=8.0 Hz, 1H), 5.12 (s, 2H), 4.87 (s, 2H), 2.00 (s, 3H). HRMS-TOF: 357.1568.

Example 1.39: Production 4-[2-amino-9-[[4-amino-3-(triflurormethyl)phenyl]methyl]purin-6-yl]pyridine-2-carbonitrile (Compound 136)

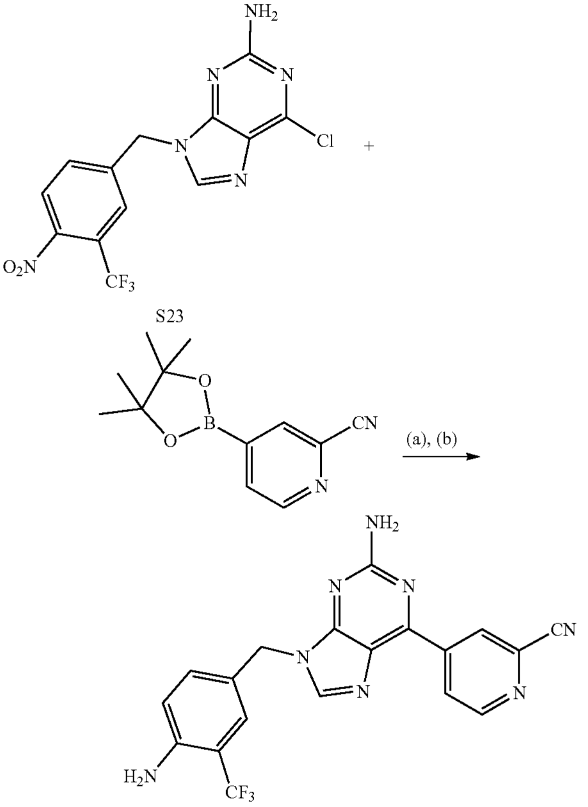

S23

136

Reagents and condition: (a) APhos-Pd-G3, $K_3PO_4$, DMAc, 60° C., 16 h (b) Fe, $NH_4Cl$, EtOH/$H_2O$, 60° C., 1 h.

Stage 1: Production of 4-[2-amino-9-[[4-nitro-3-(trifluoromethyl)phenyl]methyl]purin-6-yl]pyridine-2-carbonitrile A mixture of intermediate compound S23 or 6-chloro-9-[[4-nitro-3-(trifluoromethyl)phenyl]methyl]purin-2-amine (50 mg, 134.16 μmol, 1 eq), 4-(4,4,5,5-tetramethyl-1,3,2-dioxaborolan-2-yl)pyridine-2-carbonitrile (34 mg, 147.58 μmol, 1.1 eq), $K_3PO_4$ (1.5 M aqueous solution, 90 μL, 1 eq) and APhos-Pd-G3 (8.52 mg, 13.42 μmol, 0.1 eq) in DMAc (2 mL) was degassed and purged with nitrogen for three times, and then the mixture was stirred at 60° C. for 16 h under nitrogen atmosphere. The reaction mixture was concentrated under reduced pressure to remove solvent. The residue was purified by prep-TLC ($SiO_2$, Ethyl acetate/Petroleum ether-1:1). Compound 4-[2-amino-9-[[4-nitro-3-(trifluoromethyl)phenyl]methyl]purin-6-yl]pyridine-2-carbonitrile (40 mg, 90.84 μmol, 68% yield) was obtained as a yellow oil. MS: m/z=441.1 (M+1, ESI+).

Stage 2: Production of 4-[2-amino-9-[[4-amino-3-(trifluoromethyl)phenyl]methyl]purin-6-yl]pyridine-2-carbonitrile To a solution of 4-[2-amino-9-[[4-nitro-3-(trifluoromethyl)phenyl]methyl]purin-6-yl]pyridine-2-carbonitrile (40 mg, 90.84 μmol, 1 eq) in ethanol (15 mL) and water (5 mL) were added iron dust (25 mg, 454.2 μmol, 5 eq) and $NH_4Cl$ (39 mg, 726.72 μmol, 8 eq). The mixture was stirred at 60° C. for 1 h. The reaction mixture was filtered and concentrated under reduced pressure to give a residue. The residue was purified by prep-HPLC (column: Welch Ultimate XB-SiOH 250*50*10 μm; mobile phase: [Hexane-EtOH (0.1% ammonia hydroxide)]; B %: 10%-50%, 15 min). Compound 136 or 4-[2-amino-9-[[4-amino-3-(trifluoromethyl)phenyl]methyl]purin-6-yl]pyridine-2-carbonitrile (8.9 mg, 20.71 μmol, 23% yield, 95.51% purity) was obtained as a white solid. $^1H$ NMR (400 MHz, DMSO-$d_6$) δ=9.03 (s, 1H), 8.97 (d, J=5.1 Hz, 1H), 8.87 (dd, J=1.3, 5.1 Hz, 1H), 8.38 (s, 1H), 7.41 (s, 1H), 7.29 (br d, J=8.4 Hz, 1H), 6.84 (s, 2H), 6.79 (d, J=8.5 Hz, 1H), 5.66 (s, 2H), 5.20 (s, 2H). HRMS-TOF: 411.1305.

Example 1.40: Production 3-(6-amino-1-(4-amino-3-methylbenzyl)-1H-pyrazolo[3,4-d]pyrimidin-4-yl) benzonitrile (Compound 204)

1.40.1. Production of 3-(6-amino-1H-pyrazolo[3,4-d]pyrimidin-4-yl)benzonitrile (intermediate compound S107)

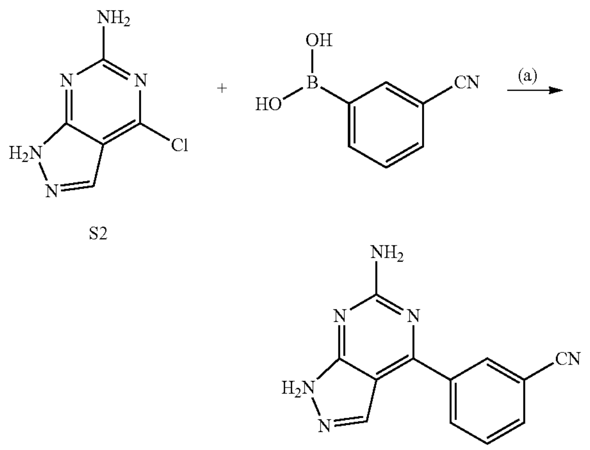

S2

S107

Reagents and Conditions: (a) $Pd(PPh_3)_4$, $Na_2CO_3$, dioxane/$H_2O$, 100° C., 16 h.

A mixture of 4-chloro-1H-pyrazolo[3,4-d]pyrimidin-6-amine (500 mg, 1 eq), (3-cyanophenyl)boronic acid (519 mg, 1.2 eq), $Pd(PPh_3)_4$ (340 mg, 0.1 eq) and $Na_2CO_3$ (625 mg, 2 eq) in dioxane (20 mL) was degassed and purged with nitrogen for three times, and then the mixture was stirred at 100° C. for 16 hr under nitrogen atmosphere. The reaction mixture was partitioned between ethyl acetate (100 mL) and water (30 mL). The organic phase was separated, washed by brine (20 mL), dried over sodium sulfate, filtered and concentrated under reduced pressure to give a residue. The crude product 3-(6-amino-1H-pyrazolo[3,4-d]pyrimidin-4-yl)benzonitrile (500 mg, crude) was obtained as a yellow solid and used into the next step without further purification. MS: m/z=237.1 (M+1, ESI+).

1.40.2. Production of 3-(6-amino-1-(4-amino-3-methylbenzyl)-1H-pyrazolo[3,4-d]pyrimidin-4-yl) benzonitrile (Compound 204)

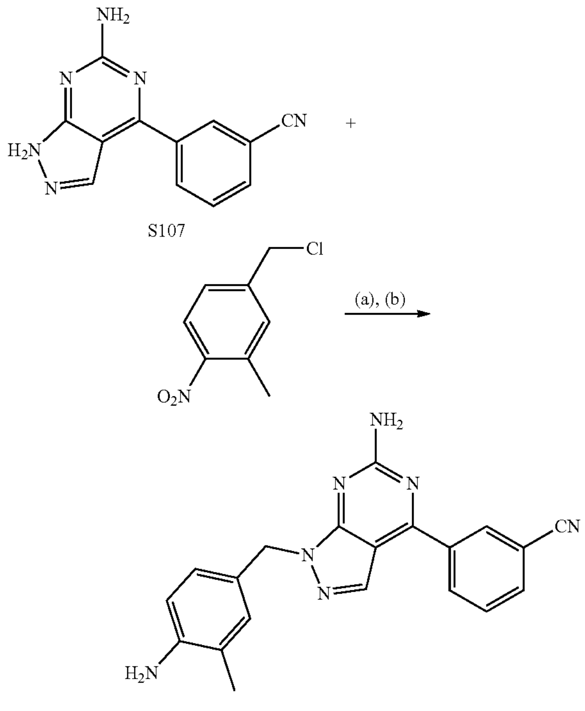

S107

204

Reagents and Conditions: (a) $K_2CO_3$, DMF, 80° C., 16 h; (b) Fe, $NH_4Cl$, EtOH/$H_2O$, 60° C., 1 h.

Stage 1: Production of 3-[6-amino-1-[(3-methyl-4-nitro-phenyl)methyl]pyrazolo[3,4-d]pyrimidin-4-yl] benzonitrile To a solution of 4-(chloromethyl)-2-methyl-1-nitro-benzene (500 mg, 1.27 eq) and intermediate compound 5107 or 3-(6-amino-1H-pyrazolo[3,4-d]pyrimidin-4-yl)benzonitrile (500 mg, 1 eq) in DMF (10 mL) was added $K_2CO_3$ (585 mg, 2 eq). The mixture was stirred at 80° C. for 16 hr. The reaction mixture was concentrated under reduced pressure to give a residue. The residue was purified by prep-HPLC (column: Phenomenex Luna C18 150*25 mm*10 μm; mobile phase: [water (0.225% FA)-ACN]; B %: 40%-70%, 10 min). Compound 3-[6-amino-1-[(3-methyl-4-nitro-phenyl)methyl]pyrazolo[3,4-d]pyrimidin-4-yl]benzonitrile (200 mg, 24% yield) was obtained as a yellow solid. $^1H$ NMR (400 MHz, DMSO-$d_6$) δ=8.56-8.42 (m, 3H), 8.10-8.06 (m, 1H), 8.00-7.92 (m, 1H), 7.86-7.76 (m, 1H), 7.40-7.30 (m, 1H), 7.24-7.08 (m, 3H), 5.65-5.43 (m, 2H), 2.49 (s, 3H). MS: m/z=386.0 (M+1, ESI+).

Stage 2: Production of 3-(6-amino-1-(4-amino-3-methylbenzyl)-1H-pyrazolo[3,4-d]pyrimidin-4-yl) benzonitrile (Compound 204)

To a solution of 3-[6-amino-1-[(3-methyl-4-nitro-phenyl) methyl]pyrazolo [3,4-d]pyrimidin-4-yl]benzonitrile (150 mg, 1 eq) in ethanol (12 mL) and water (4 mL) were added iron dust (108 mg, 1.95 mmol, 5 eq) and $NH_4Cl$ (166 mg, 8 eq). The mixture was stirred at 60° C. for 1 hr. The reaction mixture was filtered and concentrated under reduced pressure to give a residue. The residue was purified by prep-HPLC (column: Phenomenex Luna C18 150*25 mm*10 μm; mobile phase: [water (0.225% FA)-ACN]; B %: 23%-53%, 10 min). Compound 204 or 3-[6-amino-1-[(4-amino-3-methyl-phenyl)methyl]pyrazolo[3,4-d]pyrimidin-4-yl] benzonitrile (54.26 mg, 38% yield, 98.27% purity) was obtained as a white solid. $^1$H NMR (400 MHz, DMSO-$d_6$) δ=8.54-8.49 (m, 1H), 8.49-8.45 (m, 1H), 8.37-8.31 (m, 1H), 8.09-8.01 (m, 1H), 7.84-7.70 (m, 1H), 7.16-6.99 (m, 2H), 6.91-6.86 (m, 1H), 6.86-6.80 (m, 1H), 6.58-6.45 (m, 1H), 5.33-5.14 (m, 2H), 4.98-4.57 (m, 2H), 2.02-1.96 (m, 3H).

Example 1.41: Production 3-(6-amino-1-(4-amino-3-methylbenzyl)-1H-pyrazolo[3,4-d]pyrimidin-4-yl)-2-fluorobenzonitrile (Compound 206)

1.41.1. Production of 4-chloro-1-(3-methyl-4-nitrobenzyl)-1H-pyrazolo[3,4-d]pyrimidin-6-amine (intermediate compound S108)

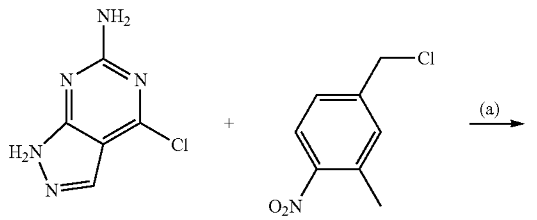

S2

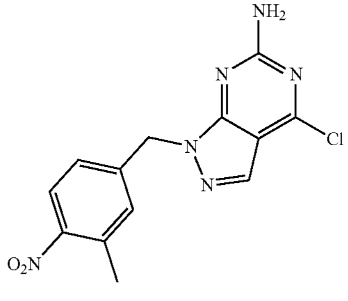

S108

Reagents and Conditions: (a) $K_2CO_3$, DMAc, 80° C., 16 h.

To a solution of 4-chloro-1H-pyrazolo[3,4-d]pyrimidin-6-amine (0.8 g, 1 eq) and 4-(chloromethyl)-2-methyl-1-nitro-benzene (720 mg, 0.8) in DMAc (50 mL) was added $K_2CO_3$ (1.30 g, 2 eq). The mixture was stirred at 80° C. for 16 hr. The reaction mixture filtered and concentrated under reduced pressure to give a residue. The crude product 4-chloro-1-[(3-methyl-4-nitro-phenyl)methyl]pyrazolo[3,4-d]pyrimidin-6-amine (800 mg, crude) was obtained as a yellow solid and used into the next step without further purification. MS: m/z=354.9 (M+1, ESI+).

1.41.2. Production of 3-(6-amino-1-(4-amino-3-methylbenzyl)-1H-pyrazolo[3,4-d]pyrimidin-4-yl)-2-fluorobenzonitrile (Compound 206)

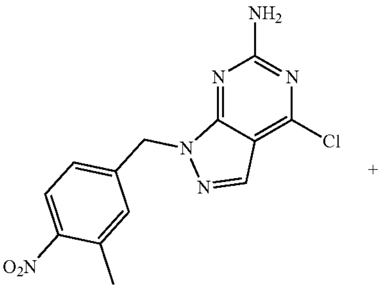

S108

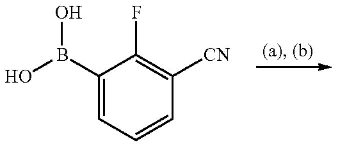

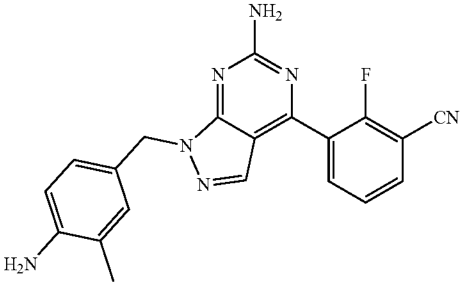

206

Reagents and condition: (a) $Pd(PPh_3)_4$, $K_2CO_3$, dioxane/$H_2O$, 100° C., 16 h; (b) Fe, $NH_4Cl$, EtOH/$H_2O$, 60° C., 1 h.

Stage 1: Production of 3-(6-amino-1-(3-methyl-4-nitrobenzyl)-1H-pyrazolo[3,4-d]pyrimidin-4-yl)-2-fluorobenzonitrile A mixture of (3-cyano-2-fluoro-phenyl)boronic acid (434 mg, 1.2 eq), intermediate compound S108 or 4-chloro-1-[(3-methyl-4-nitro-phenyl)methyl]pyrazolo[3,4-d]pyrimidin-6-amine (700 mg, 1 eq), $Pd(PPh_3)_4$ (253 mg, 219.63 μmol, 0.1 eq) and $Na_2CO_3$ (465 mg, 2 eq) in dioxane (10 mL) and water (2 mL) was degassed and purged with nitrogen for three times, and then the mixture was stirred at 110° C. for 16 hr under nitrogen atmosphere. The reaction mixture was filtered and concentrated under reduced pressure to give a residue. The residue was purified by flash silica gel chromatography (ISCO®; 40 g SepaFlash® Silica Flash Column, Eluent of 0~80% Ethyl acetate/Petroleum ether gradient @40 mL/min). Compound 3-[6-amino-1-[(3-methyl-4-nitro-phenyl)methyl]pyrazolo[3,4-d]pyrimidin-4-yl]-2-fluoro-benzonitrile (800 mg, 90% yield) was obtained as a yellow solid. MS: m/z=386.0 (M+1, ESI+).

Stage 2: Production of 3-(6-amino-1-(4-amino-3-methylbenzyl)-1H-pyrazolo[3,4-d]pyrimidin-4-yl)-2-fluorobenzonitrile (Compound 206)

To a solution of 3-[6-amino-1-[(3-methyl-4-nitro-phenyl) methyl]pyrazolo [3,4-d]pyrimidin-4-yl]-2-fluoro-benzonitrile (200 mg, 1 eq) in water (4 mL) and ethanol (12 mL) were added iron dust (138 mg, 5 eq) and $NH_4Cl$ (212 mg, 8 eq). The mixture was stirred at 60° C. for 1 hr. The reaction mixture was filtered and concentrated under reduced pressure to give a residue. The residue was purified by prep-HPLC (column: Phenomenex Synergi C18 150*25 mm*10 μm; mobile phase: [water (0.225% FA)-ACN]; B %: 16%-46%, 11 min), the 89% purity compound was obtained after first purification. The residue was purified by prep-HPLC (column: Phenomenex Luna C18 150*25 mm*10 μm; mobile phase: [water (0.225% FA)-ACN]; B %: 18%-48%, 10 min). Compound 206 or 3-[6-amino-1-[(4-amino-3-methyl-phenyl)methyl]pyrazolo[3,4-d]pyrimidin-4-yl]-2-fluoro-benzonitrile (111.35 mg, 59% yield, 97.78% purity) was obtained as a white solid. $^1H$ NMR (400 MHz, DMSO-d6) δ=8.21-8.10 (m, 2H), 8.00-7.94 (m, 1H), 7.66-7.52 (m, 1H), 7.16-7.07 (m, 2H), 6.92-6.80 (m, 2H), 6.56-6.46 (m, 1H), 5.34-5.15 (m, 2H), 4.93-4.67 (m, 2H), 2.06-1.88 (m, 3H).

Example 1.42: Production 3-(6-amino-1-(4-amino-3-(trifluoromethyl)benzyl)-1H-pyrazolo[3,4-d]pyrimidin-4-yl)benzonitrile (Compound 210)

1.42.1. Production of 4-chloro-1-(4-nitro-3-(trifluoromethyl)benzyl)-1H-pyrazolo[3,4-d]pyrimidin-6-amine (intermediate compound S109)

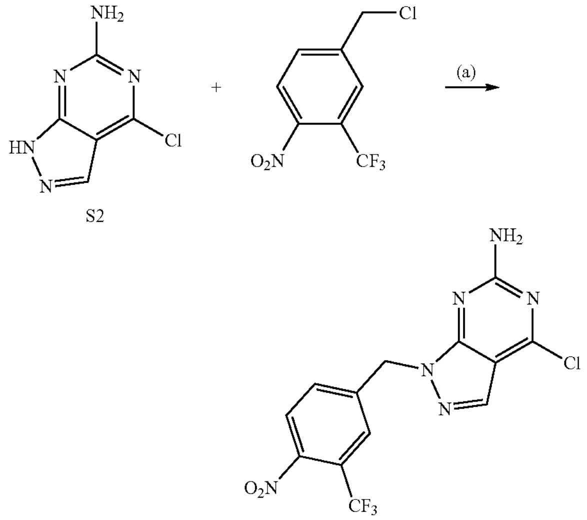

S2

S109

Reagents and Conditions: (a) $K_2CO_3$, DMAc, 80° C., 16 h.

To a solution of 4-(chloromethyl)-1-nitro-2-(trifluoromethyl)benzene (3.39 g, 1.2 eq) and 4-chloro-1H-pyrazolo[3,4-d]pyrimidin-6-amine (2 g, 1 eq) in DMF (20 mL) was added $K_2CO_3$ (3.26 g, 2 eq). The mixture was stirred at 80° C. for 16 hr. The reaction mixture was concentrated under reduced pressure to remove DMF to give a residue. The residue was purified by flash silica gel chromatography (ISCO®; 40 g SepaFlash® Silica Flash Column, Eluent of 0~100% Ethyl acetate/Petroleum ether gradient @45 mL/min). Compound 4-chloro-1-[[4-nitro-3-(trifluoromethyl)phenyl]methyl]pyrazolo[3,4-d]pyrimidin-6-amine (2 g, 45% yield) was obtained as a yellow solid. MS: m/z=373.3 (M+1, ESI+)

1.42.2. Production of 3-(6-amino-1-(4-amino-3-(trifluoromethyl)benzyl)-1H-pyrazolo[3,4-d]pyrimidin-4-yl)benzonitrile (Compound 210)

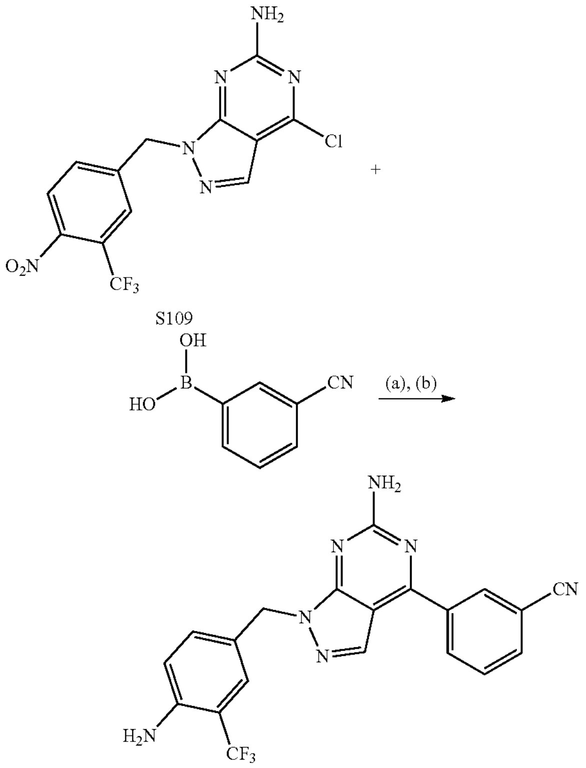

S109

210

Reagents and condition: (a) $Pd(PPh_3)_4$, $K_2CO_3$, dioxane/$H_2O$, 100° C., 15 h; (b) Fe, $NH_4Cl$, EtOH/$H_2O$, 60° C., 2 h.

Stage 1: Production of 3-(6-amino-1-(4-nitro-3-(trifluoromethyl)benzyl)-1H-pyrazolo[3,4-d]pyrimidin-4-yl)benzonitrile A mixture of (3-cyanophenyl)boronic acid (236 mg, 1.5 eq), intermediate compound S109 or 4-chloro-1-[[4-nitro-3-(trifluoromethyl) phenyl]methyl]pyrazolo[3,4-d]pyrimidin-6-amine (400 mg, 1 eq), $Pd(PPh_3)_4$ (124 mg, 0.1 eq), $K_2CO_3$ (296 mg, 2 eq) in dioxane (10 mL) and water (1 mL) was degassed and purged with nitrogen for three times, and then the mixture was stirred at 100° C. for 15 hr under nitrogen atmosphere. The reaction mixture was concentrated under reduced pressure to remove dioxane and water to give a residue. The residue was purified by flash silica gel chromatography (ISCO®; 12 g SepaFlash® Silica Flash Column, Eluent of 0~100% Ethyl acetate/Petroleum ether gradient @35 mL/min). Compound 3-[6-amino-1-[[4-nitro-3-(trifluoromethyl)phenyl]methyl]pyrazolo[3,4-d]pyrimidin-4-yl]benzonitrile (300 mg, 63% yield) was obtained as a yellow oil. MS: m/z=440.1 (M+1, ESI+).

Stage 2: Production of 3-(6-amino-1-(4-amino-3-(trifluoromethyl)benzyl)-1H-pyrazolo[3,4-d]pyrimidin-4-yl)benzonitrile (Compound 210)

To a solution of 3-[6-amino-1-[[4-nitro-3-(trifluoromethyl)phenyl]methyl]pyrazolo[3,4-d]pyrimidin-4-yl]benzonitrile (290 mg, 1 eq) in water (5 mL) and ethanol (15 mL) was added iron dust (190 mg, 5 eq) and $NH_4Cl$ (292 mg, 8 eq). The mixture was stirred at 60° C. for 2 hr. The reaction mixture was concentrated under reduced pressure to remove ethanol to give a residue. The residue was purified by prep-HPLC (column: Unisil 3-100 C18 Ultra 150*50 mm*3 μm; mobile phase: [water (0.225% FA)-ACN]; B %: 43%-63%, 10 min). Compound 210 or 3-[6-amino-1-[[4-amino-3-(trifluoromethyl)phenyl]methyl]pyrazolo[3,4-d]pyrimidin-4-yl]benzonitrile (59.98 mg, 21% yield, 99.14% purity) was obtained as a white solid. $^1H$ NMR (400 MHz, DMSO-$d_6$) δ=8.52 (s, 1H), 8.47 (d, J=8.1 Hz, 1H), 8.38 (s, 1H), 8.06 (d, J=7.7 Hz, 1H), 7.79 (t, J=7.8 Hz, 1H), 7.30 (d, J=1.5 Hz, 1H), 7.23-7.17 (m, 1H), 7.10 (s, 2H), 6.78 (d, J=8.4 Hz, 1H), 5.59 (s, 2H), 5.30 (s, 2H).

Example 1.43: Production of 3-(6-amino-1-(4-amino-3-(trifluoromethyl)benzyl)-1H-pyrazolo[3,4-d]pyrimidin-4-yl)-2-fluorobenzonitrile (Compound 211)

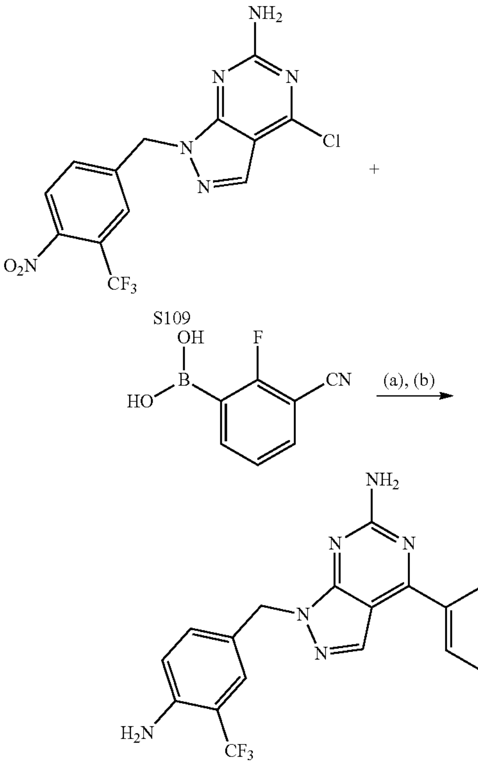

S109

211

Reagents and condition: (a) $Pd(PPh_3)_4$, $K_2CO_3$, dioxane/$H_2O$, 100° C., 15 h; (b) Fe, $NH_4Cl$, EtOH/$H_2O$, 60° C., 2 h.

Stage 1: Production of 3-(6-amino-1-(4-nitro-3-(trifluoromethyl)benzyl)-1H-pyrazolo[3,4-d]pyrimidin-4-yl)-2-fluorobenzonitrile A mixture of (3-cyano-2-fluoro-phenyl)boronic acid (265 mg, 1.5 eq), intermediate compound S109 or 4-chloro-1-[[4-nitro-3-(trifluoromethyl)phenyl]methyl]pyrazolo[3,4-d]pyrimidin-6-amine (400 mg, 1 eq), $Pd(PPh_3)_4$ (124 mg, 0.1 eq), $K_2CO_3$ (296 mg, 2 eq) in dioxane (10 mL) and water (1 mL) was degassed and purged with nitrogen for three times, and then the mixture was stirred at 100° C. for 15 hr under nitrogen atmosphere. The reaction mixture was concentrated under reduced pressure to remove dioxane and water to give a residue. The residue was purified by flash silica gel chromatography (ISCO®; 12 g Sepa Flash® Silica Flash Column, Eluent of 0~100% Ethyl acetate/Petroleum ether gradient @35 mL/min). Compound 3-[6-amino-1-[[4-nitro-3-(trifluoromethyl)phenyl]methyl]pyrazolo[3,4-d]pyrimidin-4-yl]-2-fluoro-benzonitrile (350 mg, 71% yield) was obtained as a yellow oil. MS: m/z=458.3 (M+1, ESI+).

Stage 2: Production of 3-(6-amino-1-(4-amino-3-(trifluoromethyl)benzyl)-1H-pyrazolo[3,4-d]pyrimidin-4-yl)-2-fluorobenzonitrile (Compound 211)

To a solution of 3-[6-amino-1-[[4-nitro-3-(trifluoromethyl)phenyl]methyl]pyrazolo[3,4-d]pyrimidin-4-yl]-2-fluoro-benzonitrile (300 mg, 1 eq) in ethanol (15 mL) and water (5 mL) was added iron dust (183 mg, 5 eq) and $NH_4Cl$ (280 mg, 8 eq). The mixture was stirred at 60° C. for 2 hr. The reaction mixture was concentrated under reduced pressure to remove ethanol to give a residue. The residue was purified by prep-HPLC (column: Unisil 3-100 C18 Ultra 150*50 mm*3 μm; mobile phase: [water (0.225% FA)-ACN]; B %: 43%-63%, 10 min). Compound 211 or 3-[6-amino-1-[[4-amino-3-(trifluoromethyl)phenyl]methyl]pyrazolo[3,4-d]pyrimidin-4-yl]-2-fluoro-benzonitrile (41.58 mg, 15% yield, 98.23% purity) was obtained as a solid off-white. $^1H$ NMR (400 MHz, DMSO-$d_6$) δ=8.20-8.11 (m, 2H), 8.00 (d, J=3.5 Hz, 1H), 7.60 (t, J=7.8 Hz, 1H), 7.30 (d, J=1.6 Hz, 1H), 7.23-7.17 (m, 1H), 7.15 (s, 2H), 6.78 (d, J=8.4 Hz, 1H), 5.60 (s, 2H), 5.29 (s, 2H).

Example 1.44: Production of 3-(6-amino-1-(2,6-difluorobenzyl)-1H-pyrazolo[3,4-d]pyrimidin-4-yl)-2-fluorobenzonitrile (Compound 213)

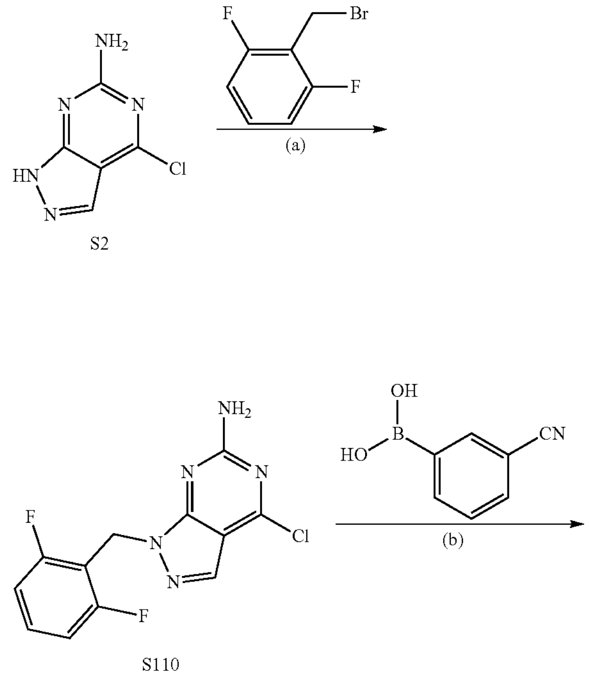

S2

S110

-continued

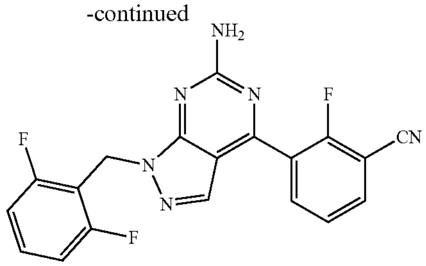

213

Reagents and Conditions: (a) $K_2CO_3$, DMAc, 80° C., 16 h; (b) $Pd(PPh_3)_4$, $K_2CO_3$, dioxane/$H_2O$, 80° C., 16 h.

Stage 1: Production of 4-chloro-1-[(2,6-difluoro-phenyl)methyl]pyrazolo[3,4-d]pyrimidin-6-amine (intermediate compound S110)

To a solution of 4-chloro-1H-pyrazolo[3,4-d]pyrimidin-6-amine (8 g, 47.18 mmol, 1 eq) and 2-(bromomethyl)-1,3-difluoro-benzene (11.72 g, 56.61 mmol, 1.2 eq) in DMAc (100 mL) was added $K_2CO_3$ (13.04 g, 94.36 mmol, 2 eq). The mixture was stirred at 80° C. for 16 hr. The reaction mixture was filtered and concentrated under reduced pressure to give a residue. The residue was purified by flash silica gel chromatography (ISCO®; 80 g Sepa Flash® Silica Flash Column, Eluent of 0~100% Ethyl acetate/Petroleum ether gradient @60 mL/min). Intermediate compound 5110 or 4-chloro-1-[(2,6-difluorophenyl)methyl]pyrazolo[3,4-d] pyrimidin-6-amine (4 g, 13.53 mmol, 29% yield) was obtained as a white solid. $^1H$ NMR (400 MHz, DMSO-$d_6$) δ=8.35-7.77 (m, 1H), 7.53-7.41 (m, 1H), 7.40-7.31 (m, 2H), 7.19-6.98 (m, 2H), 5.60-5.20 (m, 2H).

Stage 2: Production of 3-(6-amino-1-(2,6-difluorobenzyl)-1H-pyrazolo[3,4-d]pyrimidin-4-yl)-2-fluorobenzonitrile (Compound 213)

A mixture of (3-cyano-2-fluoro-phenyl)boronic acid (251 mg, 1.5 eq), intermediate compound S10 or 4-chloro-1-[(2, 6-difluorophenyl) methyl]pyrazolo[3,4-d]pyrimidin-6-amine (300 mg, 1 eq), $Pd(PPh_3)_4$ (117 mg, 0.1 eq), $K_2CO_3$ (280 mg, 2 eq) in dioxane (10 mL) and water (2 mL) was degassed and purged with nitrogen for three times, and then the mixture was stirred at 80° C. for 16 hr under nitrogen atmosphere. The reaction mixture was concentrated under reduced pressure to give a residue. The residue was purified by prep-HPLC (column: Unisil 3-100 C18 Ultra 150*50 mm*3 μm; mobile phase: [water (0.225% FA)-ACN]; B %: 45%-65%, 10 0 min). Compound 213 or 3-[6-amino-1-[(2, 6-difluorophenyl)methyl]pyrazolo[3,4-d]pyrimidin-4-yl]-2-fluoro-benzonitrile (118.51 mg, 30% yield, 98.93% purity) was obtained as a white solid. $^1H$ NMR (400 MHz, DMSO-$d_6$) δ=8.22-8.09 (m, 2H), 7.95 (d, J=3.5 Hz, 1H), 7.60 (t, J=7.8 Hz, 1H), 7.52-7.39 (m, 1H), 7.19 (s, 2H), 7.13 (t, J=8.0 Hz, 2H), 5.45 (s, 2H).

Example 1.45: Production of 3-(6-amino-1-(4-amino-2-fluorobenzyl)-1H-pyrazolo[3,4-d]pyrimidin-4-yl)benzonitrile (Compound 209)

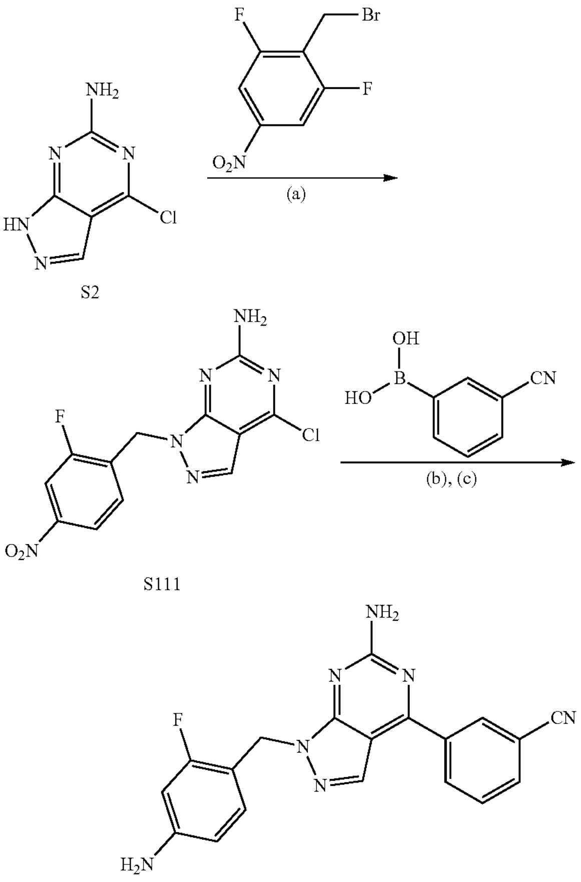

S2

S111

209

Reagents and Conditions: (a) $K_2CO_3$, DMAc, 60° C., 16 h; (b) $Pd(PPh_3)_4$, $K_2CO_3$, dioxane/$H_2O$, 80° C., 16 h; (c) Fe, $NH_4Cl$, EtOH/$H_2O$, 80° C., 3 h.

Stage 1: Production of 4-chloro-1-(2-fluoro-4-nitrobenzyl)-1H-pyrazolo[3,4-d]pyrimidin-6-amine (Intermediate Compound S111)

To a solution of 4-chloro-1H-pyrazolo[3,4-d]pyrimidin-6-amine (5.1 g, 1 eq) and 1-(bromomethyl)-2-fluoro-4-nitro-benzene (7 g, 1 eq) in DMF (20 mL) was added $K_2CO_3$ (8.3 g, 2 eq). The mixture was stirred at 60° C. for 16 hr. The reaction mixture was filtered and concentrated under reduced pressure to give a residue. The residue was purified by flash silica gel chromatography (ISCO®; 40 g Sepa-Flash® Silica Flash Column, Eluent of 0~100% Ethyl acetate/Petroleum ether gradient @40 mL/min). Intermediate compound S11 or 4-chloro-1-[(2-fluoro-4-nitro-phenyl) methyl]pyrazolo[3,4-d]pyrimidin-6-amine (5 g, 52% yield) was obtained as a yellow solid. $^1H$ NMR (400 MHz, DMSO-$d_6$) δ=8.15-8.11 (m, 1H), 8.08-8.06 (m, 1H), 8.05-8.01 (m, 1H), 7.47-7.38 (m, 2H), 7.33 (t, J=8.0 Hz, 1H), 5.57 (s, 2H). MS: m/z=323.3 (M+1, ESI+).

Stage 2: Production of 3-(6-amino-1-(2-fluoro-4-nitrobenzyl)-1H-pyrazolo [3,4-d]pyrimidin-4-yl) benzonitrile A mixture of (3-cyanophenyl)boronic acid (341 mg, 1.5 eq), intermediate compound S11 or 4-chloro-1-[(2-fluoro-4-nitro-phenyl)methyl]pyrazolo[3,4-d]pyrimidin-6-amine (500 mg, 1 eq), $Pd(PPh_3)_4$ (179 mg, 0.1 eq), $K_2CO_3$ (428 mg, 2 eq) in dioxane (10 mL) and water (2 mL) was degassed and purged with nitrogen for three times, and then the mixture was stirred at 100° C. for 16 hr under nitrogen atmosphere. The reaction mixture was concentrated under reduced pressure to remove dioxane to give a residue. The residue was purified by prep-HPLC (column: Unisil 3-100 C18 Ultra 150*50 mm*3 μm; mobile phase: [water (0.225% FA)-ACN]; B %: 45%-65%, 10 min). Compound 3-[6-amino-1-[(2-fluoro-4-nitro-phenyl)methyl]pyrazolo[3,4-d]pyrimidin-4-yl]benzonitrile (200 mg, 33% yield, 99% purity) was obtained as a yellow solid. $^1H$ NMR (400 MHz, DMSO-$d_6$) δ=8.55-8.51 (m, 1H), 8.49-8.46 (m, 1H), 8.31-8.26 (m, 1H), 8.18-8.01 (m, 4H), 7.38-7.28 (m, 1H), 7.22-7.05 (m, 2H), 5.62 (s, 2H). MS: m/z=389.9 (M+1, ESI+).

Stage 3: Production of 3-(6-amino-1-(4-amino-2-fluorobenzyl)-1H-pyrazolo[3,4-d]pyrimidin-4-yl) benzonitrile (Compound 209)

To a solution of 3-[6-amino-1-[(2-fluoro-4-nitro-phenyl) methyl]pyrazolo [3,4-d]pyrimidin-4-yl]benzonitrile (200 mg, 513.69 μmol, 1 eq) in ethanol (15 mL) and water (5 mL) were added iron dust (143 mg, 5 eq) and $NH_4Cl$ (219 mg, 8 eq). The mixture was stirred at 80° C. for 3 hr. The reaction mixture was concentrated under reduced pressure to remove ethanol and water to give a residue. The residue was purified by prep-HPLC (column: Unisil 3-100 C18 Ultra 150*50 mm*3 μm; mobile phase: [water (0.225% FA)-ACN]; B %: 30%-50%, 10 min). Compound 209 or 3-[6-amino-1-[(4-amino-2-fluoro-phenyl)methyl]pyrazolo[3,4-d]pyrimidin-4-yl]benzonitrile (36.42 mg, 19% yield, 97.66% purity) was obtained as an off-white solid. $^1H$ NMR (400 MHz, DMSO-$d_6$) δ=8.51 (s, 1H), 8.49-8.44 (m, 1H), 8.35 (s, 1H), 8.08-8.01 (m, 1H), 7.79 (t, J=7.8 Hz, 1H), 7.07 (s, 2H), 6.88 (t, J=8.5 Hz, 1H), 6.36-6.22 (m, 2H), 5.40 (s, 2H), 5.28 (s, 2H).

Example 1.46: Production of 3-(6-amino-1-(4-amino-2,6-difluorobenzyl)-1H-pyrazolo[3,4-d]pyrimidin-4-yl)benzonitrile (Compound 207)

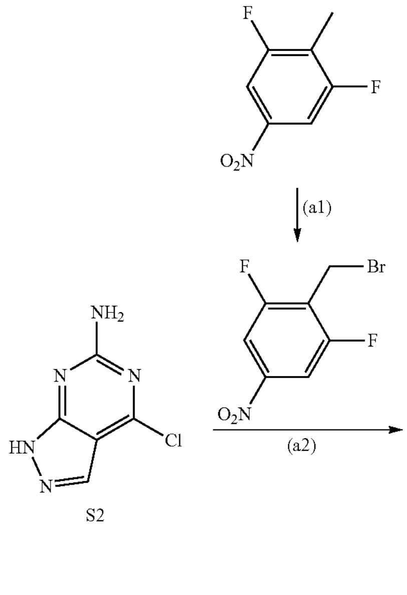

S2

-continued

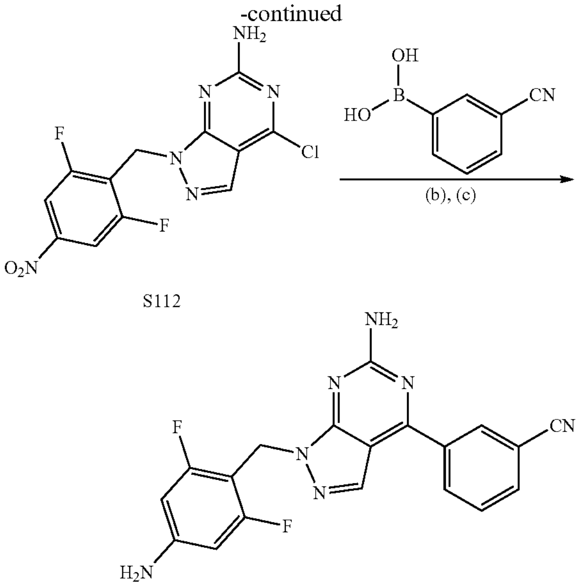

S112

207

Reagents and Conditions: (a1) NBS, AIBN, $CCl_4$, 90° C., 15 h; (a2) $K_2CO_3$, DMAc, 80° C., 3 h; (b) $Pd(dppf)Cl_2$, $K_2CO_3$, dioxane/$H_2O$, 110° C., 2 h, MW; (c) Fe, $NH_4Cl$, EtOH/$H_2O$, 80° C., 1 h.

Stage 1: Production of 4-chloro-1-[(2,6-difluoro-4-nitro-phenyl)methyl]pyrazolo[3,4-d]pyrimidin-6-amine (intermediate compound S112)

To the solution of 1,3-difluoro-2-methyl-5-nitro-benzene (2 g, 11.55 mmol, 1 eq) in tetrachloromethane (50 mL) were added NBS (3.08 g, 17.33 mmol, 1.5 eq) and AIBN (190 mg, 1.16 mmol, 0.1 eq). Then the mixture was stirred at 90° C. for 15 h. The reaction mixture was concentrated in vacuum to give a residue. To the residue was added DMAc (50 mL), 4-chloro-1H-pyrazolo[3,4-d]pyrimidin-6-amine (1.96 g, 11.55 mmol, 1 eq) and $K_2CO_3$ (3.19 g, 23.11 mmol, 2 eq). Then the mixture was stirred at 80° C. for 3 h. To the mixture was added water (130 mL) and ethyl acetate (130 mL), and the layers were separated. The aqueous was extracted with ethyl acetate (130 mL×2). Combined the organic phase to wash by brines (150 mL×2), dry over anhydrous sodium sulfate, filter and the filtrate was concentrated in vacuum to give a residue. The residue was purified by flash silica gel chromatography (40 g SepaFlash® Silica Flash Column, Eluent of 0~30% Ethyl acetate/Petroleum ether gradient @60 mL/min). Intermediate compound S112 or 4-chloro-1-[(2,6-difluoro-4-nitro-phenyl) methyl]pyrazolo[3,4-d]pyrimidin-6-amine (1.5 g, 4.26 mmol, 37% yield, 96.7% purity) was obtained as a yellow solid.

Stage 2: Production of 3-[6-amino-1-[(2,6-difluoro-4-nitro-phenyl) methyl]pyrazolo[3,4-d]pyrimidin-4-yl]benzonitrile Intermediate compound S112 or 4-chloro-1-[(2,6-difluoro-4-nitro-phenyl)methyl]pyrazolo[3,4-d]pyrimidin-6-amine (500 mg, 1.47 mmol, 1 eq), (3-cyanophenyl)boronic acid (323 mg, 2.20 mmol, 1.5 eq), $K_2CO_3$ (405 mg, 2.94 mmol, 2 eq) and $Pd(dppf)Cl_2$ (107 mg, 146.77 μmol, 0.1 eq) were taken up into a microwave tube in dioxane (6 mL) and water (2 mL). The sealed tube was heated at 110° C. for 2 h under microwave. After that the mixture was added water (80 mL) and ethyl acetate (80 mL), and the layers were separated. The aqueous was extracted with ethyl acetate (80 mL×3). Combined the organic phase to dry over anhydrous sodium sulfate, filter and the filtrate was concentrated in vacuum to give a residue. The residue was purified by flash silica gel chromatography (20 g SepaFlash® Silica Flash Column, Eluent of 0~100% Ethyl acetate/Petroleum ether gradient @50 mL/min). Compound 3-[6-amino-1-[(2,6-difluoro-4-nitro-phenyl)methyl]pyrazolo[3,4-d]pyrimidin-4-yl]benzonitrile (200 mg, 441.90 μmol, 30% yield, 90% purity) was obtained as a yellow solid. $^1$H NMR (400 MHz, DMSO-$d_6$) δ=8.49 (d, J=1.2 Hz, 1H), 8.47-8.41 (m, 1H), 8.35 (s, 1H), 8.16-8.07 (m, 2H), 8.06 (td, J=1.3, 7.8 Hz, 1H), 7.79 (t, J=7.9 Hz, 1H), 7.16 (s, 2H), 5.55 (s, 2H). MS: m/z=408.0 (M+1, ESI+).

Stage 3: Production of 3-[6-amino-1-[(4-amino-2,6-difluoro-phenyl) methyl]pyrazolo[3,4-d]pyrimidin-4-yl]benzonitrile (Compound 207)

To the solution of 3-[6-amino-1-[(2,6-difluoro-4-nitro-phenyl)methyl]pyrazolo[3,4-d]pyrimidin-4-yl]benzonitrile (200 mg, 491.00 μmol, 1 eq) in ethanol (8 mL) and water (2 mL) were added iron dust (137 mg, 2.45 mmol, 5 eq) and $NH_4Cl$ (210 mg, 3.93 mmol, 8 eq). Then the mixture was stirred at 80° C. for 1 h. The reaction mixture was filtered and the filtrate was concentrated in vacuum. After that, to the mixture was added water (30 mL) and then extracted with ethyl acetate (30 mL×3). Combined the organic phase to dry over anhydrous sodium sulfate, filter and the filtrate was concentrated in vacuum to give a residue. The residue was purified by prep-HPLC (column: Welch Ultimate XB-CN 250*70*10 μm; mobile phase: [Hexane-EtOH (0.1% ammonia hydroxide)]; B %: 30%-70%, 15 min). Compound 207 or 3-[6-amino-1-[(4-amino-2,6-difluoro-phenyl)methyl]pyrazolo[3,4-d]pyrimidin-4-yl]benzonitrile (62.95 mg, 163.33 μmol, 33% yield, 97.91% purity) was obtained as a yellow solid. $^1$H NMR (400 MHz, DMSO-$d_6$) δ=8.49 (t, J=1.4 Hz, 1H), 8.45 (td, J=1.4, 7.9 Hz, 1H), 8.29 (s, 1H), 8.05 (td, J=1.3, 7.7 Hz, 1H), 7.79 (t, J=7.8 Hz, 1H), 7.07 (s, 2H), 6.30-6.06 (m, 2H), 5.80 (s, 2H), 5.25 (s, 2H).

Example 1.47: Production of 3-(6-amino-1-(4-amino-2-fluorobenzyl)-1H-pyrazolo[3,4-d]pyrimidin-4-yl)-2-fluorobenzonitrile (Compound 203)

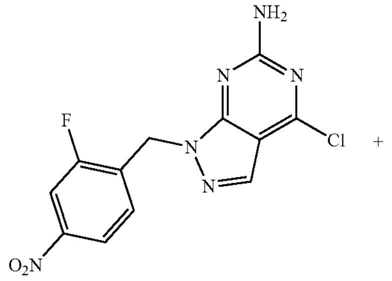

S111

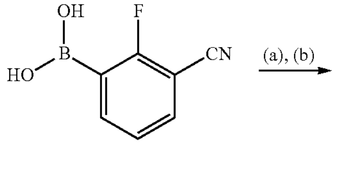

-continued

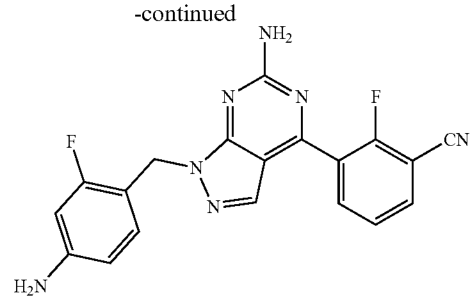

203

Reagents and condition: (a) $Pd(dppf)Cl_2$, $K_2CO_3$, dioxane/$H_2O$, 110° C., 16 h; (b) Fe, $NH_4Cl$, EtOH/$H_2O$, 80° C., 3 h.

Stage 1: Production of 3-(6-amino-1-(2-fluoro-4-nitrobenzyl)-1H-pyrazolo[3,4-d]pyrimidin-4-yl)-2-fluorobenzonitrile A mixture of (3-cyano-2-fluoro-phenyl)boronic acid (383 mg, 2.33 mmol, 1.5 eq), intermediate compound S111 or 4-chloro-1-[(2-fluoro-4-nitro-phenyl)methyl]pyrazolo[3,4-d]pyrimidin-6-amine (500 mg, 1 eq), $Pd(PPh_3)_4$ (179 mg, 0.1 eq), $K_2CO_3$ (428 mg, 2 eq) in dioxane (10 mL) and water (2 mL) was degassed and purged with nitrogen for three times, and then the mixture was stirred at 100° C. for 16 hr under nitrogen atmosphere. The reaction mixture was concentrated under reduced pressure to remove dioxane to give a residue. The residue was purified by flash silica gel chromatography (ISCO®; 12 g Sepa Flash® Silica Flash Column, Eluent of 0~80% Ethyl acetate/Petroleum ether gradient @30 mL/min). Compound 3-[6-amino-1-[(2-fluoro-4-nitro-phenyl)methyl]pyrazolo[3,4-d]pyrimidin-4-yl]-2-fluoro-benzonitrile (300 mg, 48% yield) was obtained as a yellow solid. MS: m/z=407.9 (M+1, ESI+).

Stage 2: Production of 3-(6-amino-1-(4-amino-2-fluorobenzyl)-1H-pyrazolo [3,4-d]pyrimidin-4-yl)-2-fluorobenzonitrile (Compound 203)

To a solution of 3-[6-amino-1-[(2-fluoro-4-nitro-phenyl) methyl]pyrazolo [3,4-d]pyrimidin-4-yl]-2-fluoro-benzonitrile (209 mg, 1 eq) in ethanol (15 mL) and water (5 mL) was added iron dust (143 mg, 5 eq) and $NH_4Cl$ (219 mg, 8 eq). The mixture was stirred at 80° C. for 3 hr. The reaction mixture was concentrated under reduced pressure to remove ethanol to give a residue. The residue was purified by prep-HPLC (column: Unisil 3-100 C18 Ultra 150*50 mm*3 μm; mobile phase: [water (0.225% FA)-ACN]; B %: 33%-53%, 10 min), 80% purity desired compound was obtained, then the residue was purified by second prep-HPLC (column: Phenomenex Gemini-NX C18 75*30 mm*3 μm; mobile phase: [water (0.225% FA)-ACN]; B %: 22%-52%, 7 min). Compound 203 or 3-[6-amino-1-[(4-amino-2-fluoro-phenyl)methyl]pyrazolo[3,4-d]pyrimidin-4-yl]-2-fluoro-benzonitrile (62.37 mg, 31% yield, 97.40% purity) was obtained as a white solid. $^1$H NMR (400 MHz, DMSO-$d_6$) δ=8.21-8.10 (m, 2H), 7.98 (d, J=3.7 Hz, 1H), 7.61 (t, J=7.8 Hz, 1H), 7.14 (s, 2H), 6.97-6.84 (m, 1H), 6.32 (s, 1H), 6.31-6.28 (m, 1H), 5.42 (s, 2H), 5.27 (s, 2H).

Example 1.48: Production of 3-(6-amino-1-(4-amino-2,6-difluorobenzyl)-1H-pyrazolo[3,4-d]pyrimidin-4-yl)-2-fluorobenzonitrile (Compound 208)

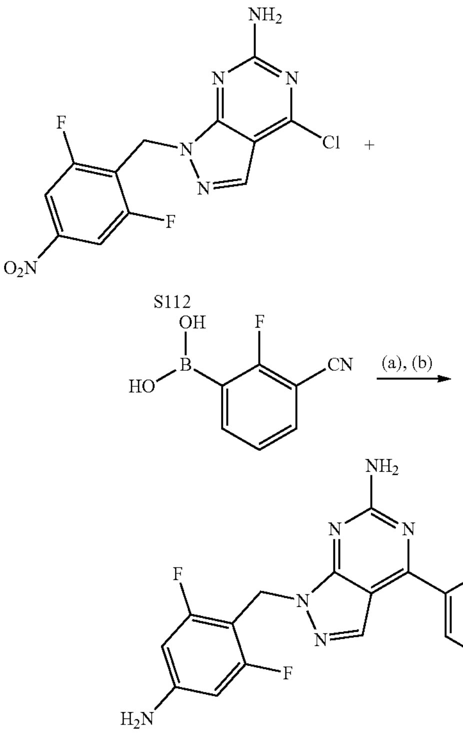

S112

208

Reagents and condition: (a) Pd(dppf)$Cl_4$, $K_2CO_3$, dioxane/$H_2O$, 110° C., 15 h; (b) Fe, $NH_4Cl$, EtOH/$H_2O$, 80° C., 1 h.

Stage 1: Production of 3-[6-amino-1-[(2,6-difluoro-4-nitro-phenyl)methyl]pyrazolo[3,4-d]pyrimidin-4-yl]-2-fluoro-benzonitrile To the solution of intermediate compound S112 or 4-chloro-1-[(2,6-difluoro-4-nitro-phenyl)methyl]pyrazolo [3,4-d]pyrimidin-6-amine (400 mg, 1.17 mmol, 1 eq) in water (2 mL) and dioxane (8 mL) were added (3-cyano-2-fluoro-phenyl)boronic acid (300 mg, 1.82 mmol, 1.55 eq), Pd(dppf)$Cl_2$ (86 mg, 117.41 μmol, 0.1 eq) and $K_2CO_3$ (325 mg, 2.35 mmol, 2 eq). Then the mixture was stirred at 110° C. for 15 h. After that the mixture was concentrated in vacuum to give a residue, and it was purified by flash silica gel chromatography (12 g SepaFlash® Silica Flash Column, Eluent of 20~100% Ethyl acetate/Petroleum ether gradient @50 mL/min). Compound 3-[6-amino-1-[(2,6-difluoro-4-nitro-phenyl)methyl]pyrazolo[3,4-d]pyrimidin-4-yl]-2-fluoro-benzonitrile (140 mg, 322.25 μmol, 27% yield, 97.9% purity) was obtained as a yellow solid. $^1H$ NMR (400 MHz, DMSO-$d_6$) δ=8.20-8.12 (m, 2H), 8.12-8.05 (m, 2H), 7.99 (d, J=3.6 Hz, 1H), 7.60 (t, J=7.8 Hz, 1H), 7.22 (s, 2H), 5.54 (s, 2H). MS: m/z=426.1 (M+1, ESI+).

Stage 2: Production of 3-(6-amino-1-(4-amino-2,6-difluorobenzyl)-1H-pyrazolo[3,4-d]pyrimidin-4-yl)-2-fluorobenzonitrile (Compound 208)

To the solution of 3-[6-amino-1-[(2,6-difluoro-4-nitro-phenyl)methyl]pyrazolo [3,4-d]pyrimidin-4-yl]-2-fluorobenzonitrile (140 mg, 329.16 μmol, 1 eq) in ethanol (8 mL) and water (2 mL) were added iron dust (92 mg, 1.65 mmol, 5 eq) and $NH_4Cl$ (140 mg, 2.63 mmol, 8 eq). Then the mixture was stirred at 80° C. for 1 h. The reaction mixture was filtered and the filtrate was concentrated in vacuum. To the mixture were added water (50 mL) and then extracted with ethyl acetate (30 mL×3). Combined the organic phase to dry over anhydrous sodium sulfate, filter and concentrate in vacuum to give a residue. The residue was purified by prep-HPLC (column: Welch Ultimate XB-CN 250*70*10 μm; mobile phase: [Hexane-EtOH (0.1% $NH_3 \cdot H_2O$)]; B %: 35%-75%, 15 min). Compound 208 or 3-[6-amino-1-[(4-amino-2,6-difluoro-phenyl)methyl]pyrazolo[3,4-d]pyrimidin-4-yl]-2-fluoro-benzonitrile (44.01 mg, 109.41 μmol, 33% yield, 98.28% purity) was obtained as a yellow solid. $^1H$ NMR (400 MHz, DMSO-$d_6$) δ=8.14 (dd, J=6.7, 7.7 Hz, 2H), 7.93 (d, J=3.6 Hz, 1H), 7.60 (t, J=7.8 Hz, 1H), 7.13 (s, 2H), 6.27-6.07 (m, 2H), 5.80 (s, 2H), 5.24 (s, 2H).

Example 1.49: Production of 4-[6-amino-1-[(2,6-difluorophenyl)methyl]pyrazolo[3,4-d]pyrimidin-4-yl]pyridine-2-carbonitrile (Compound 234)

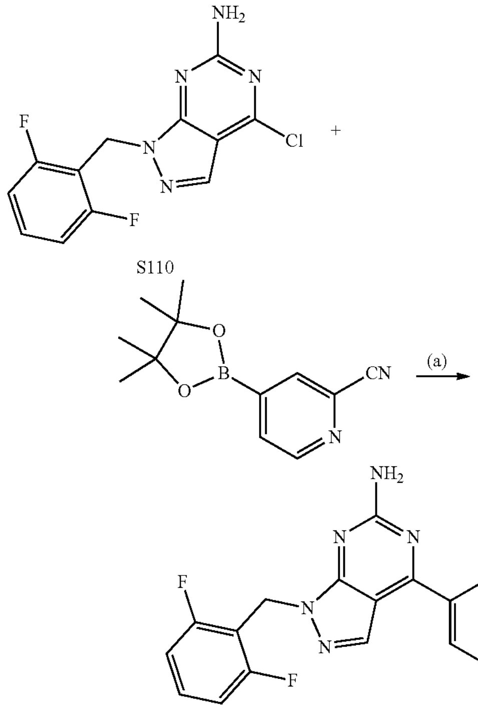

S110

234

Reagents and condition: (a) Pd(dppf)$Cl_2$, $K_2CO_3$, dioxane/$H_2O$, 80° C., 16 h.

A mixture of intermediate compound S110 or 4-chloro-1-[(2,6-difluorophenyl)methyl]pyrazolo[3,4-d]pyrimidin-6-amine (300 mg, 1 eq), 4-(4,4,5,5-tetramethyl-1,3,2-dioxaborolan-2-yl)pyridine-2-carbonitrile (279 mg, 1.2 eq), $K_2CO_3$ (279 mg, 2 eq), Pd(dppf)$Cl_2$ (74 mg, 0.1 eq) in dioxane (10 mL) and water (2 mL) was degassed and purged with nitrogen for three times, and then the mixture was stirred at 80° C. for 16 hr under nitrogen atmosphere. The reaction mixture was concentrated under reduced pressure to remove dioxane to give a residue. The residue was purified by prep-HPLC (column: Unisil 3-100 C18 Ultra 150*50 mm*3 μm; mobile phase: [water (0.225% FA)-ACN]; B %: 38%-58%, 10 min). Compound 234 or 4-[6-amino-1-[(2,6-difluorophenyl)methyl]pyrazolo[3,4-d]pyrimidin-4-yl]pyridine-2-carbonitrile (124.39 mg, 34% yield, 99.96% purity) was obtained as a white solid. $^1$H NMR (400 MHz, DMSO-$d_6$) δ=8.96 (d, J=5.1 Hz, 1H), 8.58 (d, J=0.6 Hz, 1H), 8.41-8.39 (m, 1H), 8.39-8.36 (m, 1H), 7.51-7.41 (m, 1H), 7.25 (s, 2H), 7.17-7.08 (m, 2H), 5.47 (s, 2H).

Example 1.50: Production of 4-(6-amino-1-(4-amino-2,6-difluorobenzyl)-1H-pyrazolo[3,4-d]pyrimidin-4-yl)picolinonitrile (Compound 226)

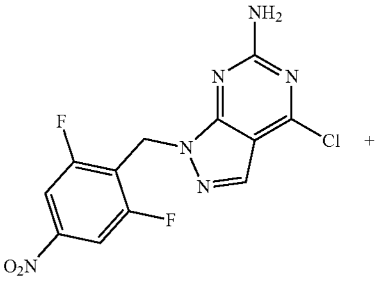

S112

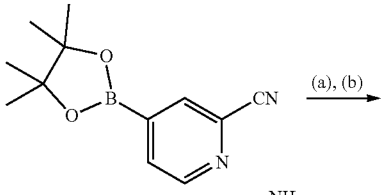

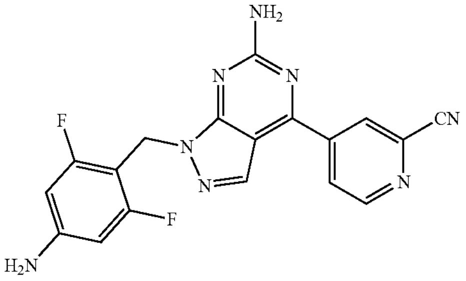

226

Reagents and condition: (a) Pd(dppf)$Cl_2$, $K_2CO_3$, dioxane/$H_2O$, 80° C., 16 h; (b) Fe, $NH_4Cl$, EtOH/$H_2O$, 80° C., 2 h.

Stage 1: Production of 4-[6-amino-1-[(2,6-difluoro-4-nitro-phenyl)methyl]pyrazolo[3,4-d]pyrimidin-4-yl]pyridine-2-carbonitrile To the solution of intermediate compound S112 or 4-chloro-1-[(2,6-difluoro-4-nitro-phenyl)methyl]pyrazolo [3,4-d]pyrimidin-6-amine (400 mg, 1.17 mmol, 1 eq) in dioxane (10 mL) and water (2 mL) were added 4-(4,4,5,5-tetramethyl-1,3,2-dioxaborolan-2-yl) pyridine-2-carbonitrile (540 mg, 2.35 mmol, 2 eq), Pd(dppf)$Cl_2$ (86 mg, 117.41 μmol, 0.1 eq) and $K_2CO_3$ (325 mg, 2.35 mmol, 2 eq). Then the mixture was stirred at 100° C. for 15 h. The mixture was concentrated in vacuum to give a residue. The residue was purified by flash silica gel chromatography (20 g Sepa-Flash® Silica Flash Column, Eluent of 0~60% Ethyl acetate/Petroleum ether gradient @50 mL/min). Compound 4-[6-amino-1-[(2,6-difluoro-4-nitro-phenyl)methyl]pyrazolo[3,4-d]pyrimidin-4-yl]pyridine-2-carbonitrile (300 mg, 625.68 μmol, 53% yield, 85% purity) was obtained as a yellow solid. $^1$H NMR (400 MHz, DMSO-$d_6$) δ=8.96 (d, J=5.1 Hz, 1H), 8.58 (s, 1H), 8.43 (s, 1H), 8.38 (dd, J=1.7, 5.1 Hz, 1H), 8.09 (br d, J=7.1 Hz, 2H), 7.28 (br s, 2H), 5.56 (s, 2H). MS: m/z=409.1 (M+1, ESI+).

Stage 2: Production of 4-[6-amino-1-[(4-amino-2,6-difluoro-phenyl) methyl]pyrazolo[3,4-d]pyrimidin-4-yl]pyridine-2-carbonitrile (Compound 226)

To the mixture of 4-[6-amino-1-[(2,6-difluoro-4-nitro-phenyl)methyl]pyrazolo [3,4-d]pyrimidin-4-yl]pyridine-2-carbonitrile (300 mg, 734.72 μmol, 1 eq) in water (3 mL) and ethanol (9 mL) were added iron dust (205 mg, 3.67 mmol, 5 eq) and $NH_4Cl$ (314 mg, 5.88 mmol, 8 eq). Then the mixture was stirred at 80° C. for 2 h. The reaction mixture was filtered and the filtrate was concentrated in vacuum. To the mixture was added water (30 mL) and extracted with ethyl acetate (30 mL×3). Combined the organic phase to dry over anhydrous sodium sulfate, filter and the filtrate was concentrated in vacuum to give a residue. The residue was purified by prep-HPLC (column: Welch Ultimate XB-CN 250*70*10 μm; mobile phase: [Hexane-ethanol (0.1% $NH_3 \cdot H_2O$)]; B %: 30%-70%, 15 min). Compound 226 or 4-[6-amino-1-[(4-amino-2,6-difluoro-phenyl)methyl]pyrazolo[3,4-d]pyrimidin-4-yl]pyridine-2-carbonitrile (70.80 mg, 178.73 μmol, 24% yield, 95.51% purity) was obtained as a yellow solid. $^1$H NMR (400 MHz, DMSO-$d_6$) δ=8.96 (dd, J=0.8, 5.1 Hz, 1H), 8.58 (dd, J=0.8, 1.6 Hz, 1H), 8.46-8.24 (m, 2H), 7.19 (s, 2H), 6.29-6.08 (m, 2H), 5.80 (s, 2H), 5.26 (s, 2H).

Example 1.51: Production of 4-(6-amino-1-(4-amino-3-methylbenzyl)-1H-pyrazolo[3,4-d]pyrimidin-4-yl)picolinonitrile (Compound 230)

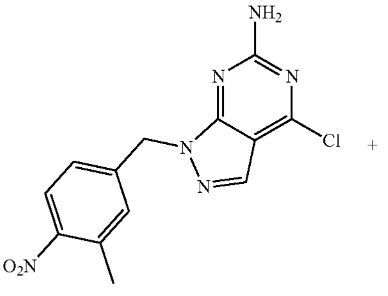

S108

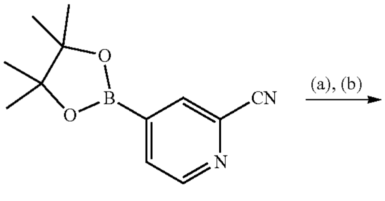

-continued

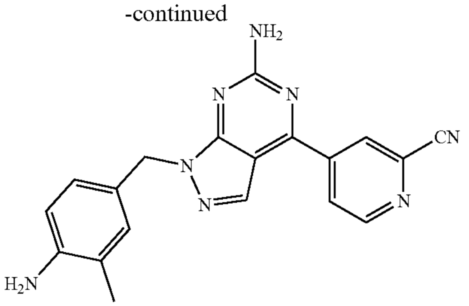

230

Reagents and condition: (a) $Pd(dppf)Cl_2$, $K_2CO_3$, dioxane/$H_2O$, 110° C., 16 h; (b) Fe, $NH_4Cl$, $EtOH/H_2O$, 60° C., 3 h.

Stage 1: Production of 4-(6-amino-1-(3-methyl-4-nitrobenzyl)-1H-pyrazolo[3,4-d]pyrimidin-4-yl)picolinonitrile A mixture of intermediate compound S108 or 4-chloro-1-[(3-methyl-4-nitro-phenyl)methyl]pyrazolo[3,4-d]pyrimidin-6-amine (500 mg, 1 eq), 4-(4,4,5,5-tetramethyl-1,3,2-dioxaborolan-2-yl)pyridine-2-carbonitrile (541 mg, 1.5 eq), $K_2CO_3$ (433 mg, 2 eq), $Pd(dppf)Cl_2$ (114 mg, 0.1 eq) in dioxane (10 mL) and water (2 mL) was degassed and purged with $N_2$ for three times, and then the mixture was stirred at 110° C. for 16 hr under $N_2$ atmosphere. The reaction mixture was filtered and concentrated under reduced pressure to give a residue. The residue was purified by flash silica gel chromatography (ISCO®; 12 g SepaFlash® Silica Flash Column, Eluent of 0~100% Ethyl acetate/Petroleum ether gradient @30 mL/min). Compound 4-[6-amino-1-[(3-methyl-4-nitro-phenyl)methyl]pyrazolo[3,4-d]pyrimidin-4-yl]pyridine-2-carbonitrile (500 mg, 82.49% yield) was obtained as a yellow solid. $^1H$ NMR (400 MHz, DMSO-$d_6$) δ=8.99 (dd, J=0.7, 5.1 Hz, 1H), 8.56 (s, 1H), 8.43 (dd, J=1.7, 5.1 Hz, 1H), 7.98-7.91 (m, 1H), 7.39-7.31 (m, 1H), 7.30-7.07 (m, 3H), 5.68-5.49 (m, 2H), 2.49-2.47 (m, 3H). MS: m/z=387.1 (M+1, ESI+).

Stage 2: Production of 4-(6-amino-1-(4-amino-3-methylbenzyl)-1H-pyrazolo[3,4-d]pyrimidin-4-yl)picolinonitrile (Compound 230)

To a solution of 4-[6-amino-1-[(3-methyl-4-nitro-phenyl)methyl]pyrazolo[3,4-d]pyrimidin-4-yl]pyridine-2-carbonitrile (400 mg, 1 eq) in ethanol (15 mL) and water (5 mL) were added iron dust (289 mg, 5 eq) and $NH_4Cl$ (443 mg, 8 eq). The mixture was stirred at 60° C. for 3 h. The reaction mixture was filtered and concentrated under reduced pressure to give a residue. The residue was purified by prep-HPLC (column: Phenomenex Gemini-NX C18 75*30 mm*3 μm; mobile phase: [water (0.05% ammonia hydroxide v/v)-ACN]; B %: 15%-45%, 11.5 min). Compound 230 or 4-[6-amino-1-[(4-amino-3-methyl-phenyl) methyl]pyrazolo[3,4-d]pyrimidin-4-yl]pyridine-2-carbonitrile (41.4 mg, 7% yield, 95.38% purity) was obtained as a yellow solid. $^1H$ NMR (400 MHz, DMSO-$d_6$) δ=8.97 (dd, J=0.6, 5.1 Hz, 1H), 8.60 (d, J=0.9 Hz, 1H), 8.44 (s, 1H), 8.40 (dd, J=1.7, 5.1 Hz, 1H), 7.17 (s, 2H), 6.93-6.79 (m, 2H), 6.52 (d, J=8.1 Hz, 1H), 5.24 (s, 2H), 4.81 (s, 2H), 1.99 (s, 3H).

Example 1.52: Production of 6-(6-amino-1-(4-aminobenzyl)-1H-pyrazolo[3,4-d]pyrimidin-4-yl)picolinonitrile (Compound 215)

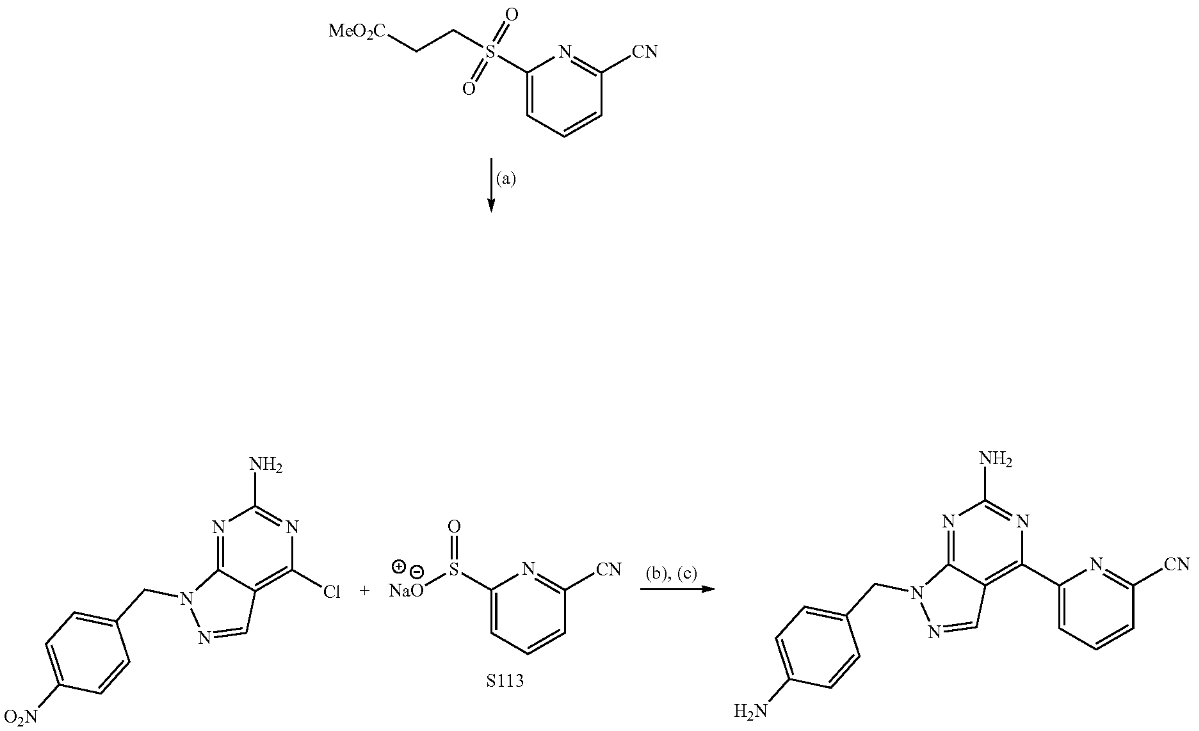

S3 S113 215

Reagents and condition: (a) NaOMe, MeOH, 25° C., 0.5 h; (b) $Pd(OAc)_2$, $K_2CO_3$, $Cy_3P$, dioxane, 120° C., 16 h; (c) Fe, $NH_4Cl$, $EtOH/H_2O$, 60° C., 3 h.

Stage 1: Production of (6-cyano-2-pyridyl)sulfinyloxy Sodium (Intermediate Compound S113)

To a solution of sodium methoxide (212 mg, 1 eq) in methanol (10 mL) was added methyl 3-[(6-cyano-2-pyridyl) sulfonyl]propanoate (1 g, 1 eq). The mixture was stirred at 25° C. for 0.5 hr. The reaction mixture was concentrated under reduced pressure to remove methanol to give a residue. The crude product of intermediate compound S113 or (6-cyano-2-pyridyl)sulfinyloxy sodium (1 g, crude) was obtained as a yellow solid and used into the next step without further purification. MS: m/z=167.0 (M+1, ESI+).

Stage 2: Production of 6-[6-amino-1-[(4-nitrophenyl)methyl]pyrazolo[3,4-d]pyrimidin-4-yl]pyridine-2-carbonitrile A mixture of intermediate compound 5113 or 4-chloro-1-[(4-nitrophenyl) methyl]pyrazolo[3,4-d]pyrimidin-6-amine (500 mg, 1 eq), (6-cyano-2-pyridyl)sulfinyloxy sodium (374 mg, 1.2 eq), palladium acetate (36 mg, 0.1 eq), $Cy_3P$ (92 mg, 0.2 eq) and $K_2CO_3$ (453 mg, 2 eq) in dioxane (5 mL) was degassed and purged with nitrogen for three times, and then the mixture was stirred at 120° C. for 16 hr under nitrogen atmosphere. The reaction mixture was filtered and concentrated under reduced pressure to give a residue. The residue was purified by flash silica gel chromatography (ISCO®; 12 g SEPAFLASH® Silica Flash Column, Eluent of 70~100% Ethyl acetate/Petroleum ether gradient @35 mL/min). Compound 6-[6-amino-1-[(4-nitrophenyl)methyl]pyrazolo[3,4-d]pyrimidin-4-yl]pyridine-2-carbonitrile (200 mg, 504.92 μmol, 31% yield, 94% purity) was obtained as a white solid. $^1H$ NMR (400 MHz, DMSO-$d_6$) δ=8.66 (dd, J=1.3, 8.0 Hz, 1H), 8.50 (s, 1H), 8.35-8.30 (m, 1H), 8.28-8.24 (m, 1H), 8.20 (d, J=8.9 Hz, 2H), 7.41 (d, J=8.9 Hz, 2H), 7.20 (s, 2H), 5.64 (s, 2H). MS: m/z=373.1 (M+1, ESI+).

Stage 3: Production of 6-(6-amino-1-(4-aminobenzyl)-1H-pyrazolo[3,4-d]pyrimidin-4-yl)picolinonitrile (Compound 215)

To a solution of 6-[6-amino-1-[(4-nitrophenyl)methyl] pyrazolo[3,4-d]pyrimidin-4-yl]pyridine-2-carbonitrile (200 mg, 1 eq) in water (5 mL) and ethanol (15 mL) was added iron dust (150 mg, 5 eq) and $NH_4Cl$ (230 mg, 8 eq). The mixture was stirred at 60° C. for 3 hr. The reaction mixture was concentrated under reduced pressure to remove ethanol and water to give a residue. The residue was purified by prep-HPLC (column: Phenomenex Gemini-NX C18 75*30 mm*3 μm; mobile phase: [water (0.05% ammonia hydroxide v/v)-ACN]; B %: 10%-40%, 11.5 min), the 89% purity desired compound was obtained, the residue was re-purified by prep-HPLC (column: Welch Ultimate XB-CN 250*50*10 μm; mobile phase: [Hexane-EtOH (0.1% $NH_3$—$H_2O$)]; B %: 20%-60%, 15 min), the 91% purity desired compound was obtained. Then the residue was purified by prep-HPLC (column: Phenomenex Luna C18 150*25 mm*10 μm; mobile phase: [water (0.225% FA)-ACN]; B %: 16%-46%, 10 min). Compound 215 or 6-[6-amino-1-[(4-aminophenyl)methyl]pyrazolo[3,4-d]pyrimidin-4-yl]pyridine-2-carbonitrile (21.55 mg, 11% yield, 98.25% purity) was obtained as a yellow solid. $^1H$ NMR (400 MHz, DMSO-$d_6$) δ=8.65 (d, J=7.6 Hz, 1H), 8.39 (s, 1H), 8.35-8.27 (m, 1H), 8.26-8.22 (m, 1H), 7.12 (s, 2H), 6.94 (br d, J=8.3 Hz, 2H), 6.48 (br d, J=8.3 Hz, 2H), 5.25 (s, 2H), 5.03 (s, 2H).

Example 1.53: Production of 6-[6-amino-1-[(4-amino-2-fluoro-phenyl)methyl]pyrazolo[3,4-d]pyrimidin-4-yl]pyridine-2-carbonitrile (Compound 219)

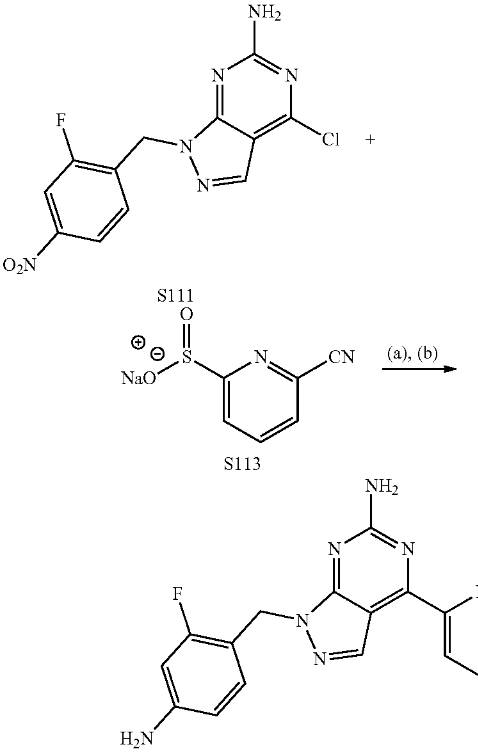

S111

S113

219

Reagents and condition: (a) $Pd(OAc)_2$, $K_2CO_3$, $Cy_3P$, dioxane, 120° C., 16 h; (b) Fe, $NH_4Cl$, $THF/H_2O$, 80° C., 4 h.

Stage 1: Production of 6-[6-amino-1-[(2-fluoro-4-nitro-phenyl)methyl]pyrazolo[3,4-d]pyrimidin-4-yl] pyridine-2-carbonitrile A mixture of intermediate compound S113 or (6-cyano-2-pyridyl)sulfinyloxy sodium (495.01 mg, 2.60 mmol, 1.2 eq), intermediate compound S11 or 4-chloro-1-[(2-fluoro-4-nitro-phenyl)methyl]pyrazolo[3,4-d]pyrimidin-6-amine (700 mg, 2.17 mmol, 1 eq), palladium acetate (48.70 mg, 216.93 μmol, 0.1 eq), $Cy_3P$ (121.67 mg, 433.86 μmol, 140.66 μL, 0.2 eq) and $K_2CO_3$ (599.64 mg, 4.34 mmol, 2 eq) in dioxane (5 mL) was degassed and purged with nitrogen for three times, and then the mixture was stirred at 120° C. for 16 hr under nitrogen atmosphere. The mixture was concentrated in vacuum to give a residue. The residue was purified by flash silica gel chromatography (12 g Sepa-Flash® Silica Flash Column, Eluent of 10~50% Ethyl acetate/Petroleum ether gradient @40 mL/min). Compound 6-[6-amino-1-[(2-fluoro-4-nitro-phenyl)methyl]pyrazolo[3,4-d]pyrimidin-4-yl]pyridine-2-carbonitrile (220 mg, 503.88

μmol, 26% yield, 89.4% purity) was obtained as a yellow solid. $^1$H NMR (400 MHz, DMSO-$d_6$) δ=8.66 (dd, J=1.1, 7.9 Hz, 1H), 8.49 (s, 1H), 8.36-8.29 (m, 1H), 8.28-8.23 (m, 1H), 8.16 (dd, J=2.3, 9.8 Hz, 1H), 8.04 (dd, J=1.8, 8.6 Hz, 1H), 7.29 (t, J=8.0 Hz, 1H), 7.22 (s, 2H), 5.64 (s, 2H).

Stage 2: Production of 6-[6-amino-1-[(4-amino-2-fluoro-phenyl)methyl]pyrazolo[3,4-d]pyrimidin-4-yl]pyridine-2-carbonitrile (Compound 219)

To the mixture of 6-[6-amino-1-[(2-fluoro-4-nitro-phenyl)methyl]pyrazolo[3,4-d]pyrimidin-4-yl]pyridine-2-carbonitrile (200 mg, 512.39 μmol, 1 eq) in THF (10 mL) and water (2 mL) was added iron dust (143 mg, 2.56 mmol, 5 eq) and $NH_4Cl$ (219.27 mg, 4.10 mmol, 8 eq). Then the mixture was stirred at 80° C. for 4 h. The reaction mixture was filtered and the filtrate was added 50 mL saturated $NaHCO_3$ aqueous solution and extracted with ethyl acetate (50 mL×3). Combined the organic layers to dry over anhydrous sodium sulfate, filter and concentrate in vacuum to give a residue. The residue was purified by prep-HPLC (column: Welch Ultimate XB-CN 250*70*10 μm; mobile phase: [Hexane-EtOH (0.1% $NH_3 \cdot H_2O$)]; B %: 35%-75%, 15 min). Compound 219 or 6-[6-amino-1-[(4-amino-2-fluoro-phenyl)methyl]pyrazolo[3,4-d]pyrimidin-4-yl]pyridine-2-carbonitrile (56.69 mg, 151.63 μmol, 30% yield, 96.38% purity) was obtained as a yellow solid. $^1$H NMR (400 MHz, DMSO-$d_6$) δ=8.65 (dd, J=1.2, 8.0 Hz, 1H), 8.39 (s, 1H), 8.34-8.29 (m, 1H), 8.26-8.22 (m, 1H), 7.13 (s, 2H), 6.95-6.79 (m, 1H), 6.31 (dd, J=1.8, 5.4 Hz, 1H), 6.28 (s, 1H), 5.40 (s, 2H), 5.29 (s, 2H).

Example 1.54: Production of 6-[6-amino-1-[(4-amino-2,6-difluoro-phenyl)methyl]pyrazolo[3,4-d]pyrimidin-4-yl]pyridine-2-carbonitrile (Compound 223)

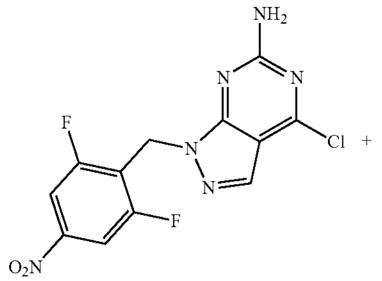

S112

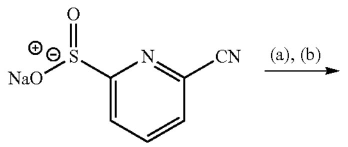

S113

-continued

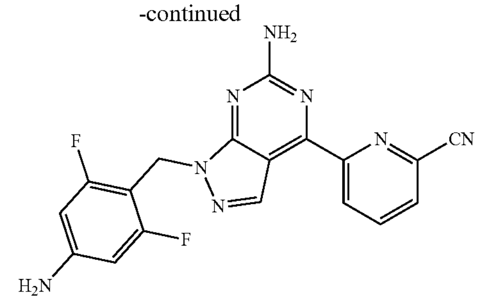

223

Reagents and condition: (a) $Pd(OAc)_2$, $K_2CO_3$, $Cy_3P$, dioxane, 120° C., 16 h; (b) Fe, $NH_4Cl$, THF/$H_2O$, 80° C., 5 h.

Stage 1: Production of 6-[6-amino-1-[(2,6-difluoro-4-nitro-phenyl)methyl]pyrazolo[3,4-d]pyrimidin-4-yl]pyridine-2-carbonitrile A mixture of intermediate compound S113 or sodium 6-cyanopyridine-2-sulfinate (530 mg, 2.79 mmol, 2 eq), intermediate compound S112 or 4-chloro-1-[(2,6-difluoro-4-nitro-phenyl)methyl]pyrazolo[3,4-d]pyrimidin-6-amine (470 mg, 1.38 mmol, 0.99 eq), palladium acetate (31 mg, 139.36 μmol, 0.1 eq), $Cy_3P$ (78 mg, 278.72 μmol, 0.2 eq) and $K_2CO_3$ (385 mg, 2.79 mmol, 2 eq) in dioxane (15 mL) was degassed and purged with nitrogen for three times, and then the mixture was stirred at 120° C. for 16 hr under nitrogen atmosphere. The mixture was concentrated in vacuum to give a residue. The residue was purified by flash silica gel chromatography (20 g SepaFlash® Silica Flash Column, Eluent of 30~60% Ethyl acetate/Petroleum ether gradient @50 mL/min). Compound 6-[6-amino-1-[(2,6-difluoro-4-nitro-phenyl)methyl]pyrazolo[3,4-d]pyrimidin-4-yl]pyridine-2-carbonitrile (180 mg, 290.95 μmol, 21% yield, 66% purity) was obtained as a yellow solid. $^1$H NMR (400 MHz, DMSO-$d_6$) δ=8.65 (dd, J=1.1, 8.0 Hz, 1H), 8.38 (s, 1H), 8.35-8.33 (m, 1H), 8.26-8.21 (m, 1H), 8.12-8.06 (m, 2H), 7.22 (s, 2H), 5.57 (s, 2H). MS: m/z=409.0 (M+1, ESI+).

Stage 2: Production of 6-[6-amino-1-[(4-amino-2,6-difluoro-phenyl)methyl]pyrazolo[3,4-d]pyrimidin-4-yl]pyridine-2-carbonitrile (Compound 223)

To the mixture of 6-[6-amino-1-[(2,6-difluoro-4-nitro-phenyl)methyl]pyrazolo[3,4-d]pyrimidin-4-yl]pyridine-2-carbonitrile (180 mg, 290.95 μmol, 66% purity, 1 eq) in THF (10 mL) and water (3 mL) was added iron dust (81 mg, 1.45 mmol, 5 eq) and $NH_4Cl$ (124 mg, 2.33 mmol, 8 eq). Then the mixture was stirred at 80° C. for 5 hr. The reaction mixture was filtered and the filtrate was added saturated $NaHCO_3$ aqueous solution (50 mL) and extracted with ethyl acetate (80 mL×3). Combined the organic phase to dry over anhydrous sodium sulfate, filter and concentrate in vacuum to give a residue. The residue was purified by prep-HPLC (column: Welch Ultimate XB-CN 250*70*10 μm; mobile phase: [Hexane-EtOH (0.1% ammonia hydroxide)]; B %: 40%-80%, 10 min). Compound 223 or 6-[6-amino-1-[(4-amino-2,6-difluoro-phenyl)methyl]pyrazolo[3,4-d]pyrimidin-4-yl]pyridine-2-carbonitrile (24.24 mg, 60.94 μmol, 21% yield, 95.11% purity) was obtained as a yellow solid. $^1$H NMR (400 MHz, DMSO-$d_6$) δ=8.65 (dd, J=0.9, 8.0 Hz, 1H), 8.35 (s, 1H), 8.34-8.29 (m, 1H), 8.27-8.21 (m, 1H), 7.13 (s, 2H), 6.18 (d, J=10.3 Hz, 2H), 5.80 (s, 2H), 5.27 (s, 2H).

Example 1.55: Production of 6-(6-amino-1-(2,6-difluorobenzyl)-1H-pyrazolo[3,4-d]pyrimidin-4-yl) picolinonitrile (Compound 231)

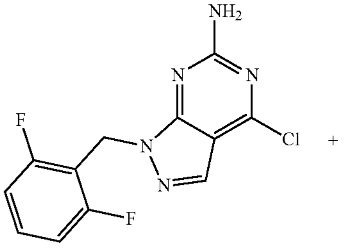

S110

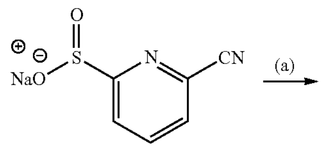

S113

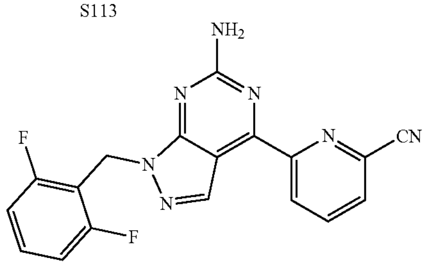

231

Reagents and condition: (a) $Pd(OAc)_2$, $K_2CO_3$, $Cy_3P$, dioxane, 120° C., 10 h, MW.

A mixture of (6-cyano-2-pyridyl)sulfinyloxysodium (231 mg, 1.2 eq), intermediate compound S110 or 4-chloro-1-[(2, 6-difluorophenyl) methyl]pyrazolo[3,4-d]pyrimidin-6-amine (300 mg, 1 eq), palladium acetate (23 mg, 0.1 eq), $Cy_3P$ (57 mg, 0.2 eq) and $K_2CO_3$ (280 mg, 2 eq) in dioxane (2 mL) was degassed and purged with nitrogen for three times, and then the mixture was stirred at 120° C. for 10 hr under microwave condition. The reaction mixture was filtered and concentrated under reduced pressure to give a residue. The residue was purified by prep-HPLC (column: Phenomenex Luna C18 150*25 mm*0 µm; mobile phase: [water (0.225% FA)-ACN]; B %: 37%-67%, 11 min). Compound 231 or 6-[6-amino-1-[(2,6-difluorophenyl)methyl] pyrazolo[3,4-d]pyrimidin-4-yl]pyridine-2-carbonitrile (70.52 mg, 18% yield, 95.65% purity) was obtained as a yellow solid. $^1H$ NMR (400 MHz, DMSO-$d_6$) δ=8.65 (dd, J=1.0, 8.0 Hz, 1H), 8.36 (s, 1H), 8.33-8.27 (m, 1H), 8.26-8.20 (m, 1H), 7.51-7.41 (m, 1H), 7.18 (s, 2H), 7.12 (t, J=8.0 Hz, 2H), 5.48 (s, 2H).

Example 1.56: Production of 6-(6-amino-1-(4-amino-3-methylbenzyl)-1H-pyrazolo[3,4-d]pyrimidin-4-yl)picolinonitrile (Compound 227)

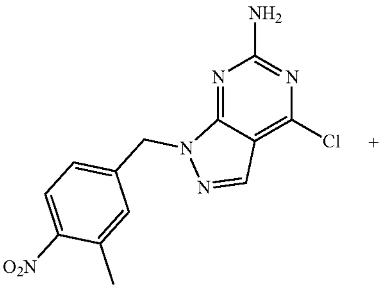

S108

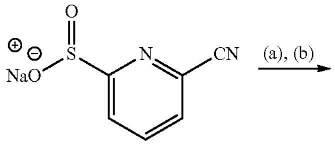

S113

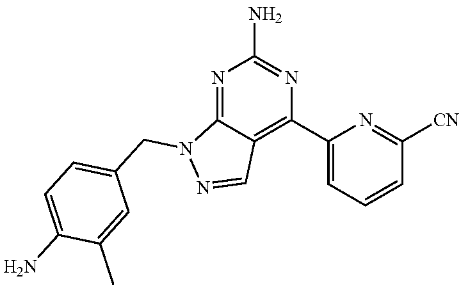

227

Reagents and condition: (a) $Pd(OAc)_2$, $K_2CO_3$, $Cy_3P$, dioxane, 120° C., 16 h; (b) Fe, $NH_4Cl$, $EtOH/H_2O$, 60° C., 2 h.

Stage 1: Production of 6-[6-amino-1-[(3-methyl-4-nitro-phenyl)methyl]pyrazolo[3,4-d]pyrimidin-4-yl] pyridine-2-carbonitrile A mixture of intermediate compound S113 or (6-cyano-2-pyridyl)sulfinyloxy sodium (356 mg, 1.2 eq), intermediate compound S108 or 4-chloro-1-[(3-methyl-4-nitro-phenyl) methyl]pyrazolo[3,4-d]pyrimidin-6-amine (500 mg, 1 eq), palladium acetate (35 mg, 0.1 eq), $Cy_3P$ (88 mg, 0.2 eq) and $K_2CO_3$ (433 mg, 2 eq) in dioxane (5 mL) was degassed and purged with nitrogen for three times, and then the mixture was stirred at 120° C. for 16 hr under nitrogen atmosphere. The reaction mixture was filtered and concentrated under reduced pressure to give a residue. The residue was purified by flash silica gel chromatography (ISCO®; 24 g Sepa Flash® Silica Flash Column, Eluent of 50~80% Ethyl acetate/Petroleum ether gradient @35 mL/min). Compound 6-[6-amino-1-[(3-methyl-4-nitro-phenyl)methyl]pyrazolo [3,4-d]pyrimidin-4-yl]pyridine-2-carbonitrile (300 mg, 40% yield, 81% purity) was obtained as a yellow solid. $^1H$ NMR (400 MHz, DMSO-$d_6$) δ=8.66 (dd, J=1.1, 7.9 Hz, 1H), 8.48 (s, 1H), 8.37-8.29 (m, 1H), 8.28-8.22 (m, 1H), 7.95 (d, J=8.5 Hz, 1H), 7.32 (s, 1H), 7.24-7.14 (m, 3H), 5.55 (s, 2H), 2.47 (s, 3H). MS: m/z=387.1 (M+1, ESI+).

Stage 2: Production of 6-(6-amino-1-(4-amino-3-methylbenzyl)-1H-pyrazolo[3,4-d]pyrimidin-4-yl)picolinonitrile (Compound 227)

To a solution of 6-[6-amino-1-[(3-methyl-4-nitro-phenyl)methyl]pyrazolo[3,4-d]pyrimidin-4-yl]pyridine-2-carbonitrile (311 mg, 1 eq) in water (5 mL) and ethanol (15 mL) were added iron dust (225 mg, 5 eq) and $NH_4Cl$ (344 mg, 8 eq). The mixture was stirred at 60° C. for 2 hr. The reaction mixture was concentrated under reduced pressure to remove ethanol and water to give a residue. The residue was purified by prep-HPLC (column: Phenomenex Gemini-NX C18 75*30 mm*3 μm; mobile phase: [water (0.05% ammonia hydroxide v/v)-ACN]; B %: 10%-40%, 11.5 min), the 88% purity desired compound was obtained, the residue was re-purified by prep-HPLC (column: Welch Ultimate XB-SiOH 250*50*10 μm; mobile phase: [Hexane-EtOH (0.1% $NH_3$—$H_2O$)]; B %: 15%-55%, 15 min), the 90% purity desired compound was obtained. Then the residue was purified by prep-HPLC (column: Welch Ultimate XB-SiOH 250*50*10 μm; mobile phase: [Hexane-EtOH (0.1% $NH_3$—$H_2O$)]; B %: 15%-55%, 15 min), 91% purity desired compound was obtained. Finally the residue was purified by prep-HPLC (column: Phenomenex Luna C18 150*25 mm*10 μm; mobile phase: [water (0.225% FA)-ACN]; B %: 21%-51%, 10 min). Compound 227 or 6-[6-amino-1-[(4-amino-3-methyl-phenyl)methyl]pyrazolo[3,4-d]pyrimidin-4-yl]pyridine-2-carbonitrile (30.69 mg, 10% yield, 98.87% purity) was obtained as a yellow solid. $^1H$ NMR (400 MHz, DMSO-$d_6$) δ=8.65 (dd, J=1.1, 8.0 Hz, 1H), 8.39 (s, 1H), 8.34-8.27 (m, 1H), 8.26-8.20 (m, 1H), 7.11 (s, 2H), 6.86 (s, 1H), 6.82 (dd, J=1.9, 8.1 Hz, 1H), 6.52 (d, J=8.0 Hz, 1H), 5.24 (s, 2H), 4.80 (s, 2H), 1.99 (s, 3H).

Example 1.57: Production of 2-(6-amino-1-(4-aminobenzyl)-1H-pyrazolo[3,4-d]pyrimidin-4-yl)isonicotinonitrile (Compound 216)

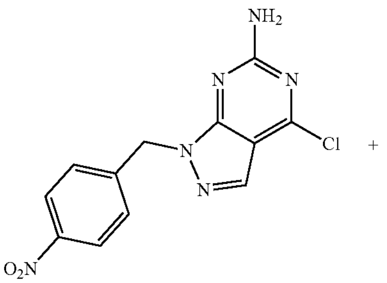

S3

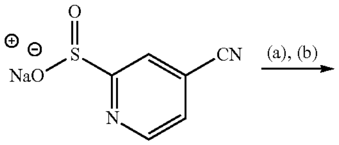

-continued

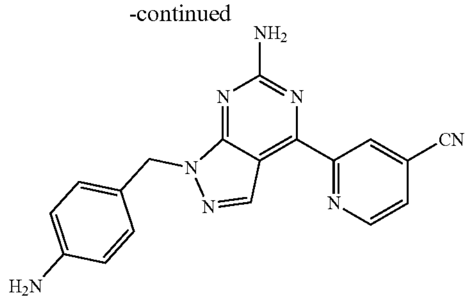

216

Reagents and condition: (a) $Pd(OAc)_2$, $K_2CO_3$, $Cy_3P$, dioxane, 120° C., 16 h; (b) Fe, $NH_4Cl$, EtOH/$H_2O$, 60° C., 2 h.

Stage 1: Production of 2-(6-amino-1-(4-nitrobenzyl)-1H-pyrazolo[3,4-d]pyrimidin-4-yl)isonicotinonitrile A mixture of sodium 4-cyanopyridine-2-sulfinate (298 mg, 1.2 eq), intermediate compound S3 or 4-chloro-1-[(4-nitrophenyl)methyl]pyrazolo[3,4-d]pyrimidin-6-amine (400 mg, 1 eq), palladium acetate (29 mg, 0.1 eq), $Cy_3P$ (73 mg, 0.2 eq) and $K_2CO_3$ (362 mg, 2 eq) in dioxane (5 mL) was degassed and purged with nitrogen for three times, and then the mixture was stirred at 120° C. for 16 hr under nitrogen atmosphere. The reaction mixture was filtered and concentrated under reduced pressure to give a residue. The residue was purified by flash silica gel chromatography (ISCO®; 12 g SepaFlash® Silica Flash Column, Eluent of 70-90% Ethyl acetate/Petroleum ether gradient @30 mL/min). Compound 2-[6-amino-1-[(4-nitrophenyl) methyl]pyrazolo[3,4-d]pyrimidin-4-yl]pyridine-4-carbonitrile (300 mg, 55% yield, 89% purity) was obtained as a yellow solid. MS: m/z=373.1 (M+1, ESI+).

Stage 2: Production of 2-(6-amino-1-(4-aminobenzyl)-1H-pyrazolo[3,4-d]pyrimidin-4-yl)isonicotinonitrile (Compound 216)

To a solution of 2-[6-amino-1-[(4-nitrophenyl)methyl]pyrazolo[3,4-d]pyrimidin-4-yl]pyridine-4-carbonitrile (300 mg, 1 eq) in water (5 mL) and ethanol (15 mL) was added iron dust (225 mg, 5 eq) and $NH_4Cl$ (345 mg, 8 eq). The mixture was stirred at 60° C. for 2 hr. The reaction mixture was concentrated under reduced pressure to remove ethanol and water to give a residue. The residue was purified by prep-HPLC (column: Phenomenex Gemini-NX C18 75*30 mm*3 μm; mobile phase: [water (10 mM $NH_4HCO_3$)-ACN]; B %: 18%-48%, 8 min), 80% purity desired compound was obtained. Then the residue was purified by the 2nd prep-HPLC (column: Welch Ultimate XB-SiOH 250*50*10 μm; mobile phase: [Hexane-EtOH (0.1% $NH_3 \cdot H_2O$)]; B %: 15%-55%, 15 min), 80% purity desired compound was obtained. Finally the residue was purified by the 3rd prep-HPLC (column: Phenomenex Luna C18 150*25 mm*10 μm; mobile phase: [water (0.225% FA)-ACN]; B %: 17%-47%, 10 min). Compound 216 or 2-[6-amino-1-[(4-aminophenyl)methyl]pyrazolo[3,4-d]pyrimidin-4-yl]pyridine-4-carbonitrile (23.18 mg, 8% yield, 95.02% purity) was obtained as a yellow solid. $^1H$ NMR (400 MHz, DMSO-$d_6$) δ=9.54 (d, J=2.1 Hz, 1H), 9.22 (d, J=2.0 Hz, 1H), 8.92 (t, J=2.1 Hz, 1H), 8.45 (s, 1H), 7.13 (s, 2H), 6.96 (d, J=8.4 Hz, 2H), 6.63-6.37 (m, 2H), 5.25 (s, 2H), 5.04 (s, 2H). HRMS-TOF: 343.1408.

Example 1.58: Production of 2-(6-amino-1-(4-amino-2-fluorobenzyl)-1H-pyrazolo[3,4-d]pyrimidin-4-yl)isonicotinonitrile (Compound 220)

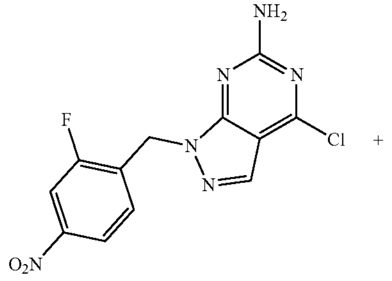

S111

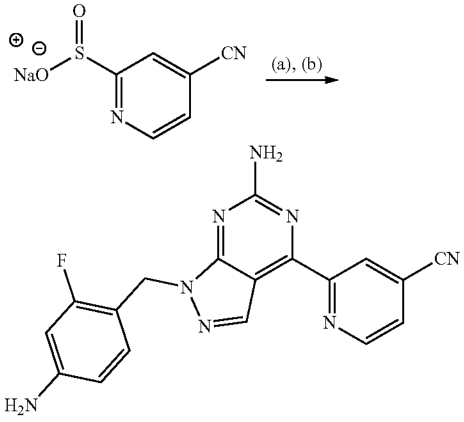

220

Reagents and condition: (a) $Pd(OAc)_2$, $K_2CO_3$, $Cy_3P$, dioxane, 120° C., 16 h; (b) Fe, $NH_4Cl$, $EtOH/H_2O$, 60° C., 1 h.

Stage 1: Production of 2-(6-amino-1-(2-fluoro-4-nitrobenzyl)-1H-pyrazolo[3,4-d]pyrimidin-4-yl)isonicotinonitrile A mixture of sodium 4-cyanopyridine-2-sulfinate (424 mg, 1.2 eq), intermediate compound S11 or 4-chloro-1-[(2-fluoro-4-nitro-phenyl)methyl]pyrazolo[3,4-d]pyrimidin-6-amine (600 mg, 1 eq), palladium acetate (41 mg, 0.1 eq), $Cy_3P$ (104 mg, 0.2 eq) and $K_2CO_3$ (513 mg, 2 eq) in dioxane (5 mL) was degassed and purged with nitrogen for three times, and then the mixture was stirred at 120° C. for 16 hr under nitrogen atmosphere. The reaction mixture was filtered and concentrated under reduced pressure to give a residue. The residue was purified by flash silica gel chromatography (ISCO®; 12 g SepaFlash® Silica flash column, eluent of 70-90% ethyl acetate/petroleum ether gradient @30 mL/min). Compound 2-[6-amino-1-[(2-fluoro-4-nitro-phenyl)methyl]pyrazolo[3,4-d]pyrimidin-4-yl]pyridine-4-carbonitrile (300 mg, 41% yield, 99% purity) was obtained as a yellow solid. $^1$H NMR (400 MHz, DMSO-$d_6$) δ=9.13-9.06 (m, 1H), 8.68 (dd, J=0.9, 1.5 Hz, 1H), 8.55 (s, 1H), 8.16 (dd, J=2.3, 9.9 Hz, 1H), 8.09 (dd, J=1.6, 4.9 Hz, 1H), 8.03 (dd, J=2.1, 8.5 Hz, 1H), 7.30 (t, J=8.0 Hz, 1H), 7.21 (s, 2H), 5.63 (s, 2H).

Stage 2: Production of 2-(6-amino-1-(4-amino-2-fluorobenzyl)-1H-pyrazolo[3,4-d]pyrimidin-4-yl)isonicotinonitrile (Compound 220)

To a solution of 2-[6-amino-1-[(2-fluoro-4-nitro-phenyl)methyl]pyrazolo[3, 4-d]pyrimidin-4-yl]pyridine-4-carbonitrile (300 mg, 1 eq) in water (5 mL) and ethanol (15 mL) was added iron dust (214 mg, 5 eq) and $NH_4Cl$ (328 mg, 8 eq). The mixture was stirred at 60° C. for 1 hr. The reaction mixture was concentrated under reduced pressure to remove ethanol and water to give a residue. The residue was purified by prep-HPLC (column: Welch Ultimate XB-CN 250*70*10 μm; mobile phase: [Hexane-EtOH column: Welch Ultimate XB-SiOH 250*50*10 μm; mobile phase: [Hexane-EtOH (0.1% $NH_3 \cdot H_2O$)]; B %: 15%-55%, 15 min (0.1% $NH_3 \cdot H_2O$)]; B %: 30%-70%, 15 min), 90% purity desired compound was obtained after prep-HPLC, the residue was purified by 2$^{nd}$ prep-HPLC (column: Welch Ultimate XB-CN 250*70*10 μm; mobile phase: [Hexane-EtOH (0.1% ammonia hydroxide)]; B %: 30%-70%, 15 min). Compound 220 or 2-[6-amino-1-[(4-amino-2-fluoro-phenyl)methyl]pyrazolo[3,4-d]pyrimidin-4-yl]pyridine-4-carbonitrile (33.67 mg, 89.81 μmol, 96.12% purity) was obtained as a yellow solid. $^1$H NMR (400 MHz, DMSO-$d_6$) δ=9.08 (dd, J=0.7, 5.0 Hz, 1H), 8.68 (d, J=1.3 Hz, 1H), 8.46 (s, 1H), 8.08 (dd, J=1.6, 5.0 Hz, 1H), 7.13 (s, 2H), 6.88 (t, J=8.4 Hz, 1H), 6.33-6.30 (m, 1H), 6.29 (s, 1H), 5.40 (s, 2H), 5.29 (s, 2H).

Example 1.59: Production of 2-[6-amino-1-[(4-amino-2,6-difluoro-phenyl)methyl]pyrazolo[3,4-d]pyrimidin-4-yl]pyridine-4-carbonitrile (Compound 224)

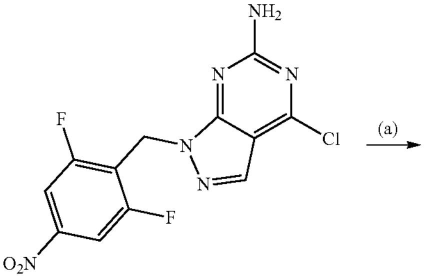

S112

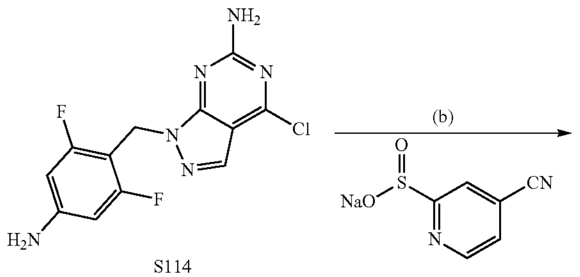

S114

-continued

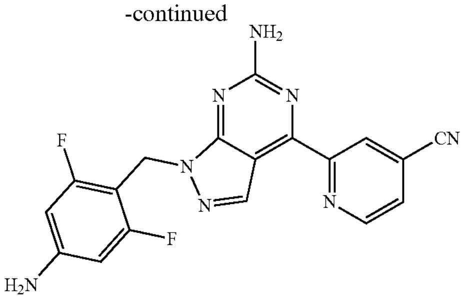

224

Reagents and condition: (a) Fe, $NH_4Cl$, $EtOH/H_2O$, 80° C., 3 h; (b) $Pd(OAc)_2$, $K_2CO_3$, $PCy_3$, dioxane, 120° C., 16 h.

Stage 1: Production of 1-(4-amino-2,6-difluorobenzyl)-4-chloro-1H-pyrazolo[3,4-d]pyrimidin-6-amine (intermediate compound S114)

To the mixture of intermediate compound S112 or 4-chloro-1-[(2,6-difluoro-4-nitro-phenyl)methyl]pyrazolo[3,4-d]pyrimidin-6-amine (700 mg, 1.38 mmol, 67% purity, 1 eq) in water (3 mL) and ethanol (10 mL) were added iron dust (385 mg, 6.88 mmol, 5 eq) and $NH_4Cl$ (590 mg, 11.01 mmol, 8 eq). Then the mixture was stirred at 80° C. for 3 h. The reaction mixture was filtered and the filtrate was concentrated in vacuum. The mixture was added water (30 mL) and extracted with ethyl acetate (30 mL×3). Combined the organic layers to dry over anhydrous sodium sulfate, filter and concentrate in vacuum. The residue was purified by prep-HPLC (column: Welch Ultimate XB-CN 250*70*10 μm; mobile phase: [Hexane-EtOH (0.1% $NH_3 \cdot H_2O$)]; B %: 20%-60%, 15 min). Intermediate compound S114 or 1-(4-amino-2,6-difluorobenzyl)-4-chloro-1H-pyrazolo[3,4-d]pyrimidin-6-amine (400 mg, 1.03 mmol, 75% yield, 88% purity) was obtained as a yellow solid. $^1H$ NMR (400 MHz, DMSO-$d_6$) δ=7.92 (s, 1H), 7.32 (s, 2H), 6.25-6.09 (m, 2H), 5.80 (s, 2H), 5.18 (s, 2H).

Stage 2: Production of 2-[6-amino-1-[(4-amino-2,6-difluoro-phenyl)methyl]pyrazolo[3,4-d]pyrimidin-4-yl]pyridine-4-carbonitrile (Compound 224)

A mixture of (4-cyano-2-pyridyl)sulfinyloxy sodium (550 mg, 2.89 mmol, 2.55 eq), intermediate compounds S114 or 1-[(4-amino-2,6-difluoro-phenyl)methyl]-4-chloro-pyrazolo[3,4-d]pyrimidin-6-amine (400 mg, 1.13 mmol, 88% purity, 1 eq), palladium acetate (25 mg, 113.30 μmol, 0.1 eq), $Cy_3P$ (63 mg, 226.59 μmol, 73.46 μL, 0.2 eq) and $K_2CO_3$ (313 mg, 2.27 mmol, 2 eq) in dioxane (10 mL) was degassed and purged with nitrogen for three times, and then the mixture was stirred at 120° C. for 16 hr under nitrogen atmosphere. The reaction mixture was filtered and the filtrate was concentrated in vacuum. The residue was purified by flash silica gel chromatography (20 g Sepa Flash® Silica Flash Column, Eluent of 20~40% Ethyl acetate/Petroleum ether gradient @40 mL/min). Compound 224 or 2-[6-amino-1-[(4-amino-2,6-difluoro-phenyl)methyl]pyrazolo[3,4-d]pyrimidin-4-yl]pyridine-4-carbonitrile (70 mg, 181.87 μmol, 16% yield, 98.30% purity) was obtained as a yellow solid. $^1H$ NMR (400 MHz, DMSO-$d_6$) δ=9.07 (dd, J=0.8, 5.0 Hz, 1H), 8.67 (dd, J=0.9, 1.5 Hz, 1H), 8.41 (s, 1H), 8.06 (dd, J=1.7, 5.0 Hz, 1H), 7.11 (s, 2H), 6.27-6.11 (m, 2H), 5.79 (s, 2H), 5.26 (s, 2H).

Example 1.60: Production of 2-(6-amino-1-(2,6-difluorobenzyl)-1H-pyrazolo[3,4-d]pyrimidin-4-yl) isonicotinonitrile (Compound 232)

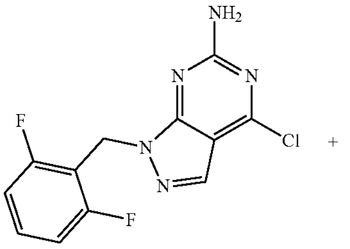

S110

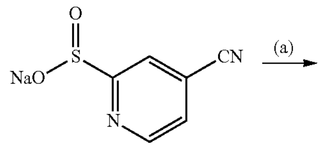

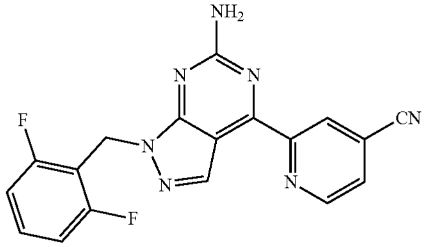

232

Reagents and condition: (a) $Pd(OAc)_2$, $K_2CO_3$, $Cy_3P$, dioxane, 120° C., 16 h.

A mixture of (4-cyano-2-pyridyl)sulfinyloxy sodium (232 mg, 1.2 eq), intermediate compound S110 or 4-chloro-1-[(2,6-difluorophenyl) methyl]pyrazolo[3,4-d]pyrimidin-6-amine (300 mg, 1 eq), palladium acetate (23 mg, 0.1 eq), $Cy_3P$ (57 mg, 0.2 eq) and $K_2CO_3$ (281 mg, 2 eq) in dioxane (5 mL) was degassed and purged with nitrogen for three times, and then the mixture was stirred at 120° C. for 16 hr under nitrogen atmosphere. The reaction mixture was filtered and concentrated under reduced pressure to give a residue. The residue was purified by prep-HPLC (column: Unisil 3-100 C18 Ultra 150*50 mm*3 μm; mobile phase: [water (0.225% FA)-ACN]; B %: 43%-63%, 10 min). Compound 232 or 2-[6-amino-1-[(2,6-difluorophenyl)methyl]pyrazolo[3,4-d]pyrimidin-4-yl]pyridine-4-carbonitrile (66.33 mg, 18% yield, 99.34% purity) was obtained as a white solid. $^1H$ NMR (400 MHz, DMSO-$d_6$) δ=9.06 (d, J=5.0 Hz, 1H), 8.67 (s, 1H), 8.44-8.38 (m, 1H), 8.09-8.03 (m, 1H), 7.51-7.39 (m, 1H), 7.22-7.15 (m, 2H), 7.14-7.09 (m, 2H), 5.47 (s, 2H).

Example 1.61: 2-(6-amino-1-(4-amino-3-methylbenzyl)-1H-pyrazolo[3,4-d]pyrimidin-4-yl)isonicotinonitrile (Compound 228)

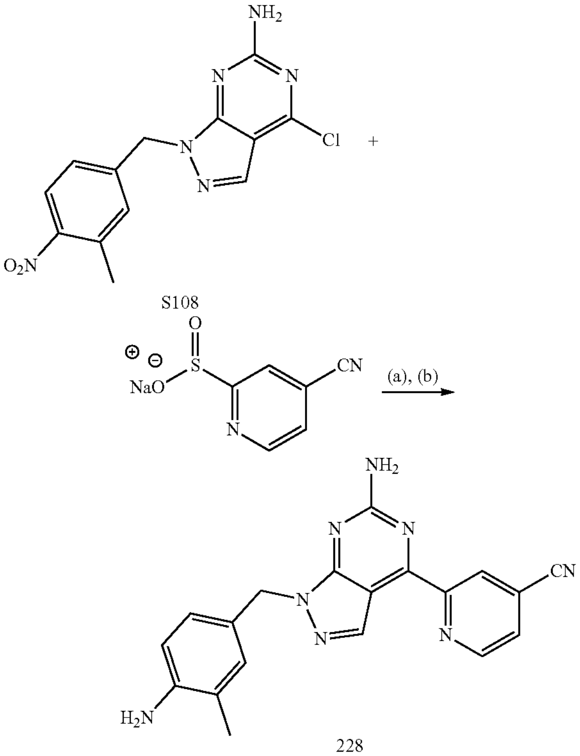

S108

228

Reagents and condition: (a) $Pd(OAc)_2$, $K_2CO_3$, $Cy_3P$, dioxane, 120° C., 16 h; (b) Fe, $NH_4Cl$, $EtOH/H_2O$, 60° C., 2 h.

Stage 1: Production of 2-(6-amino-1-(3-methyl-4-nitrobenzyl)-1H-pyrazolo[3,4-d]pyrimidin-4-yl) isonicotinonitrile A mixture of (4-cyano-2-pyridyl)sulfinyloxy sodium (215 mg, 1.2 eq), intermediate compound S108 or 4-chloro-1-[(3-methyl-4-nitro-phenyl)methyl]pyrazolo[3,4-d]pyrimidin-6-amine (300 mg, 1 eq), palladium acetate (21 mg, 0.1 eq), $Cy_3P$ (52 mg, 0.2 eq) and $K_2CO_3$ (260 mg, 2 eq) in dioxane (5 mL) was degassed and purged with nitrogen for three times, and then the mixture was stirred at 120° C. for 16 hr under nitrogen atmosphere. The reaction mixture was filtered and concentrated under reduced pressure to give a residue. The residue was purified by flash silica gel chromatography (ISCO®; 24 g SepaFlash® Silica Flash Column, Eluent of 50~80% Ethyl acetate/Petroleum ether gradient @35 mL/min). Compound 2-[6-amino-1-[(3-methyl-4-nitro-phenyl)methyl]pyrazolo[3,4-d]pyrimidin-4-yl] pyridine-4-carbonitrile (200 mg, 55% yield) was obtained as a yellow solid. MS: m/z=387.1 (M+1, ESI+).

Stage 2: Production of 2-(6-amino-1-(4-amino-3-methylbenzyl)-1H-pyrazolo[3,4-d]pyrimidin-4-yl) isonicotinonitrile (Compound 228)

To a solution of 2-[6-amino-1-[(3-methyl-4-nitro-phenyl) methyl]pyrazolo[3,4-d]pyrimidin-4-yl]pyridine-4-carbonitrile (200 mg, 1 eq) in ethanol (15 mL) and water (5 mL) was added iron dust (145 mg, 5 eq) and $NH_4Cl$ (221 mg, 8 eq). The mixture was stirred at 60° C. for 2 hr. The reaction mixture was filtered and concentrated under reduced pressure to give a residue. The residue was purified by prep-HPLC (column: Phenomenex Gemini-NX C18 75*30 mm*3 μm; mobile phase: [water (10 mM $NH_4HCO_3$)-ACN]; B %: 20%-50%, 8 min), 80% purity desired compound was obtained after prep-HPLC, the residue was purified by 2$^{nd}$ prep-HPLC (column: Shim-pack C18 150*25*10 μm; mobile phase: [water (0.225% FA)-ACN]; B %: 16%-46%, 10 min). Compound 228 or 2-[6-amino-1-[(4-amino-3-methyl-phenyl)methyl]pyrazolo[3,4-d]pyrimidin-4-yl]pyridine-4-carbonitrile (19.65 mg, 10% yield, 96.15% purity) was obtained as a yellow solid. $^1H$ NMR (400 MHz, DMSO-$d_6$) δ=9.08 (dd, J=0.8, 4.9 Hz, 1H), 8.67 (dd, J=0.9, 1.6 Hz, 1H), 8.45 (s, 1H), 8.07 (dd, J=1.6, 5.0 Hz, 1H), 7.10 (s, 2H), 6.86 (s, 1H), 6.82 (dd, J=1.9, 8.1 Hz, 1H), 6.51 (d, J=8.0 Hz, 1H), 5.23 (s, 2H), 4.80 (s, 2H), 1.98 (s, 3H).

Example 1.62: Production of 5-(6-amino-1-(4-aminobenzyl)-1H-pyrazolo[3,4-d]pyrimidin-4-yl)nicotinonitrile (Compound 217)

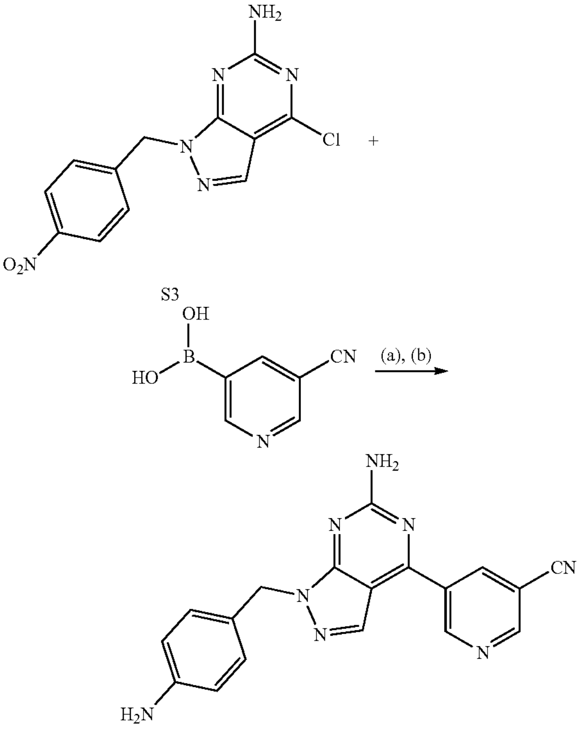

S3

217

Reagents and condition: (a) $Pd(dppf)Cl_2$, $K_2CO_3$, dioxane/$H_2O$, 110° C., 16 h; (b) Fe, $NH_4Cl$, $THF/H_2O$, 60° C., 3 h.

Stage 1: Production of 5-(6-amino-1-(4-nitrobenzyl)-1H-pyrazolo[3,4-d]pyrimidin-4-yl)nicotinonitrile A mixture of (5-cyano-3-pyridyl)boronic acid (583 mg, 1.5 eq), intermediate compound S3 or 4-chloro-1-[(4-nitrophenyl)methyl]pyrazolo[3,4-d]pyrimidin-6-amine (800 mg, 1 eq), $K_2CO_3$ (726 mg, 2 eq), Pd(dppf)$Cl_2$ (192 mg, 0.1 eq) in dioxane (10 mL) and water (2 mL) was degassed and purged with nitrogen for three times, and then the mixture was stirred at 110° C. for 16 hr under nitrogen atmosphere. The reaction mixture was filtered and concentrated under reduced pressure to give a residue. The residue was purified by flash silica gel chromatography (ISCO®; 24 g Sepa Flash® Silica Flash Column, Eluent of 0~100% Ethyl acetate/Petroleum ether gradient @30 mL/min). Compound 5-[6-amino-1-[(4-nitrophenyl)methyl]pyrazolo[3,4-d]pyrimidin-4-yl]pyridine-3-carbonitrile (800 mg, 82% yield) was obtained as a yellow solid. $^1$H NMR (400 MHz, DMSO-$d_6$) δ=9.63-9.52 (m, 1H), 9.37-9.31 (m, 2H), 9.25-9.23 (m, 1H), 9.15-9.12 (m, 2H), 7.46-7.42 (m, 2H), 5.65-5.60 (m, 2H). MS: m/z=373.1 (M+1, ESI+).

Stage 2: Production of 5-(6-amino-1-(4-aminobenzyl)-1H-pyrazolo[3,4-d]pyrimidin-4-yl)nicotinonitrile (Compound 217)

To a solution of 5-[6-amino-1-[(4-nitrophenyl)methyl]pyrazolo[3,4-d]pyrimidin-4-yl]pyridine-3-carbonitrile (300 mg, 1 eq) in THF (15 mL) and water (5 mL) was added iron dust (224 mg, 5 eq) and $NH_4Cl$ (344 mg, 8 eq). The mixture was stirred at 60° C. for 3 hr. The reaction mixture was concentrated under reduced pressure to remove THF and water to give a residue. The residue was purified by prep-HPLC (column: Phenomenex Gemini-NX C18 75*30 mm*3 μm; mobile phase: [water (0.05% ammonia hydroxide v/v)-ACN]; B %: 10%-40%, 11.5 min). Compound 217 or 5-[6-amino-1-[(4-aminophenyl)methyl]pyrazolo[3,4-d]pyrimidin-4-yl]pyridine-3-carbonitrile (27.63 mg, 7% yield, 98.17% purity) was obtained as a yellow solid. $^1$H NMR (400 MHz, DMSO-$d_6$) δ=9.54 (d, J=2.1 Hz, 1H), 9.22 (d, J=2.0 Hz, 1H), 8.92 (t, J=2.1 Hz, 1H), 8.45 (s, 1H), 7.13 (s, 2H), 6.96 (d, J=8.4 Hz, 2H), 6.63-6.37 (m, 2H), 5.25 (s, 2H), 5.04 (s, 2H).

Example 1.63: Production of 5-[6-amino-1-[(4-amino-2-fluoro-phenyl)methyl]pyrazolo[3,4-d]pyrimidin-4-yl]pyridine-3-carbonitrile (Compound 221)

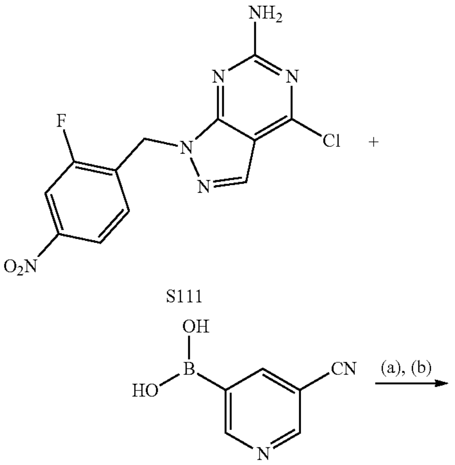

S111

-continued

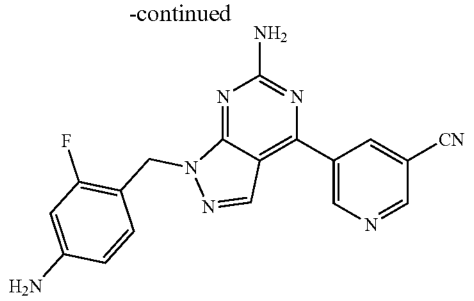

221

Reagents and condition: (a) Pd(dppf)$Cl_2$, $K_2CO_3$, dioxane/$H_2O$, 110° C., 16 h; (b) Fe, $NH_4Cl$, EtOH/$H_2O$, 60° C., 2 h.

Stage 1: Production of 5-(6-amino-1-(2-fluoro-4-nitrobenzyl)-1H-pyrazolo [3,4-d]pyrimidin-4-yl) nicotinonitrile A mixture of (5-cyano-3-pyridyl)boronic acid (343 mg, 1.5 eq), intermediate compound S11 or 4-chloro-1-[(2-fluoro-4-nitro-phenyl)methyl]pyrazolo[3,4-d]pyrimidin-6-amine (500 mg, 1 eq), $K_2CO_3$ (428 mg, 2 eq), Pd(dppf)$Cl_2$ (113 mg, 0.1 eq) in dioxane (10 mL) and water (2 mL) was degassed and purged with nitrogen for three times, and then the mixture was stirred at 110° C. for 16 hr under nitrogen atmosphere. The reaction mixture was concentrated under reduced pressure to remove dioxane to give a residue. The residue was purified by flash silica gel chromatography (ISCO®; 12 g SepaFlash® Silica Flash Column, Eluent of 0~80% Ethyl acetate/Petroleum ether gradient @30 mL/min). Compound 5-[6-amino-1-[(2-fluoro-4-nitro-phenyl)methyl]pyrazolo[3,4-d]pyrimidin-4-yl]pyridine-3-carbonitrile (300 mg, 50% yield) was obtained as a yellow solid. MS: m/z=390.9 (M+1, ESI+).

Stage 2: Production of 5-(6-amino-1-(4-amino-2-fluorobenzyl)-1H-pyrazolo [3,4-d]pyrimidin-4-yl) nicotinonitrile (Compound 221)

To a solution of 5-[6-amino-1-[(2-fluoro-4-nitro-phenyl)methyl]pyrazolo[3,4-d]pyrimidin-4-yl]pyridine-3-carbonitrile (300 mg, 1 eq) in ethanol (15 mL) and water (5 mL) was added iron dust (214 mg, 5 eq) and $NH_4Cl$ (328 mg, 8 eq). The mixture was stirred at 60° C. for 2 hr. The reaction mixture was filtered and concentrated under reduced pressure to give a residue. The residue was purified by prep-HPLC (column: Phenomenex Gemini-NX C18 75*30 mm*3 μm; mobile phase: [water (0.05% ammonia hydroxide v/v)-ACN]; B %: 13%-43%, 11.5 min). Compound 221 or 5-[6-amino-1-[(4-amino-2-fluoro-phenyl)methyl]pyrazolo[3,4-d]pyrimidin-4-yl]pyridine-3-carbonitrile (37.61 mg, 13% yield, 94.57% purity) was obtained as a yellow solid. $^1$H NMR (400 MHz, DMSO-$d_6$) δ=9.54 (d, J=2.1 Hz, 1H), 9.23 (d, J=2.0 Hz, 1H), 8.91 (t, J=2.0 Hz, 1H), 8.45 (s, 1H), 7.14 (s, 2H), 6.90 (t, J=8.4 Hz, 1H), 6.31 (d, J=10.8 Hz, 2H), 5.41 (s, 2H), 5.29 (s, 2H).

Example 1.64: Production of 5-[6-amino-1-[(4-amino-2,6-difluoro-phenyl)methyl]pyrazolo[3,4-d]pyrimidin-4-yl]pyridine-3-carbonitrile (Compound 225)

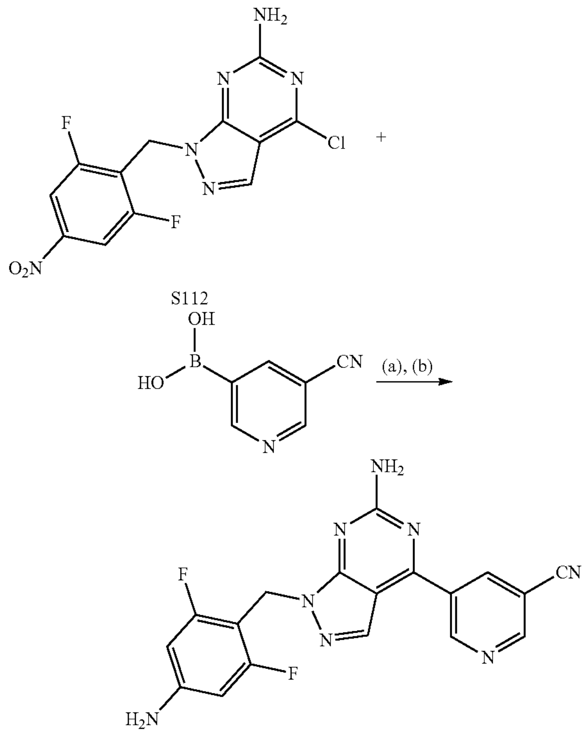

225

Reagents and conditions: (a) Pd(dppf)$Cl_2$, $K_2CO_3$, dioxane/$H_2O$, 100° C., 15 h; (b) Fe, $NH_4Cl$, EtOH/$H_2O$, 80° C., 2 h.

Stage 1: Production of 5-[6-amino-1-[(2,6-difluoro-4-nitro-phenyl)methyl]pyrazolo[3,4-d]pyrimidin-4-yl]pyridine-3-carbonitrile To the solution of intermediate compound S112 or 4-chloro-1-[(2,6-difluoro-4-nitro-phenyl)methyl]pyrazolo[3,4-d]pyrimidin-6-amine (400 mg, 1.17 mmol, 1 eq) in dioxane (10 mL) and water (2 mL) were added (5-cyano-3-pyridyl)boronic acid (346 mg, 2.34 mmol, 2 eq), Pd(dppf)$Cl_2$ (86 mg, 117.00 μmol, 0.1 eq) and $K_2CO_3$ (323 mg, 2.34 mmol, 2 eq). Then the mixture was stirred at 100° C. for 15 h. The mixture was concentrated in vacuum to give a residue. The residue was purified by flash silica gel chromatography (20 g Sepa Flash® Silica Flash Column, Eluent of 0~60% Ethyl acetate/Petroleum ether gradient @50 mL/min). Compound 5-[6-amino-1-[(2,6-difluoro-4-nitro-phenyl)methyl]pyrazolo[3,4-d]pyrimidin-4-yl]pyridine-3-carbonitrile (400 mg, 852.27 μmol, 73% yield, 87% purity) was obtained as a yellow solid. $^1H$ NMR (400 MHz, DMSO-$d_6$) δ=9.51 (d, J=2.0 Hz, 1H), 9.21 (d, J=1.9 Hz, 1H), 8.89 (t, J=2.1 Hz, 1H), 8.44 (s, 1H), 8.09 (d, J=7.3 Hz, 2H), 7.23 (s, 2H), 5.55 (s, 2H). MS: m/z=409.0 (M+1, ESI+).

Stage 2: Production of 5-[6-amino-1-[(4-amino-2,6-difluoro-phenyl) methyl]pyrazolo[3,4-d]pyrimidin-4-yl]pyridine-3-carbonitrile (Compound 225)

To the mixture of 5-[6-amino-1-[(2,6-difluoro-4-nitro-phenyl)methyl]pyrazolo[3,4-d]pyrimidin-4-yl]pyridine-3-carbonitrile (400 mg, 979.62 μmol, 1 eq) in water (3 mL) and ethanol (9 mL) were added iron dust (274 mg, 4.90 mmol, 5 eq) and $NH_4Cl$ (420 mg, 7.84 mmol, 8 eq). Then the mixture was stirred at 80° C. for 2 h. The reaction mixture was filtered and the filtrate was concentrated in vacuum. Then the mixture was added water (30 mL) and then extracted with ethyl acetate (30 mL×3). Combined the organic phase to dry over anhydrous sodium sulfate, filter and concentrate in vacuum to give a residue. The residue was purified by prep-HPLC (column: Welch Ultimate XB-CN 250*70*10 μm; mobile phase: [Hexane-EtOH (0.1% $NH_3·H_2O$)]; B %: 30%-70%, 15 min) to give a impure product. The impure product was re-purified by prep-HPLC (column: Welch Ultimate XB-CN 250*50*10 μm; mobile phase: [Hexane-EtOH (0.1% $NH_3·H_2O$)]; B %: 25%-65%, 15 min). Compound 225 or 5-[6-amino-1-[(4-amino-2,6-difluoro-phenyl)methyl]pyrazolo[3,4-d]pyrimidin-4-yl]pyridine-3-carbonitrile (113.05 mg, 297.07 μmol, 30% yield, 99.42% purity) was obtained as a yellow solid. $^1H$ NMR (400 MHz, DMSO-$d_6$) δ=9.52 (d, J=2.1 Hz, 1H), 9.21 (d, J=1.8 Hz, 1H), 8.89 (t, J=2.1 Hz, 1H), 8.38 (s, 1H), 7.13 (s, 2H), 6.18 (d, J=10.1 Hz, 2H), 5.25 (s, 2H).

Example 1.65: Production of 5-(6-amino-1-(2,6-difluorobenzyl)-1H-pyrazolo[3,4-d]pyrimidin-4-yl)nicotinonitrile (Compound 233)

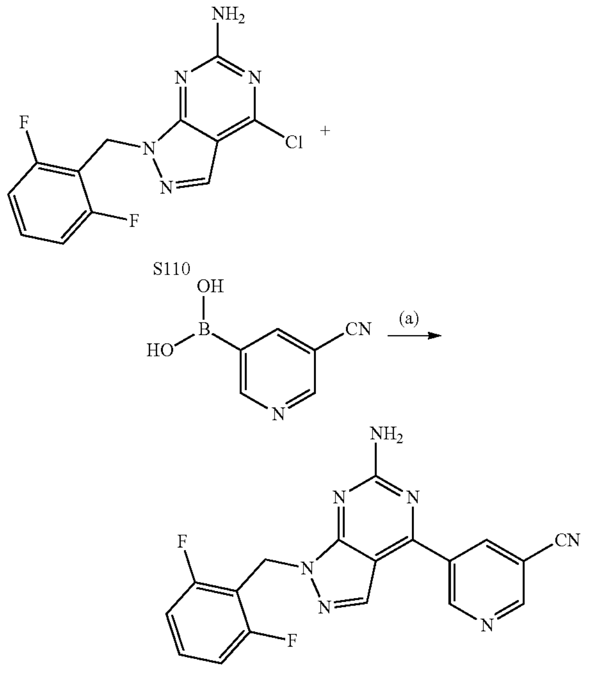

233

Reagents and condition: (a) Pd(dppf)$Cl_2$, $K_2CO_3$, dioxane/$H_2O$, 110° C., 16 h.

A mixture of intermediate compound S110 or 4-chloro-1-[(2,6-difluorophenyl)methyl]pyrazolo[3,4-d]pyrimidin-6-amine (400 mg, 1 eq), (5-cyano-3-pyridyl)boronic acid (300 mg, 1.5 eq), $K_2CO_3$ (373 mg, 2 eq), Pd(dppf)$Cl_2$ (99 mg, 0.1 eq) in dioxane (10 mL) and water (2 mL) was degassed and purged with nitrogen for three times, and then the mixture was stirred at 110° C. for 16 hr under nitrogen atmosphere. The reaction mixture was concentrated under reduced pressure to remove dioxane to give a residue. The residue was purified by prep-HPLC (column: Unisil 3-100 C18 Ultra 150*50 mm*3 μm; mobile phase: [water (0.225% FA)-ACN]; B %: 45%-65%, 10 min), 80% purity desired compound was obtained, then it was purified by second prep-HPLC (column: Phenomenex Luna C18 150*25 mm*10 μm; mobile phase: [water (0.225% FA)-ACN]; B %: 31%-61%, 10 min). Compound 233 or 5-[6-amino-1-[(2,6-difluorophenyl)methyl]pyrazolo[3,4-d]pyrimidin-4-yl]pyridine-3-carbonitrile (69.15 mg, 14% yield, 97.76% purity) was obtained as a yellow solid. $^1$H NMR (400 MHz, DMSO-$d_6$) δ=8.96 (d, J=5.1 Hz, 1H), 8.58 (d, J=0.6 Hz, 1H), 8.41-8.39 (m, 1H), 8.39-8.36 (m, 1H), 7.51-7.41 (m, 1H), 7.25 (s, 2H), 7.17-7.08 (m, 2H), 5.47 (s, 2H).

Example 1.66: Production of 5-(6-amino-1-(4-amino-3-methylbenzyl)-1H-pyrazolo[3,4-d]pyrimidin-4-yl)nicotinonitrile (Compound 229)

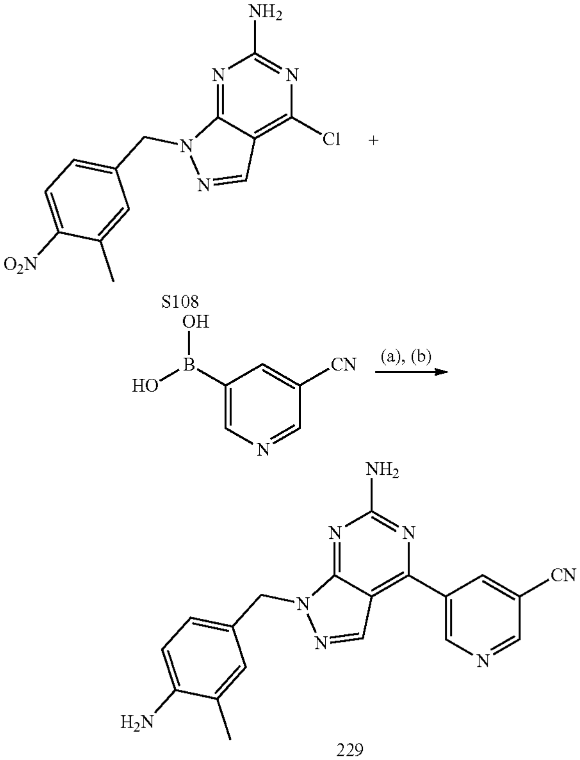

S108

229

Reagents and condition: (a) Pd(dppf)$Cl_2$, $K_2CO_3$, dioxane, 110° C., 16 h; (b) Fe, $NH_4Cl$, EtOH/$H_2O$, 60° C., 2 h.

Stage 1: Production of 5-(6-amino-1-(3-methyl-4-nitrobenzyl)-1H-pyrazolo [3,4-d]pyrimidin-4-yl) nicotinonitrile A mixture of (5-cyano-3-pyridyl)boronic acid (208 mg, 1.5 eq), intermediate compound S108 or 4-chloro-1-[(3-methyl-4-nitro-phenyl)methyl]pyrazolo[3,4-d]pyrimidin-6-amine (300 mg, 1 eq), $K_2CO_3$ (260 mg, 2 eq), Pd(dppf)$Cl_2$ (68.87 mg, 0.1 eq) in dioxane (10 mL) was degassed and purged with nitrogen for three times, and then the mixture was stirred at 110° C. for 16 hr under nitrogen atmosphere. The reaction mixture was filtered and concentrated under reduced pressure to give a residue. The residue was purified by flash silica gel chromatography (ISCO®; 24 g Sepa-Flash® Silica Flash Column, Eluent of 0~100% Ethyl acetate/Petroleum ether gradient @35 mL/min). Compound 5-[6-amino-1-[(3-methyl-4-nitro-phenyl)methyl]pyrazolo [3,4-d]pyrimidin-4-yl]pyridine-3-carbonitrile (300 mg, 82% yield) was obtained as a yellow solid. MS: m/z=386.9 (M+1, ESI+).

Stage 2: Production of 5-(6-amino-1-(4-amino-3-methylbenzyl)-1H-pyrazolo [3,4-d]pyrimidin-4-yl) nicotinonitrile (Compound 229)

To a solution of 5-[6-amino-1-[(3-methyl-4-nitro-phenyl) methyl]pyrazolo[3,4-d]pyrimidin-4-yl]pyridine-3-carbonitrile (400 mg, 1 eq) in ethanol (15 mL) and water (5 mL) was added iron dust (289 mg, 5 eq) and $NH_4Cl$ (443 mg, 8 eq). The mixture was stirred at 60° C. for 2 hr. The reaction mixture was filtered and concentrated under reduced pressure to give a residue. The residue was purified by prep-HPLC (column: Shim-pack C18 150*25*10 μm; mobile phase: [water (0.225% FA)-ACN]; B %: 12%-42%, 10 min), 92% purity desired compound was obtained, then the mixture was purified by 2$^{nd}$ prep-HPLC (column: Phenomenex Gemini-NX C18 75*30 mm*3 μm; mobile phase: [water (0.05% ammonia hydroxide v/v)-ACN]; B %: 14%-44%, 11.5 min). Compound 229 or 5-[6-amino-1-[(4-amino-3-methyl-phenyl)methyl]pyrazolo[3,4-d]pyrimidin-4-yl]pyridine-3-carbonitrile (58.12 mg, 15% yield, 97.57% purity) was obtained as a yellow solid. $^1$H NMR (400 MHz, DMSO-$d_6$) δ=9.53 (d, J=2.1 Hz, 1H), 9.22 (d, J=2.1 Hz, 1H), 8.91 (t, J=2.1 Hz, 1H), 8.43 (s, 1H), 7.12 (s, 2H), 6.91-6.77 (m, 2H), 6.52 (d, J=8.1 Hz, 1H), 5.23 (s, 2H), 4.80 (s, 2H), 1.99 (s, 3H).

Example 1.67: Production of 4-(6-amino-1-(4-aminobenzyl)-1H-pyrazolo[3,4-d]pyrimidin-4-yl)picolinonitrile (Compound 218)

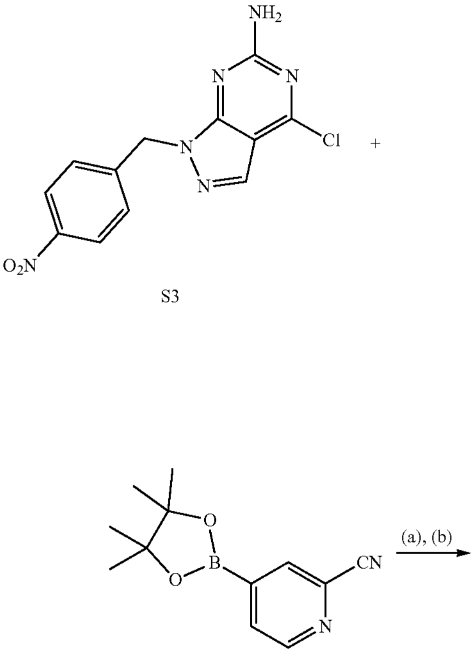

S3

-continued

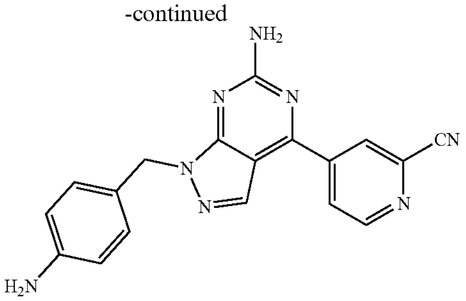

218

Reagents and condition: (a) $Pd(dppf)Cl_2$, $K_2CO_3$, dioxane/$H_2O$, 110° C., 16 h; (b) Fe, $NH_4Cl$, EtOH/$H_2O$, 60° C., 2 h.

Stage 1: Production of 4-(6-amino-1-(4-nitrobenzyl)-1H-pyrazolo[3,4-d]pyrimidin-4-yl)picolinonitrile A mixture of intermediate compound S3 or 4-chloro-1-[(4-nitrophenyl)methyl]pyrazolo[3,4-d]pyrimidin-6-amine (800 mg, 1 eq), 4-(4,4,5,5-tetramethyl-1,3,2-dioxaborolan-2-yl)pyridine-2-carbonitrile (906 mg, 1.5 eq), $K_2CO_3$ (725 mg, 2 eq), $Pd(dppf)Cl_2$ (192 mg, 0.1 eq) in dioxane (10 mL) and water (2 mL) was degassed and purged with nitrogen for three times, and then the mixture was stirred at 110° C. for 16 hr under nitrogen atmosphere. The reaction mixture was filtered and concentrated under reduced pressure to give a residue. The residue was purified by flash silica gel chromatography (ISCO®; 12 g Sepa Flash® Silica Flash Column, Eluent of 30~80% Ethyl acetate/Petroleum ether gradient @35 mL/min). Compound 4-[6-amino-1-[(4-nitrophenyl)methyl]pyrazolo[3,4-d]pyrimidin-4-yl] pyridine-2-carbonitrile (500 mg, 51% yield) was obtained as a yellow solid. $^1H$ NMR (400 MHz, DMSO-$d_6$) δ=9.05-8.94 (m, 1H), 8.84-8.71 (m, 2H), 8.58 (s, 1H), 8.43 (dd, J=1.8, 5.1 Hz, 1H), 8.09-8.07 (m, 1H), 7.46-7.41 (m, 2H), 7.31-7.24 (m, 2H), 5.67-5.61 (m, 2H). MS: m/z=372.9 (M+1, ESI+).

Stage 2: Production of 4-(6-amino-1-(4-aminobenzyl)-1H-pyrazolo[3,4-d]pyrimidin-4-yl)picolinonitrile (Compound 218)

To a solution of 4-[6-amino-1-[(4-nitrophenyl)methyl] pyrazolo[3,4-d]pyrimidin-4-yl]pyridine-2-carbonitrile (300 mg, 1 eq) in water (5 mL) and ethanol (15 mL) was added iron dust (224 mg, 5 eq) and $NH_4Cl$ (344 mg, 8 eq). The mixture was stirred at 60° C. for 2 hr. After that, the reaction mixture was concentrated under reduced pressure to remove ethanol and water to give a residue. The residue was purified by prep-HPLC (column: Phenomenex Gemini-NX C18 75*30 mm*3 μm; mobile phase: [water (0.05% ammonia hydroxide v/v)-ACN]; B %: 12%-42%, 11.5 min), 80% purity desired compound was obtained, then the residue was purified by the $2^{nd}$ prep-HPLC (column: Phenomenex Gemini-NX C18 75*30 mm*3 μm; mobile phase: [water (10 mM $NH_4HCO_3$)-ACN]; B %: 16%-46%, 8 min). Compound 218 or 4-[6-amino-1-[(4-aminophenyl)methyl]pyrazolo[3,4-d]pyrimidin-4-yl]pyridine-2-carbonitrile (52.04 mg, 18% yield, 95.28% purity) was obtained as a white solid. $^1H$ NMR (400 MHz, DMSO-$d_6$) δ=8.97 (d, J=5.1 Hz, 1H), 8.60 (d, J=0.7 Hz, 1H), 8.44 (s, 1H), 8.40 (dd, J=1.6, 5.1 Hz, 1H), 7.18 (s, 2H), 6.96 (d, J=8.3 Hz, 2H), 6.48 (d, J=8.4 Hz, 2H), 5.25 (s, 2H), 5.04 (s, 2H).

Example 1.68: Production of 4-(6-amino-1-(4-amino-2-fluorobenzyl)-1H-pyrazolo[3,4-d]pyrimidin-4-yl)picolinonitrile (Compound 222)

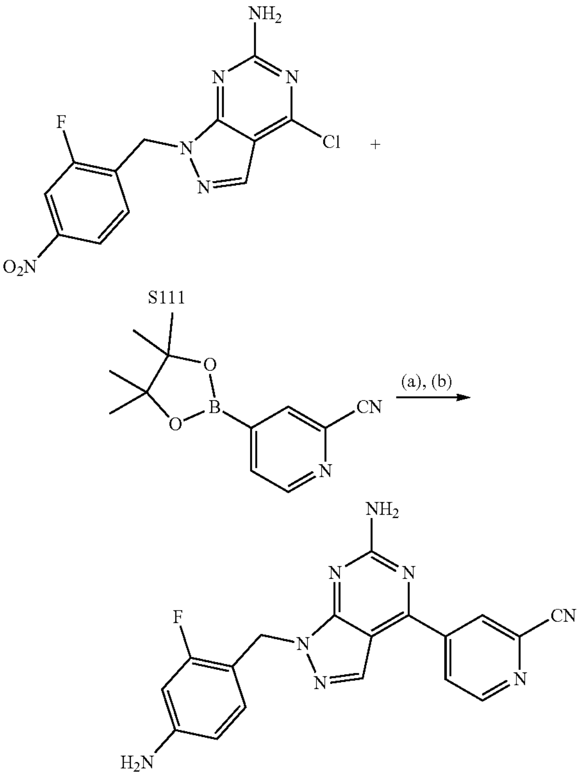

222

Reagents and condition: (a) $Pd(dppf)Cl_2$, $K_2CO_3$, dioxane/$H_2O$, 110° C., 16 h; (b) Fe, $NH_4Cl$, EtOH/$H_2O$, 60° C., 2 h.

Stage 1: Production of 4-(6-amino-1-(2-fluoro-4-nitrobenzyl)-1H-pyrazolo [3,4-d]pyrimidin-4-yl) picolinonitrile A mixture of intermediate compound S11 or 4-chloro-1-[(2-fluoro-4-nitro-phenyl)methyl]pyrazolo [3,4-d]pyrimidin-6-amine (1 g, 1 eq), 4-(4,4,5,5-tetramethyl-1,3,2-dioxaborolan-2-yl)pyridine-2-carbonitrile (784 mg, 1.1 eq), $K_2CO_3$ (856 mg, 2 eq), $Pd(dppf)Cl_2$ (226 mg, 0.1 eq) in dioxane (10 mL) and water (2 mL) was degassed and purged with nitrogen for three times, and then the mixture was stirred at 110° C. for 16 hr under nitrogen atmosphere. The reaction mixture was concentrated under reduced pressure to remove dioxane to give a residue. The residue was purified by flash silica gel chromatography (ISCO®; 12 g SepaFlash® Silica Flash Column, Eluent of 0~80% Ethyl acetate/Petroleum ether gradient @35 mL/min). Compound 4-[6-amino-1-[(2-fluoro-4-nitro-phenyl) methyl]pyrazolo[3,4-d] pyrimidin-4-yl]pyridine-2-carbonitrile (1 g, 83% yield) was obtained as a yellow solid. $^1H$ NMR (400 MHz, DMSO-$d_6$) δ=8.98 (dd, J=0.7, 5.1 Hz, 1H), 8.65-8.59 (m, 2H), 8.56 (s, 1H), 8.41 (dd, J=1.7, 5.1 Hz, 1H), 7.61-7.54 (m, 1H), 7.34 (t, J=8.0 Hz, 1H), 7.31-7.23 (m, 2H), 5.63 (s, 2H). MS: m/z=391.1 (M+1, ESI+).

Stage 2: Production of 4-(6-amino-1-(4-amino-2-fluorobenzyl)-1H-pyrazolo [3,4-d]pyrimidin-4-yl) picolinonitrile (Compound 222)

To a solution of 4-[6-amino-1-[(2-fluoro-4-nitro-phenyl) methyl]pyrazolo [3,4-d]pyrimidin-4-yl]pyridine-2-carbonitrile (500 mg, 1 eq) in ethanol (15 mL) and water (5 mL) was added iron dust (357 mg, 5 eq) and $NH_4Cl$ (548 mg, 8 eq). The mixture was stirred at 60° C. for 2 hr. The reaction mixture was filtered and concentrated under reduced pressure to give a residue. The residue was purified by prep-HPLC (column: Phenomenex Gemini-NX C18 75*30 mm*3 μm; mobile phase: [water (0.05% ammonia hydroxide v/v)-ACN]; B %: 15%-45%, 11.5 min), 79% purity desired compound obtained, the residue was purified by the $2^{nd}$ prep-HPLC (column: Phenomenex Gemini-NX C18 75*30 mm*3 μm; mobile phase: [water (10 mM $NH_4HCO_3$)-ACN]; B %: 18%-48%, 8 min), 81% purity desired compound obtained. Finally the residue was purified by the $3^{rd}$ prep-HPLC (column: Phenomenex Gemini-NX C18 75*30 mm*3 μm; mobile phase: [water (0.05% ammonia hydroxide v/v)-ACN]; B %: 16%-46%, 11.5 min). Compound 222 or 4-[6-amino-1-[(4-amino-2-fluoro-phenyl) methyl]pyrazolo[3,4-d]pyrimidin-4-yl]pyridine-2-carbonitrile (31.41 mg, 95.76% purity) was obtained as a yellow solid. $^1H$ NMR (400 MHz, DMSO-$d_6$) δ=8.97 (dd, J=0.8, 5.1 Hz, 1H), 8.60 (dd, J=0.8, 1.7 Hz, 1H), 8.44 (s, 1H), 8.40 (dd, J=1.8, 5.1 Hz, 1H), 7.19 (s, 2H), 6.89 (t, J=8.4 Hz, 1H), 6.37-6.24 (m, 2H), 5.46-5.37 (m, 2H), 5.32-5.22 (m, 2H).

Example 1.69: Production of 2-[6-amino-1-[[4-amino-3-(trifluoromethyl)phenyl]methyl]pyrazolo[3,4-d]pyrimidin-4-yl]pyridine-4-carbonitrile (Compound 235)

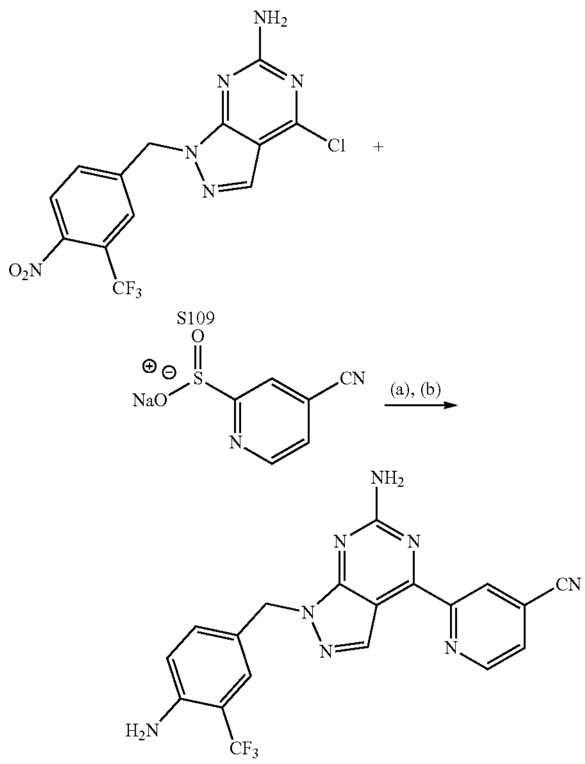

S109

235

Reagents and condition: (a) $Pd(OAc)_2$, $Cy_3P$, $K_2CO_3$, dioxane, 120° C., 16 h; (b) Fe, $NH_4Cl$, EtOH/$H_2O$, 60° C., 8 h.

Stage 1: Production of 2-[6-amino-1-[[4-nitro-3-(trifluoromethyl)phenyl]methyl]pyrazolo[3,4-d]pyrimidin-4-yl]pyridine-4-carbonitrile A mixture of sodium 4-cyanopyridine-2-sulfinate (420 mg, 2.21 mmol, 2 eq), intermediate compound S109 or 4-chloro-1-[[4-nitro-3-(trifluoromethyl)phenyl]methyl] pyrazolo[3,4-d]pyrimidin-6-amine (435 mg, 1.10 mmol, 94.74% purity, 1 eq), palladium acetate (25 mg, 110.49 μmol, 0.1 eq), $Cy_3P$ (62 mg, 220.98 μmol, 71.64 μL, 0.2 eq) and $K_2CO_3$ (305 mg, 2.21 mmol, 2 eq) in dioxane (10 mL) was degassed and purged with nitrogen for three times, and then the mixture was stirred at 120° C. for 16 hr under nitrogen atmosphere. The mixture was concentrated in vacuum to give a residue. The residue was purified by flash silica gel chromatography (12 g SepaFlash® Silica Flash Column, Eluent of 30~60% Ethyl acetate/Petroleum ether gradient @40 mL/min). Compound 2-[6-amino-1-[[4-nitro-3-(trifluoromethyl)phenyl]methyl]pyrazolo[3,4-d]pyrimidin-4-yl]pyridine-4-carbonitrile (160 mg, 354.13 μmol, 32% yield, 97.46% purity) was obtained as a yellow solid. $^1H$ NMR (400 MHz, DMSO-$d_6$) δ=9.09 (d, J=4.9 Hz, 1H), 8.68 (s, 1H), 8.57 (d, J=1.0 Hz, 1H), 8.17-8.04 (m, 2H), 7.96 (s, 1H), 7.60 (dd, J=1.2, 8.4 Hz, 1H), 7.20 (s, 2H), 5.69 (s, 2H). MS: m/z=441.1 (M+1, ESI+).

Stage 2: Production of 2-[6-amino-1-[[4-amino-3-(trifluoromethyl)phenyl]methyl]pyrazolo[3,4-d]pyrimidin-4-yl]pyridine-4-carbonitrile (Compound 235)

To the solution of 2-[6-amino-1-[[4-nitro-3-(trifluoromethyl)phenyl]methyl]pyrazolo[3,4-d]pyrimidin-4-yl]pyridine-4-carbonitrile (150 mg, 340.65 μmol, 1 eq) in ethanol (10 mL) and water (3 mL) was added iron dust (95 mg, 1.70 mmol, 5 eq) and $NH_4Cl$ (146 mg, 2.73 mmol, 8 eq). Then the mixture was stirred at 60° C. for 8 h. The reaction mixture was filtered, to the filtrate was added saturated $NaHCO_3$ solution (50 mL) and extracted with ethyl acetate (80 mL×3). Combined the organic phase to dry over anhydrous sodium sulfate, filter and concentrate in vacuum to give a residue. The residue was purified by prep-HPLC (column: Welch Ultimate XB-CN 250*70*10 μm; mobile phase: [Hexane-ethanol (0.1% ammonia hydroxide)]; B %: 20%-60%, 15 min). Compound 235 or 2-[6-amino-1-[[4-amino-3-(trifluoromethyl)phenyl]methyl]pyrazolo[3,4-d]pyrimidin-4-yl]pyridine-4-carbonitrile (76.29 mg, 180.52 μmol, 53% yield, 97.10% purity) was obtained as a yellow solid. $^1H$ NMR (400 MHz, DMSO-$d_6$) δ=9.08 (dd, J=0.7, 5.0 Hz, 1H), 8.67 (d, J=0.9 Hz, 1H), 8.47 (s, 1H), 8.07 (dd, J=1.6, 5.0 Hz, 1H), 7.28 (d, J=1.6 Hz, 1H), 7.18 (dd, J=1.3, 8.6 Hz, 1H), 7.14 (s, 2H), 6.77 (d, J=8.4 Hz, 1H), 5.59 (s, 2H), 5.31 (s, 2H).

Example 2: Assessment of Purine Compounds

2.1 A2A Receptor (A2AR) SPA Binding Assay

General Method

Test compound is weighed, then dissolved in 100% DMSO to prepare 20 mM stock solution. Dilute the stock solution with DMSO into 100× final concentration, and then use this DMSO solution to perform 3-fold serial dilution for totally 12 concentrations with DMSO. 10-fold diluting the serial dilutions with assay buffer to the working concentrations. Compound $IC_{50}$ values are determined in an A2AR (Human recombinant adenosine A2A receptor from HKE293 cells) SPA (scintillation proximity assay) binding assay with [3H] SCH58261 as the radioligand. The assay buffer is prepared with DPBS containing 10 mM $MgCl_2$. 5 μL of compound working solutions (a total of 12 concentrations starting from 1 or 3 μM, 1/3 dilution) is transferred to the wells by the 12-channel pipette. A2AR membrane is pre-incubated with adenosine deaminase for 15 min at room temperature. Then SPA beads are added and the membrane-bead suspension mixture is incubated for 30 min at room temperature with the rotary mixer. The reaction is started by the addition to each well of 25 μL of membrane-bead suspension containing 0.04 mg/mL A2aR membrane, 0.024 mg/mL adenosine deaminase and 4 mg/mL SPA beads, and 20 μL of the 7.5 nM [3H] SCH58261 radioligand solution. Final concentration of DMSO in the A2AR SPA binding assay is 1%. Sealing the plates and incubate for 1 hr at 27° C. with vigorous mixing on a plate shaker. After 1 hr, centrifuge the plate (1000 rpm, 1 min), and settle the plate for 5 min prior to counting. The signal of radiation is measured by the Microbeta2. The readout of the signal is used to calculate compound $IC_{50}$ values. Non-specific binding refers to the wells containing reaction system with the presence of 100 μM SCH58261. The dose-response curve is fitted with GraphPad Prism 5 and $IC_{50}$ values are calculated by log(inhibitor) vs. response—Variable slope program with the following formula:

$$Y=Bottom+(Top-Bottom)/(1+10^{\wedge}((Log\ IC_{50}-X)*Hill\ Slope))$$

$$K_i=/(1+\text{radio ligand concentration used in assay}/\text{radio ligand } K_d)$$

The binding affinity of selected compounds against A2A receptor was assessed using the SPA binding assay described above. The binding affinity of reference compounds Taminadenant (CAS No. 1337962-47-6) and AZD4635 (CAS No. 1321514-06-0) was also measured in this assay.

Table 2: Binding affinity of exemplary compounds against human A2A receptor

A: $K_i \leq 10$ nM
B: 10 nM<$K_i \leq 100$ nM
C: 100 nM<$K_i \leq 500$ nM
D: $K_i$>500 nM

TABLE 2

Binding affinity of exemplary compounds against human A2A receptor

| Compd. No. | human A2A receptor $K_i$ |
|---|---|
| 101 | B |
| 102 | C |
| 103 | B |
| 104 | A |
| 105 | D |
| 106 | B |
| 107 | A |
| 108 | B |
| 109 | A |
| 110 | A |
| 111 | B |
| 112 | A |
| 113 | B |
| 114 | B |
| 118 | D |
| 119 | C |
| 120 | A |
| 124 | A |
| 125 | C |
| 126 | B |
| 128 | A |
| 132 | A |
| 134 | B |
| Taminadenant | B |
| AZD4635 | A |

A: $K_i \leq 10$ nM
B: 10 nM < $K_i \leq 100$ nM
C: 100 nM < $K_i \leq 500$ nM
D: $K_i$ > 500 nM Several tested compounds bound with high affinity to human A2A receptor and were superior to Taminadenant

2.2 Human Adenosine A1 Receptor Binding Assay

General Method

Test compound is weighed, dissolved in DMSO to make a stock solution of 10 mM, diluted with DMSO to prepare working solutions, then 100-fold diluted to the indicated concentrations. Human recombinant adenosine $A_1$ receptors expressed in CHO-K1 cells were used to prepare membranes in incubation buffer (20 mM HEPES (4-(2-hydroxyethyl)-1-piperazineethanesulfonic acid) pH 7.4, 10 mM $MgCl_2$, 100 mM NaCl). Test compound or vehicle (2.2 μL) was added in 200 μL of membranes and incubated with 20 μL of 1 nM [$^3$H] DPCPX (8-cyclopentyl-1,3-dipropylxanthine) for 90 minutes at 25° C. Non-specific binding was estimated in the presence of 100 μM R(−)-PIA ((R)—N-(1-methyl-2-phenylethyl)adenosine). The incubation was stopped by vacuum filtration onto 0.3% PEI (polyethylenimine) pre-soaked GF/B filters using a harvester followed by four washes with ice-cold 50 mM Tris-HCl, pH 7.4, and the radioactivity on GF/B filtermats counted in a scintillation counter (PerkinElmer Topcount™) to determine [$^3$H] DPCPX specifically bound. Final concentration of vehicle DMSO is 1%. Data is fitted using the non-linear curve fitting routines in Meth-IQ software (ID Business Solutions Ltd., UK). $IC_{50}$ is converted to $K_i$ by Cheng-Prusoff equation:

$K_i=IC_{50}/(1+[L]/K_D)$ where [L] is concentration of radio-labeled ligand used in the assay.

The binding affinity of selected compounds against A1 receptor was assessed using the binding assay described above.

TABLE 3

Binding affinity of exemplary compounds against human A1 receptor

| Compd. No. | human A1 receptor $K_i$ |
|---|---|
| 101 | A |
| 103 | A |
| 104 | A |
| 106 | A |
| 107 | C |

TABLE 3-continued

Binding affinity of exemplary compounds against human A1 receptor

| Compd. No. | human A1 receptor $K_i$ |
|---|---|
| 108 | B |
| 109 | B |
| 110 | B |
| 111 | A |
| 112 | C |
| 113 | B |
| 114 | A |
| 120 | B |
| 124 | C |
| 128 | B |
| 132 | C |

A: $K_i$ > 1000 nM
B: 300 nM < $K_i$ ≤ 1000 nM
C: $K_i$ ≤ 300 nM

Several tested compounds bound with low affinity to human A1 receptor. This result indicates that some compounds of this disclosure exhibit selectivity for A2A receptor over human A1 receptor.

Example 3: Assessment of Purine Compounds Using a Human A2A Functional Assay

General Method cAMP assay was performed on human recombinant A2AR stable cell line (HEK293). The cells were cultured at 37° C. and 5% $CO_2$ with culture medium (90% DMEM+10% FBS+500 μg/mL G418). The compounds and reference compound ZM241385 were diluted in 3-fold started from high concentration. Then, 100 nL compounds were transferred by Echo machine with 12 doses respectively. Cells were collected with stimulation buffer (1×HBSS with 5 mM HEPES+0.05 mM IBMX+0.1% BSA) and plated the cells at the density of 5,000 cells/well, centrifuged at 600 rpm for 3 min and then incubation with compounds at room temperature for 60 min. After that, 5 μL 4× Eu-cAMP tracer solution and 5 μL 4× ULight™-anti-cAMP solution were added into the cells, centrifuged at 600 rpm for 3 min and incubated for 60 min. cAMP signal was detected with Envision. GraphPad Prism (version 6.0) was used for the data analysis.

The A2A receptor antagonistic activity of selected compounds was assessed using the cAMP assay described above. The antagonistic activity of reference compounds Taminadenant (CAS No. 1337962-47-6) and AZD4635 (CAS No. 1321514-06-0) was also measured in this assay.

Table 4: A2A Receptor antagonistic activity of exemplary compounds in a hA2A functional assay.

A: $IC_{50}$≤300 nM

B: 300 nM<$IC_{50}$≤1000 nM

C: $IC_{50}$>1000 nM

TABLE 4

A2A Receptor antagonistic activity of exemplary compounds in a hA2A functional assay.

| Compd. No. | cAMP $IC_{50}$ |
|---|---|
| 101 | C |
| 103 | C |
| 104 | A |
| 107 | A |

TABLE 4-continued

A2A Receptor antagonistic activity of exemplary compounds in a hA2A functional assay.

| Compd. No. | cAMP $IC_{50}$ |
|---|---|
| 108 | B |
| 109 | A |
| 110 | A |
| 111 | C |
| 112 | A |
| 113 | B |
| 120 | A |
| 124 | A |
| 128 | B |
| 132 | A |
| Taminadenant | B |
| AZD4635 | A |

A: $IC_{50}$ ≤ 300 nM
B: 300 nM < $IC_{50}$ ≤ 1000 nM
C: $IC_{50}$ > 1000 nM

Several compounds of this disclosure showed strong antagonistic activity against human A2A receptor and were superior to Taminadenant

Example 4: Assessment of Activity of Pyrazolo-Pyrimidine Compounds

4.1 Human Adenosine A1 Receptor Binding Assay

General Method

Test compound is weighed, dissolved in DMSO to make a stock solution of 10 mM, diluted with DMSO to prepare working solutions, then 100-fold diluted to the indicated concentrations. Human recombinant adenosine $A_1$ receptors expressed in CHO-K1 cells were used to prepare membranes in incubation buffer (20 mM HEPES (4-(2-hydroxyethyl)-1-piperazineethanesulfonic acid) pH 7.4, 10 mM $MgCl_2$, 100 mM NaCl). Test compound or vehicle (2.2 μL) was added in 200 μL of membranes and incubated with 20 μL of 1 nM [$^3$H] DPCPX (8-cyclopentyl-1,3-dipropylxanthine) for 90 minutes at 25° C. Non-specific binding was estimated in the presence of 100 μM R(−)-PIA ((R)—N-(1-methyl-2-phenylethyl)adenosine). The incubation was stopped by vacuum filtration onto 0.3% PEI (polyethylenimine) pre-soaked GF/B filters using a harvester followed by four washes with ice-cold 50 mM Tris-HCl, pH 7.4, and the radioactivity on GF/B filtermats counted in a scintillation counter (PerkinElmer Topcount™) to determine [$^3$H] DPCPX specifically bound. Final concentration of vehicle DMSO is 1%.

Data is fitted using the non-linear curve fitting routines in Meth-IQ software (ID Business Solutions Ltd., UK). $IC_{50}$ is converted to $K_i$ by Cheng-Prusoff equation: $K_i=IC_{50}/(1+[L]/K_D)$ where [L] is concentration of radiolabeled ligand used in the assay.

4.2 Human Adenosine A2A Receptor Binding Assay

General Method

Test compound is weighed, dissolved in DMSO to make a stock solution of 10 mM, diluted with DMSO to prepare working solutions, then 100-fold diluted to the indicated concentrations. Human recombinant adenosine $A_{2A}$ receptors expressed in HEK-293 cells were used to prepare membranes in incubation buffer (50 mM Tris-HCl, pH 7.4, 10 mM $MgCl_2$, 1 mM EDTA, 2 U/ml Adenosine Deaminase). Test compound or vehicle (2.2 μL) was added in 200 μL of membranes and incubated with 20 μL of 50 nM [$^3$H] CGS-21680 for 90 minutes at 25° C. Non-specific binding was estimated in the presence of 50 μM NECA (5'-N-ethylcarboxamidoadenosine). The incubation was stopped by vacuum filtration onto 0.3% PEI (polyethylenimine) presoaked GF/B filters using a harvester followed by four washes with ice-cold 50 mM Tris-HCl, pH 7.4, and the radioactivity on GF/B filtermats counted in a scintillation counter (PerkinElmer Topcount™) to determine [$^3$H] CGS-21680 specifically bound. Final concentration of vehicle DMSO is 1%.

Data is fitted using the non-linear curve fitting routines in Meth-IQ software (ID Business Solutions Ltd., UK). $IC_{50}$ is converted to $K_i$ by Cheng-Prusoff equation: $K_i = IC_{50}/(1+[L]/K_D)$ where [L] is concentration of radiolabeled ligand used in the assay.

4.3 Results

The A2A and A1 receptor inhibition activity of select compounds was assessed using the binding assay described above in Examples 4.1 and 4.2. The activity of reference adenosine receptor an antagonist compound Istradefylline (CAS No. 155270-99-8) was also measured in this assay.

Table 5: A2A and A1 receptor inhibition activity of exemplary compounds.

For A2A receptor inhibition:
A: $K_i$<20 nM,
B: 20 nM<$K_i$≤200 nM,
C: 200 nM<$K_i$≤1000 nM,
D: 1000 nM<$K_i$≤5000 nM.
For A1 receptor inhibition:
A: $K_i$<0.1 μM,
B: 0.1 μM<$K_i$≤1 μM,
C: 1 μM<$K_i$≤10 μM,
D: $K_i$>10 μM.

TABLE 5

A2A and A1 receptor inhibition activity of exemplary compounds.

| Cmpd No. | hA1 $K_i$ (μM) | hA2A $K_i$ (nM) |
|---|---|---|
| 203 | A | A |
| 204 | B | A |
| 206 | A | A |
| 207 | A | A |
| 208 | A | A |
| 209 | B | A |
| 210 | A | A |
| 211 | A | A |
| 213 | A | A |
| 215 | B | B |
| 216 | C | C |
| 217 | D | D |
| 218 | C | D |
| 219 | B | A |
| 220 | B | B |
| 221 | D | D |
| 222 | D | D |
| 223 | B | A |
| 224 | B | B |
| 225 | C | D |
| 226 | D | D |
| 227 | B | A |
| 228 | B | B |
| 229 | D | D |
| 230 | D | D |

TABLE 5-continued

A2A and A1 receptor inhibition activity of exemplary compounds.

| Cmpd No. | hA1 $K_i$ (μM) | hA2A $K_i$ (nM) |
|---|---|---|
| 231 | B | A |
| 232 | B | B |
| 233 | C | C |
| 234 | C | C |
| 235 | B | A |
| Istradefylline | B | A |

For A2A receptor inhibition:
A: $K_i$ ≤ 20 nM,
B: 20 nM < $K_i$ ≤ 200 nM,
C: 200 nM < $K_i$ ≤ 1000 nM,
D: 1000 nM < $K_i$ ≤ 5000 nM.
For A1 receptor inhibition:
A: $K_i$ ≤ 0.1 μM,
B: 0.1 μM < $K_i$ ≤ 1 μM,
C: 1 μM < $K_i$ ≤ 10 μM,
D: $K_i$ > 10 μM.

The A2A receptor binding assay results of Table 5 indicate that the compounds of this disclosure can act as A2A receptor antagonists. Several compounds exhibited potent activity as dual antagonists of both A2A and A1 receptors. See e.g., compounds 203, 206, 207, 208, 211, and 213 in Table 5.

EQUIVALENTS AND INCORPORATION BY REFERENCE

While the invention has been particularly shown and described with reference to a preferred embodiment and various alternate embodiments, it will be understood by persons skilled in the relevant art that various changes in form and details can be made therein without departing from the spirit and scope of the invention. Therefore, it must be understood that the embodiments described above are for illustrative purposes and do not limit the present invention.

All references, issued patents and patent applications cited within the body of the instant specification, are herein incorporated by reference in their entirety for all purposes.

The invention claimed is:

1. A compound of formula (Ib)

(Ib)

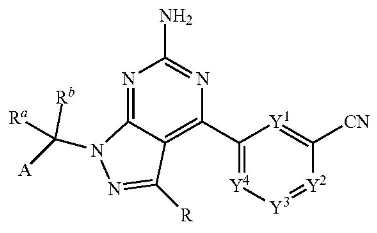

wherein:

R is H, ($C_1$-$C_3$)alkyl, or substituted ($C_1$-$C_3$)alkyl;

$Y^1$ to $Y^4$ are independently selected from $CR^{10}$;

each $R^{10}$ is independently selected from H, ($C_1$-$C_8$)alkyl, substituted ($C_1$-$C_8$)alkyl, ($C_2$-$C_8$)alkenyl, substituted ($C_2$-$C_8$)alkenyl, ($C_2$-$C_8$)alkynyl, substituted ($C_2$-$C_8$) alkynyl, ($C_1$-$C_3$)haloalkyl, ($C_1$-$C_8$)alkoxy, substituted ($C_1$-$C_8$)alkoxy, —$CONH_2$, substituted amido, —$NH_2$, substituted amino, —$CO_2H$, halogen, hydroxyl, —$NO_2$, —$SO_3H$, —$SO_2NH_2$, substituted sulfonamide, and thiol, with proviso that $Y^1$ is not CH;

$R^a$ and $R^b$ are each independently selected from H, F, $(C_1\text{-}C_3)$alkyl, and substituted $(C_1\text{-}C_3)$alkyl; and A is phenyl or phenyl substituted with one, two or three $R^{20}$ groups, each $R^{20}$ is independently selected from $(C_1\text{-}C_8)$alkyl, substituted $(C_1\text{-}C_8)$alkyl, $(C_2\text{-}C_8)$alkenyl, substituted $(C_2\text{-}C_8)$alkenyl, $(C_2\text{-}C_8)$alkynyl, substituted $(C_2\text{-}C_8)$alkynyl, $(C_1\text{-}C_3)$haloalkyl, $(C_1\text{-}C_8)$alkoxy, substituted $(C_1\text{-}C_8)$alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol;

wherein one or more substituents of substituted $(C_1\text{-}C_3)$ alkyl, substituted $(C_1\text{-}C_8)$alkyl, substituted $(C_2\text{-}C_8)$alkenyl, substituted $(C_2\text{-}C_8)$alkynyl, substituted $(C_1\text{-}C_8)$ alkoxy, substituted amido, substituted amino, and substituted sulfonamide are independently selected from halogen, hydroxy, oxo (═O), thioxo (═S), cyano (—CN), nitro (—$NO_2$), imino (═N—H), oximo (═N—OH), —$CONH_2$, —$NH_2$, —$CO_2H$, —$SO_3H$, —$SO_2NH_2$, thiol and hydrazino (═N—$NH_2$), or a solvate, a hydrate, and/or a stereoisomer thereof, or a pharmaceutically acceptable salt thereof.

2. The compound, or a solvate, a hydrate, and/or a stereoisomer thereof, or a pharmaceutically acceptable salt thereof of claim 1, wherein $R^a$ and $R^b$ are each H.

3. The compound, or a solvate, a hydrate, and/or a stereoisomer thereof, or a pharmaceutically acceptable salt thereof of claim 2, wherein A is unsubstituted or substituted phenyl represented by:

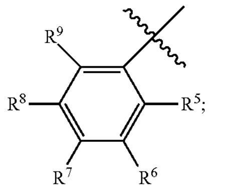

or the moiety is

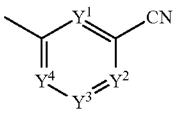

is

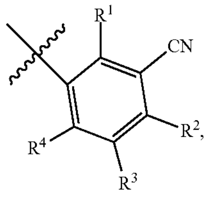

wherein $R^1$ is selected from $(C_1\text{-}C_8)$alkyl, substituted $(C_1\text{-}C_8)$alkyl, $(C_2\text{-}C_8)$alkenyl, substituted $(C_2\text{-}C_8)$ alkenyl, $(C_2\text{-}C_8)$alkynyl, substituted $(C_2\text{-}C_8)$alkynyl, $(C_1\text{-}C_3)$haloalkyl, $(C_1\text{-}C_8)$alkoxy, substituted $(C_1\text{-}C_8)$alkoxy, —$CONH_2$, substituted amido, —$NH_2$, substituted amino, —$CO_2H$, halogen, hydroxyl, —$NO_2$, —$SO_3H$, —$SO_2NH_2$, substituted sulfonamide, and thiol, and $R^2$ to $R^9$ are independently selected from H, $(C_1\text{-}C_8)$alkyl, substituted $(C_1\text{-}C_8)$alkyl, $(C_2\text{-}C_8)$alkenyl, substituted $(C_2\text{-}C_8)$alkenyl, $(C_2\text{-}C_8)$alkynyl, substituted $(C_2\text{-}C_8)$ alkynyl, $(C_1\text{-}C_3)$haloalkyl, $(C_1\text{-}C_8)$alkoxy, substituted $(C_1\text{-}C_8)$alkoxy, —$CONH_2$, substituted amido, —$NH_2$, substituted amino, —$CO_2H$, halogen, hydroxyl, —$NO_2$, —$SO_3H$, —$SO_2NH_2$, substituted sulfonamide, and thiol, wherein one or more substituents of substituted $(C_1\text{-}C_8)$ alkyl, substituted $(C_2\text{-}C_8)$alkenyl, substituted $(C_2\text{-}C_8)$ alkynyl, substituted $(C_1\text{-}C_8)$alkoxy, substituted amido, substituted amino, and substituted sulfonamide are independently selected from halogen, hydroxy, oxo (═O), thioxo (═S), cyano (—CN), nitro (—$NO_2$), imino (═N—H), oximo (═N—OH), —$CONH_2$, —$NH_2$, —$CO_2H$, —$SO_3H$, —$SO_2NH_2$, thiol and hydrazino (═N—$NH_2$).

4. The compound, or a solvate, a hydrate, and/or a stereoisomer thereof, or a pharmaceutically acceptable salt thereof of claim 3, wherein $R^1$ is selected from $NH_2$, F, $CH_3$, and $CF_3$; and $R^2$ to $R^9$ are independently selected from H, —$NH_2$, F, $CH_3$, and $CF_3$.

5. The compound, or a solvate, a hydrate, and/or a stereoisomer thereof, or a pharmaceutically acceptable salt thereof of claim 3, wherein $R^7$ is $NR^{21}R^{22}$, $R^{21}$ and $R^{22}$ are independently selected from H, $(C_1\text{-}C_8)$ alkyl, substituted $(C_1\text{-}C_8)$alkyl, $SO_2R^{30}$, and $COR^{30}$, and $R^{30}$ is $(C_1\text{-}C_8)$alkyl, or substituted $(C_1\text{-}C_8)$alkyl, wherein one or more substituents of substituted $(C_1\text{-}C_8)$ alkyl are independently selected from halogen, hydroxy, oxo (═O), thioxo (═S), cyano (—CN), nitro (—$NO_2$), imino (═N—H), oximo (═N—OH), —$CONH_2$, —$NH_2$, —$CO_2H$, —$SO_3H$, —$SO_2NH_2$, thiol and hydrazino (═N—$NH_2$).

6. The compound, or a solvate, a hydrate, and/or a stereoisomer thereof, or a pharmaceutically acceptable salt thereof of claim 5, wherein $R^{21}$ and $R^{22}$ are each H.

7. The compound, or a solvate, a hydrate, and/or a stereoisomer thereof, or a pharmaceutically acceptable salt thereof of claim 5, wherein $R^1$ is selected from $(C_1\text{-}C_5)$alkyl, substituted $(C_1\text{-}C_5)$ alkyl, $(C_1\text{-}C_3)$haloalkyl, $(C_1\text{-}C_5)$alkoxy, substituted $(C_1\text{-}C_5)$alkoxy, halogen and hydroxyl, and $R^5$, $R^6$, $R^8$ and $R^9$ are independently selected from H, $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$alkoxy, halogen, and hydroxyl, wherein one or more substituents of substituted $(C_1\text{-}C_5)$ alkyl, and substituted $(C_1\text{-}C_5)$alkoxy are independently selected from halogen, hydroxy, oxo (═O), thioxo (═S), cyano (—CN), nitro (—$NO_2$), imino (═N—H), oximo (═N—OH), —$CONH_2$, —$NH_2$, —$CO_2H$, —$SO_3H$, —$SO_2NH_2$, thiol and hydrazino (═N—$NH_2$).

8. The compound, or a solvate, a hydrate, and/or a stereoisomer thereof, or a pharmaceutically acceptable salt thereof of claim 7, wherein $R^1$ is selected from F, $CH_3$, and $CF_3$, and $R^5$, $R^6$, $R^8$ and $R^9$ are independently selected from H, F, $CH_3$, and $CF_3$; and $R^2$ to $R^4$ are each H.

9. The compound, or a solvate, a hydrate, and/or a stereoisomer thereof, or a pharmaceutically acceptable salt thereof of claim 3, wherein $R^2$ to $R^4$ are each H; and $R^1$ is selected from $(C_1\text{-}C_5)$alkyl, substituted $(C_1\text{-}C_5)$ alkyl, $(C_1\text{-}C_3)$haloalkyl, $(C_1\text{-}C_5)$alkoxy, substituted $(C_1\text{-}C_5)$alkoxy, halogen, and hydroxyl, wherein one or more substituents of substituted $(C_1\text{-}C_5)$ alkyl, and substituted $(C_1\text{-}C_5)$alkoxy are independently selected from halogen, hydroxy, oxo (═O), thioxo (=S), cyano (—CN), nitro (—$NO_2$), imino (=N—H), oximo (=N—OH), —$CONH_2$, —$NH_2$, —$CO_2H$, —$SO_3H$, —$SO_2NH_2$, thiol and hydrazino (=N—$NH_2$).

10. The compound, or a solvate, a hydrate, and/or a stereoisomer thereof, or a pharmaceutically acceptable salt thereof of claim 9, wherein $R^1$ is selected from F, $CH_3$, and $CF_3$.

11. The compound, or a solvate, a hydrate, and/or a stereoisomer thereof, or a pharmaceutically acceptable salt thereof of claim 1, wherein the compound of formula (Ib) is selected from:

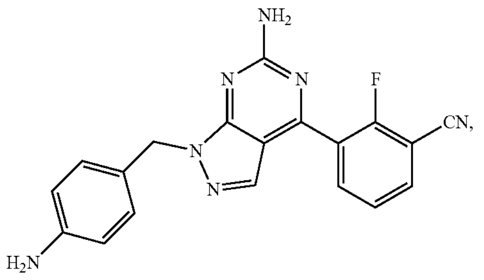

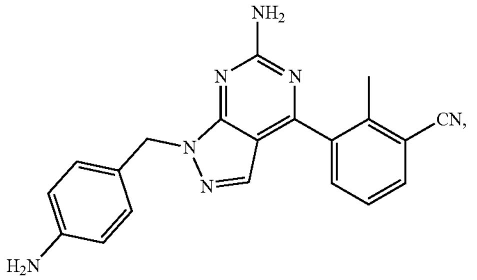

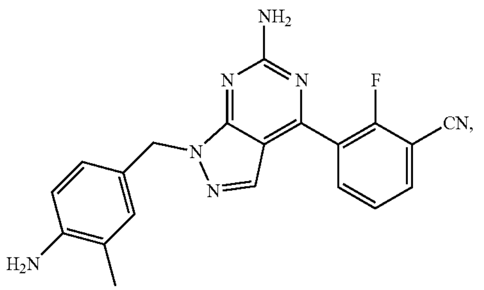

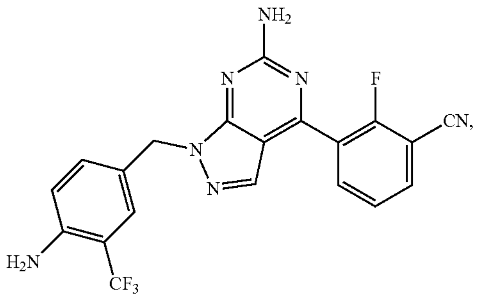

-continued

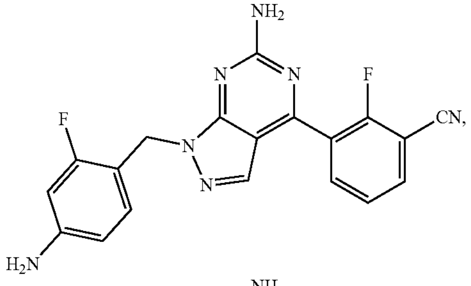

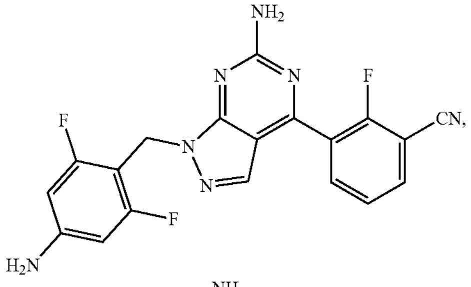

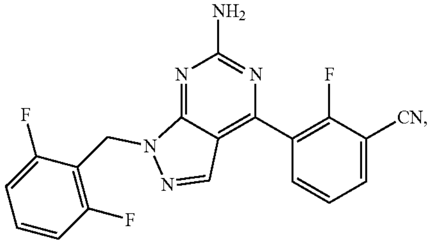

and

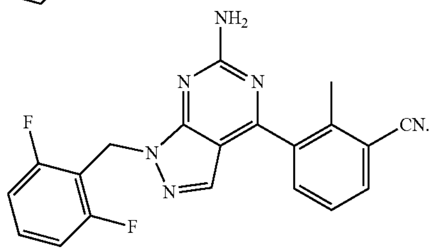

12. A pharmaceutical composition comprising:

a compound or a solvate, a hydrate, and/or a stereoisomer thereof, or a pharmaceutically acceptable salt thereof according to claim 1; and a pharmaceutically acceptable excipient.

13. A method of treating cancer, comprising administering to a subject having cancer a therapeutically effective amount of an A2A and/or A1 receptor antagonist compound or a solvate, a hydrate, and/or a stereoisomer thereof, or a pharmaceutically acceptable salt thereof according to claim 1.

14. The method of claim 13, wherein the cancer is a solid tumor cancer.

15. The method of claim 13, wherein the cancer is selected from the group consisting of lung cancer, breast cancer, prostate cancer, ovarian cancer, solenoma, cervical cancer, bladder cancer, head and neck cancer, renal cell carcinoma, cancer of the esophagus, pancreatic cancer, brain cancer, liver cancer, leukemia, lymphoma, melanoma, multiple myeloma, Ewing's sarcoma, osteosarcoma, colorectal neoplasm, cholangiocarcinoma, choriocarcinoma, mouth cancer, neuroblastoma, skin cancer, testicular cancer, stromal tumor, germ cell tumor, and thyroid cancer.

16. The method of claim 13, wherein the cancer is liver cancer that is hepatocellular carcinoma (HCC).

17. The method of claim 13, wherein the cancer is lung cancer that is non-small cell lung carcinoma (NSCLC).

18. The method of claim 13, further comprising co-administering to the subject an additional active agent.

19. The method of claim 18, wherein the additional active agent is selected from anti-angiogenesis agent, anti-inflammatory agent, immune checkpoint inhibitor, poly (ADP-ribose) polymerase (PARP) inhibitor, chemotherapeutic agent, and immunity anticancer agent.

20. The method of claim 18, wherein the additional active agent is an immune checkpoint inhibitor selected from CTLA-4 inhibitor, PD-1 inhibitors, and PD-L1 inhibitor.

21. The method of claim 19, wherein the immune checkpoint inhibitor is an antibody or antibody fragment.

22. A method of treating an inflammatory disease, comprising administering to a subject having an inflammatory disease a therapeutically effective amount of an A2A and/or A1 receptor antagonist compound or a solvate, a hydrate, and/or a stereoisomer thereof, or a pharmaceutically acceptable salt thereof according to claim 1.

23. The method of claim 22, wherein the inflammatory disease is a chronic inflammatory disease.

24. The method of claim 22, wherein the inflammatory disease is an acute inflammatory disease.

25. A compound of formula (Ib')

(Ib')

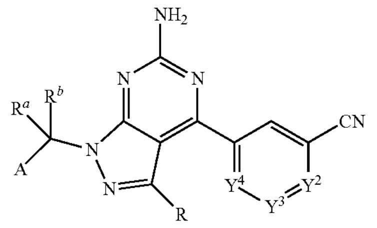

wherein:

R is H, $(C_1\text{-}C_3)$alkyl, or substituted $(C_1\text{-}C_3)$alkyl;

$Y^2$ to $Y^4$ are independently selected from $CR^{10}$;

each $R^{10}$ is independently selected from H, $(C_1\text{-}C_8)$alkyl, substituted $(C_1\text{-}C_8)$alkyl, $(C_2\text{-}C_8)$alkenyl, substituted $(C_2\text{-}C_8)$alkenyl, $(C_2\text{-}C_8)$alkynyl, substituted $(C_2\text{-}C_8)$alkynyl, $(C_1\text{-}C_3)$haloalkyl, $(C_1\text{-}C_8)$alkoxy, substituted $(C_1\text{-}C_8)$alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol;

$R^a$ and $R^b$ are each independently selected from H, F, $(C_1\text{-}C_3)$alkyl, and substituted $(C_1\text{-}C_3)$alkyl; and A is phenyl or phenyl substituted with one, two or three $R^{20}$ groups, each $R^{20}$ is independently selected from $(C_1\text{-}C_8)$alkyl, substituted $(C_1\text{-}C_8)$alkyl, $(C_2\text{-}C_8)$alkenyl, substituted $(C_2\text{-}C_8)$alkenyl, $(C_2\text{-}C_8)$alkynyl, substituted $(C_2\text{-}C_8)$alkynyl, $(C_1\text{-}C_3)$haloalkyl, $(C_1\text{-}C_8)$alkoxy, substituted $(C_1\text{-}C_8)$alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol;

wherein one or more substituents of substituted $(C_1\text{-}C_3)$alkyl, substituted $(C_1\text{-}C_8)$alkyl, substituted $(C_2\text{-}C_8)$alkenyl, substituted $(C_2\text{-}C_8)$alkynyl, substituted $(C_1\text{-}C_8)$alkoxy, substituted amido, substituted amino, and substituted sulfonamide are independently selected from halogen, hydroxy, oxo (=O), thioxo (=S), cyano (—CN), nitro (—$NO_2$), imino (N—H), oximo (=N—OH), —$CONH_2$, —$NH_2$, —$CO_2H$, —$SO_3H$, —$SO_2NH_2$, thiol and hydrazino (=N—$NH_2$), or a solvate, a hydrate, and/or a stereoisomer thereof, or a pharmaceutically acceptable salt thereof.

26. The compound, or a solvate, a hydrate, and/or a stereoisomer thereof, or a pharmaceutically acceptable salt thereof of claim 25, wherein $R^a$ and $R^b$ are each H.

27. The compound, or a solvate, a hydrate, and/or a stereoisomer thereof, or a pharmaceutically acceptable salt thereof of claim 26, wherein A is unsubstituted or substituted phenyl represented by:

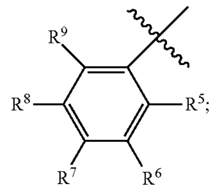

or the moiety

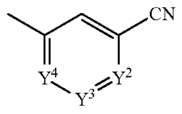

is

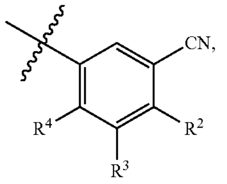

wherein $R^2$ to $R^9$ are independently selected from H, $(C_1\text{-}C_8)$alkyl, substituted $(C_1\text{-}C_8)$alkyl, $(C_2\text{-}C_8)$alkenyl, substituted $(C_2\text{-}C_8)$alkenyl, $(C_2\text{-}C_8)$alkynyl, substituted $(C_2\text{-}C_8)$alkynyl, $(C_1\text{-}C_3)$haloalkyl, $(C_1\text{-}C_8)$alkoxy, substituted $(C_1\text{-}C_8)$alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol, wherein one or more substituents of substituted $(C_1\text{-}C_8)$alkyl, substituted $(C_2\text{-}C_8)$alkenyl, substituted $(C_2\text{-}C_8)$alkynyl, substituted $(C_1\text{-}C_8)$alkoxy, substituted amido, substituted amino, and substituted sulfonamide are independently selected from halogen, hydroxy, oxo (=O), thioxo (=S), cyano (—CN), nitro (—$NO_2$), imino (=N—H), oximo (=N—OH), —$CONH_2$, —$NH_2$, —$CO_2H$, —$SO_3H$, —$SO_2NH_2$, thiol and hydrazino (=N—$NH_2$.

28. The compound, or a solvate, a hydrate, and/or a stereoisomer thereof, or a pharmaceutically acceptable salt thereof of claim 27, wherein $R^2$ to $R^9$ are independently selected from H, —$NH_2$, F, $CH_3$, and $CF_3$.

29. The compound, or a solvate, a hydrate, and/or a stereoisomer thereof, or a pharmaceutically acceptable salt thereof of claim 27, wherein $R^7$ is $NR^{21}R^{22}$, $R^{21}$ and $R^{22}$ are independently selected from H, $(C_1\text{-}C_8)$alkyl, substituted $(C_1\text{-}C_8)$alkyl, $SO_2R^{30}$, and $COR^{30}$, and $R^{30}$ is $(C_1\text{-}C_8)$alkyl, or substituted $(C_1\text{-}C_8)$alkyl, wherein one or more substituents of substituted $(C_1\text{-}C_8)$alkyl are independently selected from halogen, hydroxy, oxo (=O), thioxo (=S), cyano (—CN), nitro (—$NO_2$), imino (=N—H), oximo (=N—OH), —$CONH_2$, —$NH_2$, —$CO_2H$, —$SO_3H$, —$SO_2NH_2$, thiol and hydrazino (=N—$NH_2$.

30. The compound, or a solvate, a hydrate, and/or a stereoisomer thereof, or a pharmaceutically acceptable salt thereof of claim 29, wherein $R^{21}$ and $R^{22}$ are each H.

31. The compound, or a solvate, a hydrate, and/or a stereoisomer thereof, or a pharmaceutically acceptable salt thereof of claim 29, wherein $R^5$, $R^6$, $R^8$ and $R^9$ are independently selected from H, ($C_1$-$C_5$)alkyl, substituted ($C_1$-$C_5$)alkyl, ($C_1$-$C_3$)haloalkyl, ($C_1$-$C_5$)alkoxy, substituted ($C_1$-$C_5$)alkoxy, halogen, and hydroxyl, wherein one or more substituents of substituted ($C_1$-$C_5$) alkyl, and substituted ($C_1$-$C_8$)alkoxy are independently selected from halogen, hydroxy, oxo (=O), thioxo (=S), cyano (—CN), nitro (—$NO_2$), imino (=N—H), oximo (=N—OH), —$CONH_2$, —$NH_2$, —$CO_2H$, —$SO_3H$, —$SO_2NH_2$, thiol and hydrazino (=N—$NH_2$).

32. The compound, or a solvate, a hydrate, and/or a stereoisomer thereof, or a pharmaceutically acceptable salt thereof of claim 31, wherein $R^5$, $R^6$, $R^8$ and $R^9$ are independently selected from H, F, $CH_3$, and $CF_3$; and $R^2$ to $R^4$ are each H.

33. The compound, or a solvate, a hydrate, and/or a stereoisomer thereof, or a pharmaceutically acceptable salt thereof of claim 27, wherein $R^2$ to $R^4$ are each H.

34. The compound, or a solvate, a hydrate, and/or a stereoisomer thereof, or a pharmaceutically acceptable salt thereof of claim 25, wherein the compound of formula (Ib') is selected from:

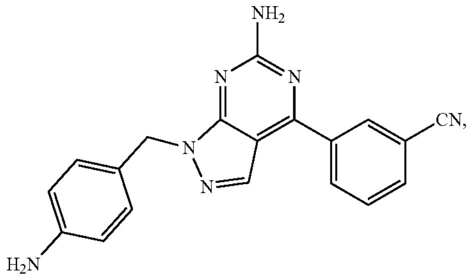

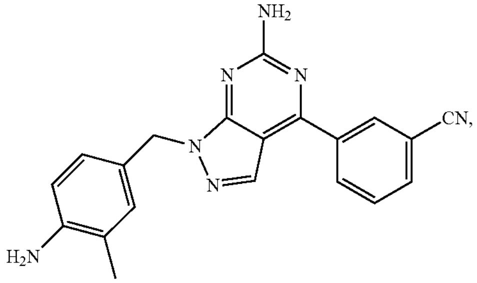

-continued

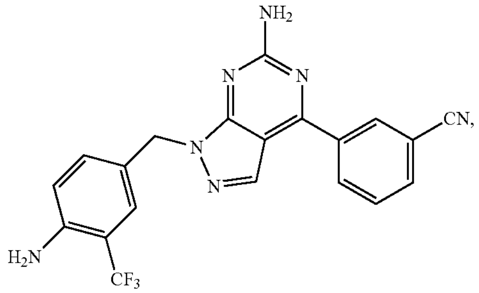

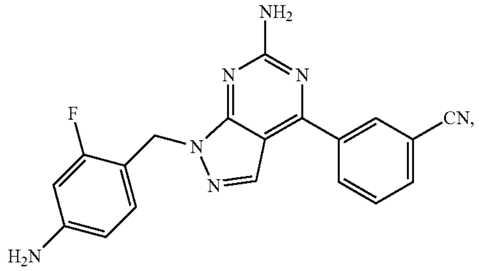

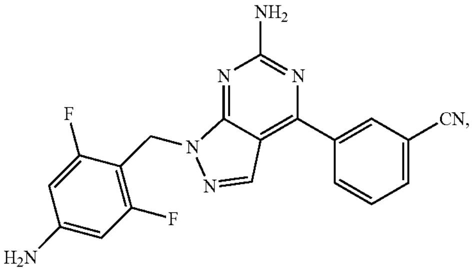

and

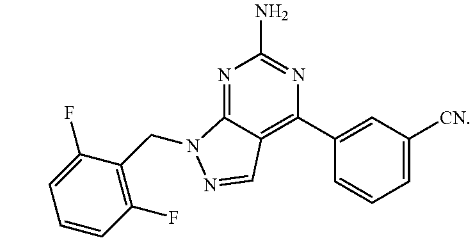

* * * * *